United States Patent
Zhang et al.

(10) Patent No.: US 10,930,367 B2
(45) Date of Patent: Feb. 23, 2021

(54) METHODS, MODELS, SYSTEMS, AND APPARATUS FOR IDENTIFYING TARGET SEQUENCES FOR CAS ENZYMES OR CRISPR-CAS SYSTEMS FOR TARGET SEQUENCES AND CONVEYING RESULTS THEREOF

(71) Applicants: THE BROAD INSTITUTE INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Feng Zhang, Cambridge, MA (US); Yinqing Li, Cambridge, MA (US); David Arthur Scott, Cambridge, MA (US); Joshua Asher Weinstein, Cambridge, MA (US); Patrick Hsu, Cambridge, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 546 days.

(21) Appl. No.: 14/738,483

(22) Filed: Jun. 12, 2015

(65) Prior Publication Data

US 2015/0356239 A1    Dec. 10, 2015

Related U.S. Application Data

(63) Continuation-in-part of application No. PCT/US2013/074812, filed on Dec. 12, 2013.

(60) Provisional application No. 61/836,080, filed on Jun. 17, 2013, provisional application No. 61/758,468, filed on Jan. 30, 2013, provisional application No. 61/769,046, filed on Feb. 25, 2013, provisional application No. 61/802,174, filed on Mar. 15, 2013, provisional application No. 61/806,375, filed on Mar. 28, 2013, provisional application No. 61/814,263, filed on Apr. 20, 2013, provisional application No. 61/819,803, filed on May 6, 2013, provisional application No. 61/828,130, filed on May 28, 2013, provisional application No. 61/736,527, filed on Dec. 12, 2012, provisional application No. 61/748,427, filed on Jan. 2, 2013, provisional application No. 61/791,409, filed on Mar. 15, 2013, provisional application No. 61/835,931, filed on Jun. 17, 2013.

(51) Int. Cl.
*G16B 20/00* (2019.01)
*C12N 15/10* (2006.01)
*C12N 9/22* (2006.01)
*C12N 15/113* (2010.01)

(52) U.S. Cl.
CPC ............... *G16B 20/00* (2019.02); *C12N 9/22* (2013.01); *C12N 15/1089* (2013.01); *C12N 15/113* (2013.01); *C12N 15/1082* (2013.01); *C12N 2310/20* (2017.05); *C12N 2320/11* (2013.01)

(58) Field of Classification Search
None
See application file for complete search history.

(56) References Cited

U.S. PATENT DOCUMENTS

| | | | |
|---|---|---|---|
| 5,622,856 A | 4/1997 | Natsoulis | |
| 6,251,677 B1 | 6/2001 | Wilson et al. | |
| 7,601,492 B2 | 10/2009 | Fu et al. | |
| 7,691,995 B2 | 4/2010 | Zamore et al. | |
| 8,697,359 B1 | 4/2014 | Zhang | |
| 8,771,945 B1 | 7/2014 | Zhang | |
| 8,865,406 B2 | 10/2014 | Zhang et al. | |
| 8,871,445 B2 | 10/2014 | Cong et al. | |
| 8,889,418 B2 | 11/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 9,549,901 B2 | 1/2017 | Shi et al. | |
| 9,597,357 B2 | 3/2017 | Gregory et al. | |
| 9,623,071 B2 | 4/2017 | Guo et al. | |
| 9,834,791 B2 | 12/2017 | Zhang et al. | |
| 9,873,894 B2 | 1/2018 | Conway et al. | |
| 10,301,651 B2 | 5/2019 | Doudna et al. | |
| 2003/0186238 A1 | 10/2003 | Allawi et al. | |
| 2004/0111221 A1 | 10/2004 | Beattie | |
| 2005/0196851 A1 | 9/2005 | Uckun | |
| 2005/0220796 A1 | 10/2005 | Dynan et al. | |
| 2006/0178297 A1 | 8/2006 | Troy et al. | |

(Continued)

FOREIGN PATENT DOCUMENTS

BR    112015013784    7/2017
CN    101228176 A    7/2008

(Continued)

OTHER PUBLICATIONS

Tulpan et al. BMC Bioinfornnatics. 2010; 11: 105. Published online Feb. 24, 2010. doi: 10.1186/1471-2105-11-105.*

(Continued)

*Primary Examiner* — Joseph Woitach
(74) *Attorney, Agent, or Firm* — Foley & Lardner LLP

(57) ABSTRACT

Disclosed are thermodynamic and multiplication methods concerning CRISPR-Cas systems, and apparatus therefor.

11 Claims, 57 Drawing Sheets
Specification includes a Sequence Listing.

(56) References Cited

U.S. PATENT DOCUMENTS

| | | |
|---|---|---|
| 2006/0234247 A1 | 10/2006 | Puttaraju et al. |
| 2007/0016012 A1 | 1/2007 | Hartlep |
| 2007/0244031 A1 | 10/2007 | Lu et al. |
| 2008/0293655 A1 | 11/2008 | Aygun et al. |
| 2010/0055798 A1 | 3/2010 | Battersby |
| 2010/0076057 A1 | 3/2010 | Sontheimer et al. |
| 2010/0081707 A1 | 4/2010 | Ali et al. |
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein |
| 2011/0059502 A1 | 3/2011 | Chalasani |
| 2011/0189776 A1 | 8/2011 | Terns et al. |
| 2011/0223638 A1 | 9/2011 | Wiedenheft et al. |
| 2011/0239315 A1 | 9/2011 | Bonas et al. |
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1 | 9/2016 | Wang et al. |
| 2016/0281072 A1 | 9/2016 | Zhang |
| 2016/0298135 A1 | 10/2016 | Chen |
| 2016/0298137 A1 | 10/2016 | Chen |
| 2016/0324938 A1 | 11/2016 | Bikard |
| 2016/0340662 A1 | 11/2016 | Zhang et al. |
| 2017/0175144 A1 | 6/2017 | Zhang et al. |
| 2018/0127783 A1 | 5/2018 | Zhang et al. |
| 2018/0230495 A1 | 8/2018 | Doudna et al. |
| 2019/0010471 A1 | 1/2019 | Zhang et al. |

FOREIGN PATENT DOCUMENTS

| | | |
|---|---|---|
| CN | 103388006 | 11/2013 |
| CN | 103668472 | 3/2014 |
| CN | 104854241 A | 8/2015 |
| EP | 2591770 | 5/2013 |
| EP | 2784162 | 1/2014 |
| EP | 2764103 | 8/2014 |
| EP | 2771468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009502170 | 1/2009 |
| JP | 2009-536827 A | 10/2009 |
| JP | 2010-522547 A | 7/2010 |
| JP | 2012-508235 | 4/2012 |
| JP | 2012-511332 A | 5/2012 |
| JP | 2012510812 | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500262 | 1/2016 |
| JP | 2016-501531 | 1/2016 |
| JP | 2016-501532 A | 1/2016 |
| JP | 2016500003 | 1/2016 |
| JP | 2016-025710 A | 2/2016 |
| JP | 2016-504026 A | 2/2016 |
| JP | 2016502840 | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-521995 | 7/2016 |
| JP | 2016-523082 A | 8/2016 |
| JP | 2016-524472 | 8/2016 |
| JP | 2016182140 | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |
| WO | WO-2004/046321 A2 | 6/2004 |
| WO | WO-2004/062618 A2 | 7/2004 |
| WO | WO-2005/014791 | 2/2005 |
| WO | 2005049642 | 6/2005 |
| WO | 2007014275 | 2/2007 |
| WO | WO-2007/134161 A2 | 11/2007 |
| WO | 2008093152 | 8/2008 |
| WO | 2008108989 | 9/2008 |
| WO | WO-2008/116860 A2 | 10/2008 |
| WO | 2010054108 | 5/2010 |
| WO | 2010065123 | 6/2010 |
| WO | WO-2010/068816 A1 | 6/2010 |
| WO | 2010079430 | 7/2010 |
| WO | WO-2010/075424 A2 | 7/2010 |
| WO | WO-2010/143917 | 12/2010 |
| WO | 2011011767 | 1/2011 |
| WO | WO-2011/016840 A2 | 2/2011 |
| WO | WO-2011/036510 A1 | 3/2011 |
| WO | 2011064736 | 6/2011 |
| WO | WO-2011/076873 A1 | 6/2011 |
| WO | WO-2011/100058 | 8/2011 |
| WO | 2011146121 | 11/2011 |
| WO | WO-2012/012738 A1 | 1/2012 |
| WO | WO-2012/031205 | 3/2012 |
| WO | WO-2012/051343 A1 | 4/2012 |
| WO | 2012149470 | 11/2012 |
| WO | 2012164565 | 12/2012 |
| WO | WO-2013/044008 A2 | 3/2013 |
| WO | WO-2013/052681 | 4/2013 |
| WO | WO-2013/071440 A1 | 5/2013 |
| WO | WO-2013/078400 A1 | 5/2013 |
| WO | 2013082519 | 6/2013 |
| WO | 2013098244 | 7/2013 |
| WO | 2013130824 | 9/2013 |
| WO | 2013141680 | 9/2013 |
| WO | 2013142578 | 9/2013 |
| WO | WO-2013/155572 | 10/2013 |
| WO | 2013176772 | 11/2013 |
| WO | WO 2013/176772 A1 | 11/2013 |
| WO | WO-2014/165349 A1 | 3/2014 |
| WO | 2014065596 | 5/2014 |
| WO | 2014089290 | 6/2014 |
| WO | 2014093479 | 6/2014 |
| WO | 2014093595 | 6/2014 |
| WO | 2014093622 | 6/2014 |
| WO | 2014093635 | 6/2014 |
| WO | 2014093661 | 6/2014 |

(56) References Cited

FOREIGN PATENT DOCUMENTS

| WO | 2014093694 | 6/2014 |
|---|---|---|
| WO | 2014093701 | 6/2014 |
| WO | 2014093709 | 6/2014 |
| WO | 2014093712 | 6/2014 |
| WO | 2014093718 | 6/2014 |
| WO | 2014099744 | 6/2014 |
| WO | 2014099750 | 6/2014 |
| WO | WO-2014/093655 | 6/2014 |
| WO | WO-2015/031775 | 8/2014 |
| WO | WO-2014/144761 | 9/2014 |
| WO | WO-2014/186585 A2 | 11/2014 |
| WO | 2014204724 | 12/2014 |
| WO | 2014204725 | 12/2014 |
| WO | 2014204727 | 12/2014 |
| WO | 2014204729 | 12/2014 |
| WO | WO-2014/191518 A1 | 12/2014 |
| WO | WO-2014/197568 A2 | 12/2014 |
| WO | WO-2014/197748 | 12/2014 |
| WO | WO-2014/204726 A1 | 12/2014 |
| WO | WO-2014/204728 | 12/2014 |
| WO | WO-2015/006747 A2 | 1/2015 |
| WO | WO-2015/035136 A2 | 3/2015 |
| WO | WO-2015/048577 | 4/2015 |
| WO | WO-2015/065964 A1 | 5/2015 |
| WO | WO-2015/070083 A1 | 5/2015 |
| WO | WO-2015/071474 | 5/2015 |
| WO | 2015089419 | 6/2015 |
| WO | WO-2015/089351 A1 | 6/2015 |
| WO | WO-2015/089364 | 6/2015 |
| WO | WO-2015/089427 A1 | 6/2015 |
| WO | WO-2015/113063 A1 | 7/2015 |
| WO | WO-2016/022866 A1 | 2/2016 |
| WO | WO-2016/141224 A1 | 9/2016 |

OTHER PUBLICATIONS

Marraffini et al. US 2010/0076057.*
Panyam, et al. "Biodegradable nanoparticles for drug and gene delivery to cells and tissue" Advanced Drug Delivery Reviews, 2003, 55:329-347.
Patterson, et al. "Codon optimization of bacterial luciferase (lux) for expression in mammalian cells" J. Ind. Microbio. Biotechnology, 2005, 32:115-123.
Pinera, et al. "RNA-guided gene activation by CRISPR-Cas9-based transcription factors" Nature Methods, 2013, 10(10):973-978.
Platt, et al. "CRISPR-Cas9 Knockin Mice for Genome Editing and Cancer Modeling" Cell, 2014, 159(2):440-455.
Porteus, et al. "Gene targeting using zinc finger nucleases" Nature Biotechnology, 2005, 23(8):967-973.
Pougach, et al. "Transcription, Processing and Function of CRISPR Cassettes in *Escherichia coli*" Mol. Microbiol, 2010, 77(6):1367-1379.
Qi, et al. "Repurposing CRISPR as an RNA-Guided Platform for Sequence-Specific Control of Gene Expression" Cell, 2013, 152(5):1173-1183.
Ran, et al, "In vivo genome editing using *Staphylococcus aureus* Cas9," Nature, 2015, doi:10.1038/nature14299.
Ran et al. "Double Nicking by RNA-Guided CRISPR Cas9 for Enhanced Genome Editing Specificity," Cell 154, 1-10, Sep. 12, 2013.
Ran, et al. "Genome engineering using the CRISPR-Cas9 system" Nature Protocols, 2013, 8(11):2281-2308.
Rand, et al. "Argonaute2 Cleaves the Anti-Guide Strand of siRNA during RISC Activation" Cell, 2005, 123:621-629.
Raymond, et al. "High-Efficiency FLP and φC31 Site-Specific Recombination in Mammalian Cells" PLoS ONE, 2007, 2(1):e162. Doi. 10.1371/journal.pone.0000162.
Rebar, et al. "Induction of angiogenesis in a mouse model using engineered transcription factors" Nature Medicine, Dec. 2002, 8(12):1427-1432.
Reiss, et al. "RecA protein stimulates homologous recombination in plants" Proc. Natl. Acad. Sci. USA, 1996, 93:3094-3098.
Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.
Sapranauskas, et al. "The *Streptococcus thermophilus* CRISPR-Cas system provides immunity in *Escherichia coli*" Nucleic Acids Research, 2011, 39(21): 9275-9282.
Sauer, "Functional Expression of the cre-lox Site-Specific Recombination System in the Yeast *Saccharomyces cerevisiae*" Mol. Cell. Biol., 1987, 7(6):2087-2096.
Sauer, et al. "Site-specific DNA recombination in mammalian cells by the Cre recombinase of bacteriophage P1" Proc. Natl. Acad. Sci. U.S.A., 1988, 85:5166-5170.
Schiffer, et al. "Predictors of Hepatitis B Cure Using Gene Therapy to Deliver DNA Cleavage Enzymes: A Mathematical Modeling Approach" PLOS Computational Biology., 2013, 9(7):e1003131. www.ploscompbiol.org.
Scholze, et al. "TAL effector-DNA specificity" Virulence, 2010, 1(5):428-432, DOI:10.4161/viru.1.5.12863.
Schramm et al. "Recruitment of RNA polymerase III to its target promoters" Genes & Development, 2002, 16:2593-2620.
Seung Woo Cho, et al., "Targeted genome engineering in human cells with the Cas9 RNA-guided endonuclease" Nature Biotechnology, Mar. 2013, 31(3):230-232.
Seung Woo Cho, et al. "Supplementary Information: Targeted genome engineering in human cells with RNA-guided endonuclease" Nature Biotechnology, Mar. 2013, 31(3):1-10.
Seung Woo Cho, et al. "Analysis off-target effects of CRISPR/Cas-derived RNA-guided endonucleases and nickases" Genome Research, Nov. 2014, 24:132-141.
Shalem et al., "Genome-Scale CRISPR-Cas9 Knockout Screening in Human Cells", Science, 2014, 343;84-87. DOI:10.1126/science.1247005.
Shen, et al. "Efficient genome modification by CRISPR-Cas9 mickase with minimal off-target effects" 2014, Nature Methods, 11(4):399-404.
Shen, et al. "Generation of gene-modified mice via Cas9/RNA-mediated gene targeting" Cell Research, 2013, 23:720-723.
Sims, et al., "High-throughput RNA interference screening using pooled shRNA libraries and next generation sequencing", Genome Biology 12(10):R104, Oct. 2011.
Sontheimer, "Project 7: Establishing RNA-Directed DNA Targeting in Eukaryotic Cells" Physical Sciences-Onc., Nov. 16, 2011-Dec. 31, 2012, htt://groups.molbiosci.northwestern.edu/sontheimer/Sontheimer_cv.php) Molecular Biosciences.
Sosa, et A. "Animal transgenesis: an overiew" Brain Struct Funct, 2010, 214:91-109.
Stolfi, et al, "Tissue-specific genome editing in Ciona embryos by CRISPR/Cas9," Development, 2014, 141:4115-4120 doi:10.1242/dev.114488.
Swiech et al., "In vivo interrogation of gene function in the mammalian brain using CRISPR-Cas9," Nature Biotechnology, 2015, doi:10.1038/nbt.3055.
Terns, et al. "Crispr-based adaptive immune systems" Current Opinion in Microbiology, 2011, 14:321-327.
Tolia, et al. "Slicer and the Argonautes" Nature Chemical Biology, 2007, 3(1):36-43.
Trevino, et al. "Genome Editing Using Cas9 Nickases" Methods in Enxymology, 2014, 546:161-174.
Urnov, et al. "Highly efficient endogenous human gene correction using designed zinc-finger nucleases" Nature, 2005, 435:646-651.
Wang, et al. One-Step Generation of Mice Carrying Mutations in Multiple Genes by CRISPR/Cas-Mediated Genome Engineering, Cell, 2013, 153:910-918.
Wiedenheft, et al. "RNA-guided genetic silencing systems in bacteria and archaea" Nature, 2012, 432:331-338.
Wu, et al. "Genome-wide binding of the CRISPR endonuclease Cas9 in mammalian cells"Nature Biotechnology, 2014, doi:10.1038/nbt.2889.

(56) References Cited

OTHER PUBLICATIONS

Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. Production of High-Titer Recombinant Adeno-Associated Virus Vectors in the Absence of Helper Adenovirus.
Zetsche et al. "A split-Cas9 architecture for inducible genome editing and transcription modulation," Nature biotechnology, 2015, 33(2): 139-142.
Zhang, X. D., et al., "cSSMD: assessing collective activity for addressing off-target effects in genome-scale RNA interference screens", Bioinformatics (Oxford), 27(20);2775-2781, Oct. 2011.
Zhang, et al. "Efficient construction of sequence-specific TAL effectors for modulating mammalian transcription" nature biotechnology, 2011, 29(2):149-154.
Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.
Geißler, et al. "Trancscriptional Activators of Human Genes with Programmable DNA-Specificity" PLos One, 2011, 6(5):e19509. Doi:10.1371/hournal.pone.0019509.
Le Rhun, et al., Small RNAs in Streptococci, RNA Biology (Apr. 4, 2012) vol. 9, Issue 4, p. 414-426.
Clark, et al., A TALE of Two Nucleases: Gene Targeting for the Masses? Zebrafish (2011) vol. 8, No. 3, p. 147-149.
Mahfouz, et al., De Novo-engineered Transcription Activator-Like Effector (TALE) Hybrid Nuclease with Novel DNA Binding Specificity Creates Double-Strand Breaks, PNAS (Feb. 8, 2011) vol. 108, No. 6, p. 2623-2628.
Bobis-Wozowicz, et al., Targeted Genome Editing in Pluripotent Stem Cells Using Zinc-Finger Nucleases, Methods (2011) vol. 53, p. 339-346.
Swarthout, et al., Zinc Finger Nucleases: A New Era for Transgenic Animals, Annals of Neurosciences (Jan. 2011) vol. 18, No. 1, p. 25-28.
Goncalves, et al., Concerted Nicking of Donor and Chromosomal Acceptor DNA Promotes Homology-Directed Gene Targeting in Human Cells, Nucleic Acids Research (2012) vol. 40, No. 8, p. 3443-3455.
Van Nierop, et al., Stimulation of Homology-Directed Gene Targeting at an Endogenous Human Locus by a Nicking Endonuclease, Nucleic Acids Research (2009) vol. 37, No. 17, p. 5725-5736.
Lee, et al., Correction of the F508 Mutation in the Cystic Fibrosis Transmembrane Conductance Regulator Gene by Zinc-Finger Nuclease Homology-Directed Repair, Bioresearch Open Access (2012) vol. 1, No. 3, p. 99-108.
Gaj, et al., Targeted Gene Knockout by Direct Delivery of Zinc-Finger Nuclease Proteins, Nature Methods (Aug. 2012) vol. 9, No. 8, p. 805-807.
Porteus, et al., Chimeric Nucleases Stimulate Gene Targeting in Human Cells, Science (May 2, 2003) vol. 300, p. 763.
Sung, et al., The Importance of Valency in Enhancing the Import and Cell Routing Potential of Protein Transduction Domain-Containing Molecules, Biochimica et Biophysica Aeta (2006) vol. 1758, p. 355-363.
Dworetzky, et al., The Effects of Variations in the Number and Sequence of Targeting Signals on Nuclear Uptake, The Journal of Cell Biology (1988) vol. 107, p. 1279-1287.
Mincer, et al., Simulations of Nuclear Pore Transport Yield Mechanistic Insights and Quantitative Predictions, PNAS (Aug. 2, 2011) vol. 108, No. 31, p. E351-E358.
U.S. Appl. No. 61/734,256, filed Dec. 6, 2012, Fuqiang Chen.
U.S. Appl. No. 61/758,624, filed Jan. 30, 2013, Fuqiang Chen.
U.S. Appl. No. 61/761,046, filed Feb. 5, 2013, Scott Knight.
U.S. Appl. No. 61/761,422, filed Mar. 15, 2013, Scott Knight.
U.S. Appl. No. 61/735,876, filed Dec. 11, 2012, Blake A. Wiedenheft.
U.S. Appl. No. 61/799,531, filed Mar. 15, 2013, Blake A. Wiedenheft.
U.S. Appl. No. 61/738,355, filed Dec. 17, 2012, George M. Church.
U.S. Appl. No. 61/799,169, filed Mar. 13, 2012, Prashant Mali.
U.S. Appl. No. 61/613,373, filed Mar. 20, 2012, Virginijus Siksnys.
U.S. Appl. No. 61/625,420, filed Apr. 17, 2012, Virginijus Siksnys.
U.S. Appl. No. 61/652,086, filed May 5, 2012, Martin Jinek.
U.S. Appl. No. 61/716,256, filed Oct. 19, 2012, Martin Jinek.
U.S. Appl. No. 61/736,527, filed Dec. 12, 2012, F. Zhang.
U.S. Appl. No. 61/757,640, filed Jan. 28, 2013, Jinek.
U.S. Appl. No. 61/794,422, filed Mar. 15, 2013, Knight.
Andreas, et al. "Enhanced efficiency through nuclear localization signal fusion on phage C31-integrase: activity comparison with Cre and FLPe recombinase in mammalian cells" Nucleic Acids Research, 2002, 30(11):2299-2306.
Asuri, et al. "Directed Evolution of Adeno-Associated Virus for Enhanced Gene Delivery and Gene Targeting in Human Pluripotent Stem Cells" Molecular Therapy, Feb. 2012, 30(2):329-338.
Al-Attar et al., "Clustered regularly interspaced short palindromic repeats (CRISPRs): the hallmark of an ingenious antiviral defense mechanism in prokaryotes" Biol Chem., 2011, 392(4):277-289.
Baker, "Gene editing at CRISPR Speed" Nature Biotechnology, 2014, 32(4):309-312.
Banaszewska, et al. "Proprotein Convertase Subtilisin/Kexin Type 9: A New Target Molecule for Gene Therapy" Cellular & Molecular Biology Letters, Feb. 2012, 17(2):228-239.
Barrangou, "RNA-mediated programmable DNA cleavage" Nature Biotechnology, Sep. 2012, 30(9):836-388.
Bergemann, et al. "Excision of specific DNA-sequences from integrated retroviral vectors via site-specific recombination" Nucleic Acids Res., 1995, 23(21):4451-4456.
Bikard, et al. "CRISPR Interference Can Prevent Natural Transformation and Virulence Acquisition During In Vivo Bacterial Infection" Cell Host & Microbe, Aug. 2012, vol. 12:177-186.
Boch, et al. "Breaking the Code of DNA Binding Specificity of TAL-Type III Effecors" Science, 2009, 326:1509-1512.
Boch, et al. "Xanthomonas AvrBs3 Family-Type III Effectors: Discovery and Function" Annu. Rev. Phytopathol, 2010, Vo. 48:419-436.
Bogdanove, et al. "TAL Effectors:Customizable Proteins for DNA Targeting" Science, 2011, 333:1843-1846.
Briner, et al. "Guide RNA Functional Modules Direct Cas9 Activity and Orthogonality" Molecular Cell, Oct. 2014, 56:333-339.
Carroll, "A CRISPR Approach to Gene Targeting" Molecular Therapy, 2012, 20(9): 1658-1660.
Cermak, et al. Efficient design and assembly of custom TALEN and other TAL Effector-Based Constructs for DNA Targeting, Nucleic Acids Research (2011) vol. 39, No. 12, e82, p. 1-11.
Chen, et al. "Dynamic Imaging of Genomic Loci in Living Human Cells by an Optimized CRISPR/Cas System" Cell, Dec. 2013, vol. 155:1479-1491.
Jieliang Chen, et al. "An Efficient Antiviral Strategy for Targeting Hepatitis B Virus Genome Using Transcription Activator-Like Effector Nucleases" Molecular Therapy, 2014, 22(2):303-311.
Sidi Chen, et al., "Genome-wide CRISPR Screen in a Mouse Model of Tumor Growth and Metastasis," Cell, 2015, 160:1-15, http://dx.doi.org/10.1016/j.cell.2015.02.038.
Cho, et al. "Generation of Transgenic Mice" Curr Protoc Cell Biol., 2011, 19.11.doi:10.1002/0471143030.cb1911s42.
Choulika, et al., "Transfer of Single Gene-Containing Long Terminal Repeats into the Genome of Mammalian Cells by a Retroviral Vector Carrying the cre Gene and the loxP site" Journal of Virology, 1996, 70(3)1792-1798.
Christian, et al. "Targeting DNA Double-Strand Breaks With TAL Effector Nucleases" Genetics, Oct. 2010, vol. 186:757-761.
Christian, et al. "Supporting Information-Targeting DNA Double-Strand Breaks With TAL Effector Nucleases" Genetics, 2010, DOI:10.1534/110.120717:1SI-8SI.
Chylinski, et al. "The tractRNA and Cas9 Families of Type II CRISPR-Cas Immunity Systems" RNA Biology, May 2013, 10(5):726-737.
Cong, et al. "Comprehensive interrogation of natural TALE DNA-binding modules and transcriptional repressor domains" Nature Communications, 2012, 3:968, DOI:10/2038/ncomms1962.
Cong, et al, "Multiplex Genome Engineering Using CRISPR-Cas Systems" Science, 2013, 339:819-823.

(56) References Cited

OTHER PUBLICATIONS

Cong, et al, "Supplementary Material: Multiplex Genome Engineering Using CRISPR-Cas Systems" Science Express, Jan. 3, 2013. http://www.sciencemag.org/content/339/6121/819/suppl/DC1.
Connor, "Scientific split—the human genome breakthrough dividing former colleagues," Science, The Independent, Apr. 25, 2014, http://www.independent.co.uk/news/science/scientific-split--the-human-genome-breakthrough-dividing-former-colleagues-9300456.html.
Dahlman, et al. "In vivo endothelial siRNA delivery using polymeric nanoparticles with low molecular weight" Nat. Nanotechnol., 2014, 9(8)648-655. doi:10.1038/nnano.2014.84.
Datsensenko, et al. "Molecular memory of prior infections activates the CRISPR/Cas adaptive bacterial immunity system" Nature Communications, Jul. 10, 2012, 3:935, DOI:10.1038/ncomms1937.
Dingwall, et al. "Abstract: A Polypeptide Domain That Specifies Migration of Nucleoplasmin into the Nucleus" Cell, 1982, 30(2):449-58.
Deltcheva, et al. "CRISPR RNA maturation by trans-encoded small RNA and host Factor RNase III" Nature, Mar. 2011, vol. 471:602-609.
Deltcheva, et al. "Supplementary Information: CRISPR RNA Maturation by Trans-Encoded Small RNA and Host Factor RNase III" www.Nature.com/doi:10.1038/nature09886:1-35.
Drittanti, et al. "High throughput production, screening and anyalysis of adeno-associated viral vectors" Gene Therapy, 2000, 7:924-929.
Ebina, et al. "Harnessing the CRISPR/Cas9 system to disrupt latent HIV-1 provirus" Scientific Reports, 2013, 2:2510, doi:10.1038/srep02510.
Ellis, et al. Macromolecular Crowding: Obvious But Underappreciated, TRENDS in Biochemical Sciences, Oct. 2001, 26(10):597-604.
Ellis, et al. "Zinc-finger nuclease-mediated gene correction using single AAV vector transduction and enhanced by Food and Drug Administration-Approved Drugs" Gene Therapy, 2013, vol. 20:35-42.
Enyeart, et al., "Biotechnological applications of mobile group II introns and their reverse transcriptases: gene targeting, RNA-seq, and non-coding RNA analysis" Mobile DNA, 2014, 5:2, http://www.mobilednajournal.com/contents5/1/2.
Gabriel, et al. "An unbiased genome-wide analysis of zinc-finger nuclease specificity" Nature Biotechnology, Aug. 2011, 29(9):816-823.
Gaj, et al. "ZFN, TALEN, and CRISPR/Cas-Based Methods for Genome Engineering" Trends in Biotechnology, Jul. 2013, 31(7):397-405.
Garneau, et al. "The CRISPR-Cas bacterial immune systems cleaves bacteriophage and plasmid DNA" Nature, Nov. 2010, 468:67-71.
Gasiunas, et al. "Cas9-crRNA ribonucleoprotein complex mediates specific DNA cleavage for adaptive immunity in bacteria" PNAS, Sep. 2012, 109(39): E2579-E2586.
Gilbert, et al. "CRISPR-Mediated Modular RNA-Guided Regulation of Transcription in Eukaryotes" Cell, Jul. 2013, 154:442-451.
Goldfarb, et al. "Synthetic peptides as nuclear localization signals" Nature, Aug. 1986, 322(14):641-644.
Grens, Enzyme Improves CRISPR a smaller Cas9 protein enables in vivo genome engineering via viral vectors, The Scientist, Apr. 1, 2015.
Gustafsson, et al. "Codon Bias and heterologous protein expression" TRENDS in Biotechnology, Jul. 2004, 22(7):346-353.
Haft, et al. "Protein Families and Multiple CRISPR/Cas Subtypes Exist in Prokaryotic Genomes" PLoS Computational Biology, 2005, 1(6):0474-483.
Haft, et al. "A Guild of 45 CRISPR-Associated (Cas) Protein Families and Multiple CRISPR/Cas Subtypes Exist in Prokaryotic Genomes" PLoS Computational Biology, 2005, 1(6):0474-0483.
Hale, et al. "Essential Features and Rational Design of CRISPR RNAs that Function With the Cas RAMP Module Complex to Cleave RNAs" Molecular Cell, 2012, 45(3):292-302.
Hale, et al. "RNA-Guided RNA Cleavage by a CRISPR RNA-Cas Protein Complex" Cell, 2009, 139:945-956.
Hale, et al. "Prokaryotic siliencing (psi) RNAs in Pyrococcus furiosus", RNA, 2008, 14:2572-2579.
Handel, et al. "Versatile and Efficient Genome Editing in Human Cells by Combining Zinc-Finger Nucleases With Adeno-Associated Viral-Vectors" Human Gene Therapy, Mar. 2012, 23:321-329.
Hibbitt, et al. "RNAi-mediated knockdown of HMG CoA reductase enhances gene expression from physiologically regulated low-density lipoprotein receptor therapeutic vectors in vivo" Gene Therapy, 2012, 19:463-467.
Hou, et al., "Efficient genome engineering in human pluripotent stem cells using Cas9 from Neisseria meningitides," PNAS, 2013, 110(39):15644-15649.
Horvath et al. "RNA-guidded genome editing a la carte" Cell Research, 2013, 23:733-734, doi:10.1038/cr.2013.39.
Hsu, et al. "Development and Applications of CRISPR-Cas9 for Genome Engineering" Cell, Jun. 2014, 157:1262-1278.
Hsu et al., "DNA targeting specificity of RNA-guided Cas9 nucleases," Nature Biotechnology, 2013, 31(9):827-834.
Hsu et al., "Supplementary Information-DNA targeting specificity of RNA-guided Cas9 nucleases," Nature Biotechnology, 2013, doi:10.1038/nbt.2647.
Hwang Woong, et al. "Efficient genome editing in zebrafish using a CRISPR-Cas System" Nature Biotechnology, Mar. 2013, 31(3):227-229.
Hwang Woong, et al. "Efficient In Vivo Genome Editing Usng RNA-Guided Nucleases" Nat. Biotechnol., 2013, 31(3):227.229. doi. 1.1038/mbt.2501.
Janssen, et al., "Mouse Models of K-ras-Initiated Carcinogenesis" Biochimicia et Biophysica Acta, 2005, 1756:145-154.
Jiang, et al. "RNA-guided editing of bacterial genomes using CRISPR-Cas systems" Nature Biotechnology, 2013, 31(3):233-239.
Jinek, et al., "RNA-programmed genome editing in human cells;" 2013, eLife 2013:e00471, DOI:10.7554/eLife.00471.
Jinek, et al, "A Programmable Dual-RNA-Guided DNA Endonuclease in Adaptive Bacterial Immunity" Science, 2012, 337:816-821.
Jinek, et al., "Figures and figure supplements—A Programmable Dual-RNA-Guided DNA Endonuclease in Adaptive Bacterial Immunity" eLife 2014;2:e00471.DOI:10.7554/eLife 00471.
Kanasty, et al. "Delivery materials for siRNA therapeutics" Nature Materials, 2013, 12:967-977.
Karvelis, et al. "crRNA and tracrRNA guide Cas9-mediated DNA interference in *Streptococcus thermophiles*" RNA Biology, 2013, 10(5):841-851.
Karvelis, et al. "Supplemental Material to: crRNA and tracrRNA guide Cas9-mediated DNA interference in *Streptococcus thermophiles*" Landes Bioscience, 2013, 10(5), http://dx.doi.org/10.4161/rna.24203.
Kim, et al. "Crystal structure of Cas1 from Archaeoglobus fulgidus and characterization of its nucleolytic activity" Biochemical and Biophysical Research Communications, 2013, 441:720-725.
Konermann, et al, "Genome-scale transcriptional activation by an engineered CRISPR-Cas9 complex" Nature, 2015, 517:583-588.
Koornneef, et al. "Apoliprotein B Knockdown by AAV-Delivered shRNA Lowers Plasma Cholesterol in Mice" Molecular Therapy, Apr. 2011, 19( 4)731-740.
Lambowitz, et al. "Group II Introns: Mobile Ribozymes that Invade DNA" Cold Spring Hart Perspect Biol., 2011, 3:a003616.
Larson, et al. "CRISPR interference (CRISPRi) for sequence-specific control of gene expression" Nature Protocols, 2013, 8(11):2180-2196.
Lewis, et al., "The c-myc and PyMT oncogenes induce different tumor types in a somatic mouse model for pancreatic cancer" Genes & Development, 2003, 17:3127-3138.
Li et al. "In vivo genome editing restores hemostasis in a mouse model of hemophilia" Nature, 2011, 475(7355):217-221. doi: 10.1038/nature10177.
Li, et al. "Multiplex and homologous recombination-mediated genome editing in *Arabidopsis* and Nicotaina benthamiana using guide RNA and Cas9" Nature Biotechnology, 2013, 31(9):688-691.

(56) References Cited

OTHER PUBLICATIONS

Lombardo, et al., "Gene editing in human stem cells using zinc finger nucleases and integrase-defective lentiviral vector delivery" Nature Biotechnology, 2007, 25(11):1298-1306.
Luo, et al., "Highly parallel identification of essential genes in cancer cells", Proceeding of the National Academy of Sciences, 2008, 105(51);20380-20385.
Ma, et al. "A Guide RNA Sequence Design Platform for the CRISPR/Cas9 System for Model Organism Genomes", BioMed Research International, 2014, 2013:270805-4. http://dx.doi.org/10.1155/2014/270805.
Maeder, et al. "CRISPR RNA-guided activation of endogenous human genes" Nature Methods, 2013, 10(10):977-979. doi.10.1038/nmeth.2556.
Makarova, et al, "Evolution and classification of the CRISPR-Cas Systems" Nature Reviews Microbiology, 2011, 9(6):467-477.
Makarova et al. "Unification of Cas protein families and a simple scenario for the origin and evolution of CRISPR-Cas systms" Biology Direct, 2011, 6:38. http:///www.biology-direct.com/content/6/1/38.
Mali, et al. "Supplementary Materials for—RNA-Guided Human Genome Engineering via Cas9" Science, 2013, 339:823-826.
Mali, et al. "RNA-Guided Human Genome engineering via Cas9" Science, 2013, DOI: 10.1126/SCIENCE.1232033.
Mali, et al. "CAS9 transcriptional activators for target specificity screening and paired nickases for cooperative genome engineering" nature biotechnology, 2013, 31(9):833-840.
Mali, et al. "Supplementary Information: Use of adjacent sgRNA:Cas9 complexes for transcriptional activation and genome engineering" Nature Biotechnoly, doi:10.1037/nbt.2675.
Malina, et al. "Repurposing CRISPR/Cas9 for in situ functional assays" Genes & Development, 2013, 27:2602-2614.
Marraffini, et al. "Self vs. non-self discrimination during CRISPR RNA-directed immunity" Nature, 2010, 463 (7280):568-571.
Mastroianni, et al. "Group II Intron-Based Gene Targeting Reactions in Eukaryotes" Plos One, 2008, 3(9):e3121. Doi:10.1371/journal.pone.0003121.
Meshorer, et al. "Chromatin in pluripotent embryonic stem cells and differentiation" Nature Reviews Molecular Cell Biology, 2006, 7:540-546.
Miller, et al. "A TALE nuclease architecture for efficient genome editing" Nature Biotechnology, 2011, 29(2):143-150.
Minton, "How can biochemical reactions within cells differ from those in test tubes?" Journal of Cell Science, 2006, 119:2863-2869.
Mojica et al. "Short motif sequences determine the targets of the prokaryotic CRISPR defence system", Microbiology, 2009, 155:733-740.
Morgan, et al. "Inducible Expression and Cytogenetic Effects of the EcoRI Restriction Endonuclease in Chinese Hamster Ovary Cells" Molecular and Cellular Biology, 1988, 8(10):4204-4211.
Mukhopadyay, "On the Same Wavelength," ASBMBTODAY, Aug. 2014, http://www.asbmb.org/asbmbtoday/201408/Features/Doudna/.
Nakamura, et al. "Codon usage tabulated from international DNA sequence databases: status for the year 2000" Nucleic Acids Research, 2000, 28(1): 292.
Nomura, et al., "Low-density lipoprotein receptor gene therapy using helper-dependent adenovirus produces long-term protection against atherosclerosis in a mouse model of familial hypercholesterolemia" Gene Therapy, 2004, 11:1540-1548.
Nishimasu et al. "Crystal Structure of *Staphylococcus aureus* Cas9," Cell 162, 1113-1126, Aug. 27, 2015.
Nishimasu, et al. Crystal Structure of Cas9 in Complex with Guide RNA and Target DNA, Cell, 2014, 156:935-949.
Oost, "New Tool for Genome Surgery" Science, Feb. 15, 2013, 399:768-770.
"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).
Addgene Materials May 2015.
Addgene Materials Oct. 2014 including Addgene News 2013.
Addgene Reagent distribution list for Zhang Lab.
*Arbitron, Inc.* v. *Kiefl*, No. 09-CV-04013 PAC, 2010 WL 3239414, at *1 (S.D.N.Y. Aug. 13, 2010).
Autofluorescence MIT Flow Cytometry Core Facility (2018), 6 pages.
Baena-Lopez, L., et al., "Accelerated homologous recombination and subsequent genome modification in *Drosophila*," Development, vol. 140, No. 23, pp. 4818-4825, dated Dec. 2013, 18 pages, including Supplementary Material.
Balboa et al., "Conditionally Stabilized dCas9 Activator for Controlling Gene Expression in Human Cell Reprogramming and Differentiation. (plus Supplemental Information)", Stem Cell Reports, vol. 5, No. 3, Sep. 8, 2015, pp. 448-459 16PP.
Barrangou and Van Der Oost (Eds.), "CRISPR-Cas Systems," Springer Heidelberg (2013; written in 2012 before the publication of Cong et al.).
Barrangou, R. et al.: "CRISPR provides acquired resistance against viruses in prokaryotes," Science, vol. 315, pp. 1709-1712, dated Mar. 23, 2007, 5 pages.
Bennett et al., "Stable transgene expression in rod photoreceptors after recombinant adeno-associated virus-mediated gene transfer to monkey retina", Proc. Natl. Acad. Sci., USA, vol. 96, Aug. 1999, pp. 9920-9925.
Berns, K., et al. "A Large-Scale RNAi Screen in Human Cells Identifies New Components of the p53 Pathway," Nature 2004, vol. 428, pp. 431-437, dated Mar. 25, 2004, 7 pages.
Bhaya, D., et al., "CRISPR-Cas Systems in Bacteria and Archaea: Versatile Small RNAs for Adaptive Defense and Regulation," Annual Review of Genetics, vol. 45, No. 1, pp. 273-297, dated Dec. 15, 2011, 27 pages.
Bikard, et al. Supplementary Information for: "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.
Bloom et al., "Inactivation of hepatitis B virus replication in cultured cells and in vivo with engineered transcription activator-like effector nucleases", Molecular Therapy, Aug. 20, 2013, vol. 21, No. 10, pp. 1889-1897.
Bohm, "The computer program LUDI: A new method for the de novo design of enzyme inhibitors", Journal of Computer-Aided Molecular Design, 1992, vol. 6, pp. 61-78.
Boutros et al.: "Genome-wide RNAi analysis of growth and viability in *Drosophila* cells," Science, American Association for the Advancement of Science, vol. 303, No. 5659, pp. 832-835, dated Feb. 6, 2004, 4 pages.
Branden, C., and Tooze, J., "Prediction, Engineering, and Design of Protein Structures," Introduction to Protein Structure, Chapter 16, p. 247, Garland Publishing, Inc., New York, dated 1991, 3 pages.
Brouns, S., et al., "Small CRISPR RNAs Guide Antiviral Defense in Prokaryotes," Science, vol. 321, pp. 960-964, dated Aug. 15, 2008, 6 pages.
Chinnasamy, D., et al., "Multicistronic lentiviral vectors containing the FMCV 2A Cleavage factor demonstrate robust expression of encoded genes at limiting MOI," Virology Journal, vol. 3, No. 4, dated Mar. 15, 2006, 16 pages.
Chou, JY, and Mansfield, BC, "Recombinant AAV-directed gene therapy for type I glycogen storage diseases," Expert Opinion on Biological Therapy, vol. 11, No. 8, pp. 1011-1024, dated Apr. 20, 2011, 21 pages.
Cockrell, "Berkeley's Wikipedian-in-residence is a first," NewsCenter, Feb. 25, 2014.
Community Corner, "CRISPR technology for gene therapy," Nature Medicine, vol. 20, No. 5, pp. 476-477, dated May 2014, 3 pages.
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.
Cong, L., et al., "In Vivo Genome Engineering With AAV Vector Carrying CRISPR-Cas9 System," Molecular Therapy, vol. 22, Supplement 1, p. S214, dated May 23, 2014, 1 page.

(56) References Cited

OTHER PUBLICATIONS

Cong, L., et al., Supplementary Material for: "Multiplex Genome Engineering Using CRISPR-Cas Systems," Science Express, dated Jul. 5, 2012.
Cotropia, et al., "Copying in Patent Law," N.C.L. Rev., Stanford Public Law Working Paper No. 1270160 (2009), 87:1421.
Cummings et al., "Fourteen and counting: unraveling trinucleotide repeat diseases", Human Molecular Genetics, 2000, vol. 9, No. 6, pp. 909-916.
Daboussi, F., et al., "Chromosomal context and epigenetic mechanisms control the efficacy of genome editing by rare-cutting designer endonucleases," Nucleic Acids Research, vol. 40, No. 13, pp. 6367-6379, dated Jul. 13, 2012, 13 pages.
Daley, J., and Wilson, T., "Rejoining of DNA Double-Strand Breaks as a Function of Overhang Length," Molecular and Cellular Biology, vol. 25, No. 3, pp. 896-906, dated Feb. 2005, 11 pages.
Damian, M., and Porteus, M., "A Crisper Look at Genome Editing: RNA-guided Genome Modification," Molecular Therapy, vol. 21, No. 4, pp. 720-722, dated Apr. 2013, 3 pages.
Database UniProtKB/TrEMBL [online], Accession No. Q0P897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.
Database WPI, Week 201437 Thomson Scientific, London, GB; AN 2014-J79552, XP-002737563, 2 pages.
Declaration of Feng Zhang for U.S. Appl. No. 14/054,414 dated Jan. 30, 2014, 10 pages.
Excerpt from Declaration of Feng Zhang, dated Sep. 9, 2015.
Federal Circuit decision in Dow Chemical Co. v. Nova Chemicals Corp., Appeal Nos. 2014-1431, 2014-1462 (Fed. Cir. Aug. 28, 2015) (Dow v. Nova), 25 pages.
Feldgarden et al., "Staphylococcus aureus M0408 acrHk-supercont1.1, whole genome shotgun sequence", NCBI Reference Sequence: NK_KB821326.1, Direct Submission, Dec. 10, 2012, pp. 1-4.
Fleming, J., et al.: "Adeno-Associated Virus and Lentivirus Vectors Mediate Efficient and Sustained Transduction of Cultured Mouse and Human Dorsal Root Ganglia Sensory Neurons," Human Gene Therapy, vol. 12, pp. 77-86, dated Jan. 1, 2001, 10 pages.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Fu et al, "Targeted genome editing in human cells using CRISPR/Cas nucleases and truncated guide RNAsc", Jan. 1, 2014, The Use of CRISPR/Cas9 ZFNs and Talens in Generating Site-Specific Genome Alterations; Methods in Enzymology; ISSN 1557-7988, vol. 546, Elsevier, NL, pp. 21-45.
Gardlik, R., et al., "Vectors and delivery systems in gene therapy," Medical Science Monitor, vol. 11, No. 4, pp. RA110-121, dated Apr. 1, 2005, 12 pages.
Garriga-Canut, M., et al., "Synthetic zinc finger repressors reduce mutant huntingtin expression in the brain of R6/2 mice," Proceedings of the National Academy of Sciences, vol. 109, No. 45, pp. E3136-E3145, dated Nov. 6, 2012, 10 pages.
Geisinger et al., "In vivo blunt-end cloning through CRISPR /CAS9-facilitated non-nomoiogous end-joining", Nucleic Acid Research Advance Access, Jan. 13, 2016, pp. 1-15.
Habib, N., Assignment to Broad Institute, dated Jun. 9, 2014, 4 pages.
Hall, B., et al., "Overview: Generation of Gene Knockout Mice," Current Protocols in Cell Biology, unit 19.12, suppl. 44, pp. 1-17, dated 2009, 17 pages.
Harrison et al., "A CRISPR view of development", Genes & Development, vol. 28, No. 17, Sep. 1, 2014, pp. 1859-1872.
Holkers, M., et al., "Adenoviral vector DNA for accurate genome editing with engineered nucleases," Nature Methods, vol. 11, No. 10, pp. 1051-1057, Aug. 24, 2014, 8 pages (Only Abstract Available).
Houdebine, L., "The methods to generate transgenic animals and to control transgene expression," Journal of Biotechnology, vol. 98, pp. 145-160, dated 2002, 16 pages.
*Huang v. California Institute of Technology*, 2004 WL 2296330 (C.D. Cal. Feb. 18, 2004).
Hung, S., et al., "AAV-Mediated CRISPR/Cas Gene Editing of Retinal Cells in Vivo," Investigative Ophthalmology & Visual Science, vol. 57, No. 7, pp. 3470-3476, dated Jun. 2016, 7 pages.
Iwamoto et al., "A General Chemical Method to Regulate Protein Stability in the Mammalian Central Nervous System", Chemistry and Biology, Current Biology, London, GB, vol. 17, No. 9, Sep. 24, 2010, pp. 981-988.
Jackson, A., et al. "Widespread siRNA "off-target" transcript silencing mediated by seed region sequence complementarity," RNA 2006, vol. 12, No. 7, dated Mar. 16, 2006, 10 pages.
Jiang, W., et al., "RNA-guided editing of bacterial genomes using CRISPR-Cas systems," Nature Biotechnology, vol. 31, No. 3, pp. 233-239, dated Mar. 2013, 30 pages, including Supplementary Materials.
Jinek, M., et al, "A programmable Dual-RNA-Guided DNA Endonuclease in adaptive bacterial immunity," Science, vol. 337, n.6096, pp. 816-821, dated Aug. 17, 2012, 7 pages.
Joseph, T., and Osman, R., "Thermodynamic basis of selectivity in guide-target-mismatched RNA interference," Proteins, vol. 80, No. 5, pp. 1283-1298, dated May 2012, 26 pages.
Kim, E., et al., "Precision genome engineering with programmable DNA-nicking enzymes," Genome Research, vol. 22, pp. 1327-1333, dated 2012, 8 pages.
Kim, S., et al., "CRISPER RNAs trigger innate immune responses in human cells," Genome Research, pp. 1-7, dated Feb. 22, 2018, 8 pages.
Kleinstiver et al., "High-fidelity CRISP-Cas9 nucleases with no detectable genome-wide off-target effects", Nature, vol. 529, No. 7587, Jan. 28, 2016, pp. 490-495.
Kowalski, Thomas J., PowerPoint Presentation, "Interview Sep. 9, 2015".
Kumar, M., et al., "Systematic Determination of the Packaging Limit of Lentiviral Vectors," Human Gene Therapy, vol. 12, pp. 1893-1905, dated Oct. 10, 2001, 21 pages.
Kuwayama, H., "Enhancement of Homologous Recombination Efficiency by Homologous Oligonucleotides," Cell Interaction Sivakumar Gowder, IntechOpen, DOI: 10.5772/47779, dated Oct. 10, 2012, 12 pages.
Lebherz, C., et al., "Gene therapy with novel adeno-associated virus vectors substantially diminished atherosclerosis in a murine model of familial hypercholesterolemia," The Journal of Gene Medicine, vol. 6, pp. 663-672, dated Mar. 2, 2004, 10 pages.
Levitt, J., et al., "Intrinsic fluorescence and redox changes associated with apoptosis of primary human epithelial cells," Journal of Biomedical Optics, vol. 11, No. 6, pp. 064012 1-10, dated Nov./Dec. 2006, 10 pages.
Li et al., "Coevolution of CRISPR-Cas system with bacteria and phages", Hereditas, vol. 33, No. 3, Mar. 31, 2011, pp. 213-218.
Ma, M., et al., "A Guide RNA Sequence Design Platform for the CRISPR/Cas9 System for Model Organism Genomes," BioMed Research International, vol. 31, No. 3, pp. 822-824, dated Nov. 2013, 4 pages.
Maczuga, P., et al., "Embedding siRNA sequences targeting Apolipoprotein B100 in shRNA and miRNA scaffolds results in differential processing and in vivo efficacy," Molecular Therapy, vol. 21, No. 1, pp. 217-227, dated Jan. 2013, 11 pages.
Maeder, M., and Gersbach, C., "Genome-editing Technologies for Gene and Cell Therapy," Molecular Therapy, vol. 24, No. 3, pp. 430-446, dated Mar. 2016, 17 pages.
Maeder, M., et al., "Robust, synergistic regulation of human gene expression using TALE activators," Nature Methods, vol. 10, No. 3, pp. 243-245, dated Mar. 2013, 9 pages.
Mali et al., "CAS9 transcriptional activators for target specificity screening and paired nickases for cooperative genome engineering", Nature Biotechnology, Sep. 2013, vol. 31, No. 9, pp. 833-837.
Mali, et al.: "Supplementary Materials for—RNA-Guided Human Genome Engineering via Cas9" Science, vol. 339, pp. 823-826, dated Feb. 15, 2013, 8 pages.

(56) References Cited

OTHER PUBLICATIONS

Mali, P., et al., Supplementary Materials for: "CAS9 transcriptional activators for target specificity screening and paired nickases for cooperative genome engineering," Nature Biotechnology, vol. 31, No. 9, pp. 833-838, dated Aug. 1, 2013, 36 pages.
Manjunath, N., et al., "Newer Gene Editing Technologies toward HIV Gene Therapy," Viruses, vol. 5, No. 11, pp. 2748-2766, dated Nov. 14, 2013, 19 pages.
*Manning v. Paradis*, 296 F.3d 1098 (Fed. Cir. 2012).
Marraffini, L., "CRISPR-Cas Immunity against Phages: Its Effects on the Evolution and Survival of Bacterial Pathogens," PLOS, Pathogens, dated Dec. 12, 2013, 6 pages.
Marraffini, L., Assignment to Rockefeller University, dated Dec. 12, 2013, 3 pages.
*Maxwell v. The Stanley Works*, 2006 WL 1967012 *5 (M.D. Tenn. Jul. 11, 2006).
Mojica, F. J., et al., Supplementary Material for: "Short motif sequences determine the targets of the prokaryotic CRISPR defence system," Microbiology, vol. 155, No. 3, pp. 733-740, dated Mar. 1, 2009, 8 pages.
Morris et al., "Distributed automated docking of flexible ligands to proteins: Parallel applications of AutoDock 2.4*", Journal of Computer-Aided Molecular Design, 1996, vol. 10, pp. 293-304.
Muther, N., et al.: "Viral Hybrid Vectors for Somatic Integration—Are They the Better Solution?" Viruses, vol. 1, pp. 1295-1324, dated Dec. 15, 2009, 30 pages.
Opposition Against Appl. Ser. No. EP13818570.7 submitted by Schlich dated Oct. 26, 2015, 8 pages.
Opposition Against EP Appl. Ser. Appl. No. 2771468-B1 dated Oct. 26, 2015.
Ozawa, K., "Gene therapy using AAV," Uirusu, vol. 57, No. 1, pp. 47-55, dated Nov. 27, 2007, 13 pages (with English Abstract; No English Translation).
Pandika, et al., www.ozy.com/rising-stars-and-provocateurs/jennifer-doudna-crispr-code-killer/4690; 2014 (Jul. 1, 2014).
Phillips, A., "The challenge of gene therapy and DNA delivery," The Journal of Pharmacy and Pharmacology, vol. 53, pp. 1169-1174, dated 2001, 6 pages.
Pougach, K.S., et al.: "CRISPR Adaptive Immunity Systems of Prokaryotes," Molecular Biology, vol. 46, No. 2, Apr. 2012, pp. 195-203, 1 page (English Abstract).
PowerPoint slide entitled "Development and Applications of CRISPR-Cas9 for Genome Editing" dated Sep. 9, 2015.
Pride, D., et al., "Analysis of Streptococcal CRISPRs from Human Saliva Reveals Substantial Sequence Diversity Within and Between Subjects Over Time," Genome Research, vol. 21, No. 1, pp. 126-136, dated Jan. 2011, 11 pages.
Qi, J., et al., "microRNAs regulate human embryonic stem cell division," Cell Cycle, vol. 8, No. 22, pp. 3729-3741, dated Nov. 15, 2009, 13 pages.
Radecke, S., et al., "Zinc-finger Nuclease-induced Gene Repair With Oligodeoxynucleotides: Wanted and Unwanted Target Locus Modifications," Molecular Therapy, vol. 18, No. 4, pp. 743-753, dated Apr. 2010, 11 pages.
Ran et al., "Double Nicking by RNA-guided CRISPR Cas9 for enhanced genome editing specificity", Cell, Sep. 2013, vol. 154, pp. 1380-1389.
Rho, M., et al., "Diverse CRISPRs Evolving in Human Microbiomes," PLOS Genetics, vol. 8, No. 6, pp. e1002441, dated Jun. 2012, 12 pages.
Rodriguez et al., "AAV-CRISPR: A New Therapeutic Approach to Nucleotide Repeat Diseases", Molecular Therapy, vol. 22, Supplement 1, Abstract 247, May 2014, p. S94.
Rolling, "Recombinant AAV-mediated gene transfer to the retina: gene therapy perspectives", Gene Therapy, Vo. 11, 2004, pp. S26-S32.
*Rubin v. The General Hospital Corp.*, 2011-1439 (Fed. Cir. Mar. 28, 2013).
Sadowski, M., and Jones, D., "The sequence-structure relationship and protein function prediction," Current Opinion in Structural Biology, vol. 19, pp. 357-362, dated May 4, 2009, 6 pages.
Sanders, UC Berkeley Jan. 7, 2013 Press Release, available at http://newscenter.berkeley.edu/2013/01/07/cheap-and-easy-technique-to-snip-dna-could-revolutionize-gene-therapy/.
Seffernick, J., et al., "Melamine Deaminase and Atrazine Chlorohydrolase: 98 Percent Identical but Functionally Different," Journal of Bacteriology, vol. 183, No. 8, pp. 2405-2410, dated Apr. 2001, 6 pages.
Senis, E., et al., "CRISPR/Cas9-mediated genome engineering: An adeno-associated viral (AAV) vector toolbox," Biotechnology Journal, vol. 9, No. 11, Sp. Iss. SI, pp. 1402-1412, dated Sep. 4, 2014, 2 pages (Only Abstract Available).
Senturk et al., "A rapid and tunable method to temporally control cas9 expression enables the identification of essential genes and the interrogation of functional gene interactions in vitro and in vivo", Jul. 28, 2015, pp. 1-27, XP002756303, doi:10.1101/023366, Retrieved from the Internet: URL:http://biorxiv.org/content/early/2015/07/28/023366 [retrieved on Apr. 11, 2016).
Shengdar Tsai et al., "Dimeric CRISPR RNS-guided FokI nucleases for highly specific genome editing", Nature Biotechnology, vol. 32, No. 6, Apr. 25, 2014, pp. 569-576.
Slaymaker et al., Rationally engineered Cas9 nucleases with improved specificity, Science, American Association for the Advancement of Science, US, vol. 351, No. 6268, Jan. 1, 2016, pp. 84-88.
Stoller, J. and Aboussouan, L., "Alpha1-antitrypsin deficiency," The Lancet, Seminar, vol. 365, No. 9478, pp. 2225-2236, dated Jun. 25, 2005, 12 pages.
Stratikopoulos, E., et al., "The hormonal action of IGF1 in postnatal mouse growth," Proceedings of the National Academy of Sciences, vol. 105, No. 49, pp. 19378-19383, dated Dec. 9, 2008, 6 pages.
Straub, C., et al., "CRISPR/Cas9-Mediated Gene Knock-Down in Post-Mitotic Neurons," PLOS One, vol. 9, No. 8, art. E105584, pp. 1-5, dated Aug. 2014, 6 pages.
Suzuki, K., et al., "In vivo genome editing via CRISPR/Cas9 mediated homology-independent targeted integration," Nature, vol. 540, art. 7631, pp. 144-149, dated Dec. 1, 2016, 44 pages.
Tang, T., et al., "A mouse knockout library for secreted and transmembrane proteins," Nature Biotechnology, vol. 28, No. 7, pp. 749-755, dated Jul. 2010, 9 pages.
Third Party Observations Concerning App. No. GB1420270.9 dated Jun. 30, 2015.
Third Party Observations Concerning Appl. No. EP2800811, dated Jul. 24, 2015.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, Feb. 16, 2015.
*Ultra-Precision Mfg. Ltd. v. Ford Motor Co.*, 2004 WL 3507671, *7, *11-12 (E.D. Mich. Mar. 30, 2004).
Van Der Oost, "New tool for genome surgery", Science, Feb. 2013, vol. 339, pp. 768-770.
Wienert, B., et al., "In vitro transcribed guide RNAs trigger an innate immune response via the RIG-I pathway," BioRxiv Preprint, dated Mar. 3, 2018, 28 pages.

(56) References Cited

OTHER PUBLICATIONS

Witkowski, A., et al., "Conversion of a Beta-Ketoacyl Synthase to a Malonyl Decarboxylase by Replacement of the Active-Site Cysteine with Glutamine," Biochemistry, vol. 38, pp. 11643-11650, dated Aug. 18, 1999, 8 pages.
Wittmann et al., "Engineered riboswitches: Expanding researchers' toolbox with synthetic RNA regulators", FEBS Letters, vol. 586, No. 15, Feb. 28, 2012, pp. 2076-2083.
Yanfang Fu et al., "Improving CRISPR-Cas nuclease specificity using truncated guide RNAs" (with Supplement Table), Nature Biotechnology, vol. 32, No. 3, Jan. 26, 2014, pp. 279-284.
Yin, H., et al., "Structure-guided chemical modification of guide RNA enables potent non-viral in vivo genome editing," Nature Biotechnology, vol. 35, pp. 1179-1187, dated Nov. 13, 2017, 22 pages.
Yu, W., et al., "Nrl knockdown by AAV-delivered CRISPR/Cas9 prevents retinal degeneration in mice," Nature Communications, vol. 8, art. 14716, dated Mar. 14, 2017, 15 pages.
Yusuke Miyazaki et al., Destabilizing Domains Derived from the Human Estrogen Receptor:, Journal of the American Chemical Society, vol. 134, No. 9, Mar. 7, 2012, pp. 3942-3945.
Zhang, F., PowerPoint Presentation: "Development and Applications of CRISPR-Cas9 for Genome Edition," Broad Institute/MIT, dated Sep. 9, 2015, 50 pages.
Schunder, et al. "First indication for a functional CRISPR/Cas system in Francisella tularensis" International Journal of Medical Microbiology, 2013, 303:1438-4221.
Singer, et al. "Applications of Lentiviral Vectors for shRNA Delivery and Transgenesis" Curr Gene Ther., 2008, 8(6):483-488.
Sung, et al. "An rpsL Cassette, Janus, for Gene Replacement through Negative Selectionin Streptococcus pneumoniae" Applied and Environmental Microbiology, 2001, 67(11):5190-5196.
Sung, Young Hoon, et al. "Mouse genetics: Catalogue and scissors" BMB Reports, 2012, 45(12):686-692.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transfer-Delivery and Expression of DNA and RNA—A Laboratory Manual, 2007, Chapter 3:23-34.
Urrutia, et al. "KRAB-containing zing finger repressor proteins" Genome Biology, 2003, 4(10):231-231.8.
Urnov, et al. "Genome editing with engineered zinc finger nucleases" Nature Reviews, Genetics, 2010, 11:637-646.
Van Den Ackerveken, et al. "Recognition of the Bacterial Avirulence Protein AvrBs3 Occurs inside the Host Plant Cell" Cell, 1996, 87:1307-1316.
Vestergaard, et al. "CRISPR adaptive immune systems of Archaea" RNA Biology, 2014, 11(2):156-167.
Villion, et al. "The double-edged sword of CRISPR-Cas systems" Cell Research, 2013, 23:15-17.
Wang, et al. "Genetic Screens in Human Cells Using the CRISPR-Cas9 System", Science, 2014, 343:80-84.
Welch, et al. "Designing Genes for Successful Protein Expression" Methods in Enzymology, 2011, 498:43-66, DOI: 10.1016/B978-0-12-385120-8.00003-6.
Wolff, et al. "Nuclear security breached" Nature Biotechnology, 2001, 19:1118-1120.
Wu, Zhijian, et al. "Effect of Genome Size on AAV Vector Packaging" The American Society of Gene & Cell Therapy, (Jan. 2010), 18(1):80-86.
Xie, et al. "RNA-Guided Genome Editing in Plants Using a CRISPR-Cas System" Molecular Plant, 2013, 6(6):1975-1983.
Yaghmai, et al. "Optimized Regulation of Gene Expression Using Artificial Transcription Factors", Molecular Therapy, 2002, 5(6):685-694.
Yang, et al. "One-Step Generation of Mice Carrying Reporter and Conditional Alleles by CRISPR/Cas-Mediated Genome Engineering" Cell, 2013, 154:1370-1379.

Yi, et al. "Current Advances in Retroviral Gene Therapy" Current Gene Therapy, 2011, 11:218:228.
Yu, et al. "An efficient recombination system for chromosome engineering in *Escherichia coli*" PNAS, 2000, 97(11):5978-5983.
Yu, Zhongshen, et al. "Highly Efficient Genome Modifications Mediated by CRISPR/Cas9 in *Drosophila*" Genetics, 2013, 195:289-291.
Zetsche, et al. "CPF1 is a Single RNA-Guided Endonuclease of a Class 2 CRISPR-Cas System" Cell, 2015, 163:759-771.
Zhang, et al., Efficient Expression of CFTR Function with Adeno-Associated Virus Vectors that Carry Shortened CFTR Genes, PNAS (USA) (1998) vol. 95, p. 10158-10163.
Zhang, et al., "Optimized CRISPR Design", XP055167487, Oct. 23, 2013, URL:http//crispr.mit.edu/about[retrieved on Feb. 5, 2015].
Zhang, et al. "Optogenetic interrogation of neural circuits: technology for probing mammalian brain structures" Nat Protoc., 2010, 5(3):439-456, doi:10.1038/nprot.2009.226.
Zolkiewska, et al. "ADAM Proteases:Ligand Processing and Modulation of the Notch Pathway" Cell Mol Life Sci, 2008, 65(13):2056-2068.
Notice of Opposition filed by Aug. 16, 2017 by Vossius against EP Patent No. 2840140.
Notice of Opposition filed Aug. 14, 2017 by Grund against EP Patent No. 2840140.
Notice of Opposition filed Aug. 11, 2017 by Schlich against EP Patent No. 2840140.
Notice of Opposition filed Aug. 16, 2017 by Mathys & Squire LLP against EP Patent No. 2840140.
*The Broad Inst. v. The Regents of University of UCA*—Decision on Motions for Patent Interference No. 106,048 filed Feb. 15, 2017.
Declaration of Paul Simons dated Dec. 22, 2015.
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-1/rziHxKT76pYJ [retrieved on Feb. 6, 2015].
Imagawa, et al. "Two nuclear localization signals are required for nuclear translocation of nuclear factor 1-A" FEBS Letters, 2000, 484118-124.
Jao, et al. "Efficient multiplex biallelic zebrafish genome editing using a CRISPR nuclease system" Proceeding of the National Academy of Sciences, 2013, www.pnas.org/cgi/doi/10.1073/pnas.1308335110.
Jinek, et al., "Supplementary Materials for a Programmable Dual-RNA-Guided DNA Endonuclease in Adaptive Bacterial Immunity" Science Express, 2012, DOI:10.1126/science.1225829.
Joshi, et al., "Evolution of I-SceI homing endonucleases with increased DNA recognition site specificity" Journal of Molecular Biology, 2011, 405(1):185-200; ePub: Oct. 26, 2010.
Joung, et al. "TALENs: a widely applicable technology for targeted genome editing" Nat Ref. Mol. Cell Biol., 2013, 14(1):49-55. doi:10.1038/nrm3586.
Kalderon, et al. "A Short Amino Acid Sequence Able to Specify Nuclear Location" Cell, 1984, 39:499-509.
Kiani, et al. "CAS9 gRNA engineering for genome editing, activation and repression" Nature Methods, Advanced Online Publication, 2015, DOI:10.1038/NMETH.3580.
Kinnevery, et al. "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals" Antimicrobial Agents and Chemotherapy, 2013, 57(1):524-531.
Kondo, et al. "Highly Improved Gene Targeting by Germline-Specific Cas9 Expression in *Drosphila*" Genetics, 2013, 195:715-721.
Kosugi, et al. "Six Classes of Nuclear Localization Signals Specific to Different Binding Grooves of Importin α.." The Journal of Biological Chemistry, 2009, 284(1):478-485.
Krauer, et al. "Identification of the nuclear localization signals within the Epstein-Barr virus EBNA-6 protein" Journal of General Virology, 2004, 85:165-172.
Kuhlman, et al. "Site-specific chromosomal integration of large synthetic constructs" Nucleic Acids Research, 2010, 38(6):1-10, doi:10.1093/nar/gkp1193.

(56) References Cited

OTHER PUBLICATIONS

Kuhlman, et al. "A place for everything Chromosomal intergration of large constructs" Bioengineered Bugs, Jul./Aug. 2010, 1(4)296-299.

Lanford, et al. "Induction of Nuclear Transport with a Synthetic Peptide Homologous to the SV40 T Antigen Transport Signal" Cell, 1986, 46:575-582.

Lange, et al. "Classical Nuclear Localization Signals: Definition, Function, and Interaction with Importin . . . " J. Biol. Chem., 2007, 282(8):5101-5105.

Lemay, et al. "Folding of the Adenine Riboswitch" Chemistry & Biology, 2006, 13:857-868.

Lewin, et al. "Nuclear localization sequences target proteins to the nucleus" Cells, 2006, 5:224.

Li, Ting, et al. "Modularly assembled designer TAL effector nucleases for targeted gene knockout and gene replacement in eukaryotes" Nucleic Acids Research, 2011, 39(14):6315-6325.

Liu, et al. "Epstein-Barr Virus DNase Contains Two Nuclear Localization Signals Which Are Different in Sensitivity to the Hydrophobic Regions" Virology, 1998, 247:62-73.

Los, et al. "Halotag Technology: Cell Imaging and Protein Analysis" Cell Notes, 2006, 14:10-14.

Luo, Ming, et al. "Multiple Nuclear Localization Sequences Allow Modulation of 5-Lipoxygenase Nuclear Import" Traffic, 2004, 5:847-854.

Lyssenko, et al. "Cognate putative nuclear localization signal effects strong nuclear localization of a GFP reporter and facilitates gene expression studies in Caenorhabditis elegans" BioTechniques, 2007, 43:596-600.

Mahfouz, et al. "Targeted transcriptional repression using a chimeric TALE-SRDX repressor protein" Plant Mol Biol, 2012, 78:311-321.

Makarova, et al. "An updated evolutionary classification of CRISPR-Cas systems" Nature Reviews—Microbiology, 2015, 13:722-736.

Morbitzer, et al. "Regulation of selected genome loci using de novo-engineered transcription activator-like effector (TALE)-type transcription factors" PNAS, 2010, 108(50):21617-21622.

Morbitzer, et al. "Assembly of custom TALE-type DNA binding domains by modular cloning" 2011, 39(13):5790-5799.

Morin, et al. "Nuclear Localization of the Adenovirus DNA-Binding Protein: Requirement for Two Signals and Complementation during Viral Infection" Molecular and Cellular Biology, 1989, 9(10):4372-4380.

Moscou, et al. "A Simple Cipher Governs DNA Regognition by TAL Effectors" Science, 2009, 326:1501.

Mussolino, et al. "TALE nucleases: tailored genome engineering made easy" Current Opinion in Biotechnology, 2012, 23(5):644-650.

Nagarajan, et al. "A Hierarchy of Nuclear Localization Signals Governs the Import of the Regulatory Factor X Complex Subunits and MHC Class II Expression" The Journal of Immunology, 2004, 173:410.419.

Nakai, et al. "PSORT: a program for detecting sorting signals in proteins and predicting their subcellular localization" Trends in Biochem Sciences, 1999 24:34-35.

Noguchi, et al. "PDX-1 Protein Containing Its Own Antennapedia-Like Protein Transduction Domain Can Transduce Pancreatic Duct and Islet Cells" Diabetes, 2003, 52:1732-1737.

O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.

Park, et al. "Regulation of Ribosomal S6 Kinase 2 by Mammalian Target of Rapamycin", The Journal of Biological Chemistry, 2002, 277(35):31423-31429.

Perez-Pinera, et al. "Advances in Targeted Genome Editiong" Curr Opin Chem Biol., 2012, 16(3-4):268.277, doi:10.1016/j.cbpa.2012.06.007.

Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.

Posfai, et al. "Markerless gene replacement in *Escherichia coli* stimulated by a double-strand break in the chromosome"??, 1999, 27(22):4409-15.

Primo, et al. "Lentiviral vectors for cutaneous RNA managing" Experimental Dermatology, 2012, 21:162-170.

Radulovich, et al. "Modified gateway system for double shRNA expression and Cre/lox based gene expression" BMC Biotechnology, 2011, 11(24):1-9.

Roberts, et al. "The Effect of Protein Content on Nuclear Location Signal Function" Cell, 1987, 50:465-475.

Roberts, et al. "Nuclear location signal-mediated protein transport" Biochimica et Biophysica Acta, 1989, 1008:263-280.

Rodrigues, et al. "Red Fluorescent Protein (DsRed) as a Reporter in *Saccharomyces cerevisiae*" Journal of Bacteriology, 2001, 183(12):3791-3794.

Sambrook, et al., Molecular Cloning, A Laboratory Manual on the Web, 2001, Chapter 16.

Sanjana, et al. "A Transcription Activator-Like Effector (TALE) Toolbox for Genome Engineering" Nat. Protoc, 2011, 7(1):171-192, doi:10.1038/nprot.2011.431.

Sato, et al. "Generation of Adeno-Associated Virus Vector Enabling Functional Expressionof Oxytocin Receptor and Fluorescence Marker Genes Using the Human elF4G Internal Ribosome Entry Site Elemet" Biosci. Biotechno. Biochem, 2009, 73(9):2145-2148.

Sebo, et al. "A simplified and efficient germline-specific CRISPR/Cas9 system for *Drosophila* genomic engineering" Fly, 2014, 8(1):52-57.

Sharan, et al. "Recombineering: A Homologous Recombination-Based Method of Genetic Engineering" Nat. Protoc., 2009, 4(2):206-223, doi:10.1038/nprot.2008.227.

Shieh, et al. "Nuclear Targeting of the Maize R. Protein Requires Two Nuclear Localization Sequences" Plant Physiol, 1993, 101:353-361.

Siegl, et al. "I-SceI endonuclease: a new tool for DNA repair studies and genetic manipulations in streptomycetes" Appl Microbiol Bitotechnol, 2010, 87:1525-1532.

Joseph, et al. "Thermodynamic basis of selectivity in guide-target-mismatched RNA interference" NIH Public Access Author Manuscript 2012, 80(5):1283-1298, doi:10.1002/prot.24025.

A. Amsterdam et al., "Identification of 315 genes essential for early zebrafish development," proc Natl Acad Sci., vol. 101, Aug. 31, 2004, pp. 12792-12797, 6 pages.

A. Fire et al., "Potent and specific genetic interference by double-stranded RNA in Caenorhabditis elegans," Nature, vol. 391, Feb. 19, 1998, pp. 806-811, 6 pages.

A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.

A.C. Spradling et al., "The Berkeley *Drosophila* Genome Project Gene Disruption Project: Single P-Element Insertions Mutating 25% of Vital *Drosophila* Genes," Genetics, vol. 153, Sep. 1999, pp. 135-177, 43 pages.

A.H. Tong et al., "Global mapping of the yeast genetic interaction network," Science, vol. 303, Feb. 6, 2004, pp. 808-813, 6 pages.

A.L. Lin and D.H Gutmann, "Advances in the treatment of neurofibromatosis-associated tumours," Nature, vol. 10, Nov. 2013, pp. 616-624, 9 pages.

A.P. Blanchard and L. Hood, "Sequence to array: probing the genome's secrets," Nat Biotechnol, vol. 14, Dec. 14, 1996, p. 1649.

Addgene, "gRNA_Cloning Vector", retrieved on Jan. 30, 2019, <https://www/addgenen.org/41824/>2 pages.

Allen, et al., "Liposomal drug delivery systems: From concept to clinical applications" Advanced Drug Delivery Reviews, vol. 65, 2013, pp. 36-48, 13 pages.

B. Langmead et al., "Ultrafast and memory-efficient alignment of short DNA sequences to the human genome," Genome biology, vol. 10, Mar. 4, 2009, 10 pages.

(56) References Cited

OTHER PUBLICATIONS

B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counter-selection," Plasmid, vol. 55, 2006, pp. 58-63, 6 pages.
Botta, S. et al, "Transcriptional Repression with Zinc-Finger and Tale Protein Scaffold", Molecular Therapy, 2013, Supplement 1, p. S208, Abstract No. 539.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Carte, J., et al., "Cas6 is an endoribonuclease that generates guide RNAs for invader defense in prokaryotes," Genes Dev., vol. 22, 2008, pp. 3489-3496.
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chevalier et al., "Homing endonuclease: structural and functional insight into the catalysts of intron/intein mobility," Oxford University Press., vol. 29, 2001, pp. 3757-3774.
Cho, Minseon, et al., "Quantitative selection and parallel characterization of aptamers," PNAS, vol. 110, Nov. 12, 2013, pp. 18460-18465.
D.J.Burgess et al., "Topoisomerase levels determine chemotherapy response in vitro and in vivo," Proceedings of the National Academy of Sciences, vol. 105, Jul. 1, 2008, pp. 9053-9058.
Dean., "Recent Advances in Drug Design Methods: Where Will They Lead?", BioEssays, vol. 16, Sep. 1994, pp. 683-687.
Deveau, H. et al., "Phage response to CRISPR-encoded resistance in *Streptococcus thermophilus*," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
E.S. Lander, "Initial impact of the sequencing of the human genome," Nature, vol. 470, Feb. 10, 2011, p. 187-197.
Edgar, R. and Qimron, U., "The *Escherichia coli* CRISPR system protects from Λ lysogenization, lysogens, and prophage induction," Journal of Bacteriology, vol. 192, Dec. 2010, pp. 6291-6294.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Flannery, J. G., "Ribozyme-Mediated Gene Therapy for Autosomal Dominant Retinal Degeneration", Retinal Degenerative Diseases and Experimental Therapy, 1999, pp. 277-291.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.
Gao, et al., "A Sustained, Cytoplasmic Transgene Expression System delivered by Cationic Liposomes", Biochemical and Biophysical Research Communications, vol. 200, May 16, 1994, pp. 1201-1206.
GenBank: "CRISPR-associated protein Cas9/Csn1 [*Staphylococcus aureus* subsp. *aureus*]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grosse, et al. "Meganuclease-mediated Inhibition of HSV1 Infection in Cultured Cells", Molecular Therapy, vol. 19, No. 4, Apr. 1, 2011, pp. 694-702.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
H. Davies et al., "Mutations of the BRAF gene in human cancer," Nature, vol. 417, Jun. 27, 2002, p. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.
Hemann et al., "An epi-allelic series of p53 hypomorphs created by stable RNAi produces distinct tumor phenotypes in vivo," Nat Genetics, vol. 33, Mar. 2003, pp. 396-400.
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Husmann, L.K.,et al., "Expression of the Arp protein, a member of the M protein family, is not sufficient to inhibit phagocytosis of *Streptococcus pyogenes*," Infection and immunity, vol. 63, Jan. 1995, pp. 345-348.

(56) References Cited

OTHER PUBLICATIONS

Hwang, W.Y., et al., "Efficient Genome Editing in Zebrafish Using a CRISPR-Cas System", Nature Biotechnology, vol. 31, No. 3, Jan. 29, 2013, pp. 227-229.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist lncRNA exploits three-dimensional genome architecture to spread across the X chromosome," Science, vol. 341, Aug. 16, 2013, pp. 1-8, 8 pages.
Jansen R. et al., "Identification of genes that are associated with DNA repeats in prokaryotes," Molecular Microbiology, vol. 43, 2002, pp. 1565-1575, 11 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Kim et al., "High Cleavage Efficiency of a 2A Peptide Derived from Porcine Teschovirus-1 in Human Cell Lines, Zebrafish and Mice," PLoS One, vol. 6, Apr. 2011, pp. 1-8, 8 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt. 2800.
Koo et al., "Measuring and Reducing Off-Target Activities of Programmable Nucleases Including CRISPR-Cas9", Molecules and Cells, vol. 38, 2015, pp. 475-481, 7 pages.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Madisen et al., "A robust and high-throughput Cre reporting and characterization system for the whole mouse brain," Nat. Neuroscience, vol. 13, Jan. 2010, pp. 133-140, 8 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Moffat J et al., "A lentiviral RNAi library for human and mouse genes applied to an arrayed viral high-content screen," Cell, vol. 124, Mar. 24, 2006, pp. 1283-1298, 16 pages.

Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Motamedi, M.R., et al., "Double-strand-break repair recombination in *Escherichia coli*: physical evidence for a DNA replication mechanism in vivo," Genes Dev., vol. 13, 1999, pp. 2889-2903.
Musunuru, "Abstract 18593: Use of a CRISPR/Cas System for Cardiovascular Disease Modeling and Therapeutic Applications", Circulation, vol. 128, 2013, 4 pages (Meeting info: American Heart Association, 2013 Scientific Sessions and Resuscitation Science Symposium, Dallas, TX, US, Nov. 16-20, 2013).
Paddison et al., "A resource for large-scale RNA-interference-based screens in mammals," Nature, vol. 428, Mar. 25, 2004, pp. 427-431, 5 pages.
Podbielski, A., et al., "R. Novel series of plasmid vectors for gene inactivation and expression analysis in group A streptococci (GAS)," Gene, vol. 177, 1996, pp. 137-147, 11 pages.
R. Rad et al., "PiggyBac transposon mutagenesis: a tool for cancer gene discovery in mice," Science, vol. 330, Nov. 19, 2010, p. 1104-1107, 4 pages.
R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1α localization in erythroblasts," Blood, vol. 117, Jun. 2011, pp. 6928-6938, 11 pages.
Response to Third Party Observations in EP No. 13824232.6 filed Oct. 2, 2014, with Redlined and Clean Amended Claims, 14 pages.
S. Huang et al., "MED12 Controls the Response to Multiple Cancer Drugs through Regulation of TGF-β; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Schiffer, et al. "Targeted DNA Mutagenesis for the Cure of Chronic Viral Infections" Journal of Virology, vol. 86, No. 17, Jun. 20, 2012, pp. 8920-8936.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Spencer, J.M., et al., "Development of a Nuclease Screen to Improve Cas9 Targeting Specificity", Molecular Therapy, May 2015, vol. 23, Suppl. 1, S136(340).
Stewart SA et al., "Lentivirus-delivered stable gene silencing by RNAi in primary cells," RNA, vol. 9, 2003, pp. 493-501, 9 pages.
Swiech et al., "CRISPR-Mediated Genome Editing in the Mammalian Brain", Molecular Therapy, 747, vol. 22, 2014, p. S289.
Symington et al., "Double-Strand Break End Resection and Repair Pathway Choice", Annual Review of Genetics, vol. 45, 2011, pp. 247-271, 25 pages.
T. Horii et al., "Generation of an ICF Syndrome Model by Efficient Genome Editing of Human Induced Pluripotent Stem Cells Using

(56) References Cited

OTHER PUBLICATIONS the CRISPR System," International Journal of Molecular Sciences, vol. 14, 2013, p. 19774-19781, 9 pages.

T.J. Cradick et al., "CRISPR/Cas9 systems targeting β-globin and CCR5 genes have substantial off-target activity," Nucleic Acids Research, vol. 41, 2013, 9584-9592, 9 pages.

T.Yan et al., "DNA mismatch repair (MMR) mediates 6-thioguanine genotoxicity by introducing single-strand breaks to signal a G2-M arrest in MMR-proficient RKO cells," Clinical Cancer Research, vol. 9, Jun. 2003, p. 2327-2334, 9 pages.

Takara Bio USA, Inc., "Lenti-X™ Tet-on © 3G CRISPR/Cas9 System User Manual", 2016, pp. 1-35.

Third Party Observation for Application No. EP20130824232 dated Sep. 22, 2014, 19 pages.

Third Party Observation in Application No. PCT/US2013/074819 dated Apr. 10, 2015, 10 pages.

Third Party Observation Under Article 115 EPC in Application No. 13818570.7 dated Oct. 1, 2014.

Third-Party Observation for Application No. EP20130824232 dated Sep. 8, 2014, 47 pages.

V.N. Ngo et al., "A loss-of-function RNA interference screen for molecular targets in cancer," Nature, vol. 441, May 4, 2006, pp. 106-110, 5 pages.

Van Der Oost, J., et al., "CRISPR-based adaptive and heritable immunity in prokaryotes," Trends. Biochem. Sci., vol. 34, 2009, pp. 401-407, 7 pages.

Venken et al., "P[acman]: A BAC Transgenic Platform for Targeted Insertion of Large DNA Fragments in D. melanogaster", Science, vol. 314, Dec. 15, 2006, pp. 1747-1751, 5 pages.

W.G. Kaelin., "Use and Abuse of RNAi to Study Mammalian Gene Function," Science, vol. 337, Jul. 27, 2012, p. 421-422, 2 pages.

Wang, H.H. et al., "Genome-scale promoter engineering by coselection MAGE," Nat methods, vol. 9, Jun. 2012, pp. 591-593, 3 pages.

Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.

Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.

Weber et al., "TALENs Targeting HBV: Designer Endonuclease Therapies for Viral Infections", Molecular Therapy, vol. 21, Oct. 2013, pp. 1819-1821, 3 pages.

Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.

X.Liu et al., "STAGA recruits Mediator to the MYC oncoprotein to stimulate transcription and cell proliferation," Molecular and cellular biology, vol. 28, Jan. 2008, p. 108-121, 14 pages.

Xiao, W., et al, "Gene Therapy Vectors Based on Adeno-Associated Virus Type 1", Journal of Virology, May 1999, vol. 73, No. 5, p. 3994-4003.

Xu, Zhi-Li et al., "Regulated gene expression from adenovirus vectors: a systematic comparison of various inducible systems," Gene, vol. 309, 2003, pp. 145-151, 7 pages.

Yang et al., "HIV-1 TAT-mediated protein transduction and subcellular localization using novel expression vectors," FEBS Letters, vol. 532, 2012, pp. 36-44, 9 pages.

Zahner, D. and Hakenbeck, R. "The *Streptococcus pneumoniae* beta-galactosidase is a surface protein," J. Bacteriology, vol. 182, Oct. 2000, pp. 5919-5921, 3 pages.

Zeng Y et al., "Both natural and designed micro RNAs can inhibit the expression of cognate mRNAs when expressed in human cells," Mol Cell., vol. 9, Jun. 2002, pp. 1327-1333, 7 pages.

Zhang, "Processing-Independent CRISPR RNAs Limit Natural Transformation in Neisseria meningitidis", Molecular Cell, vol. 50, May 23, 2013 pp. 488-503.

Zuris, et al., "Cationic lipid-mediated delivery proteins enables efficient protein-based genome editing in vitro and in vivo", Nature Biotechnology, vol. 33, No. 1, Jan. 2015, pp. 73-80.

Zuris, et al., "Efficient Delivery of Genome-Editing Proteins in Vitro and in Vivo" Nature Biotechnology, vol. 33, No. 1, Jan. 2015, pp. 1-26.

Zuris, et al., Supplementary Information—"Cationic lipid-mediated delivery proteins enables efficient protein-based genome editing in vitro and in vivo" Nature Biotechnology, vol. 33, No. 1, Jan. 2015, pp. 1-49. doi:10.1038/nbt.3081.

U.S. Appl. No. 14/054,414, filed Oct. 15, 2013.
U.S. Appl. No. 14/104,837, filed Dec. 12, 2013.
U.S. Appl. No. 14/104,900, filed Dec. 12, 2013.
U.S. Appl. No. 14/104,977, filed Dec. 12, 2013.
U.S. Appl. No. 14/104,990, filed Dec. 12, 2013.
U.S. Appl. No. 14/105,017, filed Dec. 12, 2013.
U.S. Appl. No. 14/105,031, filed Dec. 12, 2013.
U.S. Appl. No. 14/105,035, filed Dec. 12, 2013.
U.S. Appl. No. 14/183,429, filed Feb. 18, 2014.
U.S. Appl. No. 14/183,471, filed Feb. 18, 2014.
U.S. Appl. No. 14/183,486, filed Feb. 18, 2014.
U.S. Appl. No. 14/183,512, filed Feb. 18, 2014.
U.S. Appl. No. 14/222,930, filed Mar. 24, 2014.
U.S. Appl. No. 14/226,274, filed Mar. 26, 2014.
U.S. Appl. No. 14/256,912, filed Apr. 18, 2014.
U.S. Appl. No. 14/258,458, filed Apr. 22, 2014.
U.S. Appl. No. 14/259,420, filed Apr. 23, 2014.
U.S. Appl. No. 14/290,575, filed May 29, 2014.
U.S. Appl. No. 14/293,498, filed Jun. 2, 2014.
U.S. Appl. No. 14/293,674, filed Jun. 2, 2014.
U.S. Appl. No. 14/324,960, filed Jul. 7, 2014.
U.S. Appl. No. 14/463,253, filed Aug. 19, 2014.
U.S. Appl. No. 14/481,339, filed Sep. 9, 2014.
U.S. Appl. No. 14/497,627, filed Sep. 26, 2014.
U.S. Appl. No. 14/523,799, filed Oct. 24, 2014.
U.S. Appl. No. 14/681,382, filed Apr. 8, 2015.
U.S. Appl. No. 14/703,511, filed May 4, 2015.
U.S. Appl. No. 14/704,551, filed May 5, 2015.
U.S. Appl. No. 14/705,719, filed May 6, 2015.
U.S. Appl. No. 14/738,398, filed Jun. 12, 2015.
U.S. Appl. No. 14/738,483, filed Jun. 12, 2015.
U.S. Appl. No. 14/970,967, filed Dec. 16, 2015.
U.S. Appl. No. 14/971,169, filed Dec. 16, 2015.
U.S. Appl. No. 14/971,356, filed Dec. 16, 2015.
U.S. Appl. No. 14/972,523, filed Dec. 17, 2015.
U.S. Appl. No. 14/972,927, filed Dec. 17, 2015.
U.S. Appl. No. 14/973,062, filed Dec. 17, 2015.
U.S. Appl. No. 14/990,444, filed Jan. 7, 2016.
U.S. Appl. No. 14/991,083, filed Jan. 8, 2016.
U.S. Appl. No. 15/160,710, filed May 20, 2016.
U.S. Appl. No. 15/171,141, filed Jun. 2, 2016.
U.S. Appl. No. 15/172,636, filed Jun. 3, 2016.
U.S. Appl. No. 15/179,711, filed Jun. 10, 2016.
U.S. Appl. No. 15/179,799, filed Jun. 10, 2016.
U.S. Appl. No. 15/179,912, filed Jun. 10, 2016.
U.S. Appl. No. 15/179,938, filed Jun. 10, 2016.
U.S. Appl. No. 15/179,941, filed Jun. 10, 2016.
U.S. Appl. No. 15/217,489, filed Jul. 22, 2016.
U.S. Appl. No. 15/229,702, filed Aug. 5, 2016.
U.S. Appl. No. 15/230,025, filed Aug. 5, 2016.
U.S. Appl. No. 15/230,161, filed Aug. 5, 2016.
U.S. Appl. No. 15/330,876, filed Nov. 7, 2016.
U.S. Appl. No. 15/349,603, filed Nov. 11, 2016.
U.S. Appl. No. 15/430,260, filed Feb. 10, 2017.
U.S. Appl. No. 15/436,396, filed Feb. 17, 2017.
U.S. Appl. No. 15/620,098, filed Jun. 12, 2017.
U.S. Appl. No. 15/620,391, filed Jun. 12, 2017.
U.S. Appl. No. 15/633,126, filed Jun. 26, 2017.
U.S. Appl. No. 15/834,736, filed Dec. 7, 2017.
U.S. Appl. No. 15/838,064, filed Dec. 11, 2017.
U.S. Appl. No. 15/838,720, filed Dec. 12, 2017.
U.S. Appl. No. 15/844,528, filed Dec. 16, 2017.
U.S. Appl. No. 15/887,377, filed Feb. 2, 2018.

(56) References Cited

OTHER PUBLICATIONS

U.S. Appl. No. 15/967,464, filed Apr. 30, 2018.
U.S. Appl. No. 15/967,495, filed Apr. 30, 2018.
U.S. Appl. No. 15/967,510, filed Apr. 30, 2018.
U.S. Appl. No. 16/012,692, filed Jun. 19, 2018.
U.S. Appl. No. 16/158,295, filed Oct. 11, 2018.
U.S. Appl. No. 16/177,403, filed Oct. 31, 2018.
U.S. Appl. No. 16/178,551, filed Nov. 1, 2018.
U.S. Appl. No. 16/262,905, filed Jan. 30, 2019.
U.S. Appl. No. 61/748,427, filed Jan. 2, 2012, Zhang.
Abudayyeh, et al. "C2c2 is a single-component programmable RNA-guided RNA-targeting CRISPR effector" Science, 2016, 10.1126/science.aaf5573 (2016).
Bauer, et al., "An Erythroid Enhancer of BCL11A Subject to Genetic Variation Determines Fetal Hemoglobin Level" Science, 2013, 342:253-257.
Bassett, et al. "A Genome-Wide CRISPR Library for High-Throughput Genetic Screening in *Drosophila* Cells" Journal of Genetics and Genomics, 2015, 42:301-309.
Canver, et al. "BCL11A enhancer dissection by Cas9-mediated in situ saturating mutagenesis" Nature, 2015, 527:192-197, including Supplementary material.
"CRISPR-associated protein" UniProtKB/TrEMBL, Accession No. Q73QW6, uploaded Nov. 28, 2012, retrieved on Nov. 22, 2017, http://www.uniprot.org/uniprot/Q73Qw6.txt?version4.
CRISPR-associated protein, Csn1 family, UniProtKB/TrEMBL, Accession No. D0W2Z9, uploaded Oct. 3, 2012, retrieved Nov. 22, 2017, http://www.uniprot.org/uniprot/D0W2Z9.txt?version=4.
CRISPR-associated protein, Csn2 family [*Staphylococcus pseudintermedius* ED99] GenBank, Accession No. ADX75954, uploaded on Nov. 21, 2011, retrieved on Nov. 22, 2017, http://www.uniprot.org/uniprot/G1UFN3.txt?version=3.
"Crispr genome engineering" XP055167591, Oct. 5, 2013, https://web.archive.org/web/2013100500 [retrieved on Feb. 5, 2015.
"Csn1 family CRISPR-associated protein" UniProtKB/TrEMBL, Accession No. J3TRJ9, uploaded Oct. 31, 2012, retrieved on Dec. 14, 2017, http://www.uniprot.org/uniprot/J3TRJ9.txt?version=2.
Doench, et al., "Rational design of highly active sgRNAs for CRISPR-Cas9-mediated gene inactivation" Nature Biotechnology, 2014, 32(12):1262-1267, including Supplementary material.
Dong, et al. "The crystal structure of Cpf1 in complex with CRISPR RNA" Nature, 2016, 532:523-525, including Research Letter, doi:10.1038/nature17944.
Gao, et al. "Engineered Cpf1 Enzymes with Altered PAM Specificities" BioRxiv Preprint, XP-002769442, 2016, doi: http://dx.doi.org/10.1101/091611, 1-13, including Figure Legends.
Gao, et al. "Engineered Cpf1 variants with altered PAM specificities" Nature Biotechnology, 2017, 1-4, doi:10.1038/nbt.3900, advanced online publication including Supplementary Information.
Grissa, et al. "CRISPRFinder: a web tool to identify clustered regularly interspaced short palindromic repeats" Nucleic Acids Research, 2007, 35:W52-W57, doi:10.1093/nar/gkm360.
Ho, et al. "Targeting non-coding RNAs with the CRISPR/Cas9 system in human cell lines" Nucleic Acids Research, 2015, 43(3):e17, doi:10.1093/narlgku1198.
Incontro, et al. "Efficient, Complete Deletion of Synaptic Proteins using CRISPR" Cell, Neuron, 2014, 83:1051-1057.
Kleinstiver, et al. "Engineered CRISPR-Cas9 nucleases with altered PAM specificities" Nature, 2015, 523:481-485, including Research Letter, doi:10.1038/nature14592.
Leenay, et al. "Identifying and Visualizing Functional PAM Diversity across CRISPR-Cas Systems" Molecular Cell, 2016, 62:137-147.
Li, Ping, et al. "Biallelic knockout of α-1,3 galactosyltransferase gene in porcine liver-derived cells using zing finger nucleases" Journal of Surgical Research, 2013, E39-E45.
Pattanayak, et al. "High-throughput profiling of off-target DNA cleavage reveals RNA-programmed Cas9 nuclease specificity" Nature Biotechnology, 2013, 31(9):839-843, including Supplementary Materials.

"Putative uncharacterized protein" UniProtKB/TrEMBL, Accession No. Q6NK13, uploaded Jun. 13, 2012, retrieved on Nov. 22, 2017, http://www.uniprot.org/uniprot/Q6NK13.txt?version=43.
"Putative CRISPR-associated protein", UniProtKB/TrEMBL, Accession No. Q0P897, uploaded Oct. 3, 2012, retrieved on Nov. 22, 2017, http://www.uniprot.org/uniprot/Q0P897.txt?version=28.
Putative CRISPR associated protein, UniProtKB/TrEMBL, Accession No. G1UFN3, uploaded Oct. 3, 2012, retrieved on Nov. 22, 2017, http://www.uniprot.org/uniprot/G1UFN3.txt?version=3.
Sander, et al. "CRISPR-Cas systems for editing, regulating and targeting genomes" Nature Biotechnology, 2014, 32:347-355.
Sanjana, et al. "Improved vectors and genome-wide libraries for CRISPR screening", HHS Public Access Author Manuscript, 2014, 11(8):783-784.
Sebastiani, et al. "BCL11A enhancer haplotypes and fetal hemoglobin in sickle cell anemia" Blood Cells, 2015, 54(3):1079-9796.
Shalem, et al. "High-throughput functional genomics using CRISPR-Cas9" Nature Reviews Genetics, 2015, 16(5):1471-0056.
Trafton, et al. "CRISPR-carrying nanoparticles edit the genome" MIT News, Nov. 13, 2017, http://news.mit.edu/2017/crispr-carrying-nanoparticles-edit-genome-1113.
Type V CRISPR-associated protein Cpf1 [*Acidaminococcus* sp. Bv3L6], 2017, NCBI Reference Sequence: WP_02173622.1, Non-redundant Protein Sequence.
Van Nierop, et al. "Stimulation of homology-directed gene targeting at an endogenous human locus by a nicking endonuclease" Nucleic Acids Research, 2009, 37(17):5725-5736.
Wu, Yuxuan, et al. "Correction of a Genetic Disease in Mouse via Use of CRISPR—Cas9" Cell Stem Cell, 2013, 13:659-662.
Yamano, et al. "Crystal Structure of Cpf1 in Complex with Guide RNA and Target DNA" Cell, 2016, 165:949-962.
Zhou, et al. "High-throughput screening of a CRISPR/Cas9 library for functional genomics in human cells" Nature, 2014, 509:487-491.
Press Release dated Jan. 15, 2018 "The Rockefeller University and Broad Institute of MIT and Harvard announce update to CRISPR-Cas9 Portfolio filed by Broad" Copyright by Broad Institute.
U.S. Appl. No. 16/445,150, filed Jun. 18, 2019.
U.S. Appl. No. 16/445,156, filed Jun. 18, 2019.
U.S. Appl. No. 16/525,531, filed Jul. 29, 2019.
U.S. Appl. No. 16/532,442, filed Aug. 5, 2019.
U.S. Appl. No. 16/535,043, filed Aug. 7, 2019.
U.S. Appl. No. 16/800,988, filed Feb. 25, 2020.
U.S. Appl. No. 16/844,548, filed Apr. 9, 2020.
U.S. Appl. No. 16/906,580, filed Jun. 19, 2020.
U.S. Appl. No. 16/938,110, filed Jul. 24, 2020.
U.S. Appl. No. 61,769,046, filed Feb. 25, 2013, Zhang.
U.S. Appl. No. 61/835,931, filed Jun. 17, 2013, Zhang.
U.S. Appl. No. 61/757,972, filed Jan. 29, 2013, Zhang.
U.S. Appl. No. 61/768,959, filed Feb. 25, 2013, Zhang.
U.S. Appl. No. 61/791,409, filed Mar. 15, 2013, Zhang.
U.S. Appl. No. 61/717,324, filed Oct. 23, 2012, Seung Woo Kim.
U.S. Appl. No. 61/803,599, filed Mar. 20, 2013, Jin-Soo Kim.
U.S. Appl. No. 61/837,481, filed Jun. 20, 2013, Seung Woo Cho.
U.S. Appl. No. 61/765,576, filed Feb. 15, 2013, Wendell Lim.
U.S. Appl. No. 61/716,256, filed Oct. 10, 2012, Jinek.
U.S. Appl. No. 61/758,468, filed Jan. 30, 2013, Zhang.
U.S. Appl. No. 61/802,174, filed Mar. 15, 2013, Zhang.
U.S. Appl. No. 61/806,375, filed Mar. 28, 2013, Zhang.
U.S. Appl. No. 61/814,263, filed Apr. 20, 2013, Zhang.
U.S. Appl. No. 61/819,803, filed May 6, 2013, Zhang.
U.S. Appl. No. 61/828,130, filed May 28, 2013, Zhang.
U.S. Appl. No. 61/836,127, filed Jun. 17, 2013, Zhang.
U.S. Appl. No. 61/842,322, filed Jul. 2, 2013, Zhang.
U.S. Appl. No. 61/836,101, filed Jun. 17, 2013, Zhang.
U.S. Appl. No. 61/835,936, filed Jun. 17, 2013, Zhang.
Alberts, et al., Molecular Biology of the Cell, fourth edition, 2002, 671-676.
Au, et al. "Characterization of a baculovirus nuclear localization signal domain in the late express factor 3 protein" Virology, 2009, 385:209-217.

(56) References Cited

OTHER PUBLICATIONS

Ausubel, et al. "A Compendium of Methods from Current Protocols in Molecular Biology" Short Protocols in Molecular Biology, Fourth Edition, 1999, 9: 9-3-9-4.

Baiker, et al. "The Immediate-Early 63 Protein of Varicella-Zoster Virus: Analysis of Functional Domains Required for Replication in Vitro and for T-Cell and Skin Tropism in the SCIDhu Model in Vivo" Journal of Virology, 2004, 78(3):1181-1194.

Bassett, et al. "Highly Efficient Targeted Mutagenesis of *Drosophila* with the CRISPR/Cas9 System" Cell Reports, 2013, 4:220-228.

Beerli, et al. "Toward controlling gene expression at will: Specific regulation of the erbB-2/HER-2 promoter by using polydactyl zinc finger proteins constructed from modular building blocks", Proc. Natl. Acad. Sci., 1998, 95:14628-14633.

Beerli, et al. "Positive and negative regulation of endogenous genes by designed transcription factors:" PNAS, 2000, 97(4):1495-1500.

Beerli, et al. "Enginnering polydactyl zinc-finger transcription factors" Nature Biotechnology, 2002, 20:135-141.

Birch, et al. "Plant Transformation: Problems and Strategies for Practical Application" Annu. Rev. Plant Physiol. Plant Mol. Biol., 1997, 48:297-326.

Boden, et al. "Efficient Gene Transfer of HIV-1-Specific Short Hairpin RNA into Human Lymphocytic Cells Using Recombinant Adeno-associated Virus Vectors" Molecular Therapy, 2004, 9(3):396-402.

Bouard, et al. "Themed Section: Vector Design and Drug Delivery Review, Viral vectors: from virology to transgene expression" British Journal of Pharmacology, 2009, 157:153-165.

Brouns, "A Swiss Army Knife of Immunity" Science, 2012, 337:808-809, DOI:10.1126/science.1227253.

Campeau, et al. "A Versatile Viral System for Expression and Depletion of Proteins in Mammalian Cells" PLoS One, 2009, 4(8):e6529.

Carr, et al. "Genome engineering" Nature Biotechnology, 2009, 27(12):1151-1162.

Carroll, "Progress and prospects: Zinc-finger nucleases as gene therapy agents" Gene Therapy, 2008, 15:1463-1468.

Carroll, "Genome Engineering With Zing-Finger Nucleases" Genetics, 2011, 188:773.782.

Chan, et al. "Characterization of the Kinetochore Binding Domain of CENP-E Reveals Interactions with the Kinetochore Proteins CENP-F and hBuBR1" The Journal of Cell Biology, 1998, 143:49-63.

Chan, Wai-Ting, et al. "Toxin-Antitoxin Genes of the Gram-Positive Pathogen *Streptococcus pneumoniae*: So Few and Yet So Many" Microbiology and Molecular Biology Reviews, 2012, 76(4):773-791.

Chang, et al. "Genome editing with RNA-guided Cas9 nuclease in Zebrafish embryos" Cell Research, 2013, 23:465-472.

Chen, Fuqiang et al. "High-frequency genome editing using ssDNA oligonucleotides with zinc-finger nucleases" Nature Methods, 2011, 8(9):753-755, including Supplemental Online Methods.

Chylinksi, et al. "Classification and evolution of type II CRISPR-Cas systems" Nucleic Acids Research, 2014, 42(10):6091-6105, doi:10.1093lnarlgku241.

Chiu, et al. "Engineered GFP as a vital reporter in plants" Current Biology, 1996, 6(3):325-330.

Costantino, et al., "Enhanced levels of λ Red-mediated recombinants in mismatch repair mutants" PNAS, 100 (26):15748-15753.

CRISPR-associated endonuclease Cas9; Oct. 21, 2012, XP002738511M, http://ibis/exam/dbfetch.jsp?id=uniprot:J7RUA5.

Dai, et al. "Genes:Structures and Regulation: The Transcription Factors GATA4 and dHAND Physically Interact to Synergistically Activate Cardiac Gene Expression through a p300-dependent Mechanism", J. Biol. Chem., 2002, 277:24390-24398.

DiCarlo, et al. "Genome engineering in *Saccharomyces cerevisiae* using CRISPTR-Cas systems", Nucleic Acids Research, 2013, 41(7):4336-4343, doi:10.1093/nar/gkt135.

Dingwall, et al. "The Nucleoplasmin Nuclear Location Sequence Is Larger and More Complex than That of SV-40 Large T Antigen" The Journal of Cell Biology, 1988, 107:841-849.

Do, et al. "Identification of multiple nuclear localization signals in murine EIf3, an ETS transcription factor" FEBS Letters, 2006, 580:1865-1871.

Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.

Ellis, Hilary, et al. "High efficiency mutagenesis, repair, and engineering of chromosomal DNA using single-stranded oligonucleotids" PNAS, 2001, 98(12):6742-6746.

Espinoza, et al., "Characterization of the structure, function, and mechanism of B2 RNA, an ncRNA repressor of RNA polymerase II transcription" RNA, 2007, 13(4):583-596.

Fieck, et al. "Modifications of the *E. coli* Lac repressor for expression in eukaryotic cells: effects of nuclear signal sequences on protein activity and nuclear accumulation" Nucleic Acids Research, 1992, 20(7):1785-1791.

Fischer-Fantuzzi, et al. "Molecular and Cellular Biology" Mol. Cell. Biol., 1988, 8(12):5495, DOI:10.1128/MCB.8.12.5495.

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

Foecking, et al. "Powerful and versatile enhance-promoter unit for mammalian expression vectors" Gene, 1986, 101-105.

Freitas, et al. "Mechanisms and Signals for the Nuclear Import of Proteins" Current Genomics, 2009, 10:550-557.

Fu, et al. "High-frequency off-target mutagenesis induced by CRISPR-Cas nucleases in human cells", Nature Biotechnology, 2013, 31(9):822-826.

Garcia-Bustos, et al. "Nuclear protein localization" Biochimica et Biophysica Acta, 1991, 1071:83-101.

Garg, et al. "Engineering synthetic TAL effectors with orthogonal target sites" Nucleic Acids Research, 2012, 40(15):7584-7595, doi:10.1093/nar/gks404.

Genbank, Accession No. HE980450—"*Staphylococcus aureus* subsp. *aureus* ORFX gene and pseudo SCCmec-SCC-SCCCRISPR element, strain M06/0171", http://www.ncbi.nlm.nih.gov/nuccore/HE980450, Retrieved Aug. 18, 2016.

Gomaa, et al. "Programmable removal of bacterial strains by use of genome-targeting CRISPR-Cas systems", MBio., 2014, 5(1):e00928-13.

Gratz, et al. "Genome Engineering of *Drosophila* with the CRISPR RNA-Guided Cas9 Nuclease" Genetics, 2013, 194:1029-1035.

Greenspan, et al. "Two Nuclear Location Signals in the Influenza Virus NS1 Nonstructural Protein" Journal of Virology, 1988, 62(8):3020-3026.

Greiger, et al. "Packaging Capacity of Adeno-Associated Virus Serotypes: Impact of Larger Genomes on Infectivity and Postentry Steps" Journal of Virology, 2005, 79(15): 9933-9944.

Guan, et al. "Heritable endogenous gene regulation in plants with designed polydactyl zinc finger transcription factors" PNAS, 2002, 99(20):13296-13301.

Haft, D.H., "HMM Summary Page: TIGR04330" 2012, XP-002757584, http://jcvi.org/cgi-bin/tigrfams/HmmReportPage.cgi?acc=TIGR04330.

Heintze, et al. "A CRISPR CASe for high-throughput silencing", Frontiers in Genetics, Oct. 2013, 4(193): DOI:10.3389/gfene.2013.00193.

Hicks, et al. "Protein Import Into the Nucleus: An Integrated View" Annu. Rev. Cell Dev. Biol., 1995, 11:155-88.

Hockemeyer, et al. "Highly efficient gene targeting of expressed and silent genes in human ESCs and iPSCs using zinc finger nucleases" Nat Biotechnol., 2009, 27(9):851-857, doi:10.1038/nbt.1562.

Holmes, "CRISPR Genome Engineering Resources" XP055167586, Oct. 2, 2013, https://groups.google/forum/#!top1c/crispr/5BpJj_Y3ylG [retreieved on Feb. 5, 2015].

Decision on Motions—PTAB, *The Regents of the University of California v. The Broad Institute, Inc.*, filed Sep. 10, 2020, in Patent Interference No. 106,115 (DK), 113 pages.

(56) References Cited

OTHER PUBLICATIONS

Redeclaration—PTAB, *The Regents of the University of California v. The Broad Institute, Inc.*, filed Sep. 10, 2020, in Patent Interference No. 106,115 (DK), 3 pages.

\* cited by examiner

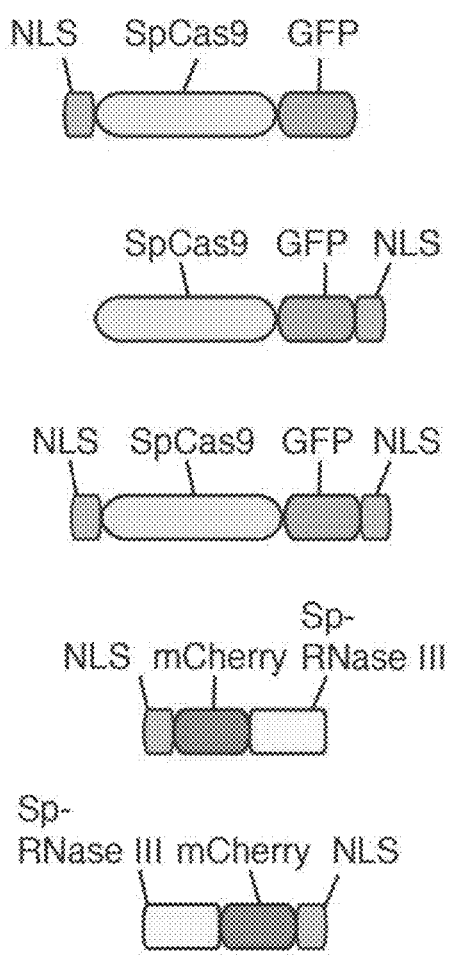
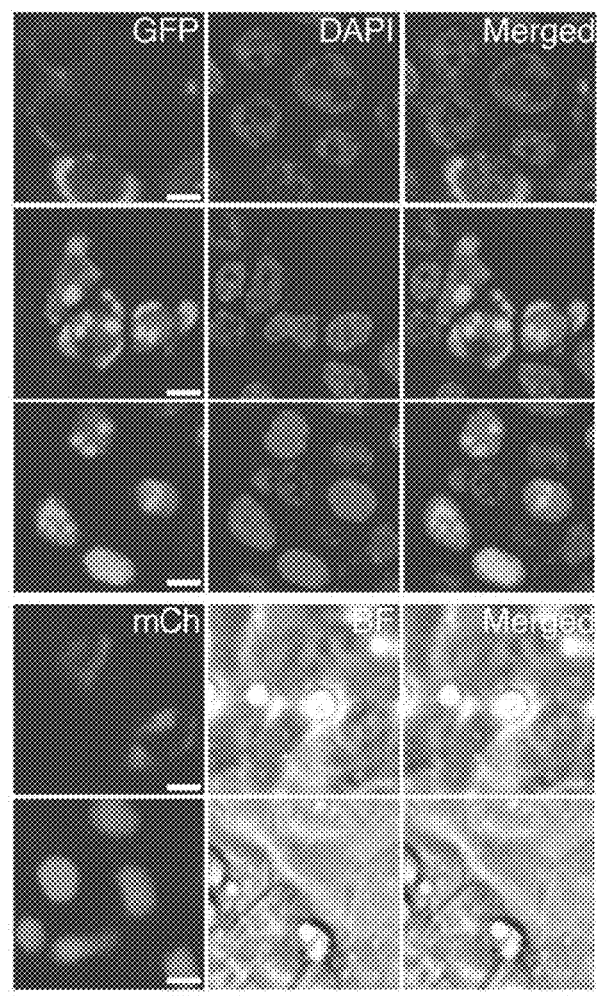
FIG. 2B

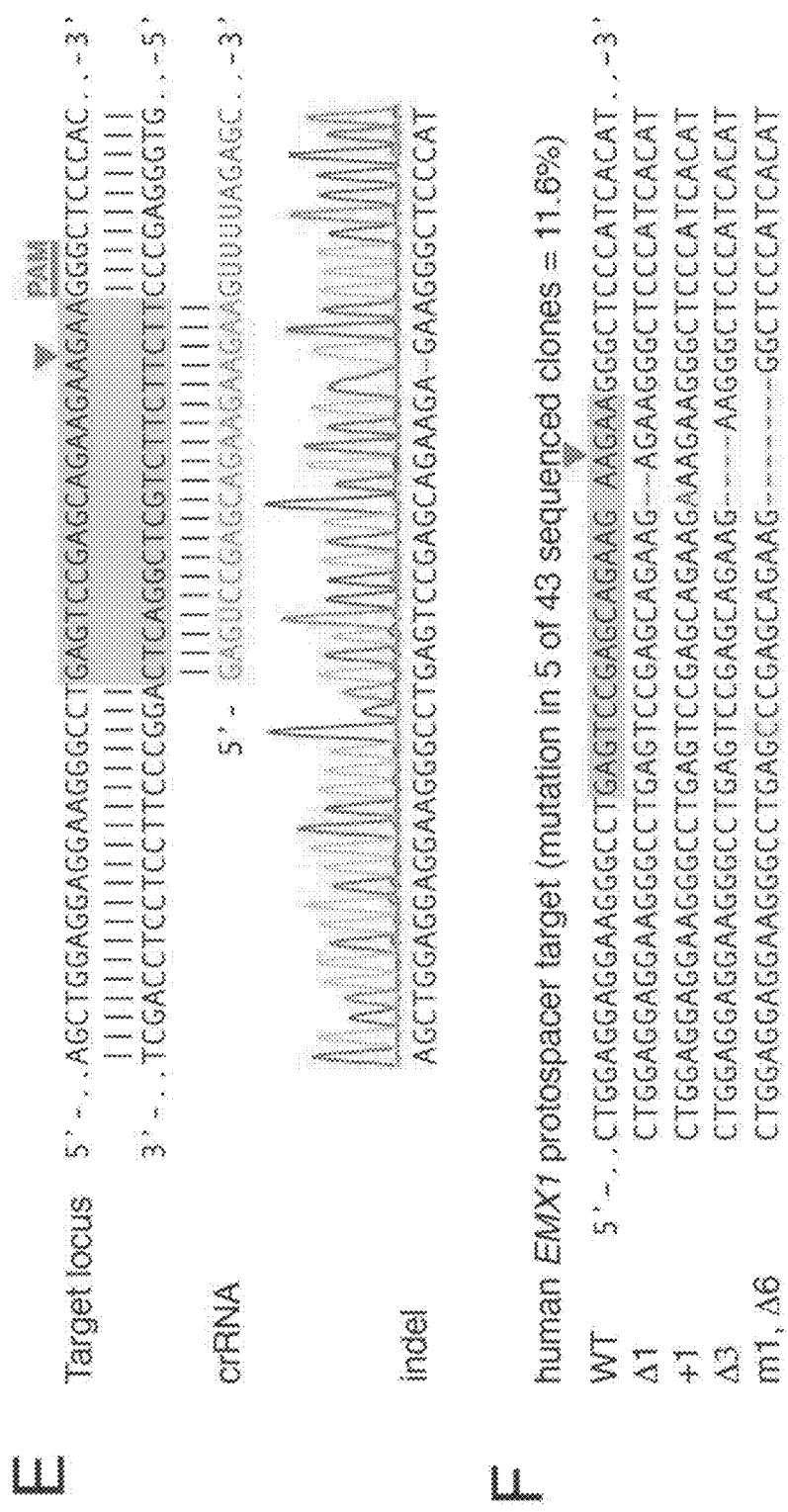
FIG. 2E-F

FIG. 3

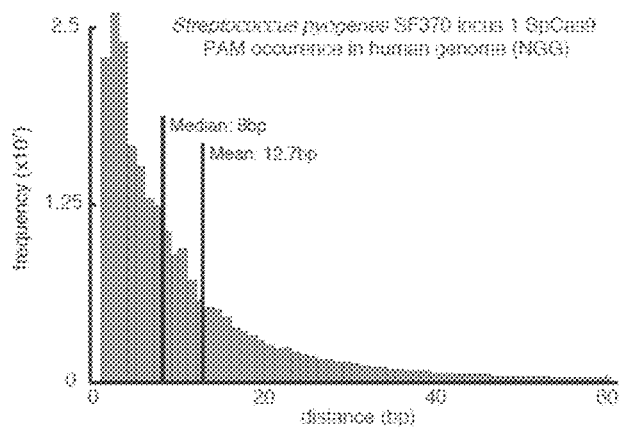
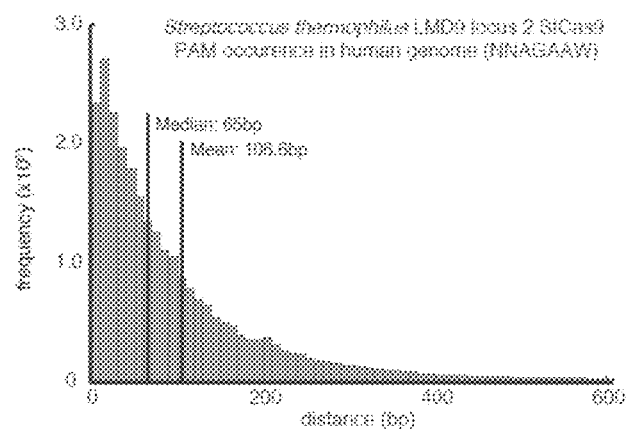
FIG. 5A-C

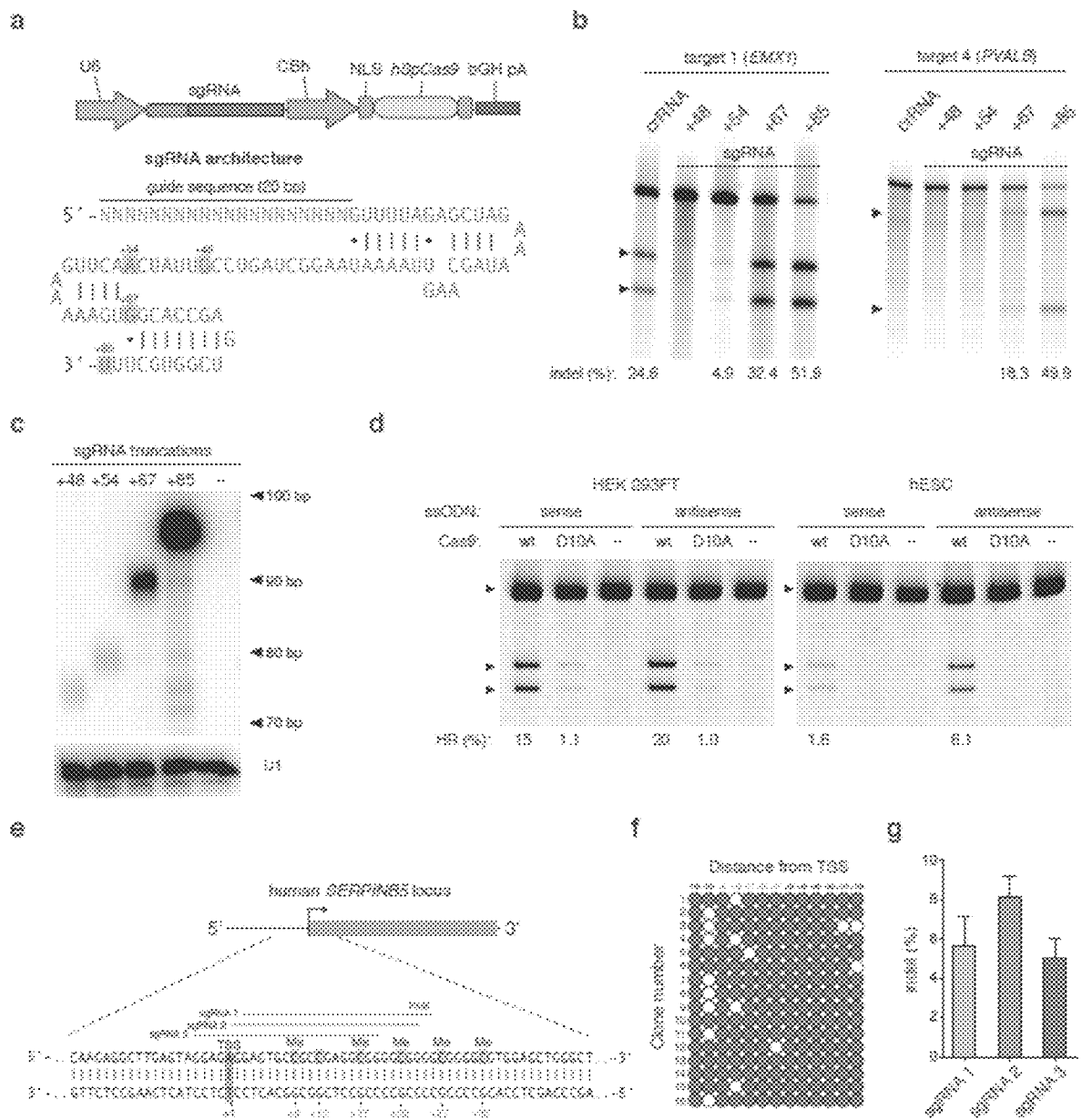
FIG. 9A-G

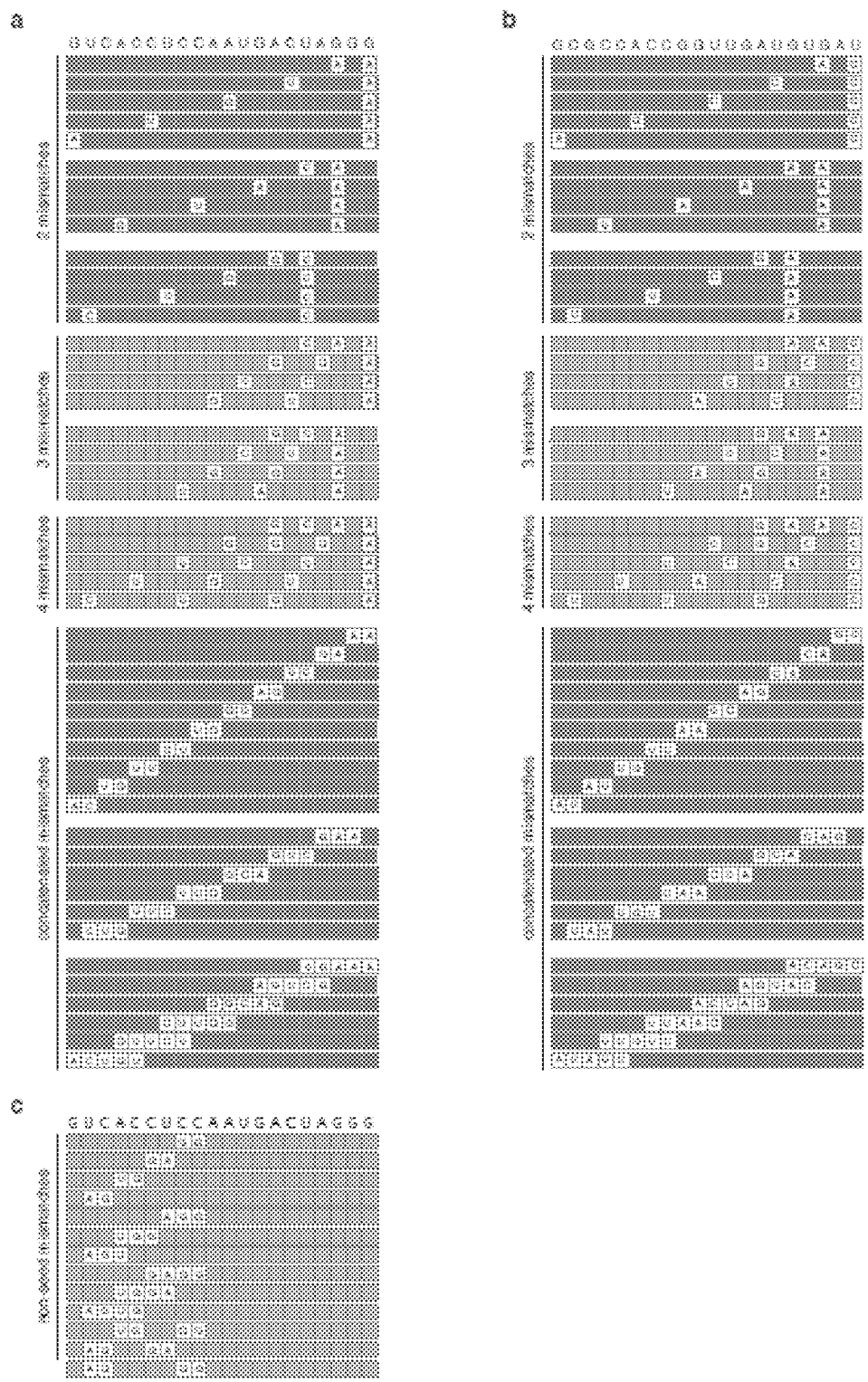
FIG. 10A-C

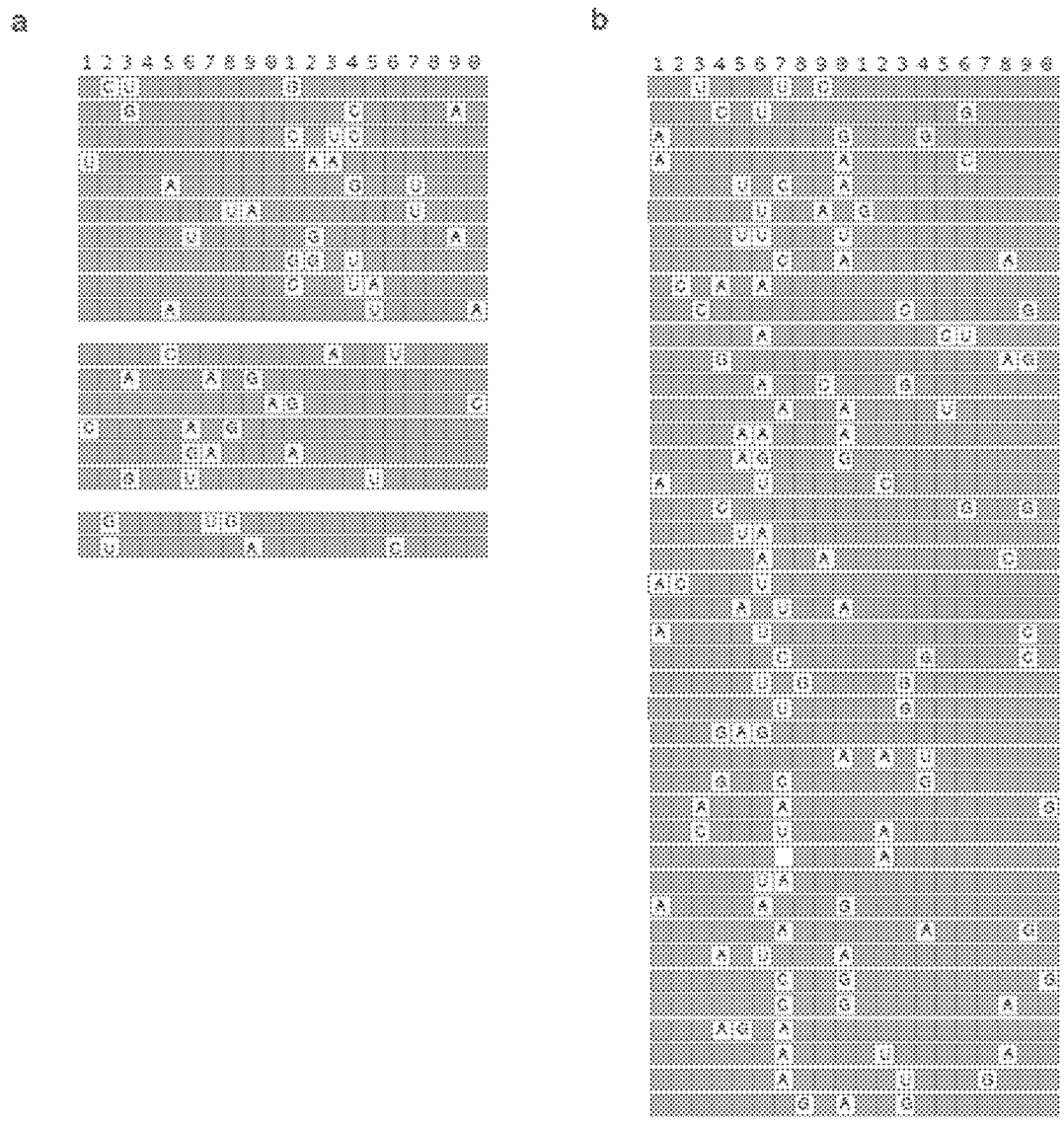
FIG. 11A-B

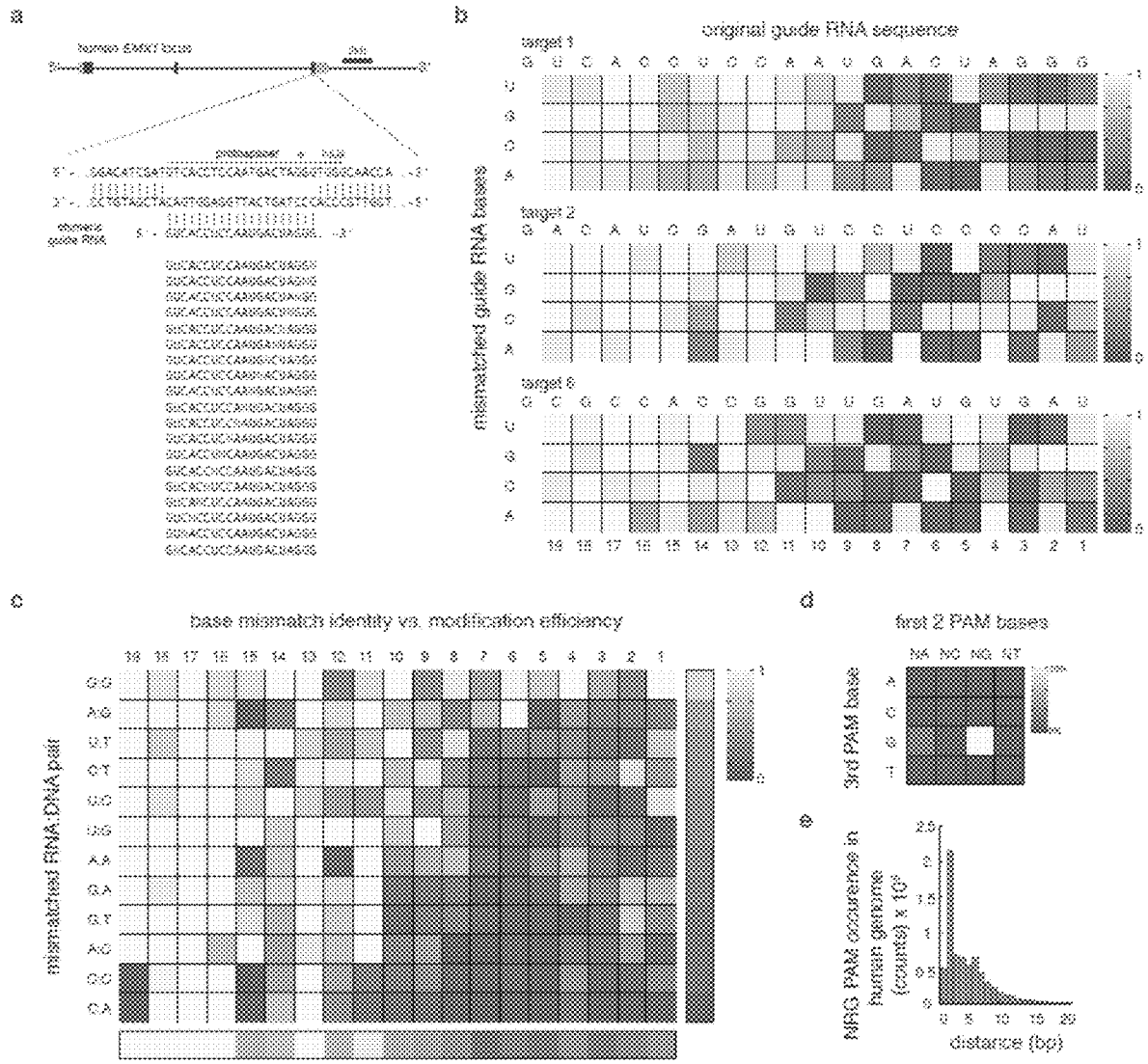
FIG. 12A-E

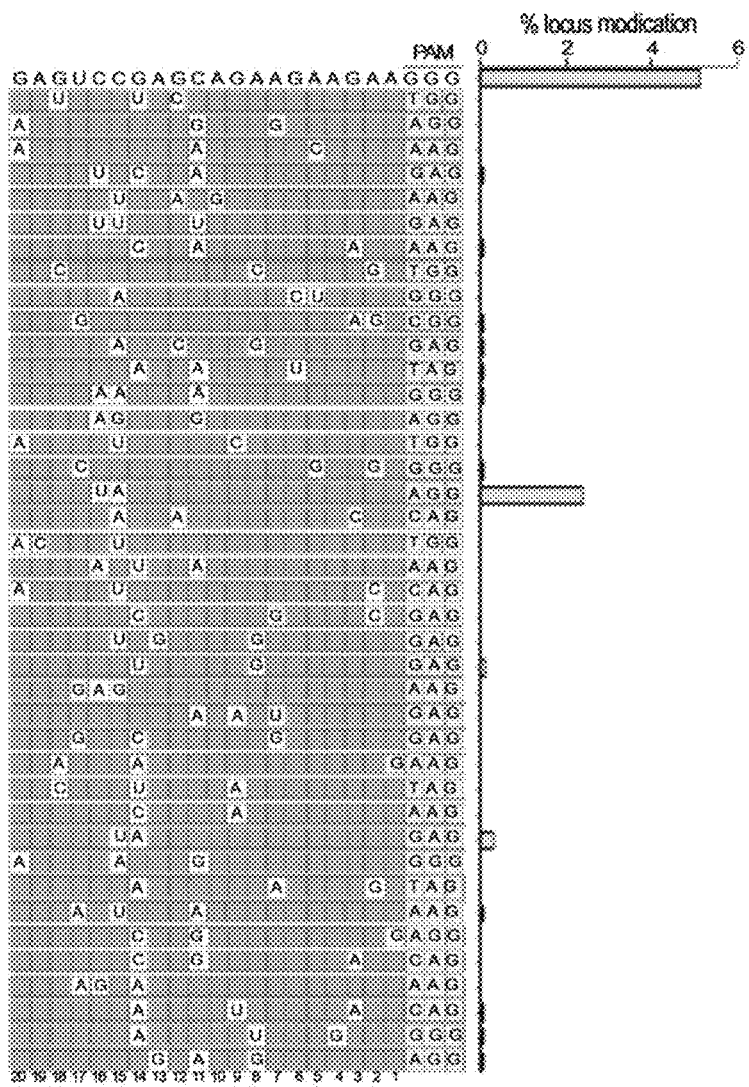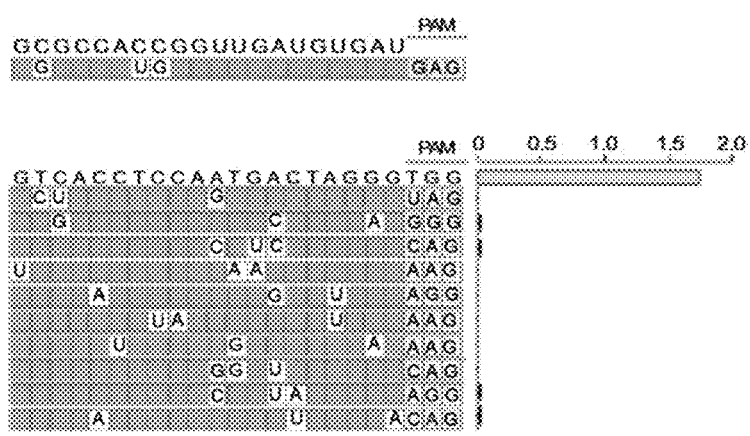
FIG. 13C

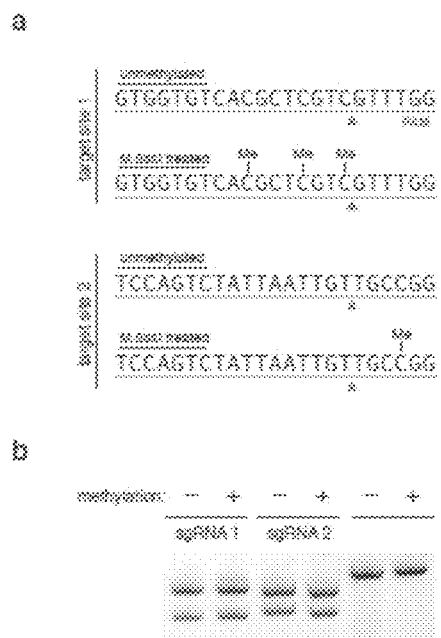
FIG. 14A-B

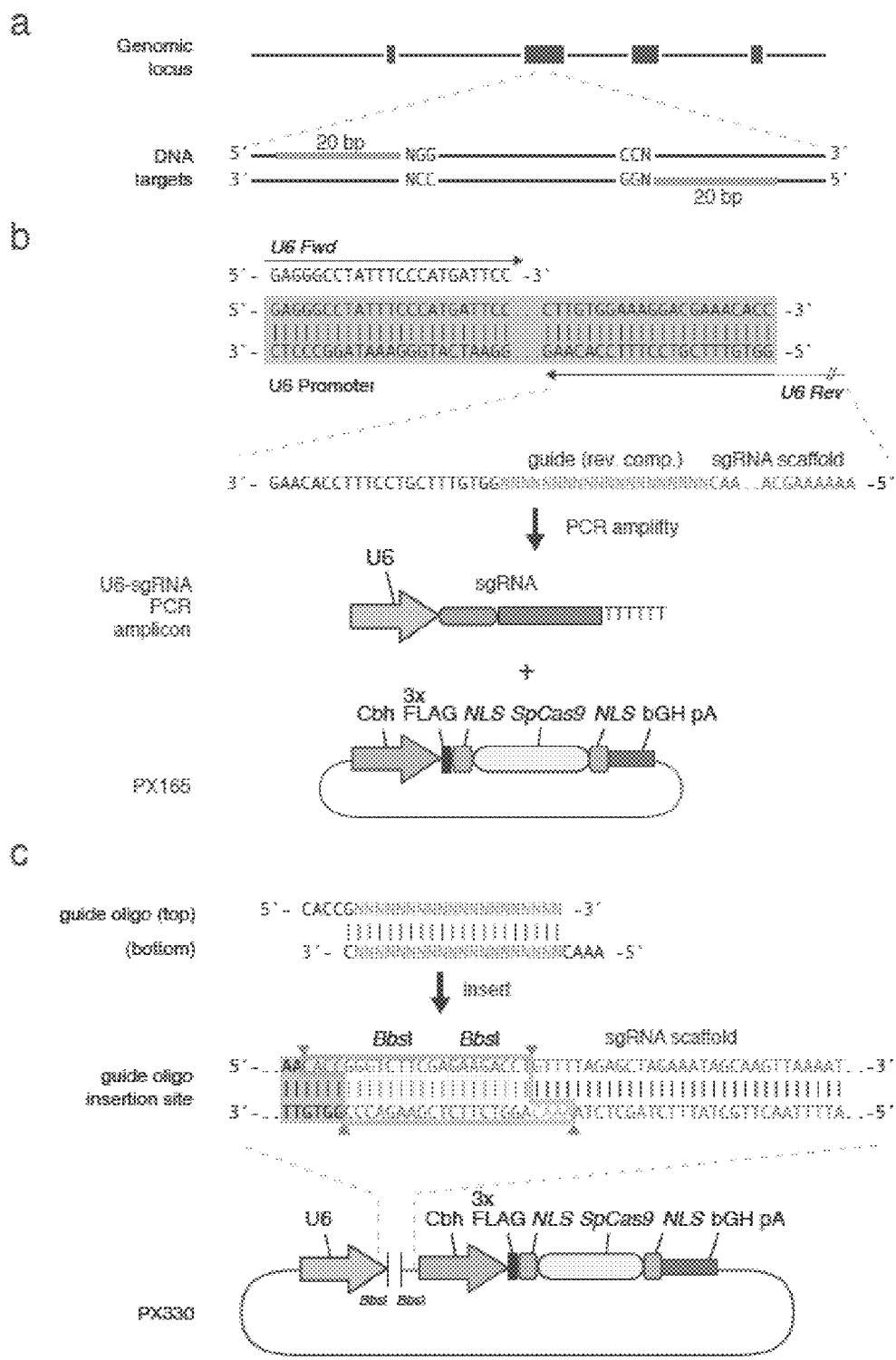
FIG. 24A-C

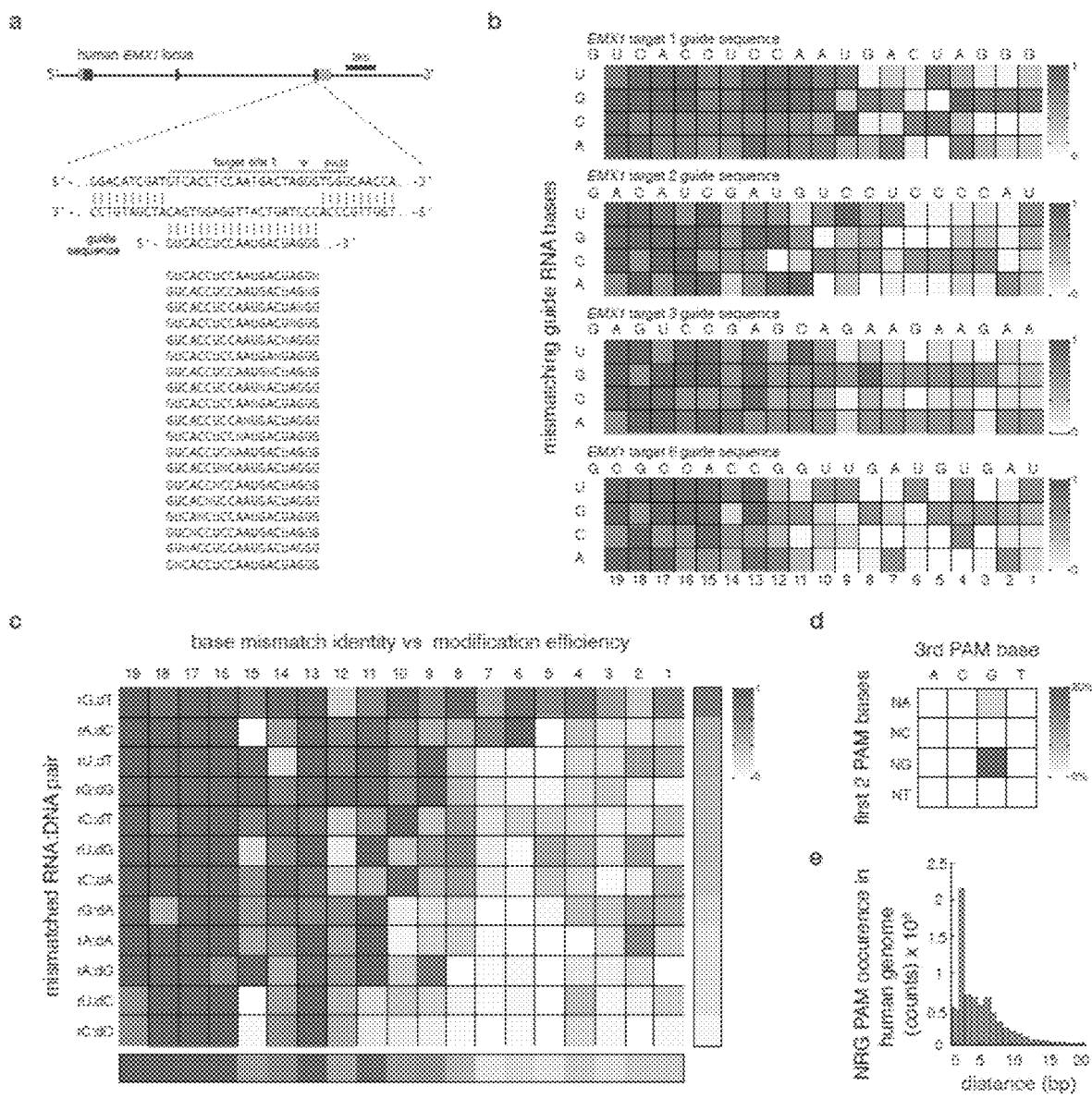
FIG. 25A-E

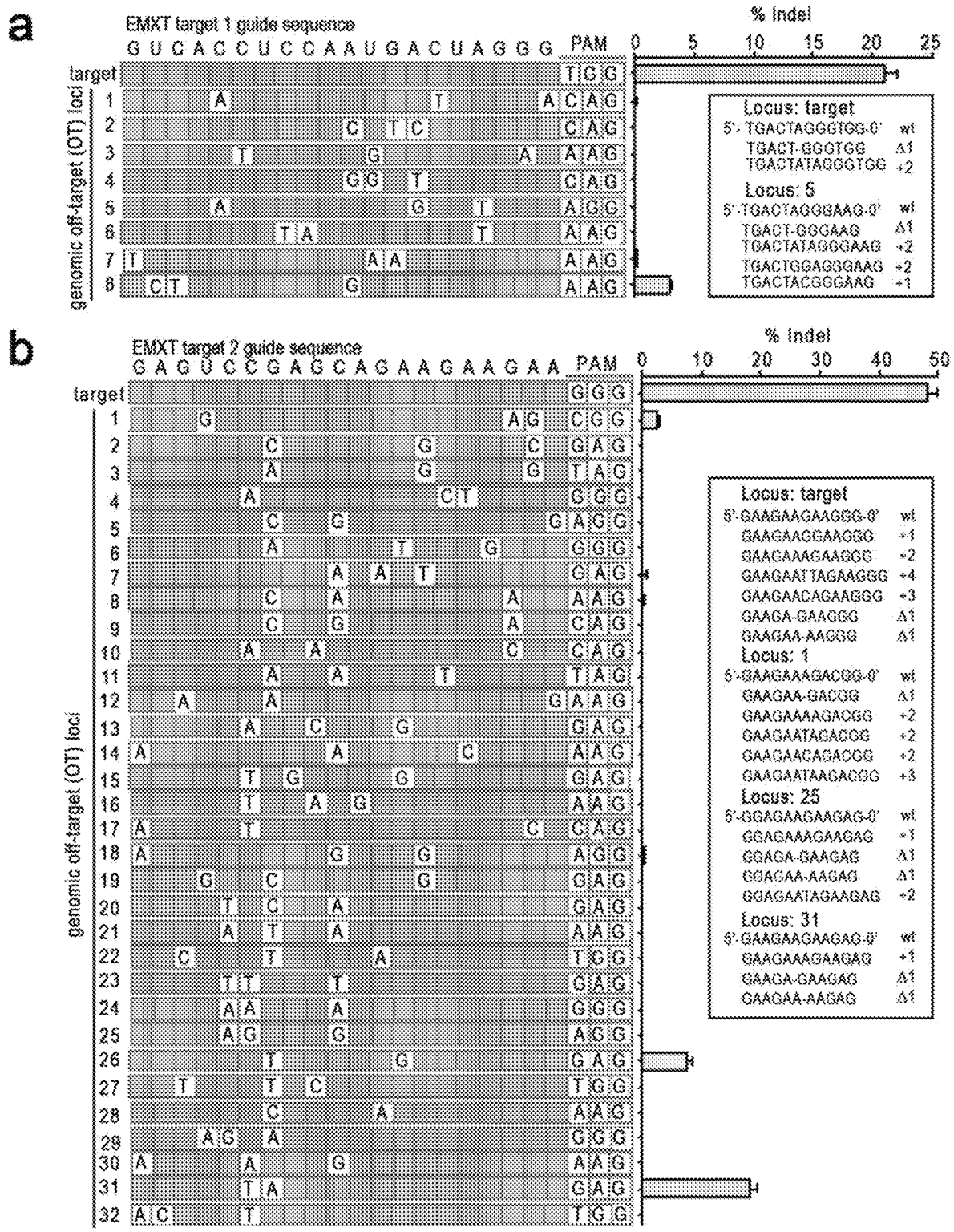
FIG. 27A-B

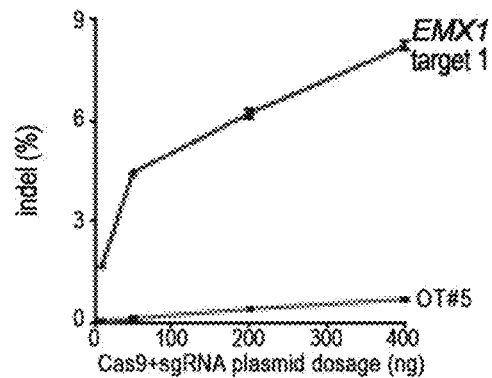
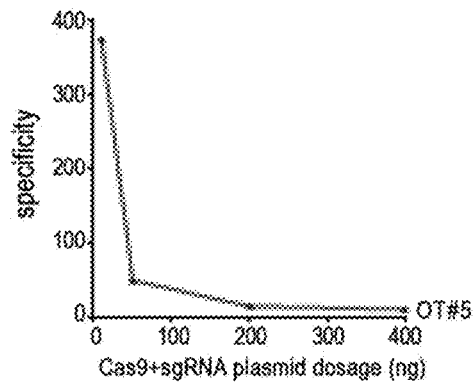
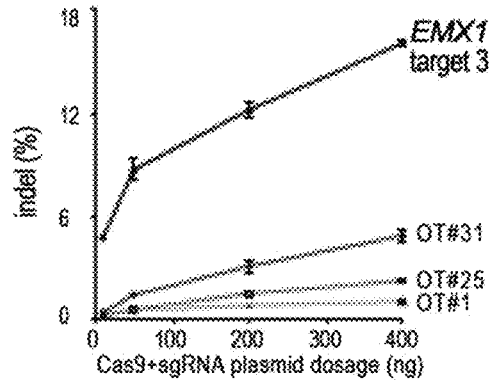
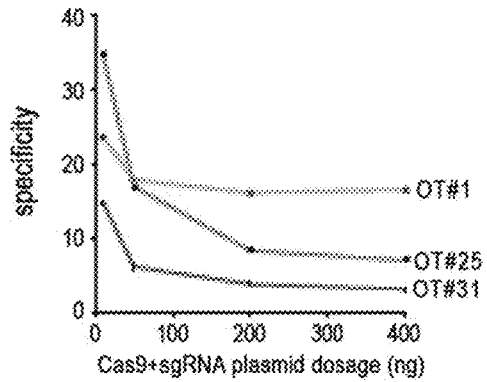
FIG. 27C-D

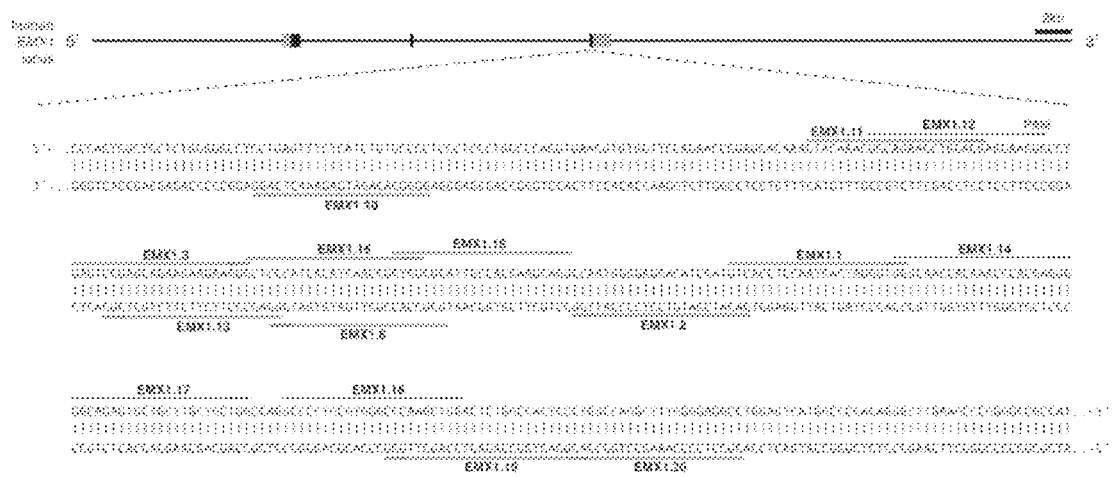
FIG. 28A-B

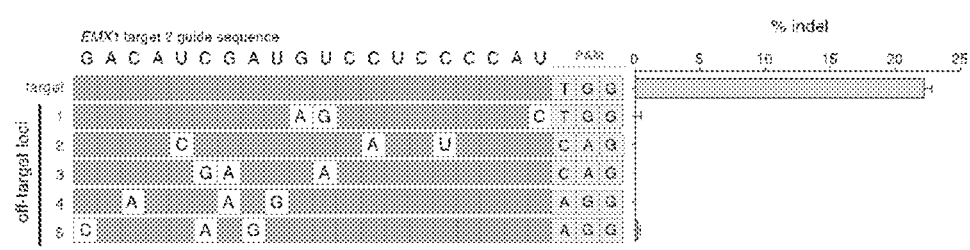
FIG. 29A-B

METHODS, MODELS, SYSTEMS, AND APPARATUS FOR IDENTIFYING TARGET SEQUENCES FOR CAS ENZYMES OR CRISPR-CAS SYSTEMS FOR TARGET SEQUENCES AND CONVEYING RESULTS THEREOF

RELATED APPLICATIONS AND INCORPORATION BY REFERENCE

This application is a continuation-in-part of international patent application serial no. PCT/US2013/074812 filed Dec. 12, 2013 and published as WO2014093709, which claims priority to U.S. provisional patent application 61/836,080 entitled METHODS, SYSTEMS, AND APPARATUS FOR IDENTIFYING TARGET SEQUENCES FOR CAS ENZYMES OR CRISPR-CAS SYSTEMS FOR TARGET SEQUENCES AND CONVEYING RESULTS THEREOF filed on Jun. 17, 2013, and which also claims priority to US provisional patent applications 61/758,468; 61/769,046; 61/802,174; 61/806,375; 61/814,263; 61/819,803 and 61/828,130 each entitled ENGINEERING AND OPTIMIZATION OF SYSTEMS, METHODS AND COMPOSITIONS FOR SEQUENCE MANIPULATION, filed on Jan. 30, 2013; Feb. 25, 2013; Mar. 15, 2013; Mar. 28, 2013; Apr. 20, 2013; May 6, 2013 and May 28, 2013, respectively, and which also claims priority to US provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively, and which also claims priority to US provisional patent applications 61/791,409 and 61/835,931 filed on Mar. 15, 2013 and Jun. 17, 2013 respectively.

STATEMENT AS TO FEDERALLY SPONSORED RESEARCH

This invention was made with government support under Grant Nos. MH100706 and DK097768 awarded by the National Institutes of Health. The government has certain rights in the invention.

Reference is also made to international patent applications PCT/US2013/074611 filed Dec. 12, 2013 and published as WO 2014/093595; PCT/US2013/074743 filed Dec. 12, 2013 and published as WO 2014/093661; PCT/US2013/074790 filed Dec. 12, 2013 and published as WO 2014/093694; PCT/US2013/074825 filed Dec. 12, 2013 and published as WO 2014/093718; PCT/US2013/074667 filed Dec. 12, 2013 and published as WO 2014/093622; PCT/US2013/074691 filed Dec. 12, 2013 and published as WO 2014/093635; PCT/US2013/074736 filed Dec. 12, 2013 and published as WO 2014/093655; PCT/US2013/074819 filed Dec. 12, 2013 and published as WO 2014/093712; and PCT/US2013/074800 filed Dec. 12, 2013 and published as WO 2014/093701.

Reference is also made to US provisional patent applications 61/757,972, filed Jan. 29, 2013, 61/799,800 filed Mar. 15, 2013, 61/835,936, 61/835,973, 61/836,080, 61/836,101, 61/836,123, 61/836,127, and 61/847,537, each filed Jun. 17, 2013, 61/862,468 and 61/862,355, each filed Aug. 5, 2013; 61/871,301 filed Aug. 28, 2013; 61/969,777 filed Sep. 25, 2013; and 61/961,980 filed Oct. 28, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention generally relates to the engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

BACKGROUND OF THE INVENTION

The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand methods, systems and apparatus for identifying target sequences for Cas enzymes or CRISPR-Cas systems for target sequences of interest and conveying the results, which are aspects of the claimed invention.

SUMMARY OF THE INVENTION

The CRISPR/Cas or the CRISPR-Cas system (both terms may be used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

In some aspects the invention relates to a non-naturally occurring or engineered composition comprising a CRISPR/Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, wherein the CRISPR complex comprises a CRISPR enzyme complexed with (1) the guide sequence that is hybridized to the target sequence, and (2) the tracr mate sequence that is hybridized to the tracr sequence, or an CRISPR enzyme system, wherein the system is encoded by a vector system comprising one or more vectors comprising I. a first regulatory element operably linked to a CRISPR/Cas system chimeric RNA (chiRNA) polynucleotide sequence, wherein the polynucleotide sequence comprises (a) one or more guide sequences capable of hybridizing to one or more target sequences in a eukaryotic cell, (b) a tracr mate sequence, and (c) one or more tracr sequences, and II. a second regulatory element operably linked to an enzyme-coding sequence encoding a CRISPR enzyme comprising at least one or more nuclear localization sequences, wherein (a), (b) and (c) are arranged in a 5' to 3'orientation, wherein components I and II are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, or a multiplexed CRISPR enzyme system, wherein the system is encoded by a vector system comprising one or more vectors comprising I. a first regulatory element operably linked to (a) one or more guide sequences capable of hybridizing to a target sequence in a cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridized to the target sequence, and (2) the tracr mate sequence that is hybridized to the tracr sequence, and wherein in the multiplexed system multiple guide sequences and a single tracr sequence is used.

Without wishing to be bound by theory, it is believed that the target sequence should be associated with a PAM (protospacer adjacent motif); that is, a short sequence recognized by the CRISPR complex. This PAM may be considered a CRISPR motif.

With regard to the CRISPR system or complex discussed herein, reference is made to FIG. 2. FIG. 2 shows an exemplary CRISPR system and a possible mechanism of action (A), an example adaptation for expression in eukaryotic cells, and results of tests assessing nuclear localization and CRISPR activity (B-F).

The invention provides a method of identifying one or more unique target sequences. The target sequences may be in a genome of an organism, such as a genome of a eukaryotic organism. Accordingly, through potential sequence-specific binding, the target sequence may be susceptible to being recognized by a CRISPR-Cas system. (Likewise, the invention thus comprehends identifying one or more CRISPR-Cas systems that identifies one or more unique target sequences.) The target sequence may include the CRISPR motif and the sequence upstream or before it. The method may comprise: locating a CRISPR motif, e.g., analyzing (for instance comparing) a sequence to ascertain whether a CRISPR motif. e.g., a PAM sequence, a short sequence recognized by the CRISPR complex, is present in the sequence; analyzing (for instance comparing) the sequence upstream of the CRISPR motif to determine if that upstream sequence occurs elsewhere in the genome; selecting the upstream sequence if it does not occur elsewhere in the genome, thereby identifying a unique target site. The sequence upstream of the CRISPR motif may be at least 10 bp or at least 11 bp or at least 12 bp or at least 13 bp or at least 14 bp or at least 15 bp or at least 16 bp or at least 17 bp or at least 18 bp or at least 19 bp or at least 20 bp in length, e.g., the sequence upstream of the CRISPR motif may be about 10 bp to about 20 bp, e.g., the sequence upstream is 10, 11, 12, 13, 14, 15, 16, 17, 18, 19, 20, 21, 22, 23, 24, 25, 26, 27, 28, 29 or 30 bp in length. The CRISPR motif may be recognized by a Cas enzyme such as a Cas9 enzyme, e.g., a SpCas9 enzyme. Further, the CRISPR motif may be a protospacer-adjacent motif (PAM) sequence, e.g., NGG or NAG. Accordingly, as CRISPR motifs or PAM sequences may be recognized by a Cas enzyme in vitro, ex vivo or in vivo, in the in silico analysis, there is an analysis, e.g., comparison, of the sequence in interest against CRISPR motifs or PAM sequences to identify regions of the sequence in interest which may be recognized by a Cas enzyme in vitro, ex vivo or in vivo. When that analysis identifies a CRISPR motif or PAM sequence, the next analysis e.g., comparison is of the sequences upstream from the CRISPR motif or PAM sequence, e.g., analysis of the sequence 10, 11, 12, 13, 14, 15, 16, 17, 18, 19, 20, 21, 22, 23, 24, 25, 26, 27, 28, 29 or 30 bp in length starting at the PAM or CRISPR motif and extending upstream therefrom. That analysis is to see if that upstream sequence is unique, i.e., if the upstream sequence does not appear to otherwise occur in a genome, it may be a unique target site. The selection for unique sites is the same as the filtering step: in both cases, you filter away all target sequences with associated CRISPR motif that occur more than once in the target genome.

Eukaryotic organisms of interest may include but are not limited to *Homo sapiens* (human), *Mus musculus* (mouse), *Rattus norvegicus* (rat), *Danio rerio* (zebrafish), *Drosophila melanogaster* (fruit fly), *Caenorhabditis elegans* (roundworm), *Sus scrofa* (pig) and *Bos taurus* (cow). The eukaryotic organism can be selected from the group consisting of *Homo sapiens* (human), *Mus musculus* (mouse), *Rattus norvegicus* (rat), *Danio rerio* (zebrafish), *Drosophila melanogaster* (fruit fly), *Caenorhabditis elegans* (roundworm), *Sus scrofa* (pig) and *Bos taurus* (cow). The invention also comprehends computer-readable medium comprising codes that, upon execution by one or more processors, implements a herein method of identifying one or more unique target sequences.

The invention further comprehends a computer system for identifying one or more unique target sequences, e.g., in a genome, such as a genome of a eukaryotic organism, the system comprising: a. a memory unit configured to receive and/or store sequence information of the genome; and b. one or more processors alone or in combination programmed to perform a herein method of identifying one or more unique target sequences (e.g., locate a CRISPR motif, analyze a sequence upstream of the CRISPR motif to determine if the sequence occurs elsewhere in the genome, select the sequence if it does not occur elsewhere in the genome), to thereby identifying a unique target site and display and/or transmit the one or more unique target sequences. The candidate target sequence may be a DNA sequence. Mismatch(es) can be of RNA of the CRISPR complex and the DNA. In aspects of the invention, susceptibility of a target sequence being recognized by a CRISPR-Cas system indicates that there may be stable binding between the one or more base pairs of the target sequence and guide sequence of the CRISPR-Cas system to allow for specific recognition of the target sequence by the guide sequence.

The CRISPR/Cas or the CRISPR-Cas system utilizes a single Cas enzyme that can be programmed by a short RNA molecule to recognize a specific DNA target, in other words the Cas enzyme can be recruited to a specific DNA target using said short RNA molecule. In certain aspects, e.g., when not mutated or modified or when in a native state, the Cas or CRISPR enzyme in CRISPR/Cas or the CRISPR-Cas system, effects a cutting at a particular position; a specific DNA target. Accordingly, data can be generated—a data training set—relative to cutting by a CRISPR-Cas system at a particular position in a nucleotide, e.g., DNA, sequence at a particular position for a particular Cas or CRISPR enzyme. Similarly, data can be generated—a data training set—relative to cutting by a CRISPR-Cas system at a particular position in a nucleotide, e.g., DNA, sequence of a particular mismatch of typical nucleic acid hybridization (e.g., rather than G-C at particular position, G-T or G-U or G-A or G-G) for the particular Cas. In generating such data sets, there is the concept of average cutting frequency. The frequency by which an enzyme will cut a nucleic acid molecule, e.g., DNA, is mainly a function of the length of the sequence it is sensitive to. For instance, if an enzyme has a recognition sequence of 4 base-pairs, out of sheer probability, with 4 positions, and each position having potentially 4 different values, there are $4^4$ or 256 different possibilities for any given 4-base long strand. Therefore, theoretically (assuming completely random DNA), this enzyme will cut 1 in 256 4-base-pair long sites. For an enzyme that recognizes a sequence of 6 base-pairs, the calculation is $4^6$ or 4096 possible combinations with this length, and so such an enzyme will cut 1 in 4096 6-base-pair long sites. Of course, such calculations take into consideration only that each position has potentially 4 different values, and completely random DNA. However, DNA is not completely random; for example, the G-C content of organisms varies. Accordingly, the data training set(s) in the invention come from observing cutting by a CRISPR-Cas system at a particular position in a nucleotide, e.g., DNA, sequence at a particular position for a particular Cas or CRISPR enzyme and observing cutting by a CRISPR-Cas system at a particular position in a nucleotide, e.g., DNA, sequence of a particular mismatch of typical nucleic acid hybridization for the particular Cas, in a statistically significant number of experiments as to the particular position, the CRISPR-Cas system and the particular Cas, and averaging the results observed or obtained therefrom. The average cutting frequency may be defined as the mean of the cleavage efficiencies for all guide RNA: target DNA mismatches at a particular location.

The invention further provides a method of identifying one or more unique target sequences, e.g., in a genome, such as a genome of a eukaryotic organism, whereby the target sequence is susceptible to being recognized by a CRISPR-Cas system (and likewise, the invention also further provides a method of identifying a CRISPR-Cas system susceptible to recognizing one or more unique target sequences), wherein the method comprises: a) determining average cutting frequency at a particular position for a particular Cas from a data training set as to that Cas, b) determining average cutting frequency of a particular mismatch (e.g., guide-RNA/target mismatch) for the particular Cas from the data training set, c) multiplying the average cutting frequency at a particular position by the average cutting frequency of a particular mismatch to obtain a first product, d) repeating steps a) to c) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally d) repeating steps a) to c) to obtain second and further products for any further particular position (s) of mismatches and particular mismatches and multiplying those second and further products by the first product, for an ultimate product, and omitting this step if there is no mismatch at any position or if there is only one particular mismatch at one particular position), and e) multiplying the ultimate product by the result of dividing the minimum distance between consecutive mismatches by the distance, in bp, between the first and last base of the target sequence, e.g., 15-20, such as 18, and omitting this step if there is no mismatch at any position or if there is only one particular mismatch at one particular position (or optionally e) multiplying the ultimate product by the result of dividing the minimum distance between consecutive mismatches by the distance, in bp, between the first and last base of the target sequence, e.g., 15-20, such as 18 and omitting this step if there is no mismatch at any position or if there is only one particular mismatch at one particular position), to thereby obtain a ranking, which allows for the identification of one or more unique target sequences, to thereby obtain a ranking, which allows for the identification of one or more unique target sequences. Steps (a) and (b) can be performed in either order. If there are no other products than the first product, that first product (of step (c) from multiplying (a) times (b)) is what is used to determine or obtain the ranking.

The invention also comprehends method of identifying one or more unique target sequences in a genome of a eukaryotic organism, whereby the target sequence is susceptible to being recognized by a CRISPR-Cas system, wherein the method comprises: a) creating a data training set as to a particular Cas, b) determining average cutting frequency at a particular position for the particular Cas from the data training set, c) determining average cutting frequency of a particular mismatch for the particular Cas from the data training set, d) multiplying the average cutting frequency at a particular position by the average cutting frequency of a particular mismatch to obtain a first product, e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position), and f) multiplying the ultimate product by the result of dividing the minimum distance between consecutive mismatches by 18 and omitting this step if there is no mismatch at any position or if there is only one particular mismatch at one particular position (or optionally f) multiplying the ultimate product by the result of dividing the minimum distance between consecutive mismatches by the distance, in bp, between the first and last base of the target sequence, e.g., 15-20, such as 18, and omitting this step if there is no mismatch at any position or if there is only one particular mismatch at one particular position), to thereby obtain a ranking, which allows for the identification of one or more unique target sequences. Steps (a) and (b) can be performed in either order. Steps (a) and (b) can be performed in either order. If there are no other products than the first product, that first product (of step (c) from multiplying (a) times (b)) is what is used to determine or obtain the ranking.

The invention also comprehends a method of identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, and/or b) determining average cutting frequency of a particular mismatch-type for the particular Cas from the training data set, to thereby obtain a ranking, which allows for the identification of one or more unique target sequences. The method may comprise determining both the average cutting frequency of guide-RNA/target mismatches at a particular position for a particular Cas from a training data set as to that Cas, and the average cutting frequency of a particular mismatch-type for the particular Cas from the training data set. Where both are determined, the method may further comprise multiplying the average cutting frequency at a particular position by the average cutting frequency of a particular mismatch-type to obtain a first product, repeating the determining and multiplying steps to obtain second and further products for any further particular position(s) of mismatches and particular mismatches and multiplying those second and further products by the first product, for an ultimate product, and omitting this step if there is no mismatch at any position or if there is only one particular mismatch at one particular position, and multiplying the ultimate product by the result of dividing the minimum distance between consecutive mismatches by the distance, in bp, between the first and last base of the target sequence and omitting this step if there is no mismatch at any position or if there is only one particular mismatch at one particular position, to thereby obtain a ranking, which allows for the identification of one or more unique target sequences. The distance, in bp, between the first and last base of the target sequence may be 18. The method may comprise creating a training set as to a particular Cas. The method may comprise determining the average cutting frequency of guide-RNA/target mismatches at a particular position for a particular Cas from a training data set as to that Cas, if more than one mismatch, repeating the determining step so as to determine cutting frequency for each mismatch, and multiplying frequencies of mismatches to thereby obtain a ranking, which allows for the identification of one or more unique target sequences.

The invention further comprehends a method of identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, and average cutting frequency of a particular mismatch-type for the particular Cas from the training data set, to thereby obtain a ranking, which allows for the identification of one or more unique target sequences. The invention additionally comprehends a method of identifying one or more unique target sequences in a genome of a eukaryotic organism, whereby the target sequence is susceptible to being recognized by a CRISPR-Cas system, wherein the method comprises: a) creating a training data set as to a particular Cas, b) determining average cutting frequency of guide-RNA/target mismatches at a particular position for the particular Cas from the training data set, and/or c) determining average cutting frequency of a particular mismatch-type for the particular Cas from the training data set, to thereby obtain a ranking, which allows for the identification of one or more unique target sequences. The invention yet further comprehends a method of identifying one or more unique target sequences in a genome of a eukaryotic organism, whereby the target sequence is susceptible to being recognized by a CRISPR-Cas system, wherein the method comprises: a) creating a training data set as to a particular Cas, b) determining average cutting frequency of guide-RNA/target mismatches at a particular position for the particular Cas from the training data set, and average cutting frequency of a particular mismatch-type for the particular Cas from the training data set, to thereby obtain a ranking, which allows for the identification of one or more unique target sequences. Accordingly, in these embodiments, instead of multiplying cutting-frequency averages uniquely determined for a mismatch position and mismatch type separately, the invention uses averages that are uniquely determined, e.g., cutting-frequency averages for a particular mismatch type at a particular position (thereby without multiplying these, as part of preparation of training set). These methods can be performed iteratively akin to the steps in methods including multiplication, for determination of one or more unique target sequences.

The invention in certain aspects provides a method for selecting a CRISPR complex for targeting and/or cleavage of a candidate target nucleic acid sequence within a cell, comprising the steps of: (a) determining amount, location and nature of mismatch(es) of guide sequence of potential CRISPR complex(es) and the candidate target nucleic acid sequence, (b) determining contribution of each of the amount, location and nature of mismatch(es) to hybridization free energy of binding between the target nucleic acid sequence and the guide sequence of potential CRISPR complex(es) from a training data set, (c) based on the contribution analysis of step (b), predicting cleavage at the location(s) of the mismatch(es) of the target nucleic acid sequence by the potential CRISPR complex(es), and (d) selecting the CRISPR complex from potential CRISPR complex(es) based on whether the prediction of step (c) indicates that it is more likely than not that cleavage will occur at location(s) of mismatch(es) by the CRISPR complex Step (b) may be performed by: determining local thermodynamic contributions, $\Delta G_{ij}(k)$, between every guide sequence i and target nucleic acid sequence j at position k, wherein $\Delta G_{ij}(k)$ is estimated from a biochemical prediction algorithm and $\alpha_k$ is a position-dependent weight calculated from the training data set, estimating values of the effective free-energy $Z_{ij}$ using the relationship $p_{ij} \propto e^{-\beta Z_{ij}}$, wherein $p_{ij}$ is measured cutting frequency by guide sequence i on target nucleic acid sequence j and $\beta$ is a positive constant of proportionality, determining position-dependent weights $\alpha_k$ by fitting across spacer/target-pairs with the sum across all N bases of the guide-sequence $$Z_{ij} = \sum_{k=1}^{N} \alpha_k \Delta G_{ij}(k)$$

and wherein, step (c) is performed by determining the position-dependent weights from the effective free-energy $\vec{Z}_{est} = \vec{G} \vec{\alpha}$ between each spacer and every potential target in the genome, and determining estimated spacer-target cutting frequencies $p_{est} \propto e^{-\beta Z_{est}}$ to thereby predict cleavage. Beta is implicitly fit by fitting the values of alpha (that are completely free to be multiplied—in the process of fitting—by whichever constant is suitable for Z=sum(alpha*Delta G)).

The invention also comprises the creation of a training data set. A training data set is data of cutting frequency measurements, obtained to maximize coverage and redundancy for possible mismatch types and positions. There are advantageously two experimental paradigms for generating a training data set. In one aspect, generating a data set comprises assaying for Cas, e.g., Cas9, cleavage at a constant target and mutating guide sequences. In another aspect, generating a data set comprises assaying for Cas, e.g., Cas9, cleavage using a constant guide sequence and testing cleavage at multiple DNA targets. Further, the method can be performed in at least two ways: in vivo (in cells, tissue, or living animal) or in vitro (with a cell-free assay, using in vitro transcribed guide RNA and Cas, e.g., Cas9 protein delivered either by whole cell lysate or purified protein). Advantageously the method is performed by assaying for cleavage at a constant target with mismatched guide RNA in vivo in cell lines. Because the guide RNA may be generated in cells as a transcript from a RNA polymerase III promoter (e.g. U6) driving a DNA oligo, it may be expressed as a PCR cassette and transfect the guide RNA directly (FIG. 24c) along with CBh-driven Cas9 (PX165, FIG. 24c). By co-transfecting Cas9 and a guide RNA with one or several mismatches relative to the constant DNA target, one may assess cleavage at a constant endogenous locus by a nuclease assay such as SURVEYOR nuclease assay or next-generation deep sequencing. This data may be collected for at least one or multiple targets within a loci of interest, e.g., at least 1, at least 5, at least 10, at least 15 or at least 20 targets from the human EMX1 locus. In this manner, a data training set can be readily generated for any locus of interest. Accordingly, there are at least two ways for generating a data training set—in vivo (in cell lines or living animal) or in vitro (with a cell-free assay, using in vitro transcribed guide RNA and Cas, e.g., Cas9, protein delivered either by whole cell lysate or purified protein). Also, the experimental paradigm can differ—e.g. with mutated guide sequences or with a constant guide and an oligo library of many DNA targets. These targeting experiments can be done in vitro as well. The readout would simply be running a gel on the result of the in vitro cleavage assay—the results will be cleaved and uncleaved fractions. Alternatively or additionally, these fractions can be gel-isolated and sequencing adapters can be ligated prior to deep sequencing on these populations.

The invention comprises computer-readable medium comprising codes that, upon execution by one or more processors, implements a herein method. The invention further comprises a computer system for performing a herein method. The system can include I. a memory unit configured to receive and/or store sequence information of the genome; and II. one or more processors alone or in combination programmed to perform the herein method, whereby the identification of one or more unique target sequences is advantageously displayed or transmitted. The eukaryotic organism can be selected from the group consisting of *Homo sapiens* (human), *Mus musculus* (mouse), *Rattus norvegicus* (rat), *Danio rerio* (zebrafish), *Drosophila melanogaster* (fruit fly), *Caenorhabditis elegans* (roundworm), *Sus scrofa* (pig) and *Bos taurus* (cow). The target sequence can be a DNA sequence, and the mismatch(es) can be of RNA of the CRISPR complex and the DNA.

The invention also entails a method for selecting a CRISPR complex for targeting and/or cleavage of a candidate target nucleic acid sequence, e.g., within a cell, comprising the steps of: (a) determining amount, location and nature of mismatch(es) of potential CRISPR complex(es) and the candidate target nucleic acid sequence, (b) determining the contribution of the mismatch(es) based on the amount and location of the mismatch(es), (c) based on the contribution analysis of step (b), predicting cleavage at the location(s) of the mismatch(es), and (d) selecting the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed. The determining steps can be based on the results or data of the data training set(s) in the invention that come from observing cutting by a CRISPR-Cas system at a particular position in a nucleotide, e.g., DNA, sequence at a particular position for a particular Cas or CRISPR enzyme and observing cutting by a CRISPR-Cas system at a particular position in a nucleotide, e.g., DNA, sequence of a particular mismatch of typical nucleic acid hybridization for the particular Cas, in a statistically significant number of experiments as to the particular position, the CRISPR-Cas system and the particular Cas, and averaging the results observed or obtained therefrom. Accordingly, for example, if the data training set shows that at a particular position the CRISPR-Cas system including a particular Cas is rather promiscuous, i.e., there can be mismatches and cutting, the amount and location may be one position, and nature of the mismatch between the CRISPR complex and the candidate target nucleic acid sequence may be not serious such that the contribution of the mismatch to failure to cut/bind may be negligible and the prediction for cleavage may be more likely than not that cleavage will occur, despite the mismatch. Accordingly, it should be clear that the data training set(s) are not generated in silico but are generated in the laboratory, e.g., are from in vitro, ex vivo and/or in vivo studies. The results from the laboratory work, e.g., from in vitro, ex vivo and/or in vivo studies, are input into computer systems for performing herein methods.

In the herein methods the candidate target sequence can be a DNA sequence, and the mismatch(es) can be of RNA of potential CRISPR complex(es) and the DNA. In aspects of the invention mentioned herein, the amount of mismatches indicates the number of mismatches in DNA: RNA base pairing between the DNA of the target sequence and the RNA of the guide sequence. In aspects of the invention the location of mismatches indicates the specific location along the sequence occupied by the mismatch and if more than one mismatch is present if the mismatches are concatenated or occur consecutively or if they are separated by at least one of more residues. In aspects of the invention the nature of mismatches indicates the nucleotide type involved in the mismatched base pairing. Base pairs are matched according to G-C and A-U Watson-Crick base pairing.

The invention further involves a method for predicting the efficiency of cleavage at candidate target nucleic acid sequence, e.g., within a target in a cell, by a CRISPR complex comprising the steps of: (a) determining amount, location and nature of mismatch(es) of the CRISPR complex and the candidate target nucleic acid sequence, (b) determining the contribution of the mismatch(es) based on the amount and location of the mismatch(es), and (c) based on the contribution analysis of step (b), predicting whether cleavage is more likely than not to occur at location(s) of mismatch(es), and thereby predicting cleavage. As with other herein methods, the candidate target sequence can be a DNA sequence, and the mismatch(es) can be of RNA of the CRISPR complex and the DNA. The cell can be from a eukaryotic organism as herein discussed.

The invention even further provides a method for selecting a candidate target sequence, e.g., within a nucleic acid sequence, e.g., in a cell, for targeting by a CRISPR complex, comprising the steps of: determining the local thermodynamic contributions, $\Delta G_{ij}(k)$, between every spacer i and target j at position k, expressing an effective free-energy $Z_{ij}$ for each spacer/target-pair as the sum $$Z_{ij} = \sum_{k=1}^{N} \alpha_k \Delta G_{ij}(k)$$

wherein $\Delta G_{ij}(k)$ is local thermodynamic contributions, estimated from a biochemical prediction algorithm and $\alpha_k$ is position-dependent weights, and estimating the effective free-energy Z through the relationship $p_{ij} \propto e^{-\beta Z_{ij}}$ wherein $p_{ij}$ is the measured cutting frequency by spacer i on target j and $\beta$ is a positive constant fit across the entire data-set, and estimating the position-dependent weights $\alpha_k$ by fitting G $\vec{\alpha} = \vec{Z}$ such that each spacer-target pair (i,j) corresponds to a row in the matrix G and each position k in the spacer-target pairing corresponds to a column in the same matrix, and estimating the effective free-energy $\vec{Z}_{est} = G \vec{\alpha}$ between each spacer and every potential target in the genome by using the fitted values $\alpha_k$, and selecting, based on calculated effective free-energy values, the candidate spacer/target pair ij according to their specificity and/or the efficiency, given the estimated spacer-target cutting frequencies $p_{est} \propto e^{-\beta Z_{est}}$. The cell can be from a eukaryotic organism as herein discussed.

The invention includes a computer-readable medium comprising codes that, upon execution by one or more processors, implements a method for selecting a CRISPR complex for targeting and/or cleavage of a candidate target nucleic acid, e.g., sequence within a cell, comprising the steps of: (a) determining amount, location and nature of mismatch(es) of potential CRISPR complex(es) and the candidate target nucleic acid sequence, (b) determining the contribution of the mismatch(es) based on the amount and location of the mismatch(es), (c) based on the contribution analysis of step (b), predicting cleavage at the location(s) of the mismatch(es), and (d) selecting the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed.

Also, the invention involves computer systems for selecting a CRISPR complex for targeting and/or cleavage of a candidate target nucleic acid sequence, e.g., within a cell, the system comprising: a. a memory unit configured to receive and/or store sequence information of the candidate target nucleic acid sequence; and b. one or more processors alone or in combination programmed to (a) determine amount, location and nature of mismatch(es) of potential CRISPR complex(es) and the candidate target nucleic acid sequence, (b) determine the contribution of the mismatch(es) based on the amount and location of the mismatch(es), (c) based on the contribution analysis of step (b), predicting cleavage at the location(s) of the mismatch(es), and (d) select the CRISPR complex from potential CRISPR complex(es) based on whether the prediction of step (c) indicates that it is more likely than not that cleavage will occur at location(s) of mismatch(es) by the CRISPR complex. The cell can be from a eukaryotic organism as herein discussed. The system can display or transmit the selection.

In aspects of the invention mentioned herein, the amount of mismatches indicates the number of mismatches in DNA: RNA base pairing between the DNA of the target sequence and the RNA of the guide sequence. In aspects of the invention the location of mismatches indicates the specific location along the sequence occupied by the mismatch and if more than one mismatch is present if the mismatches are concatenated or occur consecutively or if they are separated by at least one of more residues. In aspects of the invention the nature of mismatches indicates the nucleotide type involved in the mismatched base pairing. Base pairs are matched according to G-C and A-U Watson-Crick base pairing.

Accordingly, aspects of the invention relate to methods and compositions used to determine the specificity of Cas9. In one aspect the position and number of mismatches in the guide RNA is tested against cleavage efficiency. This information enables the design of target sequences that have minimal off-target effects.

The invention also comprehends a method of identifying one or more unique target sequences in a genome of a eukaryotic organism, whereby the target sequence is susceptible to being recognized by a CRISPR-Cas system, wherein the method comprises a) determining average cutting frequency of guide-RNA/target mismatches at a particular position for a particular Cas from a training data set as to that Cas, and if more than one mismatch is present then step a) is repeated so as to determine cutting frequency for each mismatch after which frequencies of mismatches are multiplied to thereby obtain a ranking, which allows for the identification of one or more unique target sequences. The invention further comprehends a method of identifying one or more unique target sequences in a genome of a eukaryotic organism, whereby the target sequence is susceptible to being recognized by a CRISPR-Cas system, wherein the method comprises a) creating a training data set as to a particular Cas, b) determining average cutting frequency of guide-RNA/target mismatches at a particular position for a particular Cas from the training data set, if more than one mismatch exists, repeat step b) so as to determine cutting frequency for each mismatch, then multiply frequencies of mismatches to thereby obtain a ranking, which allows for the identification of one or more unique target sequences. The invention also relates to computer systems and computer readable media that executes these methods.

In various aspects, the invention involves a computer system for selecting a candidate target sequence within a nucleic acid sequence or for selecting a Cas for a candidate target sequence, e.g., selecting a target in a eukaryotic cell for targeting by a CRISPR complex.

The computer system may comprise: (a) a memory unit configured to receive and/or store said nucleic acid sequence; and (b) one or more processors alone or in combination programmed to perform as herein discussed. For example, programmed to: (i) locate a CRISPR motif sequence (e.g., PAM) within said nucleic acid sequence, and (ii) select a sequence adjacent to said located CRISPR motif sequence (e.g. PAM) as the candidate target sequence to which the CRISPR complex binds. In some embodiments, said locating step may comprise identifying a CRISPR motif sequence (e.g. PAM) located less than about 10000 nucleotides away from said target sequence, such as less than about 5000, 2500, 1000, 500, 250, 100, 50, 25, or fewer nucleotides away from the target sequence. In some embodiments, the candidate target sequence is at least 10, 15, 20, 25, 30, or more nucleotides in length. In some embodiments the candidate target sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the nucleotide at the 3' end of the candidate target sequence is located no more than about 10 nucleotides upstream of the CRISPR motif sequence (e.g. PAM), such as no more than 5, 4, 3, 2, or 1 nucleotides. In some embodiments, the nucleic acid sequence in the eukaryotic cell is endogenous to the cell or organism, e.g., eukaryotic genome. In some embodiments, the nucleic acid sequence in the eukaryotic cell is exogenous to the cell or organism, e.g., eukaryotic genome.

In various aspects, the invention provides a computer-readable medium comprising codes that, upon execution by one or more processors, implements a method described herein, e.g., of selecting a candidate target sequence within a nucleic acid sequence or selecting a CRISPR candidate for a target sequence; for instance, a target sequence in a cell such as in a eukaryotic cell for targeting by a CRISPR complex. The method can comprise: (i) locate a CRISPR motif sequence (e.g., PAM) within said nucleic acid sequence, and (ii) select a sequence adjacent to said located CRISPR motif sequence (e.g. PAM) as the candidate target sequence to which the CRISPR complex binds. In some embodiments, said locating step may comprise identifying a CRISPR motif sequence (e.g. PAM) located less than about 10000 nucleotides away from said target sequence, such as less than about 5000, 2500, 1000, 500, 250, 100, 50, 25, or fewer nucleotides away from the target sequence. In some embodiments, the candidate target sequence is at least 10, 15, 20, 25, 30, or more nucleotides in length. In some embodiments the candidate target sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. In some embodiments, the nucleotide at the 3' end of the candidate target sequence is located no more than about 10 nucleotides upstream of the CRISPR motif sequence (e.g. PAM), such as no more than 5, 4, 3, 2, or 1 nucleotides. In some embodiments, the nucleic acid sequence in the eukaryotic cell is endogenous to the cell or organism, e.g., eukaryotic genome. In some embodiments, the nucleic acid sequence in the eukaryotic cell is exogenous to the cell or organism, e.g., eukaryotic genome.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-F shows an exemplary CRISPR system and a possible mechanism of action (A), an example adaptation for expression in eukaryotic cells, and results of tests assessing nuclear localization and CRISPR activity (B-F).

FIG. 3 shows a schematic representation assay carried out to evaluate the cleavage specificity of Cas9 form *Streptococcus pyogenes*. Single base pair mismatches between the guide RNA sequence and the target DNA are mapped against cleavage efficiency in %.

FIG. 5A-C shows histograms of distances between adjacent *S. pyogenes* SF370 locus 1 PAM (NGG) (FIG. 5A) and *S. thermophilus* LMD9 locus 2 PAM (NNAGAAW) (FIG. 5B) in the human genome; and distances for each PAM by chromosome (Chr) (FIG. 5C).

FIG. 9A-G shows the optimization of guide RNA architecture for SpCas9-mediated mammalian genome editing. (a) Schematic of bicistronic expression vector (PX330) for U6 promoter-driven single guide RNA (sgRNA) and CBh promoter-driven human codon-optimized *Streptococcus pyogenes* Cas9 (hSpCas9) used for all subsequent experiments. The sgRNA consists of a 20-nt guide sequence (blue) and scaffold (red), truncated at various positions as indicated. (b) SURVEYOR assay for SpCas9-mediated indels at the human EMX1 and PVALB loci. Arrows indicate the expected SURVEYOR fragments (n=3). (c) Northern blot analysis for the four sgRNA truncation architectures, with UI as loading control. (d) Both wildtype (wt) or nickase mutant (D10A) of SpCas9 promoted insertion of a HindIII site into the human EMX1 gene. Single stranded oligonucleotides (ssODNs), oriented in either the sense or antisense direction relative to genome sequence, were used as homologous recombination templates (FIG. 68). (e) Schematic of the human SERPINB5 locus. sgRNAs and PAMs are indicated by colored bars above sequence; methylcytosine (Me) are highlighted (pink) and numbered relative to the transcriptional start site (TSS, +1). (f) Methylation status of SERPINB5 assayed by bisulfite sequencing of 16 clones. Filled circles, methylated CpG; open circles, unmethylated CpG. (g) Modification efficiency by three sgRNAs targeting the methylated region of SERPINB5, assayed by deep sequencing (n=2). Error bars indicate Wilson intervals.

FIG. 10A-C shows position, distribution, number and mismatch-identity of some mismatch guide RNAs that can be used in generating the data training set (study on off target Cas9 activity).

FIG. 11A-B shows further positions, distributions, numbers and mismatch-identities of some mismatch guide RNAs that can be used in generating the data training set (study on off target Cas9 activity).

FIG. 12A-E shows guide RNA single mismatch cleavage efficiency. a, Multiple target sites were selected from the human EMX1 locus. Individual bases at positions 1-19 along the guide RNA sequence, which complementary to the target DNA sequence, were mutated to every ribonucleotide mismatch from the original guide RNA (blue 'N'). b, On-target Cas9 cleavage activity for guide RNAs containing single base mutations (light blue: high cutting, dark blue: low cutting) relative to the on-target guide RNA (grey). c, Base transition heat map representing relative Cas9 cleavage activity for each possible RNA:DNA base pair. Rows were sorted based on cleavage activity in the PAM-proximal 10 bases of the guide RNA (high to low). Mean cleavage levels were calculated across base transitions in the PAM-proximal 10 bases (right bar) and across all transitions at each position (bottom bar). Heat map represents aggregate single-base mutation data from 15 EMX1 targets. d, Mean Cas9 locus modification efficiency at targets with all possible PAM sequences. e, Histogram of distances between 5'-NRG PAM occurrences within the human genome. Putative targets were identified using both the plus and minus strand of human chromosomal sequences.

FIG. 13A-C shows Cas9 on-target cleavage efficiency with multiple guide RNA mismatches and genome-wide specificity. a, Cas9 targeting efficiency with guide RNAs containing concatenated mismatches of 2 (top), 3 (middle), or 5 (bottom) consecutive bases for EMX1 targets 1 and 6. Rows represent different mutated guide RNAs and show the identity of each nucleotide mutation (white cells; grey cells denote unmutated bases). b, Cas9 was targeted with guide RNAs containing 3 (top, middle) or 4 (bottom) mismatches (white cells) separated by different numbers of unmutated bases (gray cells). c, Cleavage activity at targeted EMX1 target loci (top bar) as well as at candidate off-target genomic sites. Putative off-target loci contained 1-3 individual base differences (white cells) compared to the on-target loci.

FIG. 14A-B shows SpCas9 cleaves methylated targets in vitro. a, Plasmid targets containing CpG dinucleotides are either left unmethylated or methylated in vitro by M.SssI. Methyl-CpG in either the target sequence or PAM are indicated. b, Cleavage of either unmethylated or methylated targets 1 and 2 by SpCas9 cell lysate.

FIG. 24A-C shows Target selection and reagent preparation. (a) For *S. pyogenes* Cas9, 20-bp targets (highlighted in blue) must be followed by 5'-NGG, which can occur in either strand on genomic DNA. (b) Schematic for co-transfection of Cas9 expression plasmid (PX165) and PCR-amplified U6-driven sgRNA expression cassette. Using a U6 promoter-containing PCR template and a fixed forward primer (U6 Fwd), sgRNA-encoding DNA can appended onto the U6 reverse primer (U6 Rev) and synthesized as an extended DNA oligo (Ultramer oligos from IDT). Note the guide sequence (blue N's) in U6 Rev is the reverse complement of the 5'-NGG flanking target sequence. (c) Schematic for scarless cloning of the guide sequence oligos into a plasmid containing Cas9 and sgRNA scaffold (PX330). The guide oligos (blue N's) contain overhangs for ligation into the pair of BbsI sites on PS330, with the top and bottom strand orientations matching those of the genomic target (i.e. top oligo is the 20-bp sequence preceding 5'-NGG in genomic DNA). Digestion of PX330 with BbsI allows the replacement of the Type IIs restriction sites (blue outline) with direct insertion of annealed oligos. It is worth noting that an extra G was placed before the first base of the guide sequence. Applicants have found that an extra G in front of the guide sequence does not adversely affect targeting efficiency. In cases when the 20-nt guide sequence of choice does not begin with guanine, the extra guanine will ensure the sgRNA is efficiently transcribed by the U6 promoter, which prefers a guanine in the first base of the transcript.

FIG. 25A-E shows the single nucleotide specificity of SpCas9. (a) Schematic of the experimental design. sgRNAs carrying all possible single base-pair mismatches (blue Ns) throughout the guide sequence were tested for each EMX1 target site (target site 1 shown as example). (b) Heatmap representation of relative SpCas9 cleavage efficiency by 57 single-mutated and 1 non-mutated sgRNA s each for four EMX1 target sites. For each EMX1 target, the identities of single base-pair substitutions are indicated on the left; original guide sequence is shown above and highlighted in the heatmap (grey squares). Modification efficiencies (increasing from white to dark blue) are normalized to the original guide sequence. (c) Heatmap for relative SpCas9 cleavage efficiency for each possible RNA:DNA base pair, compiled from aggregate data from single-mismatch guide RNAs for 15 EMX1 targets. Mean cleavage levels were calculated for the 10 PAM-proximal bases (right bar) and across all substitutions at each position (bottom bar); positions in grey were not covered by the 469 single-mutated and 15 non-mutated sgRNAs tested. (d) SpCas9-mediated indel frequencies at targets with all possible PAM sequences, determined using the SURVEYOR nuclease assay. Two target sites from the EMX1 locus were tested for each PAM (Table 4). (e) Histogram of distances between 5'-NRG PAM occurrences within the human genome. Putative targets were identified using both strands of human chromosomal sequences (GRCh37/hg19).

FIG. 27A-D shows SpCas9-mediated indel frequencies at predicted genomic off-target loci. (a and b) Cleavage levels at putative genomic off-target loci containing 2 or 3 individual mismatches (white cells) for EMX1 target 1 and target 3 are analyzed by deep sequencing. List of off-target sites are ordered by median position of mutations. Putative off-target sites with additional mutations did not exhibit detectable indels (Table 4). The Cas9 dosage was 3×10-10 nmol/cell, with equimolar sgRNA delivery. Error bars indicate Wilson intervals. (c and d) Indel frequencies for EMX1 targets 1 and 3 and selected off target loci (OT) as a function of SpCas9 and sgRNA dosage, normalized to on-target cleavage at highest transfection dosage (n=2). 400 ng to 10 ng of Cas9-sgRNA plasmid corresponds to 7.1×10-10 to 1.8×10-11 nmol/cell. Cleavage specificity is measured as a ratio of on- to off-target cleavage.

FIG. 28A-B shows the human EMX1 locus with target sites. Schematic of the human EMX1 locus showing the location of 15 target DNA sites, indicated by blue lines with corresponding PAM in magenta.

FIG. 29A-B shows additional genomic off-target site analysis. Cleavage levels at candidate genomic off-target loci (white cells) for a, EMX1 target 2 and b, EMX1 target 6 were analyzed by deep sequencing. All indel frequencies are absolute and analyzed by deep sequencing from 2 biological replicates. Error bars indicate Wilson confidence intervals

The figures herein are for illustrative purposes only and are not necessarily drawn to scale.

DETAILED DESCRIPTION OF THE INVENTION

Figure 1:
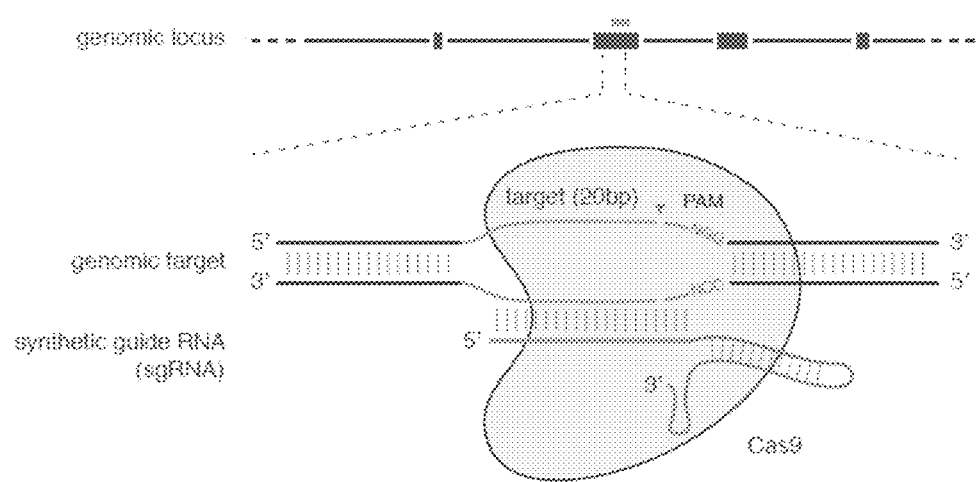
FIG. 1 shows a schematic of RNA-guided Cas9 nuclease. The Cas9 nuclease from *Streptococcus pyogenes* is targeted to genomic DNA by a synthetic guide RNA (sgRNA) consisting of a 20-nt guide sequence and a scaffold. The guide sequence base-pairs with the DNA target, directly upstream of a requisite 5'-NGG protospacer adjacent motif (PAM; magenta), and Cas9 mediates a double-stranded break (DSB) ~3 bp upstream of the PAM (indicated by triangle).
Figure 2A:
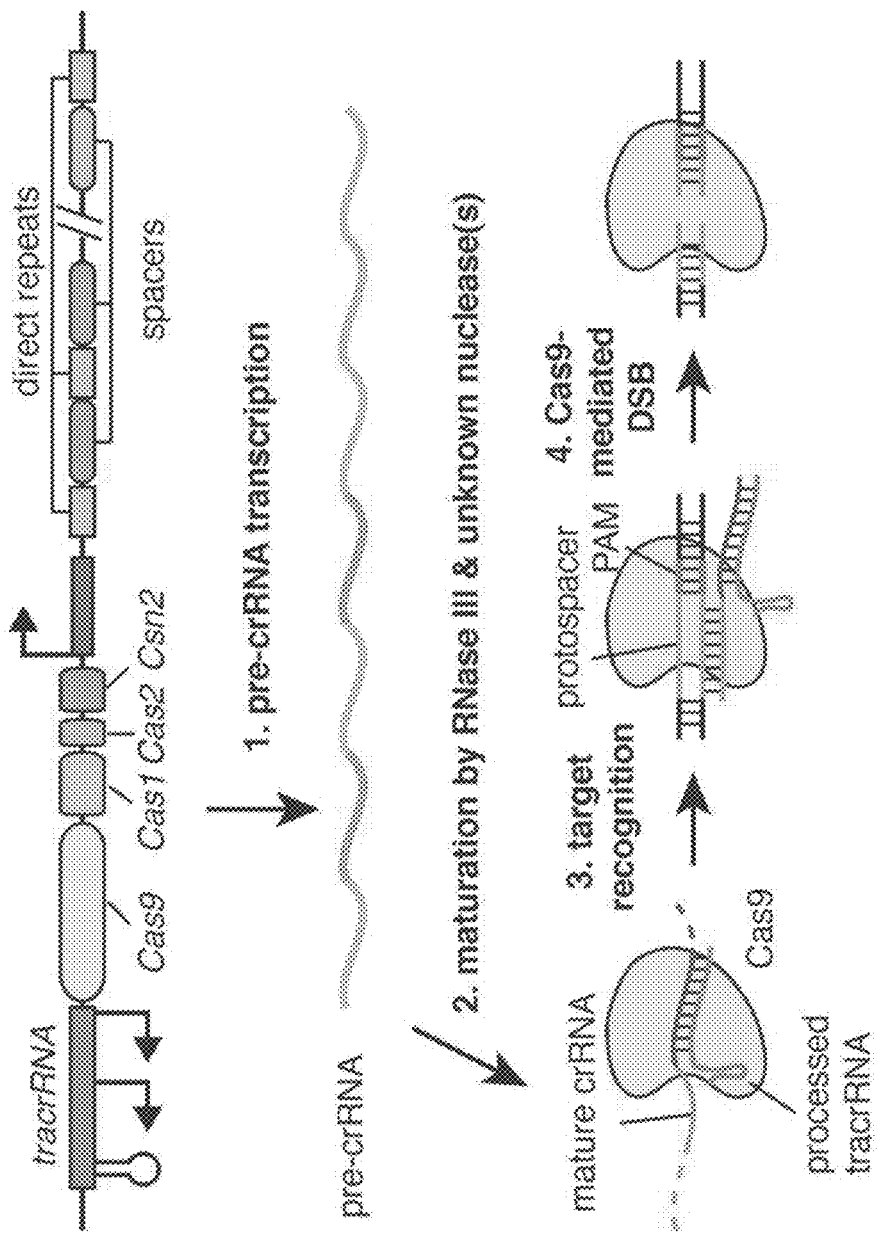
Figure 2C:
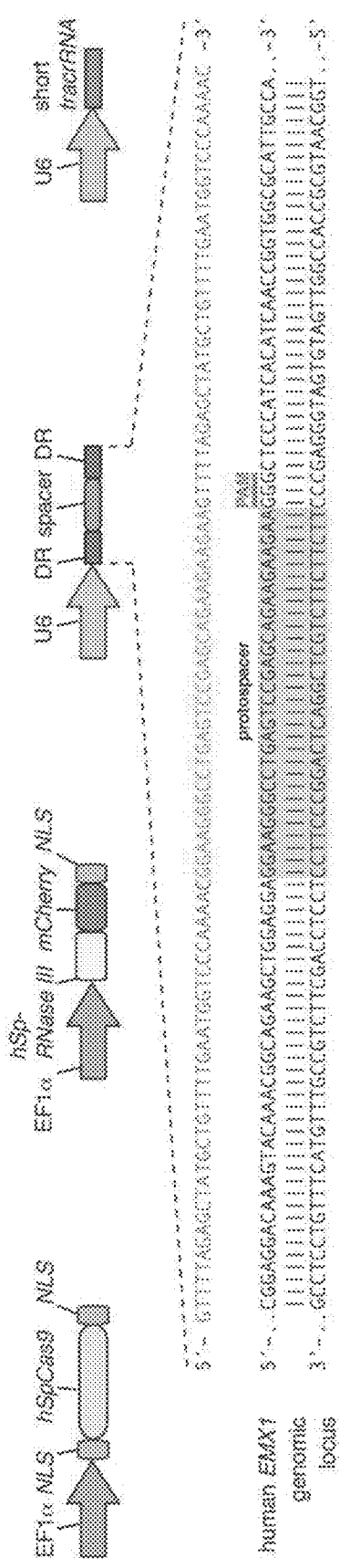
Figure 2D:
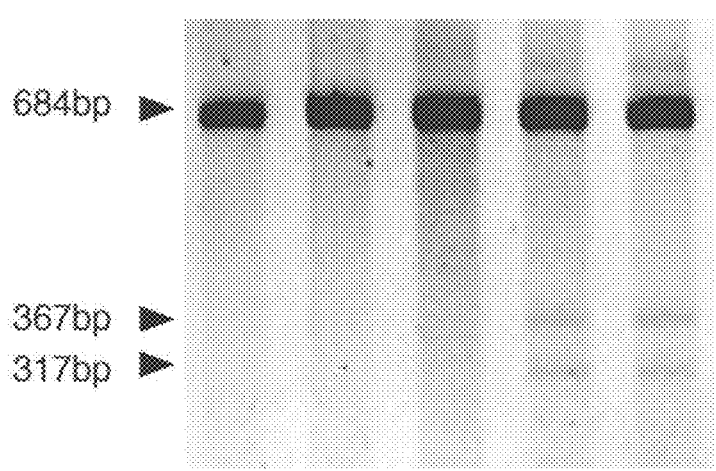

The invention relates to the engineering and optimization of systems, methods and compositions used for the control of gene expression involving sequence targeting, such as genome perturbation or gene-editing, that relate to the CRISPR/Cas system and components thereof (FIGS. 1 and 2). In advantageous embodiments, the Cas enzyme is Cas9.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M<br>I L V A G C | Aromatic<br>Aliphatic | F W Y H<br>I L V |
| Polar | W Y H K R E<br>D C S T N Q | Charged<br>Positively charged<br>Negatively charged | H K R E D<br>H K R<br>E D |
| Small | V C A G S P<br>T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides for vectors that are used in the engineering and optimization of CRISPR/Cas systems. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, the contents of which are herein incorporated by reference in their entirety.

Figure 16:
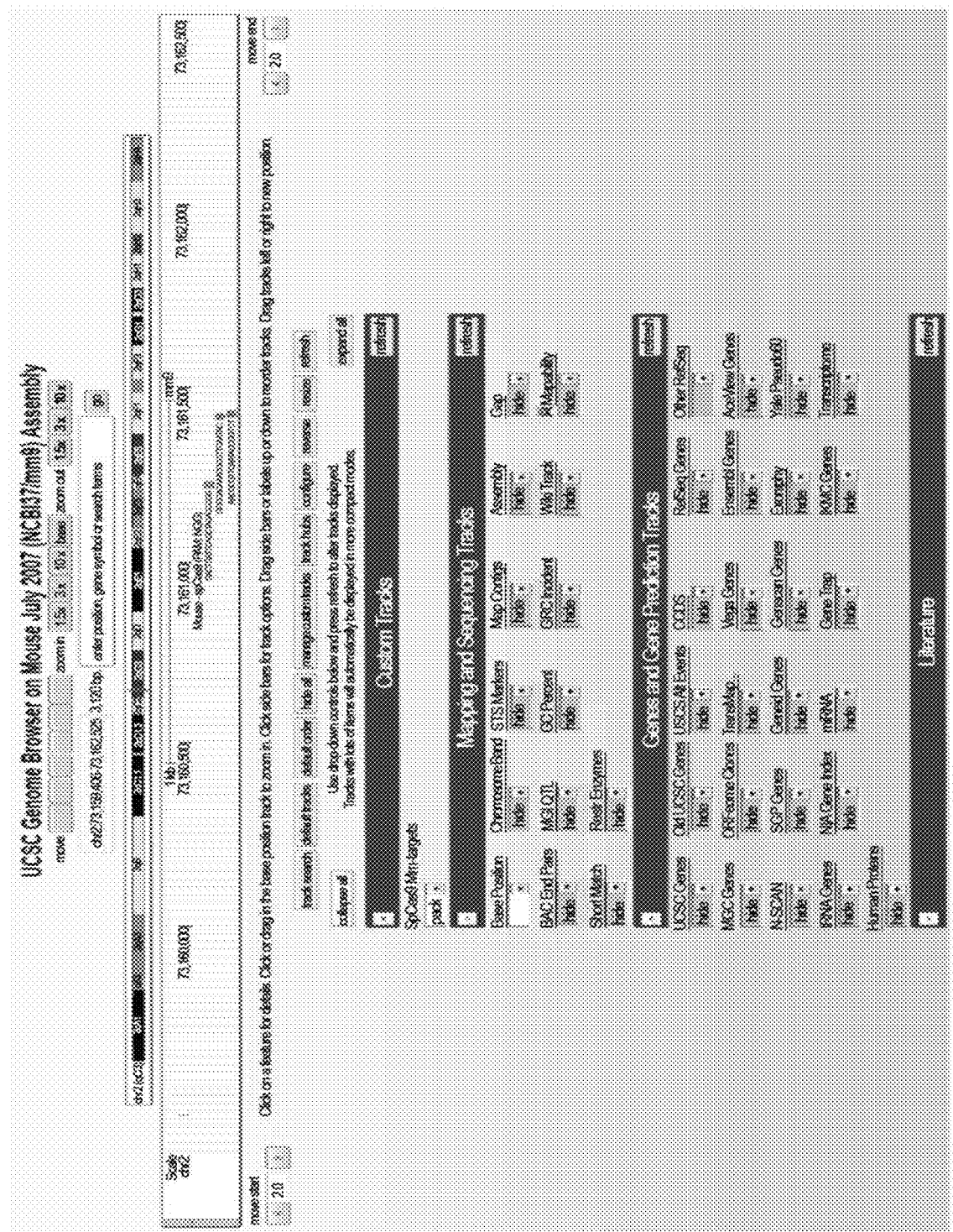
FIG. 16 shows a UCSC Genome Browser track for identifying unique *S. pyogenes* Cas9 target sites in the mouse genome.
Figure 17:
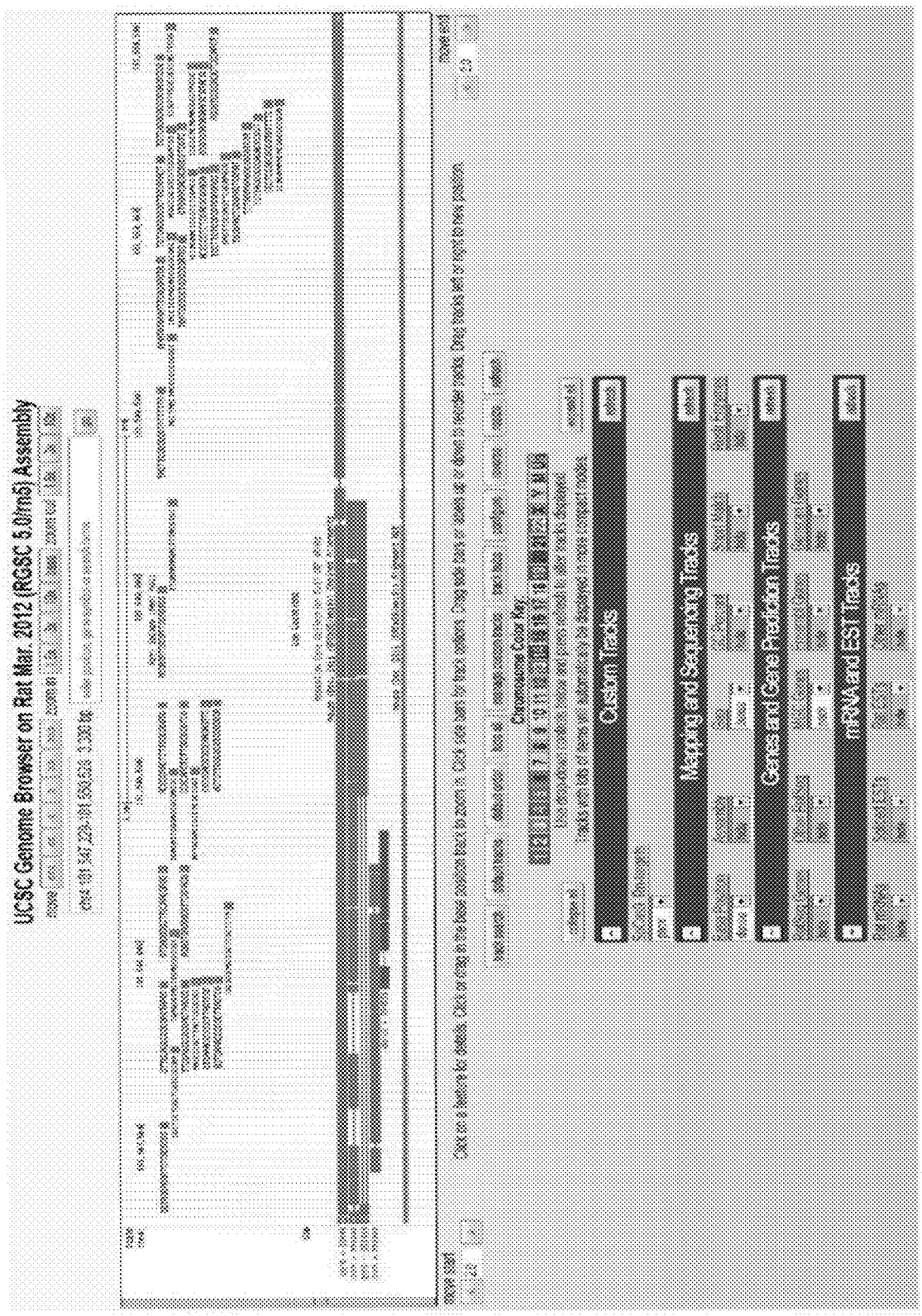
FIG. 17 shows a UCSC Genome Browser track for identifying unique *S. pyogenes* Cas9 target sites in the rat genome.
Figure 18:
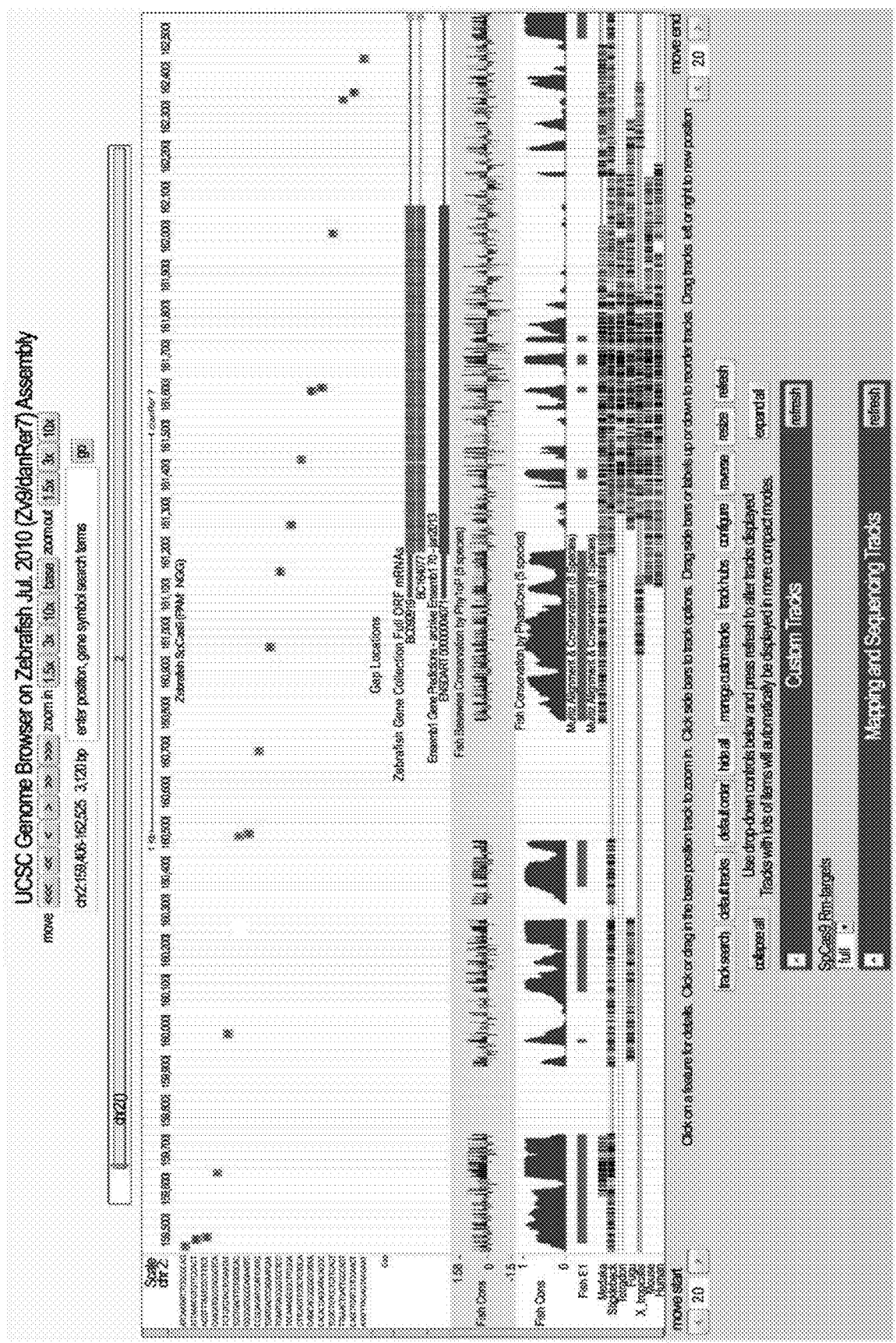
FIG. 18 shows a UCSC Genome Browser track for identifying unique *S. pyogenes* Cas9 target sites in the zebra fish genome.
Figure 19:
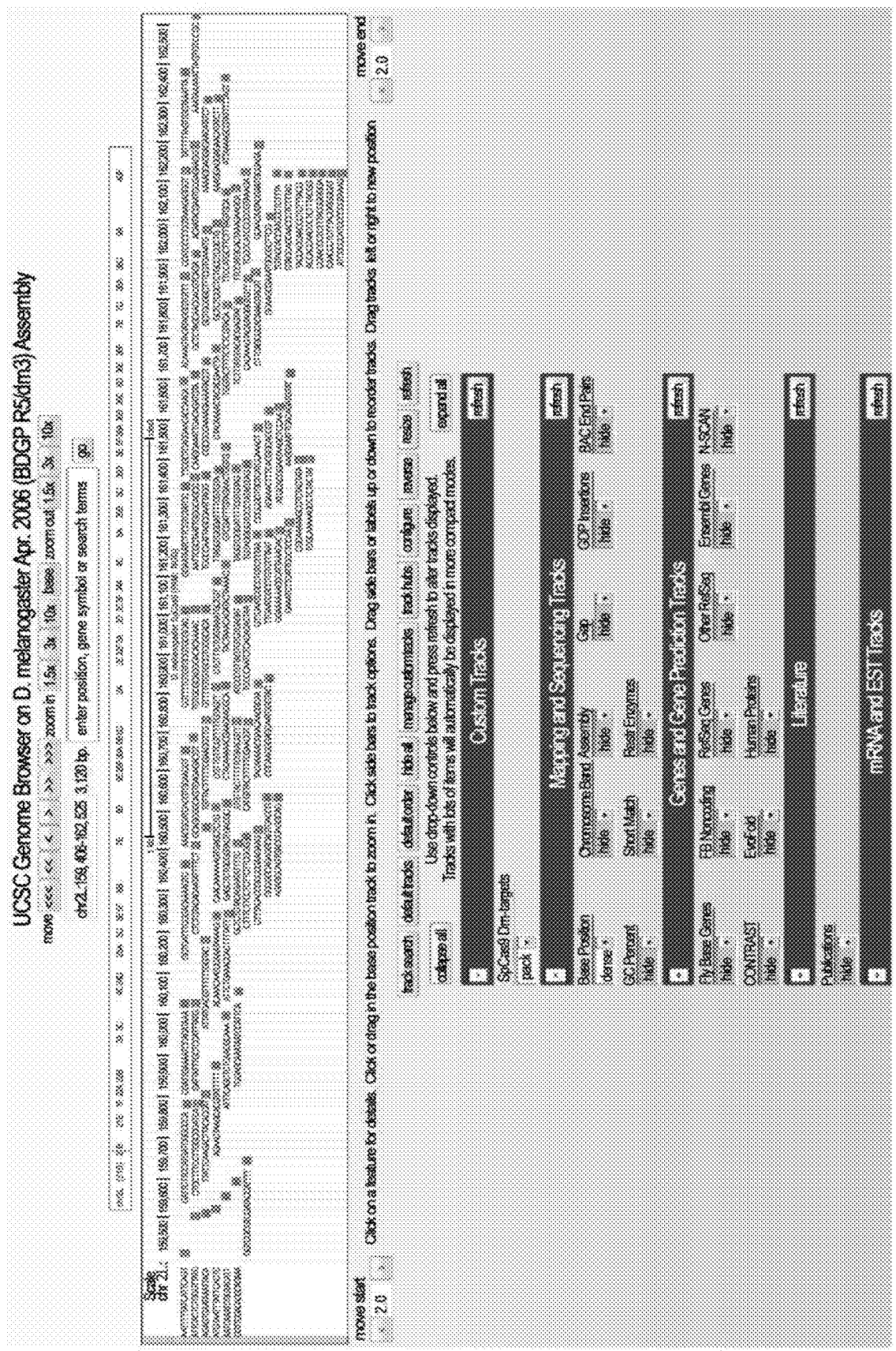
FIG. 19 shows a UCSC Genome Browser track for identifying unique *S. pyogenes* Cas9 target sites in the *D. melanogaster* genome.
Figure 20:
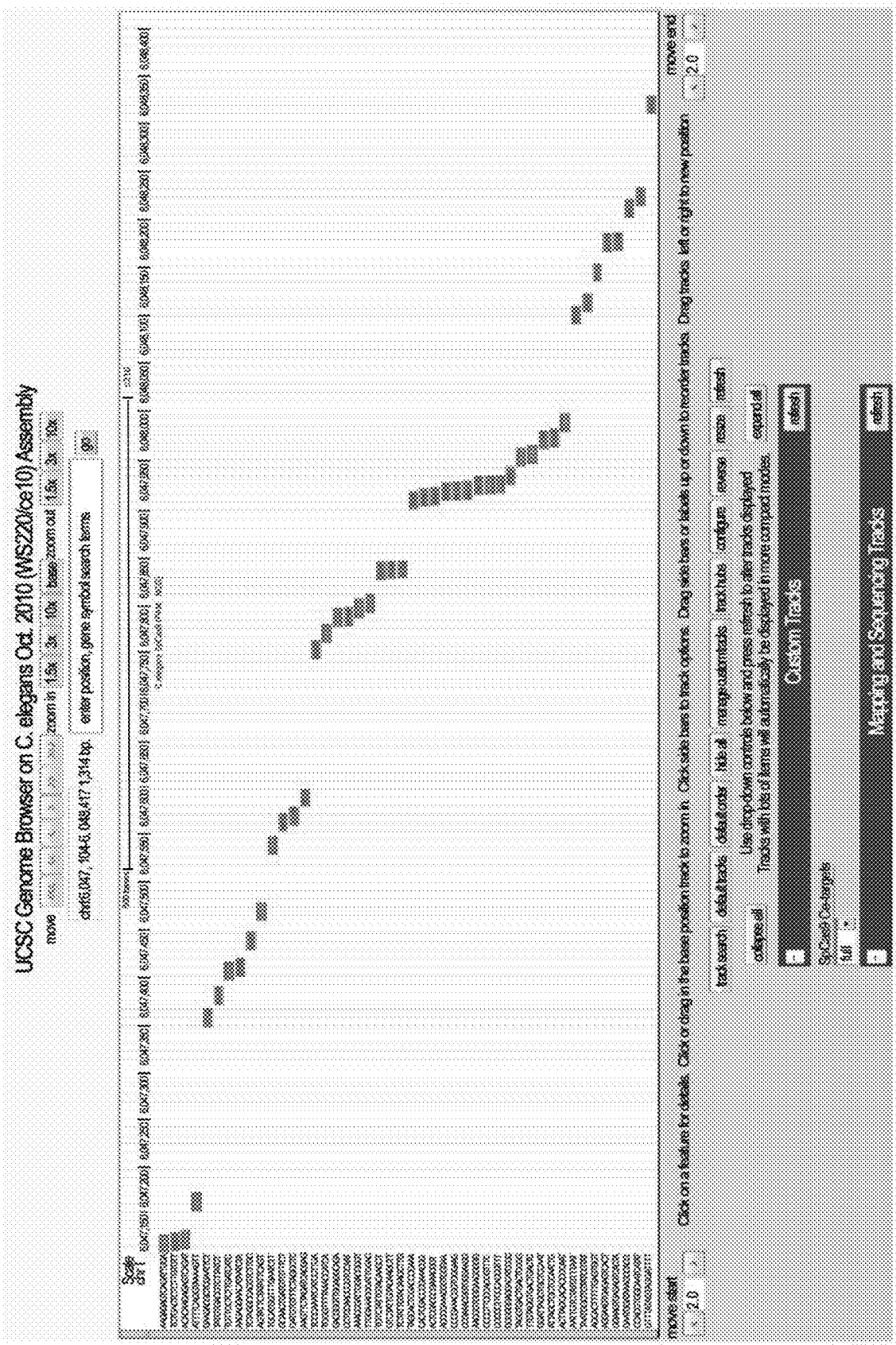
FIG. 20 shows a UCSC Genome Browser track for identifying unique *S. pyogenes* Cas9 target sites in the *C. elegans* genome.
Figure 21:
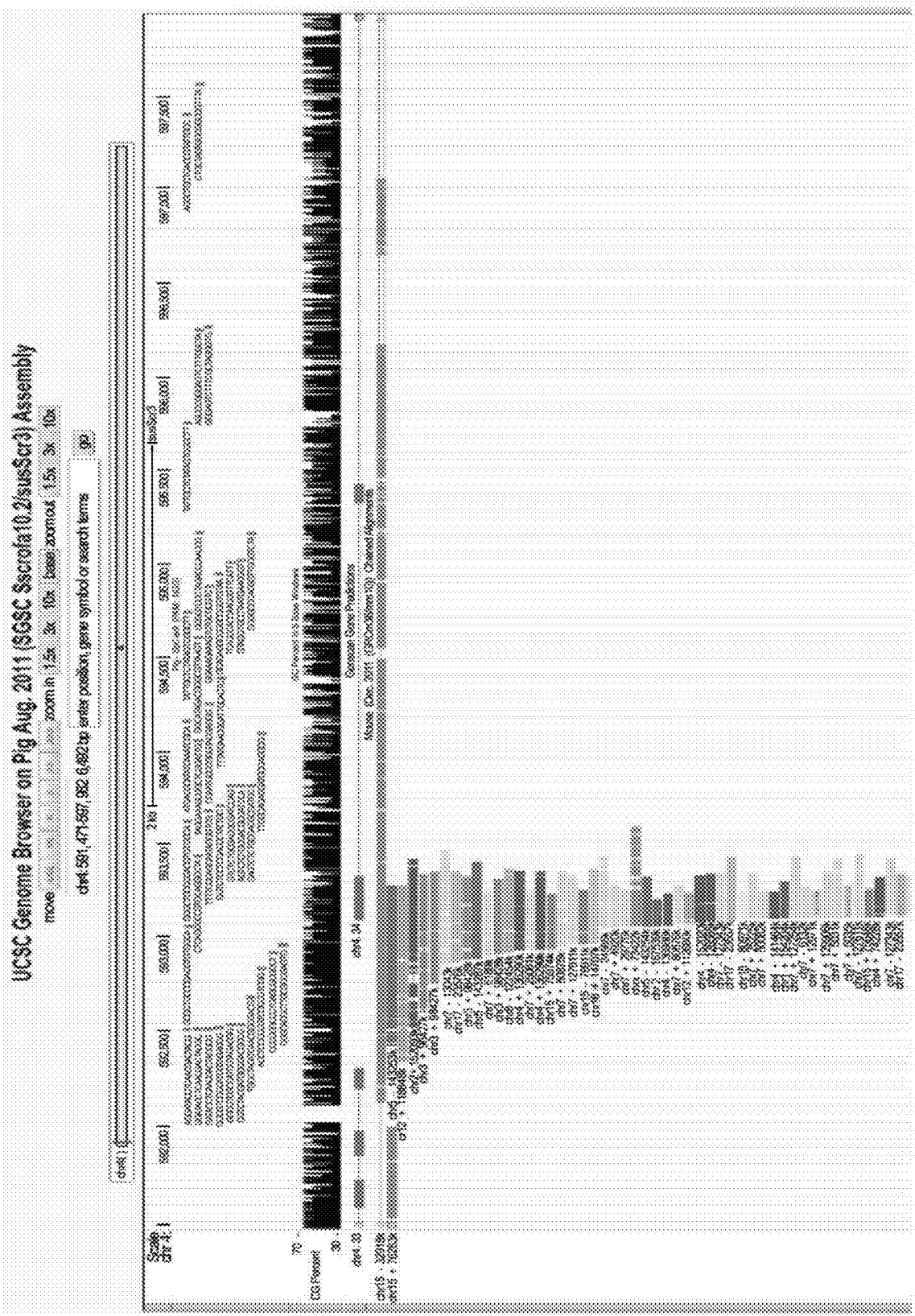
FIG. 21 shows a UCSC Genome Browser track for identifying unique *S. pyogenes* Cas9 target sites in the pig genome.
Figure 22:
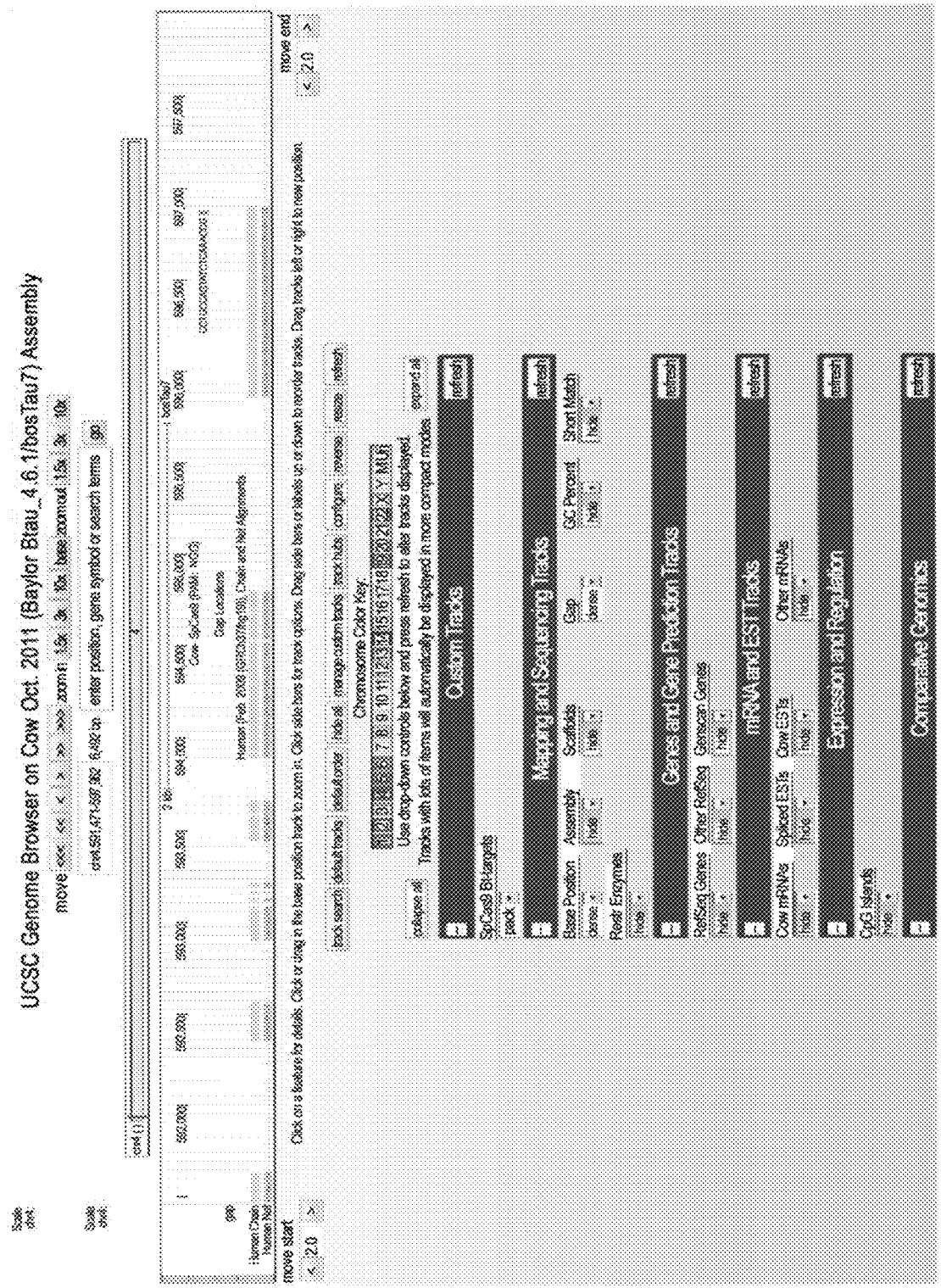
FIG. 22 shows a UCSC Genome Browser track for identifying unique *S. pyogenes* Cas9 target sites in the cow genome.

Aspects of the invention can relate to bicistronic vectors for chimeric RNA and Cas9. Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA followed by the loop sequence GAAA. Results of SURVEYOR assays for Cas9-mediated indels at the human EMX1 and PVALB loci are illustrated in FIGS. 16b and 16c, respectively. Arrows indicate the expected SURVEYOR fragments. ChiRNAs are indicated by their "+n" designation, and crRNA refers to a hybrid RNA where guide and tracr sequences are expressed as separate transcripts. Throughout this application, chimeric RNA (chiRNA) may also be called single guide, or synthetic guide RNA (sgRNA).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase. Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39). In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regard to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556

[1989]), and associated genes. Similar interspersed SSRs have been identified in *Haloferax mediterranei*, *Streptococcus pyogenes*, *Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum*, *Pyrobaculum*, *Sulfolobus*, *Archaeoglobus*, *Halocarcula*, *Methanobacterium*, *Methanococcus*, *Methanosarcina*, *Methanopyrus*, *Pyrococcus*, *Picrophilus*, *Thermoplasma*, *Corynebacterium*, *Mycobacterium*, *Streptomyces*, *Aquifex*, *Porphyromonas*, *Chlorobium*, *Thermus*, *Bacillus*, *Listeria*, *Staphylococcus*, *Clostridium*, *Thermoanaerobacter*, *Mycoplasma*, *Fusobacterium*, *Azarcus*, *Chromobacterium*, *Neisseria*, *Nitrosomonas*, *Desulfovibrio*, *Geobacter*, *Myxococcus*, *Campylobacter*, *Wolinella*, *Acinetobacter*, *Erwinia*, *Escherichia*, *Legionella*, *Methylococcus*, *Pasteurella*, *Photobacterium*, *Salmonella*, *Xanthomonas*, *Yersinia*, *Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence NGG following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archae, Mole Cell 2010, Jan. 15; 37(1): 7.

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. Several aspects of the CRISPR system can be further improved to increase the efficiency and versatility of CRISPR targeting. Optimal Cas9 activity may depend on the availability of free Mg2+ at levels higher than that present in the mammalian nucleus (see e.g. Jinek et al., 2012, Science, 337:816), and the preference for an NGG motif immediately downstream of the protospacer restricts the ability to target on average every 12-bp in the human genome.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. An aspartate-to-alanine substitution (D10A) in the RuvC I catalytic domain of SpCas9 converts the nuclease into a nickase (see e.g. Sapranauskas et al., 2011, Nucleic Acis Research, 39: 9275; Gasiunas et al., 2012, Proc. Natl. Acad. Sci. USA, 109:E2579), such that nicked genomic DNA undergoes the high-fidelity homology-directed repair (HDR). In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, See Nakamura. Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV; the NLS from nucleoplasmin (e.g. the nucleoplasmin bipartite NLS with the sequence KRPAATKKAGQAKKKK); the c-myc NLS having the amino acid sequence PAAKRVKLD or RQRRNELKRSP; the hRNPA1 M9 NLS having the sequence NQSSNFGPMKGGNFGGRSSGPYGGGGQYFAKPRNQGGY; the sequence RMRIZFKNKGKDTAELRRRVEVSVELRKAKKDEQILKRRNV of the IBB domain from importin-alpha; the sequences VSRKRPRP and PPKKARED of the myoma T protein; the sequence POPKKKPL of human p53; the sequence SALIKKKKKMAP of mouse c-abl IV; the sequences DRLRR and PKQKKRK of the influenza virus NS1; the sequence RKLKKKIKKL of the Hepatitis virus delta antigen; the sequence REKKKFLKRR of the mouse Mx1 protein; the sequence KRKGDEVDGVDEVAKKKSKK of the human poly(ADP-ribose) polymerase; and the sequence RKCLQAGMNLEARKTKK of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of nuclear localization sequence(s) (NLS(s)) in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. Throughout this application the guide sequence may be interchangeably referred to as a guide or a spacer. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by SURVEYOR assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome. A unique target sequence in a genome may include an S. pyogenes Cas9 target site of the form MMMMMMMMNNNNNNNNNNNNXGG where NNNNNNNNNNNXGG (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW where NNNNNNNNNNNNXXAGAAW (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNNXXAGAAW where NNNNNNNNNNNXXAGAAW (N is A, G, T, or C; X can be anything; and W is A or T) has a single occurrence in the genome. For the S. pyogenes Cas9, a unique target sequence in a genome may include a Cas9 target site of the form MMMMMMMMNNNNNNNNNNNNXGGXG where NNNNNNNNNNNNXGGXG (N is A, G, T, or C; and X can be anything) has a single occurrence in the genome. A unique target sequence in a genome may include an S. pyogenes Cas9 target site of the form MMMMMMMMMNNNNNNNNNNNNXGGXG where NNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

Figure 15:
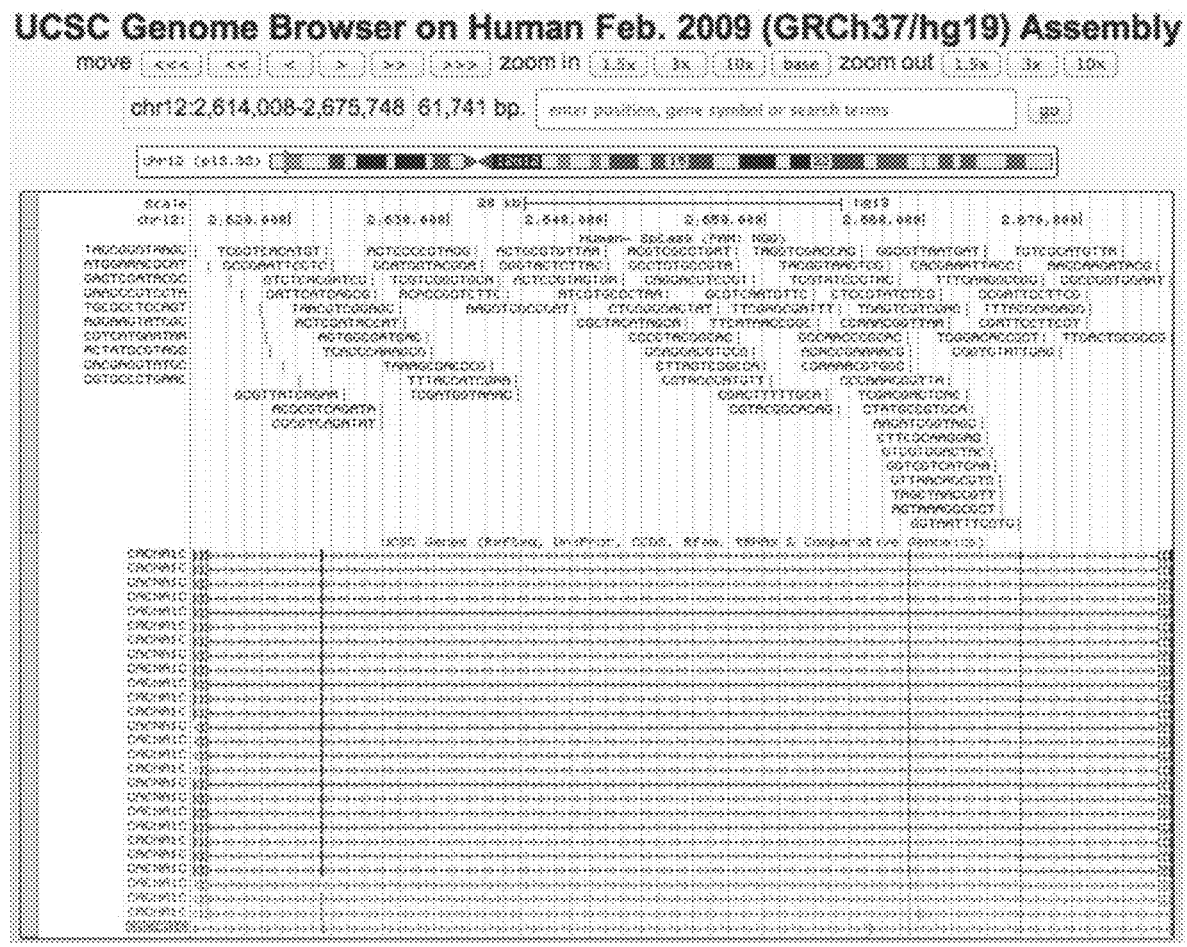
FIG. 15 shows a UCSC Genome Browser track for identifying unique *S. pyogenes* Cas9 target sites in the human genome. A list of unique sites for the human, mouse, rat, zebrafish, fruit fly, and *C. elegans* genomes have been computationally identified and converted into tracks that can be visualized using the UCSC genome browser. Unique sites are defined as those sites with seed sequences (3'-most 12 nucleotides of the spacer sequence plus the NGG PAM sequence) that are unique in the entire genome.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence An example illustration of such a hairpin structure is provided in the lower portion of FIG. 15B. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactct-caagatttaGAAAtaaatcttgcagaagctacaaagataaggctt catgccgaaatcaacacccctgtcattttatggcagggtgttttcgttatttaaT-TTTTT; (2)
NNNNNNNNNNNNNNNgttttgtacttcaGAAAtgcagaagcta-caaagataaggcttcatgccgaaatca acacccctgtcattt-tatggcagggtgttttcgttatttaaTTTTTT; (3)
NNNNNNNNNNNNNNNNNNNNgttttgtactctcaGAAAtgcag jaagctacaaagataaggcttcatgccgaaatca acacccctgtcattt-tatggcagggtgtTTTTTT; (4)
NNNNNNNNNNNNNNNNNNNNgttt-tagagctaGAAAtagcaagttaaaataaggctagtccgttatcaacttgaaaa agtggcaccgagtcggtgcTTTTTT; (5)
NNNNNNNNNNNNNNNNNNNNgttt-tagagctaGAAATAGcaagttaaaataaggctagtccgttatcaacttgaa aaagtgTTTTTT; and (6)
NNNNNNNNNNNNNNNNNNNNgttt-tagagctagAAATAGcaagttaaaataaggctagtccgttatcaTTTTT TTT. In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GALA DNA binding domain fusions, and herpes simplex virus (HSV) BP16 protein fusions. Additional domains that may form part of a fusion protein comprising a CRISPR enzyme are described in US20110059502, incorporated herein by reference. In Chalasani, US2011/0059502, it is stated, "In certain embodiments, the activity of a second domain in a fusion protein can be about 25% to about 90% more specific than the activity of a second domain not in a fusion protein. In some embodiments, a second domain can comprise an endonuclease activity. In certain embodiments, a second domain can comprise a type II endonuclease activity . . . type IIs endonuclease activity (e.g., Fok I . . . )." Accordingly, a functional domain as herein can be a FokI domain. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochorome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In some aspects, the invention comprehends delivering one or more polynucleotides, such as or one or more vectors as described herein, one or more transcripts thereof, and/or one or proteins transcribed therefrom, to a host cell. In some aspects, the invention comprehends cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

In some embodiments, a host cell contains the target sequence, and the cell can be derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds. Target sequence(s) can be in such cells.

With recent advances in crop genomics, the ability to use CRISPR-Cas9 systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications" Nat Rev Genet. 2011 Dec. 29; 13(2):85-96 are also herein incorporated by reference in their entirety. In an advantageous embodiment of the invention, the CRISPR/Cas9 system is used to engineer microalgae. Thus, target polynucleotides in the invention can be plant, algae, prokaryotic or eukaryotic.

CRISPR systems can be useful for creating an animal or cell that may be used as a disease model. Thus, identification of target sequences for CRISPR systems can be useful for creating an animal or cell that may be used as a disease model. As used herein, "disease" refers to a disease, disorder, or indication in a subject. For example, a method of the invention may be used to create an animal or cell that comprises a modification in one or more nucleic acid sequences associated with a disease, or an animal or cell in which the expression of one or more nucleic acid sequences associated with a disease are altered. Such a nucleic acid sequence may encode a disease associated protein sequence or may be a disease associated control sequence.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

CRISPR systems can be used to develop a biologically active agent that modulates a cell signaling event associated with a disease gene; and hence, identifying target sequences can be so used.

CRISPR systems can be used to develop a cell model or animal model can be constructed in combination with the method of the invention for screening a cellular function change; and hence, identifying target sequences can be so used. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product. To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody. The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal. A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

It may be desirable to discern the expression pattern of an protein associated with a signaling biochemical pathway in different bodily tissue, in different cell types, and/or in different subcellular structures. These studies can be performed with the use of tissue-specific, cell-specific or sub-cellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™

(available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex may include a number of disease-associated genes and polynucleotides as well as signaling biochemical pathway-associated genes and polynucleotides as listed in US provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. Mclvor EI, Polak U. Napierala M. RNA Biol. 2010 September-October; 7(5):551-8). The CRISPR-Cas system may be harnessed to correct these defects of genomic instability. And thus, target sequences can be found in these defects of genomic instability.

Further embodiments of the invention relate to algorithms that lay the foundation of methods relating to CRISPR enzyme, e.g. Cas, specificity or off-target activity. In general, algorithms refer to an effective method expressed as a finite list of well defined instructions for calculating one or more functions of interest. Algorithms may be expressed in several kinds of notation, including but not limited to programming languages, flow charts, control tables, natural languages, mathematical formula and pseudocode. In a preferred embodiment, the algorithm may be expressed in a programming language that expresses the algorithm in a form that may be executed by a computer or a computer system.

Methods relating to CRISPR enzyme, e.g. Cas, specificity or off-target activity are based on algorithms that include but are not limited to the thermodynamic algorithm, multiplicative algorithm and positional algorithm. These algorithms take in an input of a sequence of interest and identify candidate target sequences to then provide an output of a ranking of candidate target sequences or a score associated with a particular target sequence based on predicted off-target sites. Candidate target sites may be selected by an end user or a customer based on considerations which include but are not limited to modification efficiency, number, or location of predicted off-target cleavage. In a more preferred embodiment, a candidate target site is unique or has minimal predicted off-target cleavage given the previous parameters. However, the functional relevance of potential off-target modification should also be considered when choosing a target site. In particular, an end user or a customer may consider whether the off-target sites occur within loci of known genetic function, i.e. protein-coding exons, enhancer regions, or intergenic regulatory elements. There may also be cell-type specific considerations, i.e. if an off-target site occurs in a locus that is not functionally relevant in the target cell type. Taken together, a end user or customer may then make an informed, application-specific selection of a candidate target site with minimal off-target modification.

The thermodynamic algorithm may be applied in selecting a CRISPR complex for targeting and/or cleavage of a candidate target nucleic acid sequence within a cell. The first step is to input the target sequence (Step S400) which may have been determined using the positional algorithm. A CRISPR complex is also input (Step S402). The next step is to compare the target sequence with the guide sequence for the CRISPR complex (Step S404) to identify any mismatches. Furthermore, the amount, location and nature of the mismatch(es) between the guide sequence of the potential CRISPR complex and the candidate target nucleic acid sequence may be determined. The hybridization free energy of binding between the target sequence and the guide sequence is then calculated (Step S406). For example, this may be calculated by determining a contribution of each of the amount, location and nature of mismatch(es) to the hybridization free energy of binding between the target nucleic acid sequence and the guide sequence of potential CRISPR complex(es). Furthermore, this may be calculated by applying a model calculated using a training data set as explained in more detail below. Based on the hybridization free energy (i.e. based on the contribution analysis) a prediction of the likelihood of cleavage at the location(s) of the mismatch(es) of the target nucleic acid sequence by the potential CRISPR complex(es) is generated (Step S408). The system then determines whether or not there are any additional CRISPR complexes to consider and if so repeats the comparing, calculating and predicting steps. Each CRISPR complex is selected from the potential CRISPR complex(es) based on whether the prediction indicates that it is more likely than not that cleavage will occur at location(s) of mismatch(es) by the CRISPR complex (Step S410). Optionally, the probabilities of cleavage may be ranked so that a unique CRISPR complex is selected. Determining the contribution of each of the amount, location and nature of mismatch(es) to hybridization free energy includes but is not limited to determining the relative contribution of these factors. The term "location" as used in the term "location of mismatch(es)" may refer to the actual location of the one or more base pair mismatch(es) but may also include the location of a stretch of base pairs that flank the base pair mismatch(es) or a range of locations/positions. The stretch of base pairs that flank the base pair mismatch(es) may include but are not limited to at least one, at least two, at least three base pairs, at least four or at least five or more base pairs on either side of the one or more mismatch(es). As used herein, the "hybridization free energy" may be an estimation of the free energy of binding, e.g. DNA:RNA free energy of binding which may be estimated from data on DNA:DNA free energy of binding and RNA:RNA free energy of binding.

In methods relating to the multiplicative algorithm applied in identifying one or more unique target sequences in a genome of a eukaryotic organism, whereby the target sequence is susceptible to being recognized by a CRISPR-Cas system, wherein the method comprises: a) creating a data training set as to a particular Cas, b) determining average cutting frequency at a particular position for the particular Cas from the data training set, c) determining average cutting frequency of a particular mismatch for the particular Cas from the data training set, d) multiplying the average cutting frequency at a particular position by the average cutting frequency of a particular mismatch to obtain a first product, e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position (or optionally e) repeating steps b) to d) to obtain second and further products for any further particular position (s) of mismatches and particular mismatches and multiplying those second and further products by the first product, for an ultimate product, and omitting this step if there is no mismatch at any position or if there is only one particular mismatch at one particular position), and f) multiplying the ultimate product by the result of dividing the minimum distance between consecutive mismatches by 18 and omitting this step if there is no mismatch at any position or if there is only one particular mismatch at one particular position (or optionally f) multiplying the ultimate product by the result of dividing the minimum distance between consecutive mismatches by 18 and omitting this step if there is no mismatch at any position or if there is only one particular mismatch at one particular position), to thereby obtain a ranking, which allows for the identification of one or more unique target sequences, the predicted cutting frequencies for genome-wide targets may be calculated by multiplying, in series: $f_{est}=f(1)g(N_1,N_1')\times f(2)g(N_2,N_2')\times \ldots f(19)g(N_{19},N_{19}')\times h$ with values f(i) and $g(N_i,N_i')$ at position i corresponding, respectively, to the aggregate position- and base-mismatch cutting frequencies for positions and pairings indicated in a generalized base transition matrix or an aggregate matrix, e.g. a matrix as indicated in FIG. 12*c*. Each frequency was normalized to range from 0 to 1, such that $f\rightarrow(f-f_{min})/(f_{max}-f_{min})$. In case of a match, both were set equal to 1. The value h meanwhile re-weighted the estimated frequency by the minimum pair-wise distance between consecutive mismatches in the target sequence. This value distance, in base-pairs, was divided by 18 to give a maximum value of 1 (in cases where fewer than 2 mismatches existed, or where mismatches occurred on opposite ends of the 19 bp target-window). Samples having a read-count of at least 10,000 (n=43) were plotted. Those tied in rank were given a rank-average. The Spearman correlation coefficient, 0.58, indicated that the estimated frequencies recapitulated 58% of the rank-variance for the observed cutting frequencies. Comparing $f_{est}$ with the cutting frequencies directly yielded a Pearson correlation of 0.89. While dominated by the highest-frequency gRNA/target pairs, this value indicated that nearly 90% of all cutting-frequency variance was explained by the predictions above. In further aspects of the invention, the multiplicative algorithm or the methods mentioned herein may also include thermodynamic factors, e.g. hybridization energies, or other factors of interest being multiplied in series to arrive at the ultimate product.

In embodiments of the invention, determining the off-target activity of a CRISPR enzyme may allow an end user or a customer to predict the best cutting sites in a genomic locus of interest. In a further embodiment of the invention, one may obtain a ranking of cutting frequencies at various putative off-target sites to verify in vitro, in vivo or ex vivo if one or more of the worst case scenario of non-specific cutting does or does not occur. In another embodiment of the invention, the determination of off-target activity may assist with selection of specific sites if an end user or customer is interested in maximizing the difference between on-target cutting frequency and the highest cutting frequency obtained in the ranking of off-target sites. Another aspect of selection includes reviewing the ranking of sites and identifying the genetic loci of the non-specific targets to ensure that a specific target site selected has the appropriate difference in cutting frequency from say targets that may encode for oncogenes or other genetic loci of interest. Aspects of the invention may include methods of minimizing therapeutic risk by verifying the off-target activity of the CRISPR-Cas complex. Further aspects of the invention may include utilizing information on off-target activity of the CRISPR-Cas complex to create specific model systems (e.g. mouse) and cell lines. The methods of the invention allow for rapid analysis of non-specific effects and may increase the efficiency of a laboratory.

Figure 23:
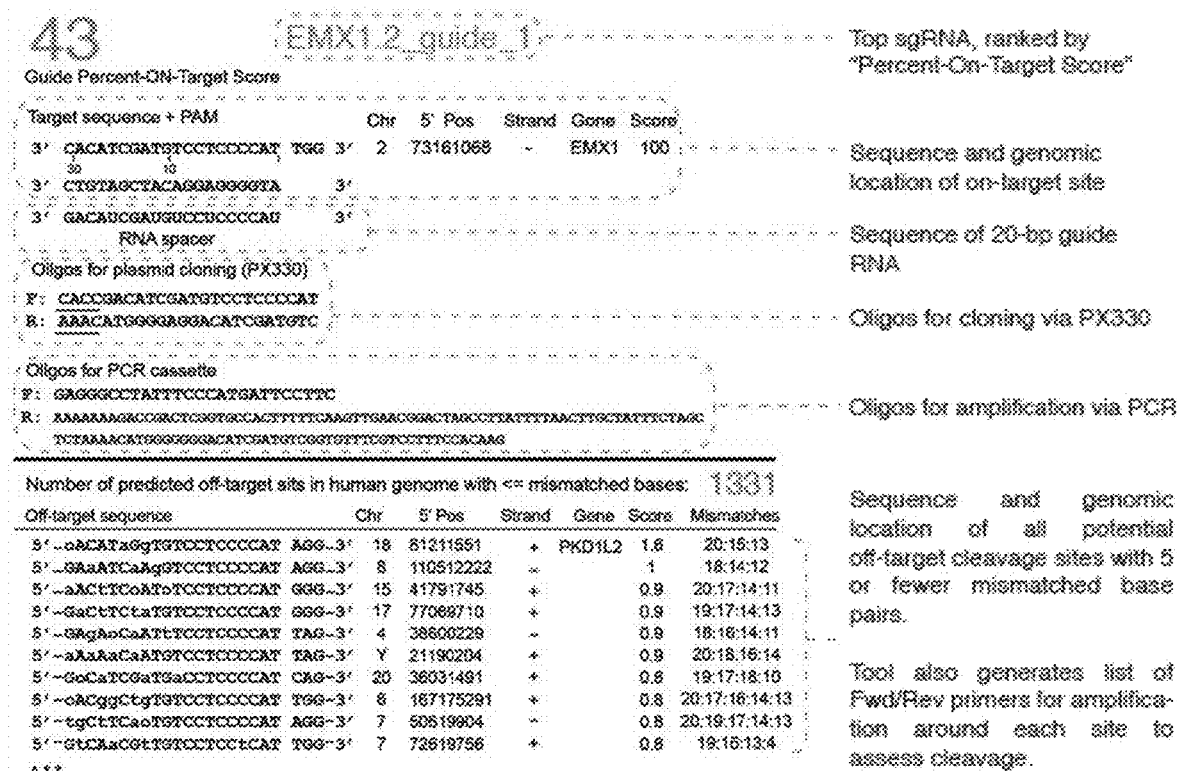
FIG. 23 shows CRISPR Designer, a web app for the identification of Cas9 target sites. Most target regions (such as exons) contain multiple possible CRISPR sgRNA+PAM sequences. To minimize predicted off-targeted cleavage across the genome, a web-based computational pipeline ranks all possible sgRNA sites by their predicted genome-wide specificity and generates primers and oligos required for construction of each possible CRISPR as well as primers (via Primer3) for high-throughput assay of potential off-target cleavage in a next-generation sequencing experiment. Optimization of the choice of sgRNA within a user's target sequence: The goal is to minimize total off-target activity across the human genome. For each possible sgRNA choice, there is identification of off-target sequences (preceding either NAG or NGG PAMs) across the human genome that contain up to 5 mismatched base-pairs. The cleavage efficiency at each off-target sequence is predicted using an experimentally-derived weighting scheme. Each possible sgRNA is then ranked according to its total predicted off-target cleavage; the top-ranked sgRNAs represent those that are likely to have the greatest on-target and the least off-target cleavage. In addition, automated reagent design for CRISPR construction, primer design for the on-target SURVEYOR assay, and primer design for high-throughput detection and quantification of off-target cleavage via next-gen sequencing are advantageously facilitated.

In methods relating to the positional algorithm applied in identifying one or more unique target sequences in a genome of a eukaryotic organism, whereby the target sequence is susceptible to being recognized by a CRISPR-Cas system, wherein the method comprises: a) determining average cutting frequency of guide-RNA/target mismatches at a particular position for a particular Cas from a training data set as to that Cas, if more than one mismatch, repeat step a) so as to determine cutting frequency for each mismatch, multiply frequencies of mismatches to thereby obtain a ranking, which allows for the identification of one or more unique target sequences, an example of an application of this algorithm may be seen in FIG. 23.

Figure 32:
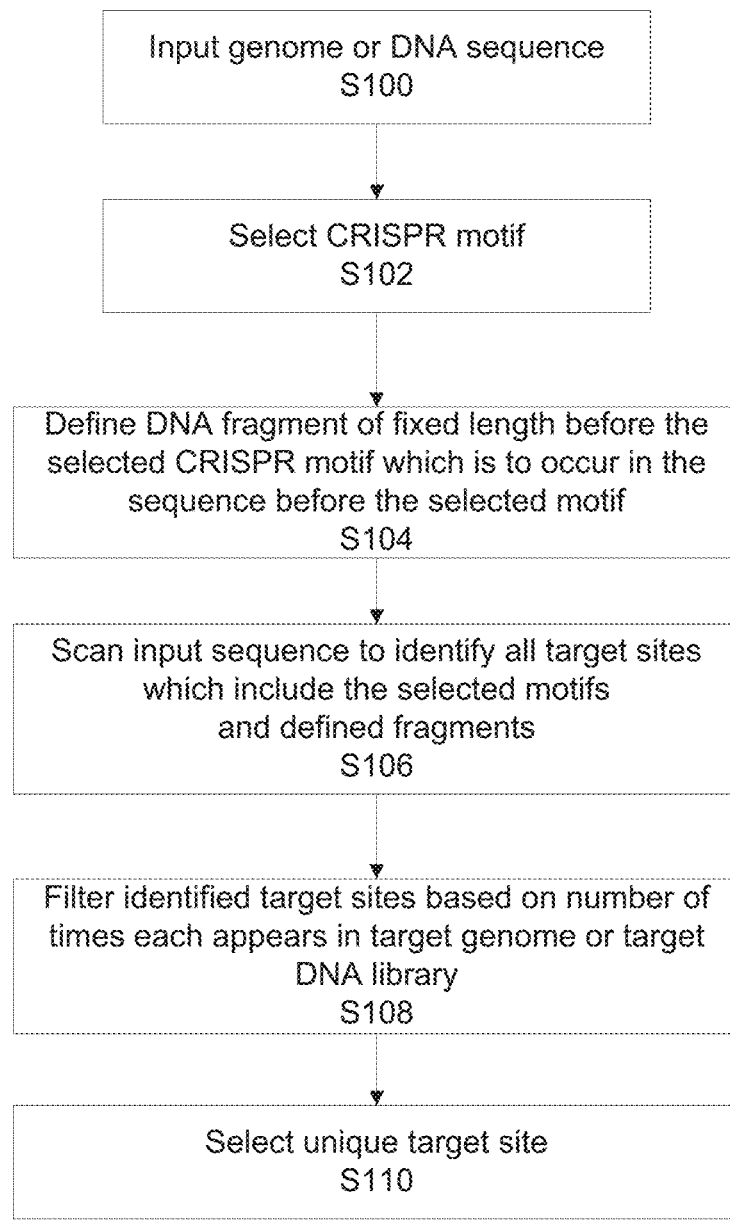
FIG. 32 shows a flow diagram as to locational methods of the invention.

FIGS. 32, 33A, 33B and 34, respectively, each show a flow diagram of methods of the invention. FIG. 32 provides a flow diagram as to locational or positional methods of the invention, i.e., with respect to computational identification of unique CRISPR target sites: To identify unique target sites for a Cas, e.g., a Cas9, e.g., the S. pyogenes SF370 Cas9 (SpCas9) enzyme, in nucleic acid molecules, e.g., of cells, e.g., of organisms, which include but are not limited to human, mouse, rat, zebrafish, fruit fly, and C. elegans genome, Applicants developed a software package to scan both strands of a DNA sequence and identify all possible SpCas9 target sites. The method is shown in FIG. 32 which shows that the first step is to input the genome sequence (Step S100). The CRISPR motif(s) which are suitable for this genome sequence are then selected (Step S102). For this example, the CRISPR motif is an NGG protospacer adjacent motif (PAM) sequence. A fragment of fixed length which needs to occur in the overall sequence before the selected motif (i.e. upstream in the sequence) is then selected (Step S102). In this case, the fragment is a 20 bp sequence. Thus, each SpCas9 target site was is operationally defined as a 20 bp sequence followed by an NGG protospacer adjacent motif (PAM) sequence, and all sequences satisfying this 5'-N20-NGG-3' definition on all chromosomes were identified (Step S106). To prevent non-specific genome editing, after identifying all potential sites, all target sites were filtered based on the number of times they appear in the relevant reference genome (Step S108). (Essentially, all the 20-bp fragments (candidate target sites) upstream of the NGG PAM motif are aggregated. If a particular 20-bp fragment occurs more than once in your genome-wide search, it is considered not unique and 'strikes out', aka filtered. The 20-bp fragments that REMAIN therefore occur only once in the target genome, making it unique; and, instead of taking a 20-bp fragment (the full Cas9 target site), this algorithm takes the first, for example, 11-12 bp upstream of the PAM motif and requires that to be unique.) Finally, a unique target site is selected (Step S110), e.g. To take advantage of sequence specificity of Cas, e.g., Cas9 activity conferred by a 'seed' sequence, which can be, for example, approximately 11-12 bp sequence 5' from the PAM sequence, 5'-NNNNNNNNNNN-NGG-3' sequences were selected to be unique in the relevant genome. Genomic sequences are available on the UCSC Genome Browser and sample visualizations of the information for the Human genome hg, Mouse genome mm, Rat genome rn, Zebrafish genome danRer, D. melanogaster genome dm, C. elegans genome cc, the pig genome and cow genome are shown in FIGS. 15 through 22 respectively.

Figure 33A:
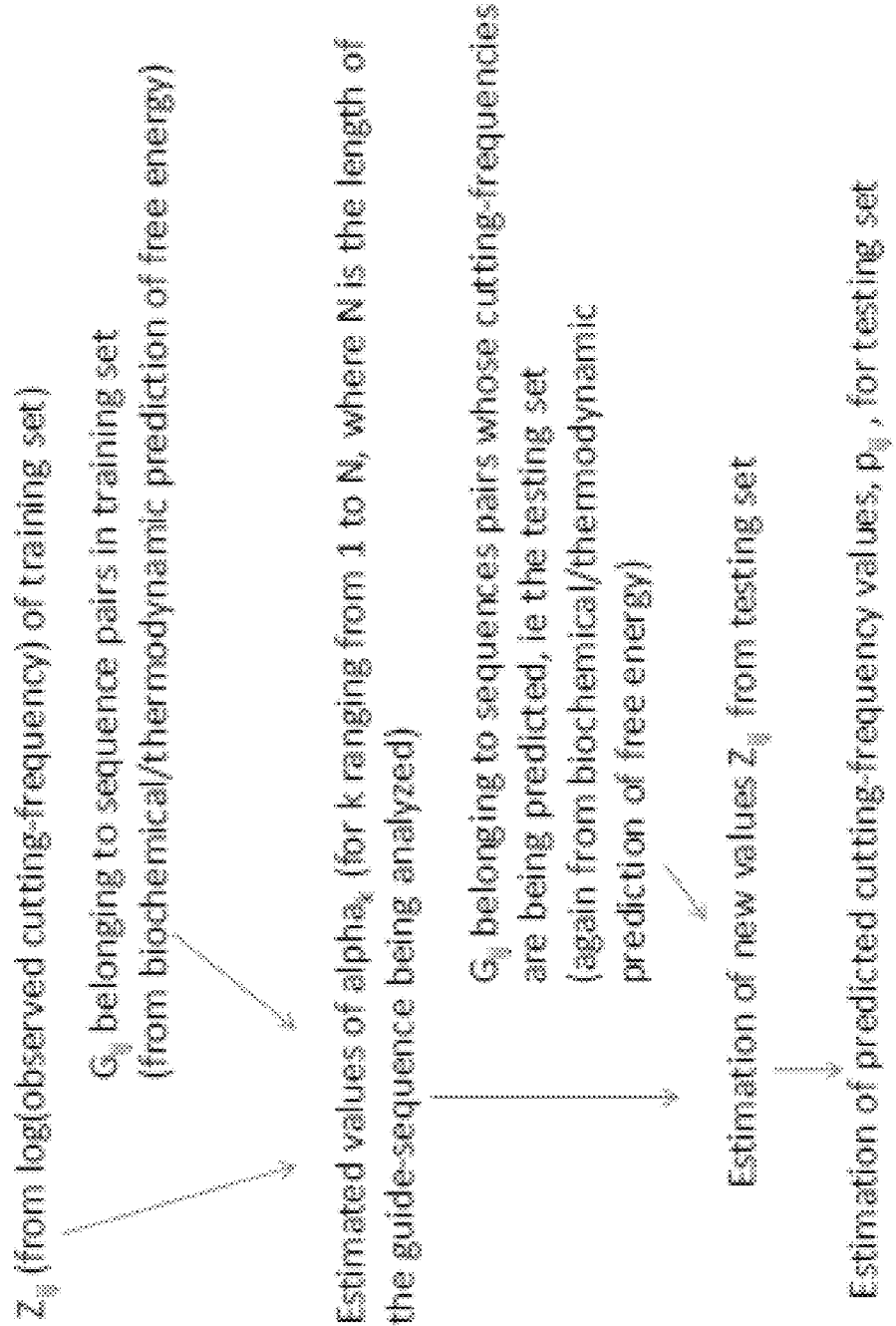
FIG. 33A-B shows a flow diagram as to thermodynamic methods of the invention.
Figure 33B:
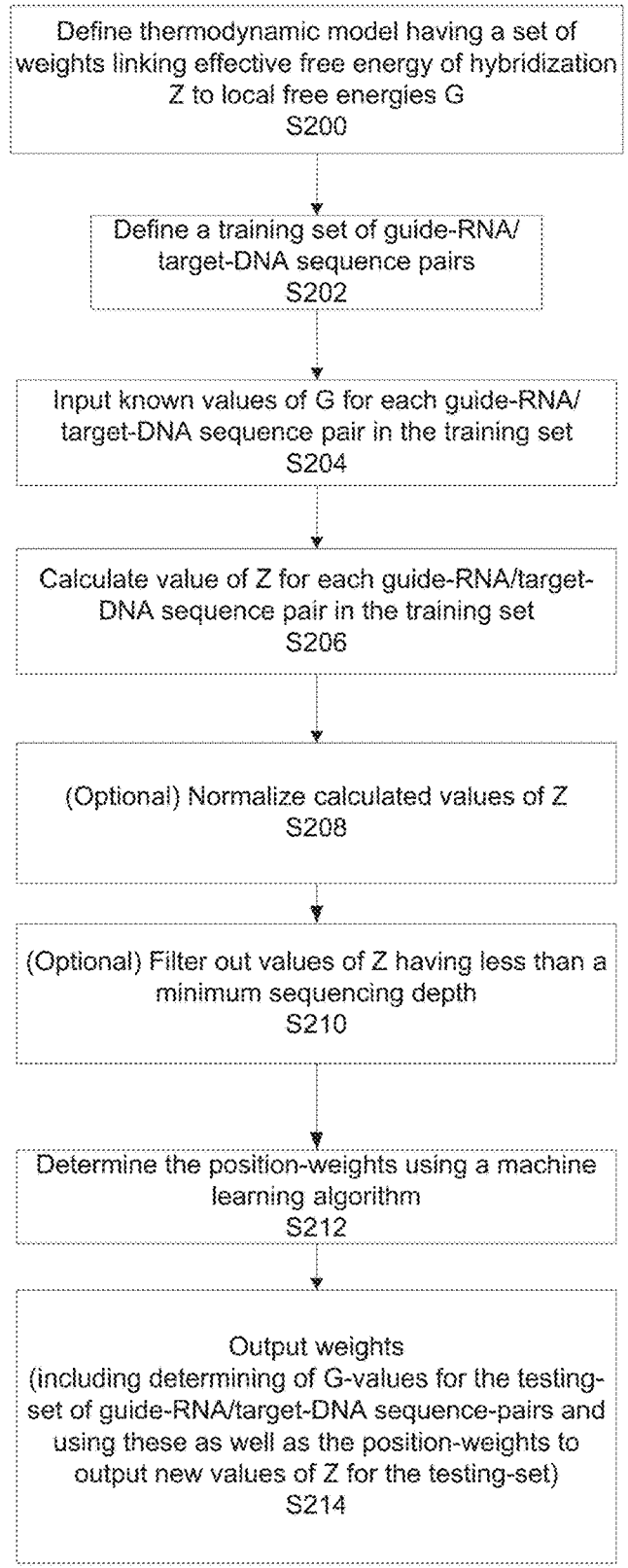
Figure 34:
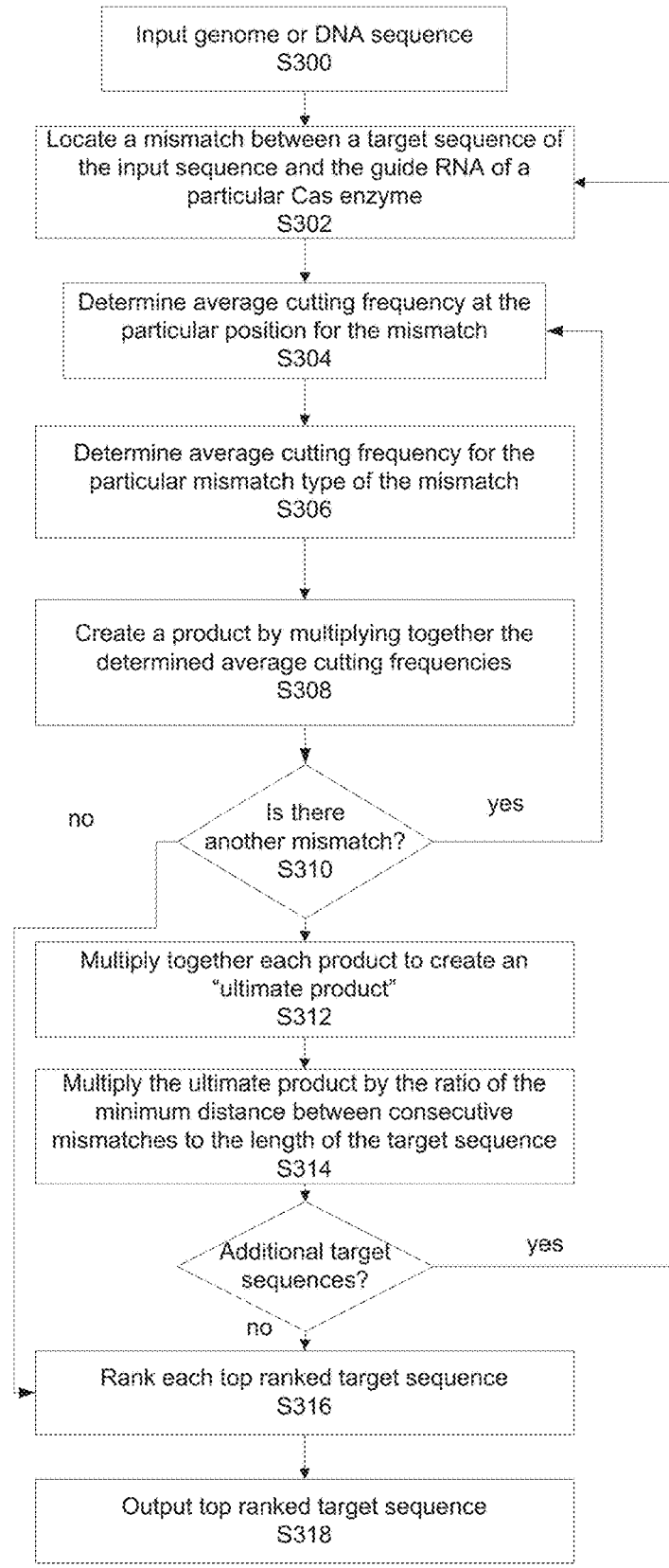
FIG. 34 shows a flow diagram as to multiplication methods of the invention.

FIGS. 33A and 33B each provides a flow diagram as to thermodynamic methods of the invention. FIG. 34 provides a flow diagram as to multiplication methods of the invention. Referring to FIGS. 33A and 33B, and considering the least squares thermodynamic model of CRISPR-Cas cutting efficiency, for arbitrary Cas9 target sites, Applicants generated a numerical thermodynamic model that predicts Cas9 cutting efficiency. Applicants propose 1) that the Cas9 guide RNA has specific free energies of hybridization to its target and any off-target DNA sequences and 2) that Cas9 modifies RNA:DNA hybridization free-energies locally in a position-dependent but sequence-independent way. Applicants trained a model for predicting CRISPR-Cas cutting efficiency based on their CRISPR-Cas guide RNA mutation data and RNA:DNA thermodynamic free energy calculations using a machine learning algorithm. Applicants then validated their resulting models by comparing their predictions of CRISPR-Cas off-target cutting at multiple genomic loci with experimental data assessing locus modification at the same sites. The methodology adopted in developing this algorithm is as follows: The problem summary states that for arbitrary spacers and targets of constant length, a numerical model that makes thermodynamic sense and predicts Cas9 cutting efficiency is to be found. Suppose Cas9 modifies DNA:RNA hybridization free-energies locally in a position-dependent but sequence-independent way. The first step is to define a model having a set a weights which links the free energy of hybridization Z with the local free energies G (Step S200). Then for DNA:RNA hybridization free energies $\Delta G_{ij}(k)$ (for position k between 1 and N) of spacer i and target j $$Z_{ij} = \sum_{k=1}^{N} \alpha_k \Delta G_{ij}(k)$$

$Z_{ij}$ can be treated as an "effective" free-energy modified by the multiplicative position-weights $\alpha_k$. The "effective" free-energy $Z_{ij}$ corresponds to an associated cutting-probability $\sim e^{-\beta Z_{ij}}$ (for some constant $\beta$) in the same way that an equilibrium model of hybridization (without position-weighting) would have predicted a hybridization-probability $\sim e^{-\beta \Delta G_{ij}}$. Since cutting-efficiency has been measured, the values $Z_{ij}$ can be treated as their observables. Meanwhile, $\Delta G_{ij}(k)$ can be calculated for any experiment's spacer-target pairing. Applicants task was to find the values $\alpha_k$, since this would allow them to estimate $Z_{ij}$ for any spacer-target pair. The weights are determined by inputting known values for Z and G from a training set of sequences with the known values being determined by experimentation as necessary. Thus, Applicants need to define a training set of sequences (Step S202) and calculate a value of Z for each sequence in the training set (Step S204). Writing the above equation for $Z_{ij}$ in matrix form Applicants get:

$$\vec{Z} = G \vec{\alpha} \quad (1)$$

Figure 6A:
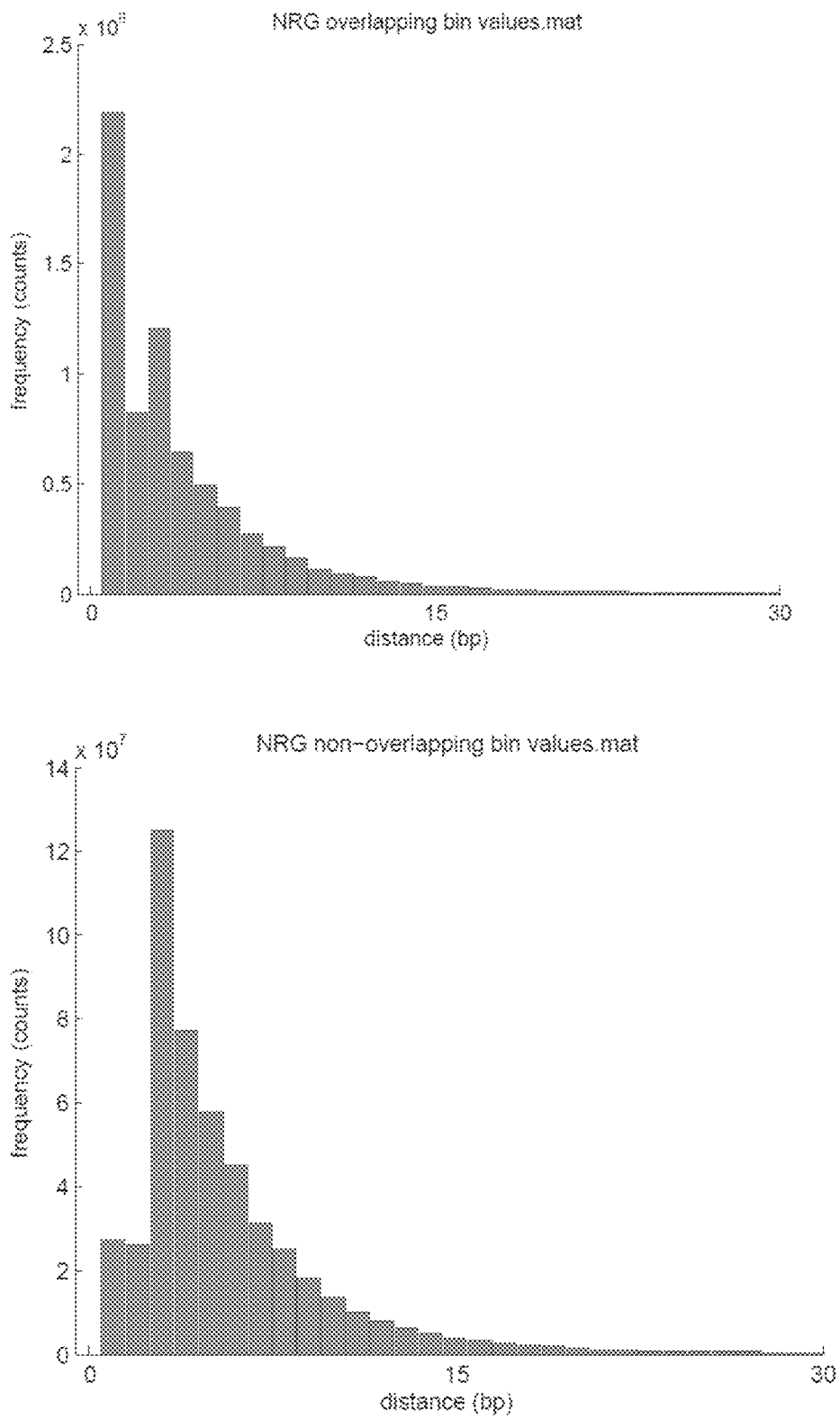
FIG. 6A-C shows the graphing of distribution of distances between NGG and NRG motifs in the human genome in an "overlapping" fashion.
Figure 6B:
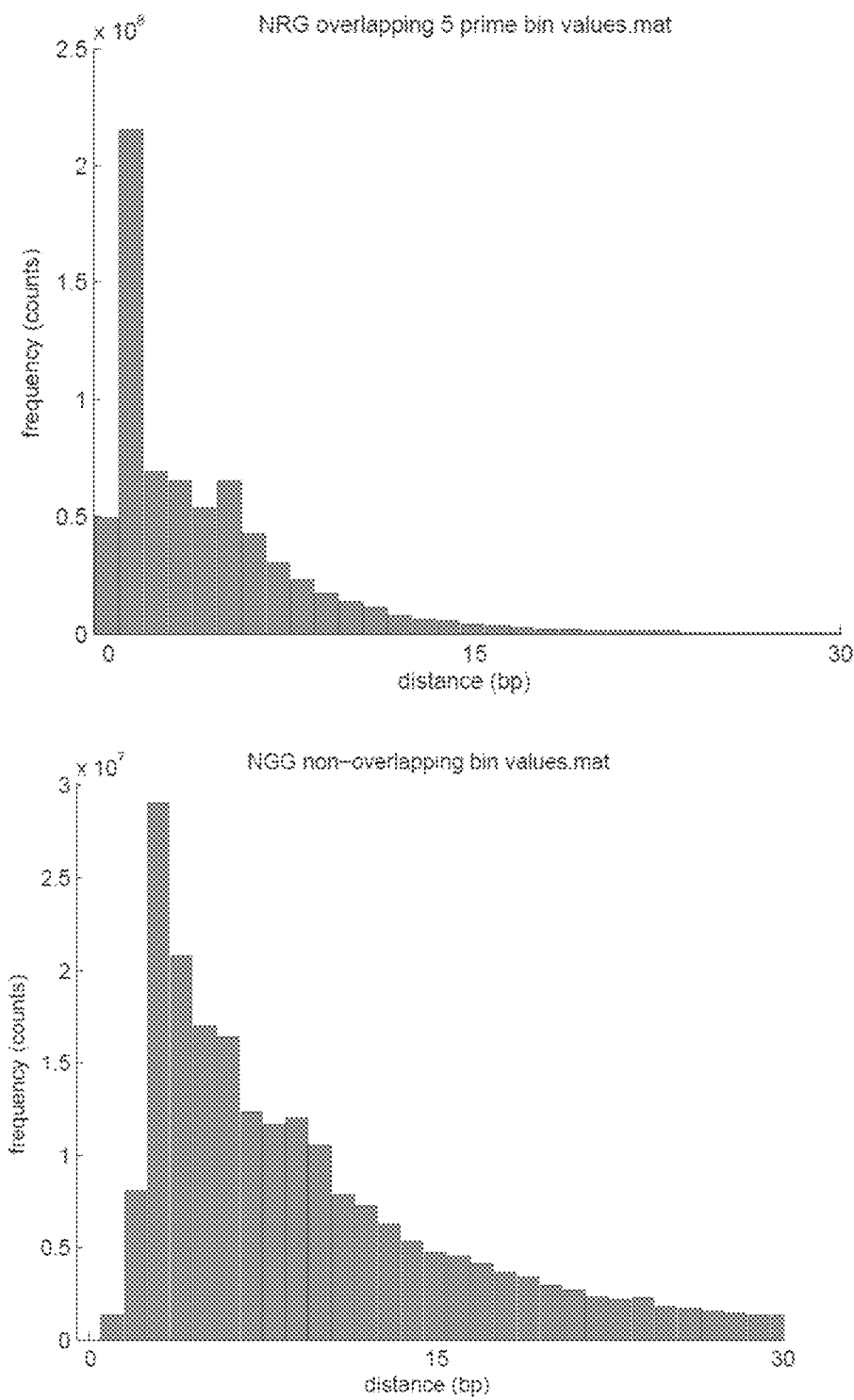
Figure 6C:
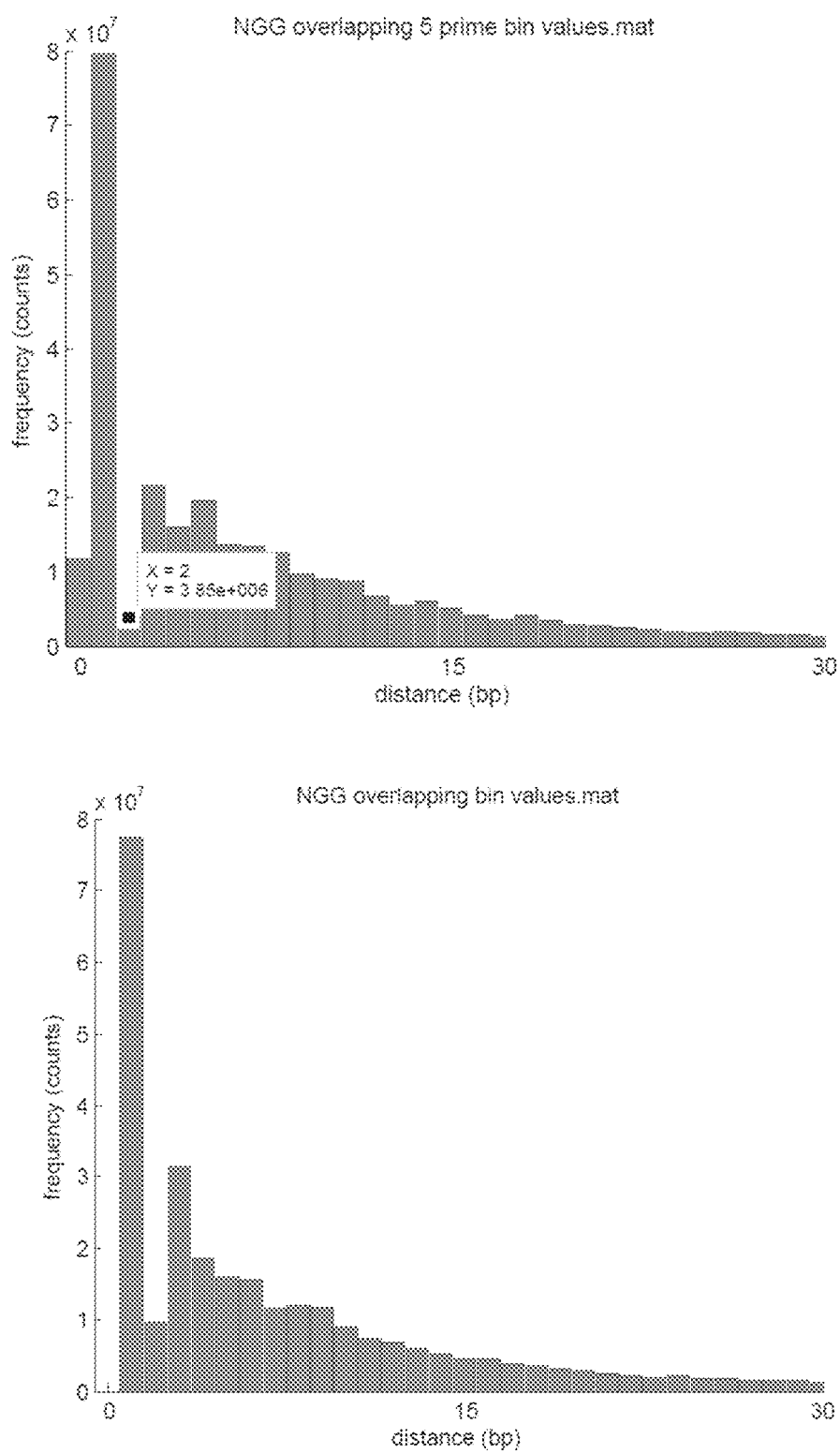
Figure 7A:
FIG. 7A-D shows a circular depiction of the phylogenetic analysis revealing five families of Cas9s, including three groups of large Cas9s (~1400 amino acids) and two of small Cas9s (~1100 amino acids).
Figure 7B:
Figure 7C:
Figure 7D:
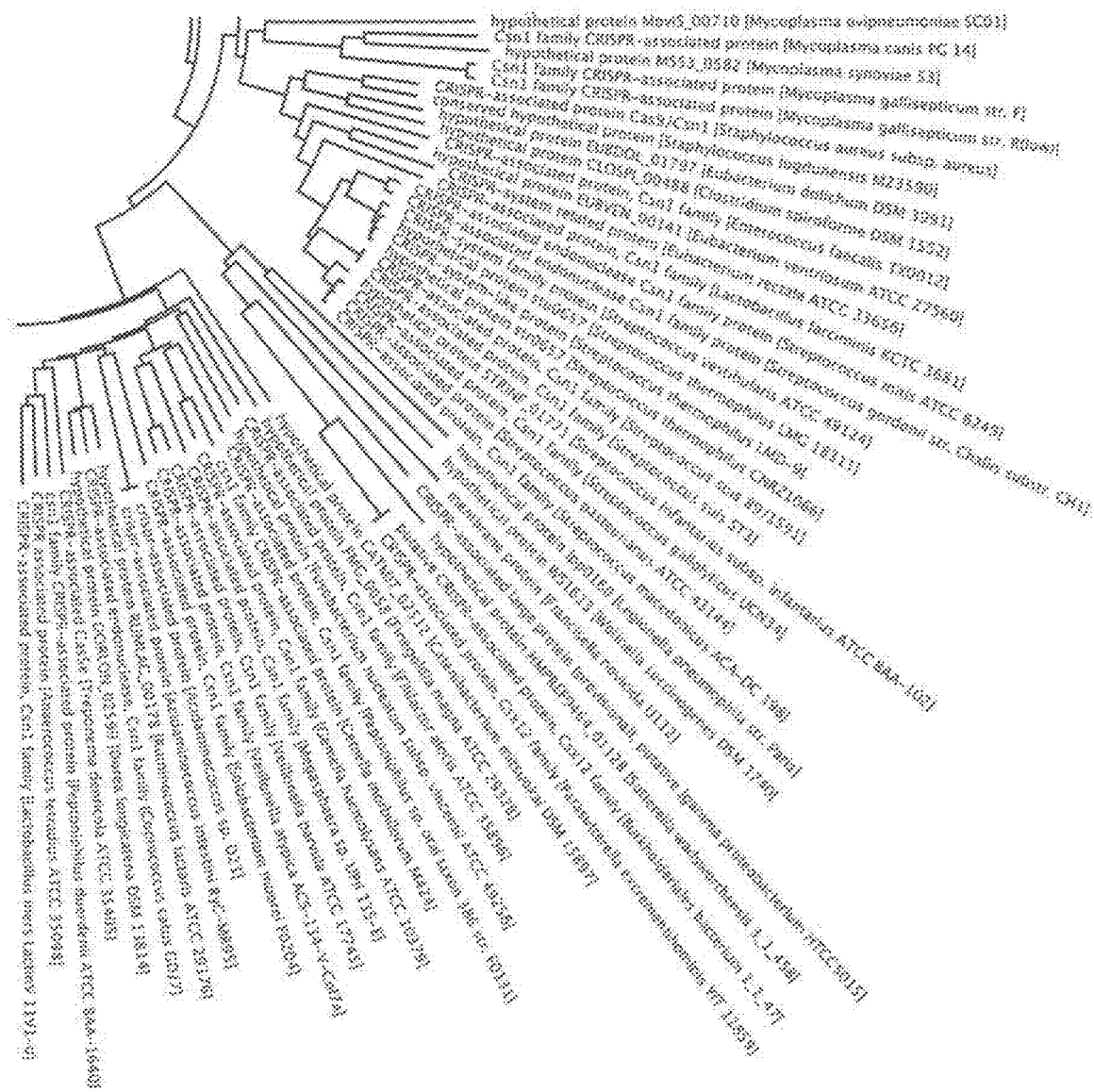
Figure 8A:
FIG. 8A-F shows a linear depiction of the phylogenetic analysis revealing five families of Cas9s, including three groups of large Cas9s (~1400 amino acids) and two of small Cas9s (~1100 amino acids).
Figure 8B:
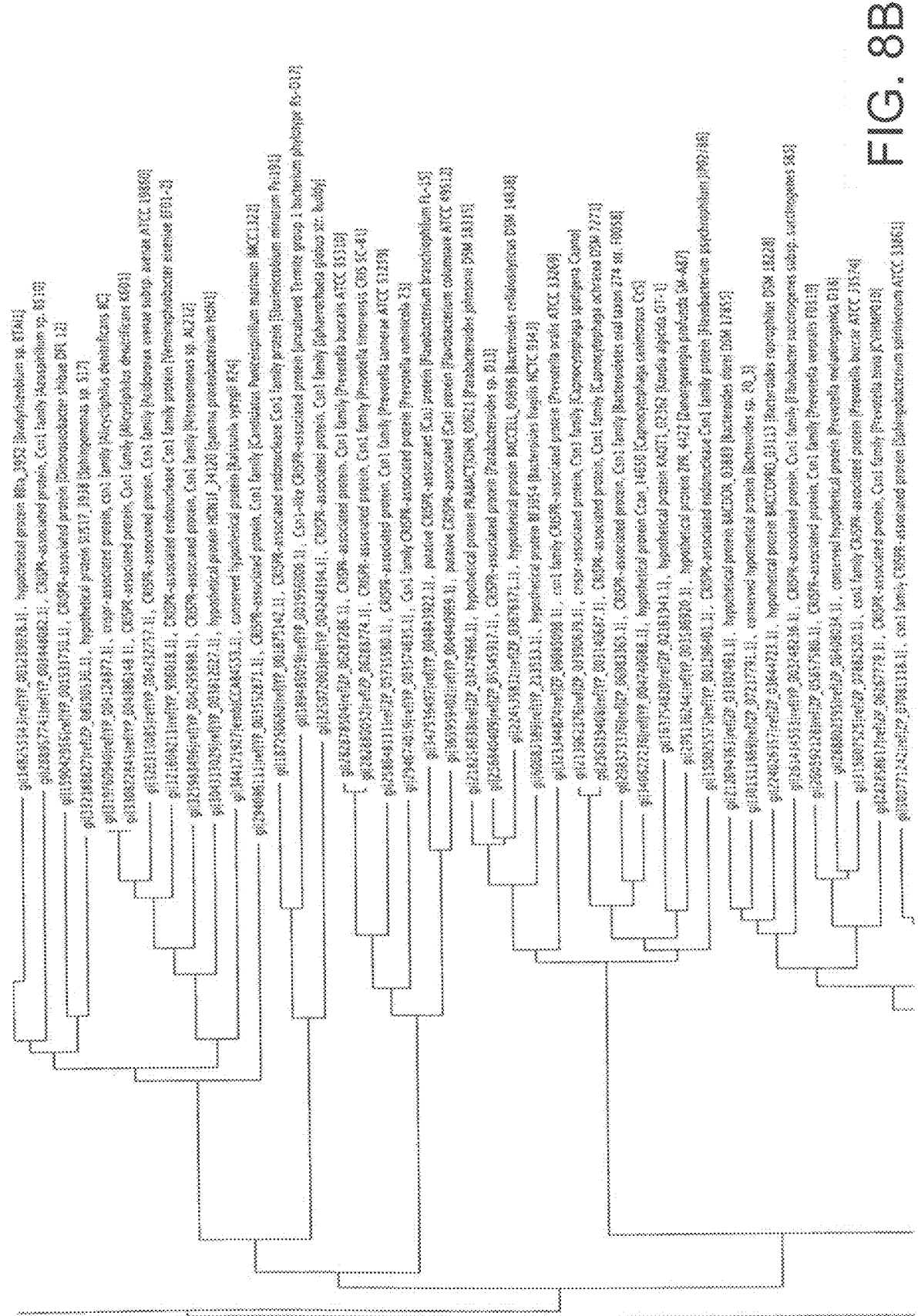
Figure 8C:
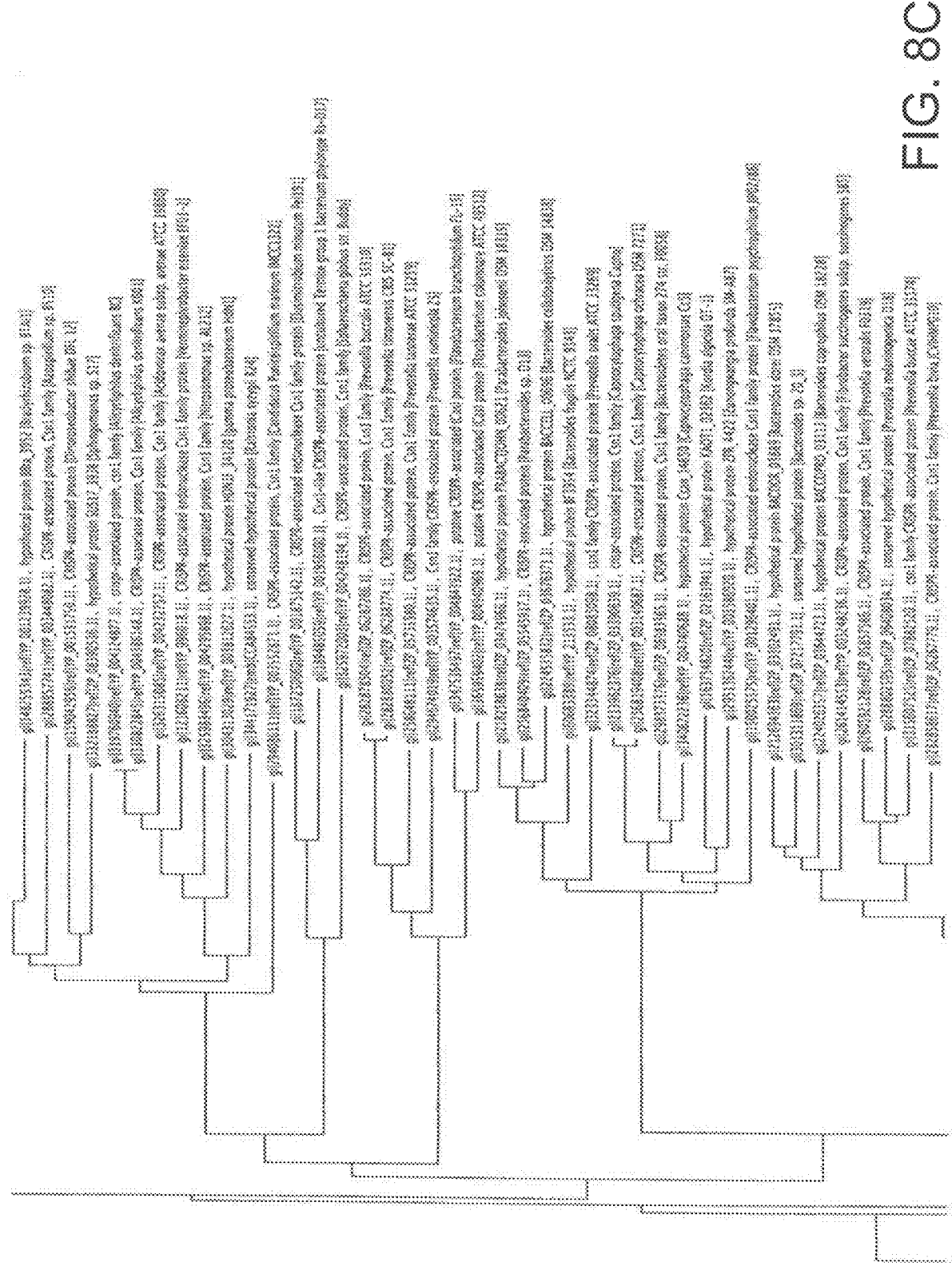
Figure 8D:
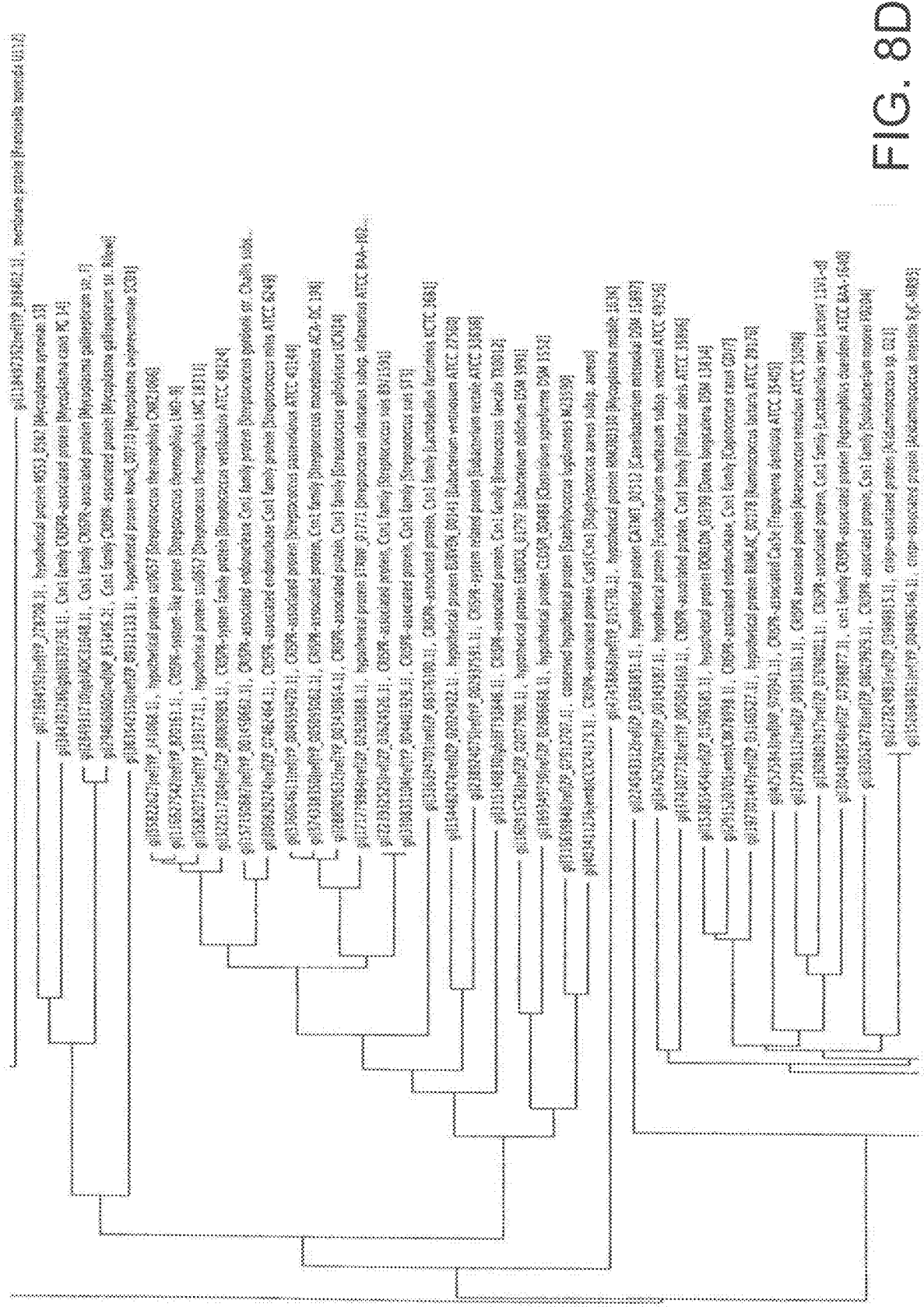
Figure 8E:
Figure 8F:
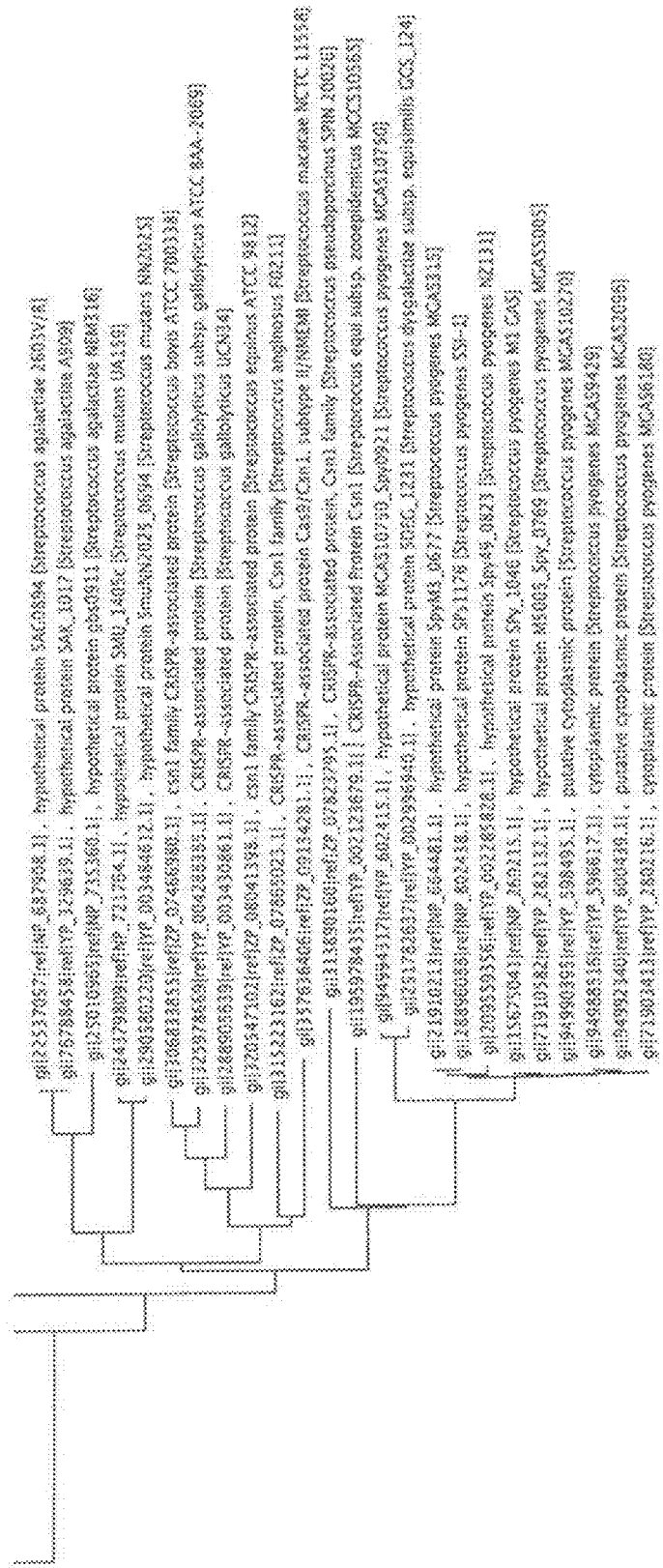

The least-squares estimate is then $$\vec{\alpha}_{est} = (G^T G)_{-1} G^T \vec{Z}$$

where $G^T$ is the matrix-transpose of the G and $(G^T G)^{-1}$ is the inverse of their matrix-product. In the above G is a matrix of local DNA:RNA free-energy values whose rth row corresponds to experimental trial r and whose kth column corresponds to the kth position in the DNA:RNA hybrid tested in that experimental trial. These values of G are thus input into the training system (Step S204). $\vec{Z}$ is meanwhile a column-vector whose rth row corresponds to observables from the same experimental trial as G's rth row. Because of the relation described above wherein the CRISPR cutting frequencies are estimated to vary as $\sim e^{-\beta Z_{ij}}$, these observables, $Z_{ij}$, were calculated as the natural logarithm of the observed cutting frequency. The observable is the cleavage efficiency of Cas, e.g., Cas9, at a target DNA for a particular guide RNA and target DNA pair. The experiment is Cas, e.g., Cas9, with a particular sgRNA/DNA target pairing, and the observable is the cleavage percentage (whether measured as indel formation percentage from cells or simply cleavage percentage in vitro) (see herein discussion on generating training data set). More in particular, every unique PCR reaction that was sequenced should be treated as a unique experimental trial to encompass replicability within the vector. This means that experimental replicates each go into separate rows of equation 1 (and because of this, some rows of G will be identical). The advantage of this is that when $\vec{\alpha}$ is fit, all relevant information—including replicability—is taken into account in the final estimate. Observable $\vec{Z}$, values were calculated as log (observed frequency of cutting) (Step S206). Cutting frequencies were optionally normalized identically (so that they all have the same "units") (Step S208). For plugging in sequencing indel-frequency values, it may be best, however, to standardize sequencing depth. The preferred way to do this would be to set a standard sequencing-depth D for which all experiments included in $\vec{Z}$ have at least that number of reads. Since cutting frequencies below 1/D cannot be consistently detected, this should be set as the minimum frequency for the data-set, and the values in $\vec{Z}$ should range from log(1/D) to log(1). One could vary the value of D later on to ensure that the $\vec{\alpha}$ estimate isn't too dependent on the value chosen. Thus, values of Z could be filtered out if they do not meet the minimum sequencing depth (Step S210). Once the values of G and Z are input to the machine learning system, the weights can be determined (Step S212) and output (Step S214). These weights can then be used to estimate the free energy Z and the cutting frequency for any sequence. In a further aspect, there are different methods of graphing NGG and NNAGAAW sequences. One is with the 'non-overlapping' method. NGG and NRG may be regraphed in an "overlapping" fashion, as indicated in FIGS. 6 A-C. Applicants also performed a study on off target Cas9 activity as indicated in FIGS. 10, 11 and 12. Aspects of the invention also relate to predictive models that may not involve hybridization energies but instead simply use the cutting frequency information as a prediction.

FIG. 34 shows the steps in one method relating to the multiplicative algorithm which may be applied in identifying one or more unique target sequences in a genome of a eukaryotic organism, whereby the target sequence is susceptible to being recognized by a CRISPR-Cas system. The method comprises: a) creating a data training set as to a particular Cas. The data training set may be created as described in more detail later by determining the weights associated with a model. Once a data training set has been established, it can be used to predict the behavior of an input sequence and to identify one or more unique target sequences therein. At step S300, the genome sequence is input to the system. For a particular Cas, the next step is to locate a mismatch between a target sequence within the input sequence and guide RNA for the particular Cas (Step S302). For the identified mismatch, two average cutting frequencies are determined using the data training set. These are the average cutting frequency at the position of the mismatch (step S304) and the average cutting frequency associated with that type of mismatch (Step S306). These average cutting frequencies are determined from the data training set which is particular to that Cas. The next step S308 is to create a product by multiplying the average cutting frequency at a particular position by the average cutting frequency of a particular mismatch to obtain a first product. It is then determined at step S310 whether or not there are any other mismatches. If there are none, the target sequence is output as the unique target sequence. However, if there are other mismatches, steps 304 to 308 are repeated to obtain second and further products for any further particular position (s) of mismatches and particular mismatches. Where second and further products are created and all products are multiplied together to create an ultimate product. The ultimate product is then multiplied by the result of dividing the minimum distance between consecutive mismatches by the length of the target sequence (e.g. 18) (step S314) which effectively scales each ultimate product. It will be appreciated that steps 312 and 314 are omitted if there is no mismatch at any position or if there is only one particular mismatch at one particular position. The process is then repeated for any other target sequences. The "scaled" ultimate products for each target sequence are each ranked to thereby obtain a ranking (Step S316), which allows for the identification of one or more unique target sequences by selecting the highest ranked one (Step S318). Thus the "scaled" ultimate product which represents the predicted cutting frequencies for genome-wide targets may be calculated by: $f_{est} = f(1)g(N_1, N_1') \times f(2)g(N_2, N_2') \times \ldots f(19)g(N_{19}, N_{19}') \times h$.

with values f(i) and $g(N_i, N_i')$ at position i corresponding, respectively, to the aggregate position- and base-mismatch cutting frequencies for positions and pairings indicated in a generalized base transition matrix or an aggregate matrix, e.g. a matrix as indicated in FIG. 12c. In other words, f(i) is the average cutting frequency at the particular position for the mismatch and $g(N_i, N_i')$ is the average cutting frequency for the particular mismatch type for the mismatch. Each frequency was normalized to range from 0 to 1, such that $f \to (f-f_{min})/(f_{max}-f_{min})$. In case of a match, both were set equal to 1. The value h meanwhile re-weighted the estimated frequency by the minimum pairwise distance between consecutive mismatches in the target sequence. This value distance, in base-pairs, was divided by a constant which was indicative of the length of the target sequence (e.g. 18) to give a maximum value of 1 (in cases where fewer than 2 mismatches existed, or where mismatches occurred on opposite ends of the 19 bp target-window). Samples having a read-count of at least 10,000 (n=43) were plotted. Those tied in rank were given a rank-average. The Spearman correlation coefficient, 0.58, indicated that the estimated frequencies recapitulated 58% of the rank-variance for the observed cutting frequencies. Comparing fir with the cutting frequencies directly yielded a Pearson correlation of 0.89. While dominated by the highest-frequency gRNA/target pairs, this value indicated that nearly 90% of all cutting-frequency variance was explained by the predictions above. In further aspects of the invention, the multiplicative algorithm or the methods mentioned herein may also include thermodynamic factors, e.g. hybridization energies, or other factors of interest being multiplied in series to arrive at the ultimate product.

Figure 35:
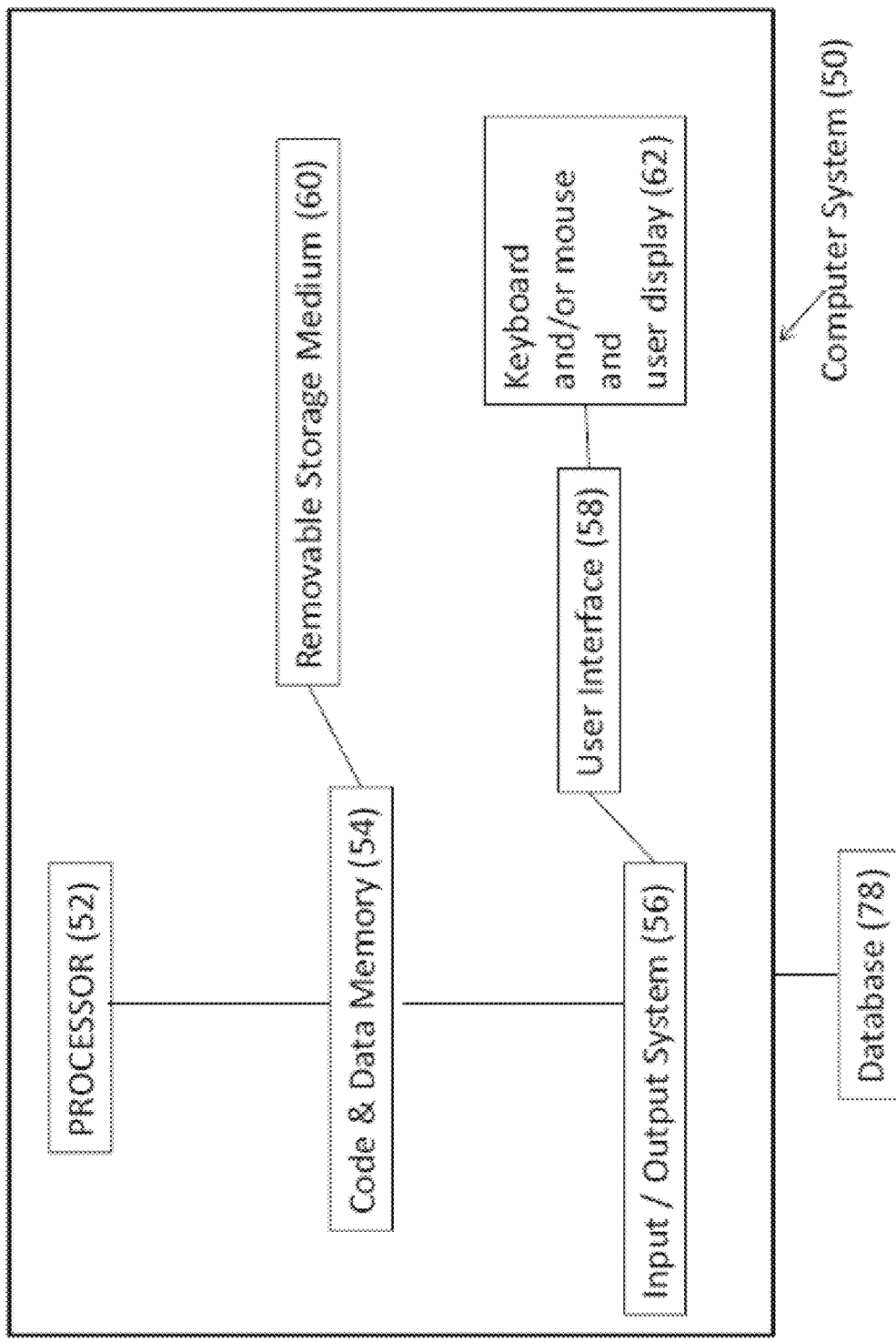
FIG. 35 shows a schematic block diagram of a computer system which can be used to implement the methods described herein.

FIG. 35 shows a schematic block diagram of a computer system which can be used to implement the methods described herein. The computer system 50 comprises a processor 52 coupled to code and data memory 54 and an input/output system 56 (for example comprising interfaces for a network and/or storage media and/or other communications). The code and/or data stored in memory 54 may be provided on a removable storage medium 60. There may also be a user interface 58 for example comprising a keyboard and/or mouse and a user display 62. The computer system is connected to a database 78. The database 78 comprises the data associated with the data training sets. The computer system is shown as a single computing device with multiple internal components which may be implemented from a single or multiple central processing units, e.g. microprocessors. It will be appreciated that the functionality of the device may be distributed across several computing devices. It will also be appreciated that the individual components may be combined into one or more components providing the combined functionality. Moreover, any of the modules, databases or devices shown may be implemented in a general purpose computer modified (e.g. programmed or configured) by software to be a special-purpose computer to perform the functions described herein. The processor may be configured to carry out the steps shown in the various flowcharts. The user interface may be used to input the genome sequence, the CRISPR motif and/or Cas for which a target sequence is to be identified. The output unique target sequence(s) may be displayed on the user display.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Evaluation of the Specificity of Cas9-Mediated Genome Cleavage

Applicants carried out an initial test to evaluate the cleavage specificity of Cas9 from *Streptococcus pyogenes*. The assay was designed to test the effect of single basepair mismatches between the guide RNA sequence and the target DNA. The results from the initial round of testing are depicted in FIG. 3.

Applicants carried out the assay using 293FT cells in 96 well plates. Cells were transfected with 65 ng of a plasmid carrying Cas9 and 10 ng of a PCR amplicon carrying the pol3 promoter U6 and the guide RNA. The experiment was conducted using a high amount of Cas9 and guide RNA, which probably explains the seemingly low specificity (i.e. single base mismatches is not sufficient to abolish cleavage). Applicants also evaluate the effect of different concentration of Cas9 and RNA on cleavage specificity. Additionally, Applicants carry out a comprehensive evaluation of every possible mismatch in each position of the guide RNA. The end goal is to generate a model to inform the design of guide RNAs having high cleavage specificity.

Additional experiments test position and number of mismatches in the guide RNA on cleavage efficiency. The following table shows a list of 48 mismatch possibilities. In the table 0 means no mutation and 1 means with mutation.

| | 20 | 19 | 18 | 17 | 16 | 15 | 14 | 13 | 12 | 11 | 10 | 9 | 8 | 7 | 6 | 5 | 4 | 3 | 2 | 1 | NGG |
|---|---|---|---|---|---|---|---|---|---|---|---|---|---|---|---|---|---|---|---|---|---|
| Test Rule 1: More mismatches = bigger effect on cutting | | | | | | | | | | | | | | | | | | | | | |
| Test Rule 2: Mismatches on 5' end have less effect than mismatches on 3' end | | | | | | | | | | | | | | | | | | | | | |
| 1 | 0 | 0 | 0 | 0 | 0 | 0 | 0 | 0 | 0 | 0 | 0 | 0 | 0 | 0 | 0 | 0 | 0 | 0 | 1 | 1 | |
| 2 | 0 | 0 | 0 | 0 | 0 | 0 | 0 | 0 | 0 | 0 | 0 | 0 | 0 | 0 | 0 | 1 | 1 | 0 | 0 | | |
| 3 | 0 | 0 | 0 | 0 | 0 | 0 | 0 | 0 | 0 | 0 | 0 | 0 | 0 | 1 | 1 | 0 | 0 | 0 | 0 | | |
| 4 | 0 | 0 | 0 | 0 | 0 | 0 | 0 | 0 | 0 | 0 | 0 | 1 | 1 | 0 | 0 | 0 | 0 | 0 | 0 | | |
| 5 | 0 | 0 | 0 | 0 | 0 | 0 | 0 | 0 | 0 | 1 | 1 | 0 | 0 | 0 | 0 | 0 | 0 | 0 | 0 | | |
| 6 | 0 | 0 | 0 | 0 | 0 | 0 | 0 | 0 | 1 | 1 | 0 | 0 | 0 | 0 | 0 | 0 | 0 | 0 | 0 | | |
| 7 | 0 | 0 | 0 | 0 | 0 | 0 | 1 | 1 | 0 | 0 | 0 | 0 | 0 | 0 | 0 | 0 | 0 | 0 | 0 | | |
| 8 | 0 | 0 | 0 | 0 | 1 | 1 | 0 | 0 | 0 | 0 | 0 | 0 | 0 | 0 | 0 | 0 | 0 | 0 | 0 | | |
| 9 | 0 | 0 | 1 | 1 | 0 | 0 | 0 | 0 | 0 | 0 | 0 | 0 | 0 | 0 | 0 | 0 | 0 | 0 | 0 | | |
| 10 | 1 | 1 | 0 | 0 | 0 | 0 | 0 | 0 | 0 | 0 | 0 | 0 | 0 | 0 | 0 | 0 | 0 | 0 | 0 | | |
| 11 | 0 | 0 | 0 | 0 | 0 | 0 | 0 | 0 | 0 | 0 | 0 | 0 | 0 | 0 | 0 | 0 | 1 | 1 | 1 | 0 | |
| 12 | 0 | 0 | 0 | 0 | 0 | 0 | 0 | 0 | 0 | 0 | 0 | 0 | 0 | 0 | 1 | 1 | 1 | 1 | 1 | | |
| 13 | 0 | 0 | 0 | 0 | 0 | 0 | 0 | 0 | 0 | 0 | 0 | 1 | 1 | 1 | 0 | 0 | 0 | 0 | | | |
| 14 | 0 | 0 | 0 | 0 | 0 | 0 | 0 | 0 | 0 | 0 | 1 | 1 | 1 | 1 | 1 | 0 | 0 | 0 | | | |
| 15 | 0 | 0 | 0 | 0 | 0 | 0 | 0 | 0 | 0 | 1 | 1 | 1 | 0 | 0 | 0 | 0 | 0 | 0 | 0 | | |
| 16 | 0 | 0 | 0 | 0 | 0 | 0 | 0 | 0 | 1 | 1 | 1 | 1 | 1 | 0 | 0 | 0 | 0 | 0 | 0 | | |

-continued

| | 20 | 19 | 18 | 17 | 16 | 15 | 14 | 13 | 12 | 11 | 10 | 9 | 8 | 7 | 6 | 5 | 4 | 3 | 2 | 1 | NGG |
|---|---|---|---|---|---|---|---|---|---|---|---|---|---|---|---|---|---|---|---|---|---|
| 17 | 0 | 0 | 0 | 0 | 0 | 0 | 0 | 1 | 1 | 1 | 0 | 0 | 0 | 0 | 0 | 0 | 0 | 0 | 0 | 0 | 0 |
| 18 | 0 | 0 | 0 | 0 | 0 | 0 | 1 | 1 | 1 | 1 | 1 | 0 | 0 | 0 | 0 | 0 | 0 | 0 | 0 | 0 | 0 |
| 19 | 0 | 0 | 0 | 0 | 1 | 1 | 1 | 0 | 0 | 0 | 0 | 0 | 0 | 0 | 0 | 0 | 0 | 0 | 0 | 0 | 0 |
| 20 | 0 | 0 | 0 | 1 | 1 | 1 | 1 | 1 | 0 | 0 | 0 | 0 | 0 | 0 | 0 | 0 | 0 | 0 | 0 | 0 | 0 |
| 21 | 0 | 1 | 1 | 1 | 0 | 0 | 0 | 0 | 0 | 0 | 0 | 0 | 0 | 0 | 0 | 0 | 0 | 0 | 0 | 0 | 0 |
| 22 | 1 | 1 | 1 | 1 | 1 | 0 | 0 | 0 | 0 | 0 | 0 | 0 | 0 | 0 | 0 | 0 | 0 | 0 | 0 | 0 | 0 |
| Test Rule 3: Mismatches more spreadout have less effect than mismatches more concentrated | | | | | | | | | | | | | | | | | | | | | |
| 23 | 0 | 0 | 0 | 0 | 0 | 0 | 0 | 0 | 0 | 0 | 0 | 0 | 0 | 0 | 0 | 0 | 0 | 1 | 0 | 1 |
| 24 | 0 | 0 | 0 | 0 | 0 | 0 | 0 | 0 | 0 | 0 | 0 | 0 | 0 | 0 | 1 | 0 | 0 | 0 | 0 | 1 |
| 25 | 0 | 0 | 0 | 0 | 0 | 0 | 0 | 0 | 0 | 0 | 1 | 0 | 0 | 0 | 0 | 0 | 0 | 0 | 0 | 1 |
| 26 | 0 | 0 | 0 | 0 | 0 | 1 | 0 | 0 | 0 | 0 | 0 | 0 | 0 | 0 | 0 | 0 | 0 | 0 | 0 | 1 |
| 27 | 1 | 0 | 0 | 0 | 0 | 0 | 0 | 0 | 0 | 0 | 0 | 0 | 0 | 0 | 0 | 0 | 0 | 0 | 0 | 1 |
| 28 | 0 | 0 | 0 | 0 | 0 | 0 | 0 | 0 | 0 | 0 | 0 | 0 | 0 | 0 | 1 | 0 | 1 | 0 | 0 | 0 |
| 29 | 0 | 0 | 0 | 0 | 0 | 0 | 0 | 0 | 0 | 0 | 0 | 1 | 0 | 0 | 0 | 0 | 1 | 0 | 0 | 0 |
| 30 | 0 | 0 | 0 | 0 | 0 | 0 | 0 | 0 | 1 | 0 | 0 | 0 | 0 | 0 | 0 | 0 | 1 | 0 | 0 | 0 |
| 31 | 0 | 0 | 0 | 1 | 0 | 0 | 0 | 0 | 0 | 0 | 0 | 0 | 0 | 0 | 0 | 0 | 1 | 0 | 0 | 0 |
| 32 | 0 | 0 | 0 | 0 | 0 | 0 | 0 | 0 | 0 | 0 | 0 | 0 | 1 | 0 | 1 | 0 | 0 | 0 | 0 | 0 |
| 33 | 0 | 0 | 0 | 0 | 0 | 0 | 0 | 0 | 0 | 1 | 0 | 0 | 0 | 0 | 1 | 0 | 0 | 0 | 0 | 0 |
| 34 | 0 | 0 | 0 | 0 | 0 | 1 | 0 | 0 | 0 | 0 | 0 | 0 | 0 | 0 | 1 | 0 | 0 | 0 | 0 | 0 |
| 35 | 0 | 1 | 0 | 0 | 0 | 0 | 0 | 0 | 0 | 0 | 0 | 0 | 0 | 0 | 1 | 0 | 0 | 0 | 0 | 0 |
| 36 | 0 | 0 | 0 | 0 | 0 | 0 | 0 | 0 | 0 | 0 | 0 | 0 | 0 | 0 | 1 | 0 | 1 | 0 | 1 |
| 37 | 0 | 0 | 0 | 0 | 0 | 0 | 0 | 0 | 0 | 0 | 0 | 1 | 0 | 0 | 1 | 0 | 0 | 1 |
| 38 | 0 | 0 | 0 | 0 | 0 | 0 | 0 | 0 | 0 | 1 | 0 | 0 | 0 | 0 | 1 | 0 | 0 | 0 | 1 |
| 39 | 0 | 0 | 0 | 0 | 0 | 0 | 0 | 0 | 1 | 0 | 0 | 0 | 1 | 0 | 0 | 0 | 0 | 1 |
| 40 | 0 | 0 | 0 | 0 | 0 | 0 | 0 | 0 | 0 | 0 | 0 | 0 | 1 | 0 | 1 | 0 | 1 | 0 | 0 |
| 41 | 0 | 0 | 0 | 0 | 0 | 0 | 0 | 0 | 0 | 0 | 1 | 0 | 0 | 1 | 0 | 0 | 1 | 0 | 0 |
| 42 | 0 | 0 | 0 | 0 | 0 | 0 | 0 | 0 | 1 | 0 | 0 | 0 | 1 | 0 | 0 | 0 | 1 | 0 | 0 |
| 43 | 0 | 0 | 0 | 0 | 0 | 0 | 1 | 0 | 0 | 0 | 0 | 1 | 0 | 0 | 0 | 0 | 1 | 0 | 0 |
| 44 | 0 | 0 | 0 | 0 | 0 | 0 | 0 | 0 | 0 | 0 | 0 | 0 | 1 | 0 | 1 | 0 | 1 | 0 | 1 |
| 45 | 0 | 0 | 0 | 0 | 0 | 0 | 0 | 0 | 0 | 1 | 0 | 0 | 1 | 0 | 1 | 0 | 0 | 0 | 1 |
| 46 | 0 | 0 | 0 | 0 | 0 | 0 | 0 | 1 | 0 | 0 | 0 | 1 | 0 | 0 | 0 | 1 | 0 | 0 | 0 | 1 |
| 47 | 0 | 0 | 0 | 0 | 1 | 0 | 0 | 0 | 0 | 1 | 0 | 0 | 0 | 0 | 1 | 0 | 0 | 0 | 0 | 1 |
| 48 | 0 | 1 | 0 | 0 | 0 | 0 | 0 | 1 | 0 | 0 | 0 | 0 | 0 | 1 | 0 | 0 | 0 | 0 | 0 | 1 |

Example 2

Evaluation of Mutations in the PAM Sequence, and its Effect on Cleavage Efficiency Applicants tested mutations in the PAM sequence and its effect on cleavage. The PAM sequence for *Streptococcus pyogenes* Cas9 is NGG, where the GG is thought to be required for cleavage. To test whether Cas9 can cleavage sequences with PAMs that are different than NGG, Applicants chose the following 30 target sites from the Emx1 locus of the human genome—2 for each of the 15 PAM possibilities: NAA, NAC, NAT, NAG, NCA, NCC, NCG, NCT, NTA, NTC, NTG, NTT, NGA, NGC, and NGT; NGG is not selected because it can be targeted efficiently.

Figure 4:
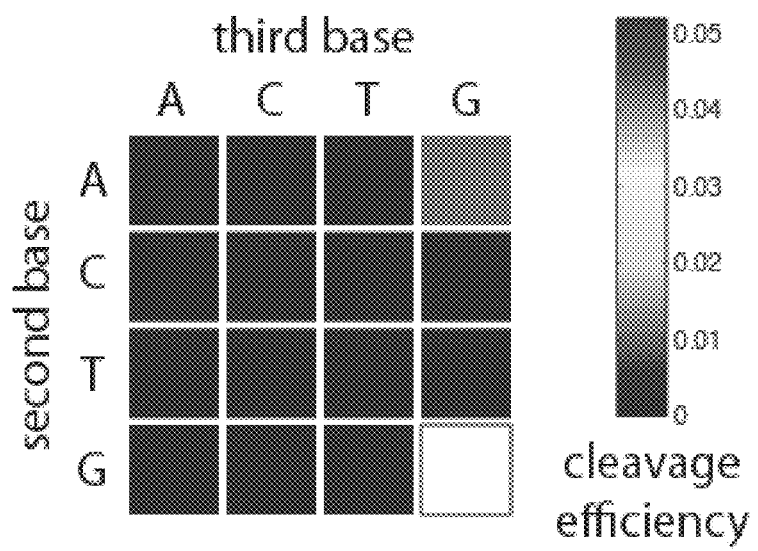
FIG. 4 shows a mapping of mutations in the PAM sequence to cleavage efficiency in %.

The cleavage efficiency data is shown in FIG. 4. The data shows that other than NGG, only sequences with NAG PAMs can be targeted.

| PAM | Target 1 | Target 2 |
|---|---|---|
| NAA | AGGCCCCAGTGGCTGCTCT | TCATCTGTGCCCCTCCCTC |
| NAT | ACATCAACCGGTGGCGCAT | GGGAGGACATCGATGTCAC |
| NAC | AAGGTGTGGTTCCAGAACC | CAAACGGCAGAAGCTGGAG |
| NAG | CCATCACATCAACCGGTGG | GGGTGGGCAACCACAAACC |
| NTA | AAACGGGAGAAGCTGGAGG | GGTGGGCAACCACAAACCC |
| NTT | GGCAGAAGCTGGAGGAGGA | GGCTCCCATCACATCAACC |
| NTC | GGTGTGGTTCCAGAACCGG | GAAGGGCCTGAGTCCGAGC |
| NTG | AACCGGAGGACAAAGTACA | CAACCGGTGGCGCATTGCC |
| NCA | TTCCAGAACCGGAGGACAA | AGGAGGAAGGGCCTGAGTC |
| NCT | GTGTGGTTCCAGAACCGGA | AGCTGGAGGAGGAAGGGCC |
| NCC | TCCAGAACCGGAGGACAAA | GCATTGCCACGAAGCAGGC |
| NCG | CAGAAGCTGGAGGAGGAAG | ATTGCCACGAAGCAGGCCA |
| NGA | CATCAACCGGTGGCGCATT | AGAACCGGAGGACAAAGTA |
| NGT | GCAGAAGCTGGAGGAGGAA | TCAACCGGTGGCGCATTGC |
| NGC | CCTCCCTCCCTGGCCCAGG | GAAGCTGGAGGAGGAAGGG |

Example 3

Cas9 Diversity and RNAs, PAMS, Targets

The CRISPR-Cas system is an adaptive immune mechanism against invading exogenous DNA employed by diverse species across bacteria and archaea. The type II CRISPR-Cas9 system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracrRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom (FIGS. 7 and 8A-F) and highly diverse in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species (FIG. 8A-F) identified based on sequence homology to known Cas9s and structures orthologous to known subdomains. Using the method of Example 1, Applicants will carry out a comprehensive evaluation of every possible mismatch in each position of the guide RNA for these different Cas9s to generate a model to inform the design of guide RNAs having high cleavage specificity for each based on the impact of the test position and number of mismatches in the guide RNA on cleavage efficiency for each Cas9.

The CRISPR-Cas system is amenable for achieving tissue-specific and temporally controlled targeted deletion of candidate disease genes. Examples include but are not limited to genes involved in cholesterol and fatty acid metabolism, amyloid diseases, dominant negative diseases, latent viral infections, among other disorders. Accordingly, target sequences can be in candidate disease genes, e.g.:

| Disease | GENE | SPACER | PAM | Mechanism | References |
|---|---|---|---|---|---|
| Hypercholes-terolemia | HMG-CR | GCCAAATTG GACGACCCT CG | CGG | Knockout | Fluvastatin: a review of its pharmacology and use in the management of hypercholesterolaemia. (Plosker GL et al. Drugs 1996, 51(3):433-459) |
| Hypercholes-terolemia | SQLE | CGAGGAGAC CCCCGTTTC GG | TGG | Knockout | Potential role of nonstatin cholesterol lowering agents (Trapani et al. IUBMB Life, Volume 63, Issue 11, pages 964-971, November 2011) |
| Hyper-lipidemia | DGAT1 | CCCGCCGCC GCCGTGGCT CG | AGG | Knockout | DGAT1 inhibitors as anti-obesity and anti-diabetic agents. (Birch AM et al. Current Opinion in Drug Discovery & Development [2010, 13(4):489-496) |
| Leukemia | BCR-ABL | TGAGCTCTA CGAGATCCA CA | AGG | Knockout | Killing of leukemic cells with a BCR/ABL fusion gene by RNA interference (RNAi). (Fuchs et al. Oncogene 2002, 21(37):5716-5724) |

Examples of a pair of guide-RNA to introduce chromosomal microdeletion at a gene locus

| Disease | GENE | SPACER | PAM | Mechanism | References |
|---|---|---|---|---|---|
| Hyperlip-idemia | PLIN2 guide1 | CTCAAAATT CATACCGGT TG | TGG | Micro-deletion | Perilipin-2 Null Mice are Protected Against Diet-Induced Obesity, Adipose Inflammation and Fatty Liver Disease (McManaman JL et al. The Journal of Lipid Research, jlr.M035063. First Published on February 12, 2013) |
| Hyperlip-idemia | PLIN2 guide2 | CGTTAAACA ACAACCGGA CT | TGG | Micro-deletion | |
| Hyperlip-idemia | SREBP guide1 | TTCACCCCG CGGCGCTGA AT | ggg | Micro-deletion | Inhibition of SREBP by a Small Molecule, Betulin, Improves Hyperlipidemia and Insulin Resistance and Reduces Atherosclerotic Plaques (Tang J et al. Cell Metabolism, Volume 13, Issue 1, 44-56, 5 January 2011) |
| Hyperlip-idemia | SREBP guide2 | ACCACTACC AGTCCGTCC AC | agg | Micro-deletion | |

Examples of potential HIV-1 targeted spacers adapted from Mcintyre et al, which generated shRNAs against HIV-1 optimized for maximal coverage of HIV-1 variants.

CACTGCTTAAGCCTCGCTCG<u>AGG</u>

TCACCAGCAATATTCGCTCG<u>AGG</u>

CACCAGCAATATTCCGCTCG<u>AGG</u>

TAGCAACAGACATACGCTCG<u>AGG</u>

GGGCAGTAGTAATACGCTCG<u>AGG</u>

<u>CCA</u>ATTCCCATACATTATTGTAC

Identification of Cas9 target site: Applicants analyzed the human CFTR genomic locus and identified the Cas9 target site (PAM may contain a NGG or a NNAGAAW motif). The frequency of these PAM sequences in the human genome are shown in FIG. 5.

Protospacer IDs and their corresponding genomic target, protospacer sequence, PAM sequence, and strand location are provided in the below Table. Guide sequences were designed to be complementary to the entire protospacer sequence in the case of separate transcripts in the hybrid system, or only to the underlined portion in the case of chimeric RNAs.

TABLE

Protospacer IDs and their corresponding genomic target, protospacer sequence, PAM sequence, and strand location

| proto-spacer ID | genomic target | protospacer sequence (5' to 3') | PAM | strand |
|---|---|---|---|---|
| 1 | EMX1 | GGACATCGAT<u>GTCAC CTCCAATGACTAGGG</u> | TGG | + |
| 2 | EMX1 | CATTGGAGGT<u>GACAT CGATGTCCTCCCCAT</u> | TGG | − |
| 3 | EMX1 | GGAAGGGCCT<u>GAGTC CGAGCAGAAGAAGAA</u> | GGG | + |
| 4 | PVALB | GGTGGCGAGA<u>GGGGC CGAGATTGGGTGTTC</u> | AGG | + |
| 5 | PVALB | ATGCAGGAGG<u>GTGGC GAGAGGGGCCGAGAT</u> | TGG | + |

Computational Identification of Unique CRISPR Target Sites:

To identify unique target sites for a Cas, e.g., a Cas9, e.g., the S. pyogenes SF370 Cas9 (SpCas9) enzyme, in nucleic acid molecules, e.g., of cells, e.g., of organisms, which include but are not limited to human, mouse, rat, zebrafish, fruit fly, and C. elegans genome, Applicants developed a software package to scan both strands of a DNA sequence and identify all possible SpCas9 target sites. For this example, each SpCas9 target site was operationally defined as a 20 bp sequence followed by an NGG protospacer adjacent motif (PAM) sequence, and all sequences satisfying this 5'-$N_{20}$-NGG-3' definition on all chromosomes were identified. To prevent non-specific genome editing, after identifying all potential sites, all target sites were filtered based on the number of times they appear in the relevant reference genome. To take advantage of sequence specificity of Cas, e.g., Cas9 activity conferred by a 'seed' sequence, which can be, for example, approximately 11-12 bp sequence 5' from the PAM sequence, 5'-NNNNNNNNNN-NGG-3' sequences were selected to be unique in the relevant genome. Genomic sequences are available on the UCSC Genome Browser and sample visualizations of the information for the Human genome hg, Mouse genome mm, Rat genome rn, Zebrafish genome danRer, D. melanogaster genome dm, C. elegans genome ce, the pig genome and cow genome are shown in FIGS. 15 through 22 respectively.

Figure 31:
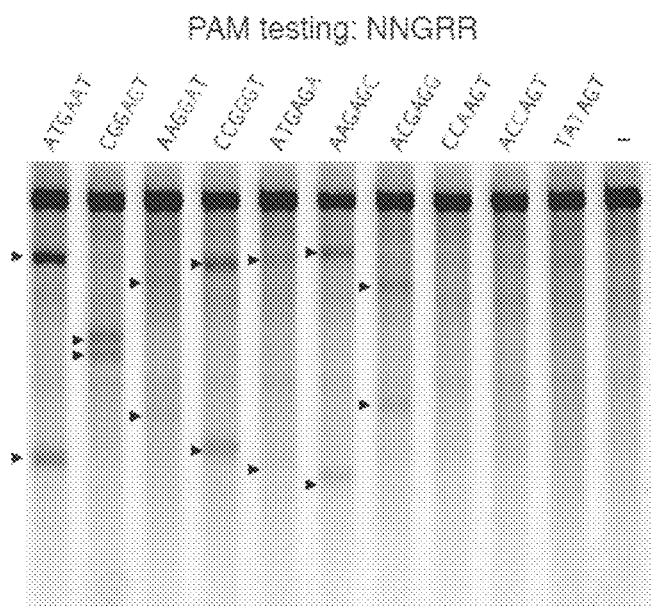
FIG. 31 shows that the PAM for *Staphylococcus aureus* sp. *Aureus* Cas9 is NNGRR.

A similar analysis may be carried out for other Cas enzymes utilizing their respective PAM sequences, for e.g. Staphylococcus aureus sp. Aureus Cas9 and its PAM sequence NNGRR (FIG. 31).

Example 4

Experimental Architecture for Evaluating CRISPR-Cas Target Activity and Specificity Targeted nucleases such as the CRISPR-Cas systems for gene editing applications allow for highly precise modification of the genome. However, the specificity of gene editing tools is a crucial consideration for avoiding adverse off-target activity. Here, Applicants describe a Cas9 guide RNA selection algorithm that predicts off-target sites for any desired target site within mammalian genomes.

Applicants constructed large oligo libraries of guide RNAs carrying combinations of mutations to study the sequence dependence of Cas9 programming. Using next-generation deep sequencing, Applicants studied the ability of single mutations and multiple combinations of mismatches within different Cas9 guide RNAs to mediate target DNA locus modification. Applicants evaluated candidate off-target sites with sequence homology to the target site of interest to assess any off-target cleavage.

Algorithm for Predicting CRISPR-Cas Target Activity and Specificity:

Data from these studies were used to develop algorithms for the prediction of CRISPR-Cas off-target activity across the human genome. The Applicants' resulting computational platform supports the prediction of all CRISPR-Cas system target activity and specificity in any genome. Applicants evaluate CRISPR-Cas activity and specificity by predicting the Cas9 cutting efficiency for any CRISPR-Cas target against all other genomic CRISPR-Cas targets, excluding constraining factors, i.e., some epigenetic modifications like repressive chromatin/heterochromatin.

The algorithms Applicants describe 1) evaluate any target site and give potential off-targets and 2) generate candidate target sites for any locus of interest with minimal predicted off-target activity.

Least Squares Thermodynamic Model of CRISPR-Cas Cutting Efficiency:

For arbitrary Cas9 target sites, Applicants generated a numerical thermodynamic model that predicts Cas9 cutting efficiency. Applicants propose 1) that the Cas9 guide RNA has specific free energies of hybridization to its target and any off-target DNA sequences and 2) that Cas9 modifies RNA:DNA hybridization free-energies locally in a position-dependent but sequence-independent way. Applicants trained a model for predicting CRISPR-Cas cutting efficiency based on their CRISPR-Cas guide RNA mutation data and RNA:DNA thermodynamic free energy calculations using a machine learning algorithm. Applicants then validated their resulting models by comparing their predictions of CRISPR-Cas off-target cutting at multiple genomic loci with experimental data assessing locus modification at the same sites.

The methodology adopted in developing this algorithm is as follows: The problem summary states that for arbitrary spacers and targets of constant length, a numerical model that makes thermodynamic sense and predicts Cas9 cutting efficiency is to be found.

Suppose Cas9 modifies DNA:RNA hybridization free-energies locally in a position-dependent but sequence-independent way. Then for DNA:RNA hybridization free energies $\Delta G_{ij}(k)$ (for position k between 1 and N) of spacer i and target j $$Z_{ij} = \sum_{k=1}^{N} \alpha_k \Delta G_{ij}(k)$$

$Z_{ij}$ can be treated as an "effective" free-energy modified by the multiplicative position-weights $\alpha_k$.

The "effective" free-energy $Z_{ij}$ corresponds to an associated cutting-probability $e^{-\beta Z_{ij}}$ (for some constant $\beta$) in the same way that an equilibrium model of hybridization (without position-weighting) would have predicted a hybridization-probability $\sim e^{-\beta \Delta G_{ij}}$. Since cutting-efficiency has been measured, the values $Z_{ij}$ can be treated as their observables. Meanwhile, $\Delta G_{ij}(k)$ can be calculated for any experiment's spacer-target pairing. Applicants task was to find the values $\alpha_k$, since this would allow them to estimate $Z_{ij}$ for any spacer-target pair.

Writing the above equation for $Z_{ij}$ in matrix form Applicants get:

$$\vec{Z} = G\vec{\alpha} \quad (1)$$

The least-squares estimate is then $$\vec{\alpha}_{est} = (G^T G)^{-1} G^T \vec{Z}$$

where $G^T$ is the matrix-transpose of the G and $(G^T G)^{-1}$ is the inverse of their matrix-product.

In the above G is a matrix of local DNA:RNA free-energy values whose rth row corresponds to experimental trial r and whose kth column corresponds to the kth position in the DNA:RNA hybrid tested in that experimental trial. $\vec{Z}$ is meanwhile a column-vector whose rth row corresponds to observables from the same experimental trial as G's rth row. Because of the relation described above wherein the CRISPR cutting frequencies are estimated to vary as $e^{-\beta Z_{ij}}$, these observables, $Z_{ij}$, were calculated as the natural logarithm of the observed cutting frequency. The observable is the cleavage efficiency of Cas, e.g., Cas9, at a target DNA for a particular guide RNA and target DNA pair. The experiment is Cas, e.g., Cas9, with a particular sgRNA/DNA target pairing, and the observable is the cleavage percentage (whether measured as indel formation percentage from cells or simply cleavage percentage in vitro) (see herein discussion on generating training data set). More in particular, every unique PCR reaction that was sequenced should be treated as a unique experimental trial to encompass replicability within the vector. This means that experimental replicates each go into separate rows of equation 1 (and because of this, some rows of G will be identical). The advantage of this is that when a is fit, all relevant information—including replicability—is taken into account in the final estimate.

Observable $\vec{Z}$, values were calculated as log (observed frequency of cutting). Cutting frequencies were normalized identically (so that they all have the same "units"). For plugging in sequencing indel-frequency values, it may be best, however, to standardize sequencing depth.

The preferred way to do this would be to set a standard sequencing-depth D for which all experiments included in $\vec{Z}$ have at least that number of reads. Since cutting frequencies below 1/D cannot be consistently detected, this should be set as the minimum frequency for the data-set, and the values in $\vec{Z}$ should range from log(1/D) to log(1). One could vary the value of D later on to ensure that the $\vec{\alpha}$ estimate isn't too dependent on the value chosen.

In a further aspect, there are different methods of graphing NGG and NNAGAAW sequences. One is with the 'non-overlapping' method. NGG and NRG may be regraphed in an "overlapping" fashion, as indicated in FIGS. 6 A-C.

Applicants also performed a study on off target Cas9 activity as indicated in FIGS. 10, 11 and 12. Aspects of the invention also relate to predictive models that may not involve hybridization energies but instead simply use the cutting frequency information as a prediction (See FIG. 29).

Example 5

DNA Targeting Specificity of the RNA-Guided Cas9 Nuclease

Here, Applicants report optimization of various applications of SpCas9 for mammalian genome editing and demonstrate that SpCas9-mediated cleavage is unaffected by DNA methylation (FIG. 14). Applicants further characterize SpCas9 targeting specificity using over 700 guide RNA variants and evaluate SpCas9-induced indel mutation levels at over 100 predicted genomic off-target loci. Contrary to previous models, Applicants found that SpCas9 tolerates mismatches between guide RNA and target DNA at different positions in a sequence-context dependent manner, sensitive to the number, position and distribution of mismatches. Finally, Applicants demonstrate that the dosage of SpCas9 and sgRNA can be titrated to minimize off-target modification. To facilitate mammalian genome engineering applications, Applicants used these results to establish a computational platform to guide the selection and validation of target sequences as well as off-target analyses.

The bacterial type II CRISPR system from *S. pyogenes* may be reconstituted in mammalian cells using three minimal components: the Cas9 nuclease (SpCas9), a specificity-determining CRISPR RNA (crRNA), and an auxiliary transactivating crRNA (tracrRNA). Following crRNA and tracrRNA hybridization, SpCas9 is localized to the genomic target matching a 20-nt guide sequence within the crRNA, immediately upstream of a required 5'-NGG protospacer adjacent motif (PAM). Each crRNA and tracrRNA duplex may also be fused to generate a chimeric single guide RNA (sgRNA) that mimics the natural crRNA-tracrRNA hybrid. Both crRNA-tracrRNA duplexes and sgRNAs can be used to target SpCas9 for multiplexed genome editing in eukaryotic cells.

Although an sgRNA design consisting of a truncated crRNA and tracrRNA had been previously shown to mediate efficient cleavage in vitro, it failed to achieve detectable cleavage at several loci that were efficiently modified by crRNA-tracrRNA duplexes bearing identical guide sequences. Because the major difference between this sgRNA design and the native crRNA-tracrRNA duplex is the length of the tracrRNA sequence, Applicants tested whether extension of the tracrRNA tail was able to improve SpCas9 activity.

Applicants generated a set of sgRNAs targeting multiple sites within the human EMX1 and PVALB loci with different tracrRNA 3' truncations. Using the SURVEYOR nuclease assay, Applicants assessed the ability of each Cas9 sgRNA complex to generate indels in HEK 293FT cells through the induction of DNA double-stranded breaks (DSBs) and subsequent non-homologous end joining (NHEJ) DNA damage repair (Methods and Materials). sgRNAs with +67 or +85 nucleotide (nt) tracrRNA tails mediated DNA cleavage at all target sites tested, with up to 5-fold higher levels of indels than the corresponding crRNA-tracrRNA duplexes. Furthermore, both sgRNA designs efficiently modified PVALB loci that were previously not targetable using crRNA-tracrRNA duplexes. For all five tested targets, Applicants observed a consistent increase in modification efficiency with increasing tracrRNA length. Applicants performed Northern blots for the guide RNA truncations and found increased levels expression for the longer tracrRNA sequences, suggesting that improved target cleavage was due to higher sgRNA expression or stability. Taken together, these data indicate that the tracrRNA tail is important for optimal SpCas9 expression and activity in vivo.

Applicants further investigated the sgRNA architecture by extending the duplex length from 12 to the 22 nt found in the native crRNA-tracrRNA duplex. Applicants also mutated the sequence encoding sgRNA to abolish any poly-T tracts that could serve as premature transcriptional terminators for U6-driven transcription. Applicants tested these new sgRNA scaffolds on 3 targets within the human EMX1 gene and observed only modest changes in modification efficiency. Thus, Applicants established sgRNA(+85), identical to some sgRNAs previously used, as an effective SpCas9 guide RNA architecture and used it in all subsequent studies.

Applicants have previously shown that a catalytic mutant of SpCas9 (D10A nickase) can mediate gene editing by homology-directed repair (HR) without detectable indel formation. Given its higher cleavage efficiency, Applicants tested whether sgRNA(+85), in complex with the Cas9 nickase, can likewise facilitate HR without incurring on-target NHEJ. Using single-stranded oligonucleotides (ssODNs) as repair templates, Applicants observed that both the wild-type and the D10A SpCas9 mediate HR in HEK 293FT cells, while only the former is able to do so in human embryonic stem cells. Applicants further confirmed using SURVEYOR assay that no target indel mutations are induced by the SpCas9 D10A nickase.

To explore whether the genome targeting ability of sgRNA(+85) is influenced by epigenetic factors that constrain the alternative transcription activator-like effector nuclease (TALENs) and potentially also zinc finger nuclease (ZFNs) technologies, Applicants further tested the ability of SpCas9 to cleave methylated DNA. Using either unmethylated or M. SssI-methylated pUC19 as DNA targets (FIG. 14a,b) in a cell-free cleavage assay, Applicants showed that SpCas9 efficiently cleaves pUC19 regardless of CpG methylation status in either the 20-bp target sequence or the PAM (FIG. 14c). To test whether this is also true in vivo, Applicants designed sgRNAs to target a highly methylated region of the human SERPINB5 locus. All three sgRNAs tested were able to mediate indel mutations in endogenously methylated targets.

Having established the optimal guide RNA architecture for SpCas9 and demonstrated its insensitivity to genomic CpG methylation, Applicants sought to conduct a comprehensive characterization of the DNA targeting specificity of SpCas9. Previous studies on SpCas9 cleavage specificity were limited to a small set of single-nucleotide mismatches between the guide sequence and DNA target, suggesting that perfect base-pairing within 10-12 bp directly 5' of PAM determines Cas9 specificity, whereas PAM-distal multiple mismatches can be tolerated. In addition, a recent study using catalytically inactive SpCas9 as a transcriptional repressor found no significant off-target effects throughout the E. coli transcriptome. However, a systematic analysis of Cas9 specificity within the context of a larger mammalian genome has not yet been reported.

To address this, Applicants first evaluated the effect of imperfect guide RNA identity for targeting genomic DNA on SpCas9 activity, and then assessed the cleavage activity resulting from a single sgRNA on multiple genomic off-target loci with sequence similarity. To facilitate large scale testing of mismatched guide sequences, Applicants developed a simple sgRNA testing assay by generating expression cassettes encoding U6-driven sgRNAs by PCR and transfecting the resulting amplicons. Applicants then performed deep sequencing of the region flanking each target site for two independent biological replicates. From these data, Applicants applied a binomial model to detect true indel events resulting from SpCas9 cleavage and NHEJ misrepair and calculated 95% confidence intervals for all reported NHEJ frequencies.

Applicants used a linear model of free energy position-dependence to investigate the combined contribution of DNA:RNA sequence and mismatch-location on Cas9 cutting efficiency. While sequence composition and mismatch location alone generated Spearman correlations between estimated and observed cutting efficiencies for EMX1 target site 1 and 0.78, respectively, integration of the two parameters greatly improved this agreement, with Spearman correlation 0.86 ($p<0.001$). Furthermore, the incorporation of nupac RNA:RNA hybridization energies into Applicants' free energy model resulted in a 10% increase in the Spearman correlation coefficient. Taken together, the data suggests an effect of SpCas9-specific perturbations on the Watson-Crick base-pairing free energies. Meanwhile, sequence composition did not substantially improve agreement between estimated and observed cutting efficiencies for EMX1 target site 6 (Spearman correlation 0.91, $p<0.001$). This suggested that single mismatches in EMX1 target site 6 contributed minimally to the thermodynamic binding free energy itself.

Potential genomic off-target sites with sequence similarity to a target site of interest may often have multiple base mismatches. Applicants designed a set of guide RNAs for EMX1 targets 1 and 6 that contains different combinations of mismatches to investigate the effect of mismatch number, position, and spacing on Cas9 target cleavage activity (FIG. 13a,b).

Figure 13A:
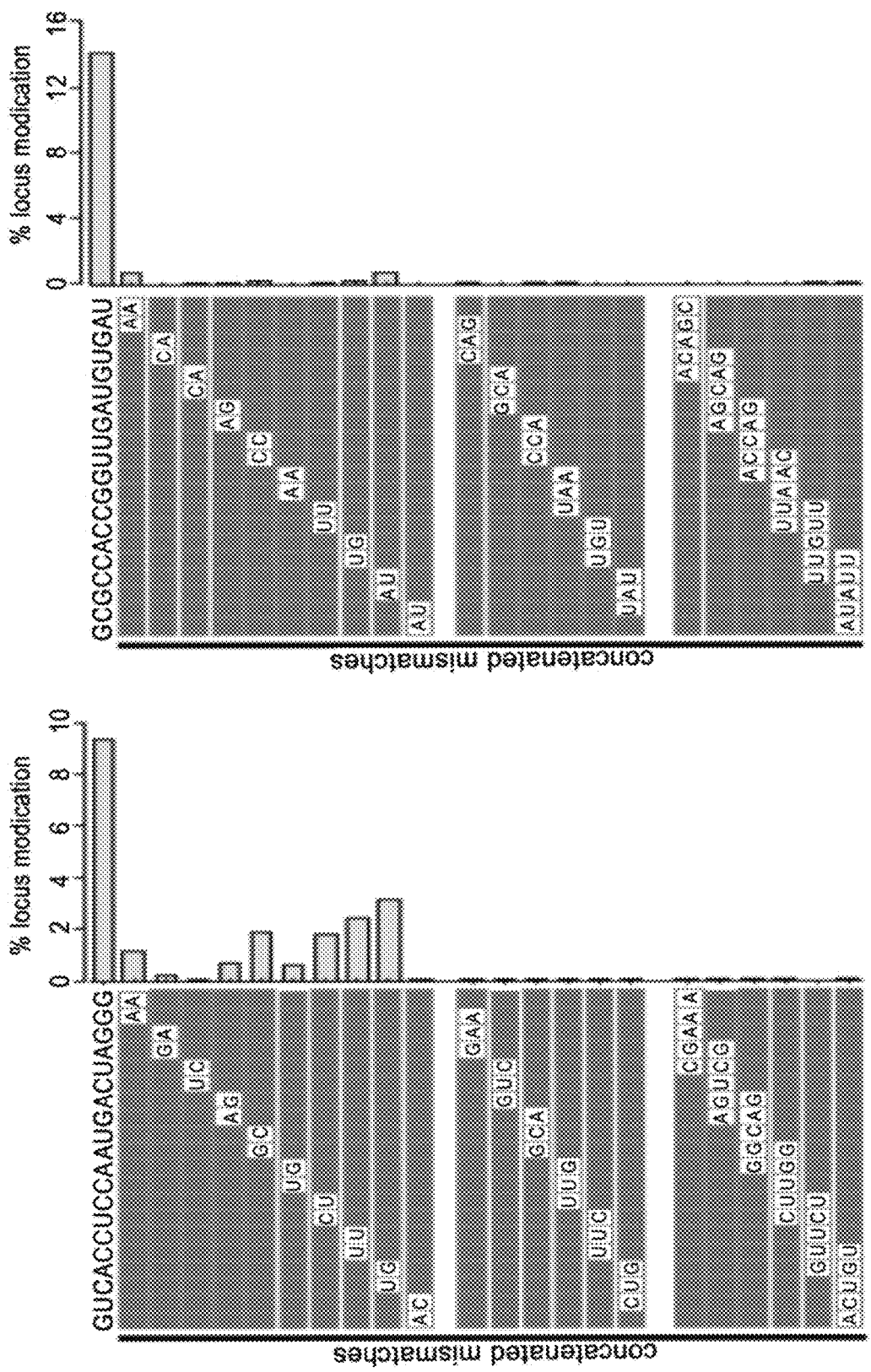

By concatenating blocks of mismatches, Applicants found that two consecutive mismatches within the PAM-proximal sequence reduced Cas9 cutting for both targets to <1% (FIG. 13a; top panels). Target site 1 cutting increased as the double mismatches shifted distally from the PAM, whereas observed cleavage for target site 6 consistently remained <0.5%. Blocks of three or five consecutive mismatches for both targets diminished Cas9 cutting to levels <0.5% regardless of position (FIG. 13, lower panels).

Figure 13B:
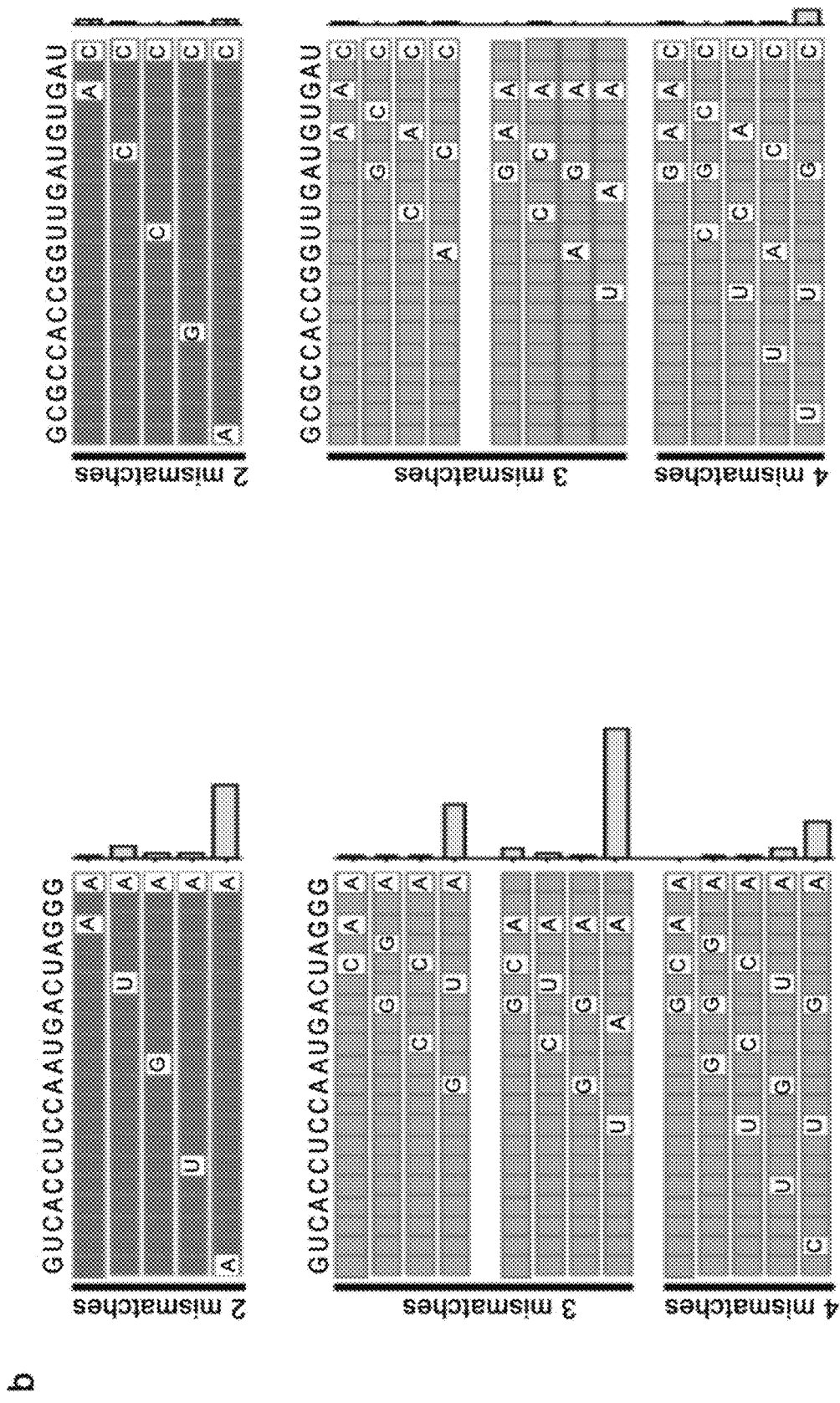

To investigate the effect of mismatch spacing, Applicants anchored a single PAM-proximal mutation while systematically increasing the separation between subsequent mismatches. Groups of 3 or 4 mutations each separated by 3 or fewer bases diminished Cas9 nuclease activity to levels <0.5%. However, Cas9 cutting at target site 1 increased to 3-4% when the mutations were separated by 4 or more unmutated bases (FIG. 13b). Similarly, groups of 4 mutations separated by 4 or more bases led to indel efficiencies from 0.5-1%. However, cleavage at target site 6 consistently remained below 0.5% regardless of the number or spacing of the guide RNA mismatches.

The multiple guide RNA mismatch data indicate that increasing the number of mutations diminishes and eventually abolishes cleavage. Unexpectedly, isolated mutations are tolerated as separation increased between each mismatch. Consistent with the single mismatch data, multiple mutations within the PAM-distal region are generally tolerated by Cas9 while clusters of PAM-proximal mutations are not. Finally, although the mismatch combinations represent a limited subset of base mutations, there appears to be target-specific susceptibility to guide RNA mismatches. For example, target site 6 generally showed lower cleavage with multiple mismatches, a property also reflected in its longer 12-14 bp PAM-proximal region of mutation intolerance (FIG. 12). Further investigation of Cas9 sequence-specificity may reveal design guidelines for choosing more specific DNA targets.

To determine if Applicants' findings from the guide RNA mutation data generalize to target DNA mismatches and allow the prediction of off-target cleavage within the genome, Applicants transfected cells with Cas9 and guide RNAs targeting either target 3 or target 6, and performed deep sequencing of candidate off-target sites with sequence similarity. No genomic loci with only 1 mismatch to either targets was identified. Genomic loci containing 2 or 3 mismatches relative to target 3 or target 6 revealed cleavage at some of the off-targets assessed (FIG. 13c). Targets 3 and 6 exhibited cleavage efficiencies of 7.5% and 8.0%, whereas off-target sites 3-1, 3-2, 3-4, and 3-5 were modified at 0.19%, 0.42%, 0.97%, and 0.50%, respectively. All other off-target sites cleaved at under 0.1% or were modified at levels indistinguishable from sequencing error. The off-target cutting rates were consistent with the collective results from the guide RNA mutation data: cleavage was observed at a small subset of target 3 off-targets that contained either very PAM-distal mismatches or had single mismatches separated by 4 or more bases.

Given that the genome targeting efficiencies of TALENs and ZFNs may be sensitive to confounding effects such as chromatin state or DNA methylation, Applicants sought to test whether RNA-guided SpCas9 cleavage activity would be affected by the epigenetic state of a target locus. To test this, Applicants methylated a plasmid in vitro and performed an in vitro cleavage assay on two pairs of targets containing either unmethylated or methylated CpGs. SpCas9 mediated efficient cleavage of the plasmid whether methylation occurred in the target proper or within the PAM, suggesting that SpCas9 may not be susceptible to DNA methylation effects.

The ability to program Cas9 to target specific sites in the genome by simply designing a short sgRNA has enormous potential for a variety of applications. Applicants' results demonstrate that the specificity of Cas9-mediated DNA cleavage is sequence-dependent and is governed not only by the location of mismatching bases, but also by their spacing. Importantly, while the PAM-proximal 9-12 nt of the guide sequence generally defines specificity, the PAM-distal sequences also contribute to the overall specificity of Cas9-mediated DNA cleavage. Although there are off-target cleavage sites for a given guide sequence, expected off-target sites are likely predictable based on their mismatch locations. Further work looking at the thermodynamics of sgRNA-DNA interaction will likely yield additional predictive power for off-target activity, and exploration of alternative Cas9 orthologs may also yield novel variants of Cas9s with improved specificity. Taken together, the high efficiency of Cas9 as well as its low off-target activity make CRISPR-Cas an attractive genome engineering technology.

Example 6

Use of Cas9 to Target a Variety of Disease Types

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species.

Target selection for sgRNA: There are two main considerations in the selection of the 20-nt guide sequence for gene targeting: 1) the target sequence should precede the 5'-NGG PAM for *S. pyogenes* Cas9, and 2) guide sequences should be chosen to minimize off-target activity. Applicants provided an online Cas9 targeting design tool (available at the website genome-engineering.org/tools; see Examples above and FIG. 23) that takes an input sequence of interest and identifies suitable target sites. To experimentally assess off-target modifications for each sgRNA, Applicants also provide computationally predicted off-target sites for each intended target, ranked according to Applicants" quantitative specificity analysis on the effects of base-pairing mismatch identity, position, and distribution.

The detailed information on computationally predicted off-target sites is as follows: Considerations for Off-target Cleavage Activities: Similar to other nucleases, Cas9 can cleave off-target DNA targets in the genome at reduced frequencies. The extent to which a given guide sequence exhibit off-target activity depends on a combination of factors including enzyme concentration, thermodynamics of the specific guide sequence employed, and the abundance of similar sequences in the target genome. For routine application of Cas9, it is important to consider ways to minimize the degree of off-target cleavage and also to be able to detect the presence of off-target cleavage.

Minimizing off-target activity: For application in cell lines, Applicants recommend following two steps to reduce the degree of off-target genome modification. First, using Applicants' online CRISPR target selection tool, it is possible to computationally assess the likelihood of a given guide sequence to have off-target sites. These analyses are performed through an exhaustive search in the genome for off-target sequences that are similar sequences as the guide sequence. Comprehensive experimental investigation of the effect of mismatching bases between the sgRNA and its target DNA revealed that mismatch tolerance is 1) position dependent—the 8-14 bp on the 3' end of the guide sequence are less tolerant of mismatches than the 5' bases, 2) quantity dependent—in general more than 3 mismatches are not tolerated, 3) guide sequence dependent—some guide sequences are less tolerant of mismatches than others, and 4) concentration dependent—off-target cleavage is highly sensitive to the amount of transfected DNA. The Applicants' target site analysis web tool (available at the website genome-engineering.org/tools) integrates these criteria to provide predictions for likely off-target sites in the target genome. Second, Applicants recommend titrating the amount of Cas9 and sgRNA expression plasmid to minimize off-target activity.

Detection of off-target activities: Using Applicants' CRISPR targeting web tool, it is possible to generate a list of most likely off-target sites as well as primers performing SURVEYOR or sequencing analysis of those sites. For isogenic clones generated using Cas9, Applicants strongly recommend sequencing these candidate off-target sites to check for any undesired mutations. It is worth noting that there may be off target modifications in sites that are not included in the predicted candidate list and full genome sequence should be performed to completely verify the absence of off-target sites. Furthermore, in multiplex assays where several DSBs are induced within the same genome, there may be low rates of translocation events and can be evaluated using a variety of techniques such as deep sequencing (48).

The online tool (FIG. 23) provides the sequences for all oligos and primers necessary for 1) preparing the sgRNA constructs, 2) assaying target modification efficiency, and 3) assessing cleavage at potential off-target sites. It is worth noting that because the U6 RNA polymerase III promoter used to express the sgRNA prefers a guanine (G) nucleotide as the first base of its transcript, an extra G is appended at the 5' of the sgRNA where the 20-nt guide sequence does not begin with G (FIG. 24).

Example 7

Base Pair Mismatching Investigations

Applicants tested whether extension of the tracrRNA tail was able to improve SpCas9 activity. Applicants generated a set of sgRNAs targeting multiple sites within the human EMX1 and PVALB loci with different tracrRNA 3' truncations (FIG. 9*a*). Using the SURVEYOR nuclease assay, Applicants assessed the ability of each Cas9 sgRNA complex to generate indels in HEK 293FT cells through the induction of DNA double-stranded breaks (DSBs) and subsequent non-homologous end joining (NHEJ) DNA damage repair (Methods and Materials). sgRNAs with +67 or +85 nucleotide (nt) tracrRNA tails mediated DNA cleavage at all target sites tested, with up to 5-fold higher levels of indels than the corresponding crRNA-tracrRNA duplexes (FIG. 9). Furthermore, both sgRNA designs efficiently modified PVALB loci that were previously not targetable using crRNA-tracrRNA duplexes (1) (FIG. 9*b* and FIG. 9*b*). For all five tested targets, Applicants observed a consistent increase in modification efficiency with increasing tracrRNA length. Applicants performed Northern blots for the guide RNA truncations and found increased levels expression for the longer tracrRNA sequences, suggesting that improved target cleavage was due to higher sgRNA expression or stability (FIG. 9*c*). Taken together, these data indicate that the tracrRNA tail is important for optimal SpCas9 expression and activity in vivo.

Applicants have previously shown that a catalytic mutant of SpCas9 (D10A nickase) can mediate gene editing by homology-directed repair (HR) without detectable indel formation. Given its higher cleavage efficiency, Applicants tested whether sgRNA(+85), in complex with the Cas9 nickase, can likewise facilitate HR without incurring on-target NHEJ. Using single-stranded oligonucleotides (ssODNs) as repair templates, Applicants observed that both the wild-type and the D10A SpCas9 mediate HR in HEK 293FT cells, while only the former is able to do so in human embryonic stem cells (hESCs; FIG. 9*d*).

To explore whether the genome targeting ability of sgRNA(+85) is influenced by epigenetic factors that constrain the alternative transcription activator-like effector nuclease (TALENs) and potentially also zinc finger nuclease (ZFNs) technologies, Applicants further tested the ability of SpCas9 to cleave methylated DNA. Using either unmethylated or M. SssI-methylated pUC19 as DNA targets (FIG. 14*a,b*) in a cell-free cleavage assay, Applicants showed that SpCas9 efficiently cleaves pUC19 regardless of CpG methylation status in either the 20-bp target sequence or the PAM. To test whether this is also true in vivo, Applicants designed sgRNAs to target a highly methylated region of the human SERPINB5 locus (FIG. 9*e,f*). All three sgRNAs tested were able to mediate indel mutations in endogenously methylated targets (FIG. 9*g*).

Applicants systematically investigated the effect of base-pairing mismatches between guide RNA sequences and target DNA on target modification efficiency. Applicants chose four target sites within the human EMX1 gene and, for each, generated a set of 57 different guide RNAs containing all possible single nucleotide substitutions in positions 1-19 directly 5' of the requisite NGG PAM (FIG. 25*a*). The 5' guanine at position 20 is preserved, given that the U6 promoter requires guanine as the first base of its transcript. These 'off-target' guide RNAs were then assessed for cleavage activity at the on-target genomic locus.

Consistent with previous findings, SpCas9 tolerates single base mismatches in the PAM-distal region to a greater extent than in the PAM-proximal region. In contrast with a model that implies a prototypical 10-12 bp PAM-proximal seed sequence that determines target specificity, Applicants found that most bases within the target site are specifically recognized, although mismatches are tolerated at different positions in a sequence-context dependent manner. Single-base specificity generally ranges from 8 to 12 bp immediately upstream of the PAM, indicating a sequence-dependent specificity boundary that varies in length (FIG. 25b).

To further investigate the contributions of base identity and position within the guide RNA to SpCas9 specificity, Applicants generated additional sets of mismatched guide RNAs for eleven more target sites within the EMX1 locus (FIG. 28) totaling over 400 sgRNAs. These guide RNAs were designed to cover all 12 possible RNA:DNA mismatches for each position in the guide sequence with at least 2× coverage for positions 1-10. Applicants' aggregate single mismatch data reveals multiple exceptions to the seed sequence model of SpCas9 specificity (FIG. 25c). In general, mismatches within the 8-12 PAM-proximal bases were less tolerated by SpCas9, whereas those in the PAM-distal regions had little effect on SpCas9 cleavage. Within the PAM-proximal region, the degree of tolerance varied with the identity of a particular mismatch, with rC:dC base-pairing exhibiting the highest level of disruption to SpCas9 cleavage (FIG. 25c).

In addition to the target specificity, Applicants also investigated the NGG PAM requirement of SpCas9. To vary the second and third positions of PAM, Applicants selected 32 target sites within the EMX1 locus encompassing all 16 possible alternate PAMs with 2× coverage (Table 4). Using SURVEYOR assay, Applicants showed that SpCas9 also cleaves targets with NAG PAMs, albeit 5-fold less efficiently than target sites with NGG PAMs (FIG. 25d). The tolerance for an NAG PAM is in agreement with previous bacterial studies (12) and expands the S. pyogenes Cas9 target space to every 4-bp on average within the human genome, not accounting for constraining factors such as guide RNA secondary structure or certain epigenetic modifications (FIG. 25e).

Figure 26A:
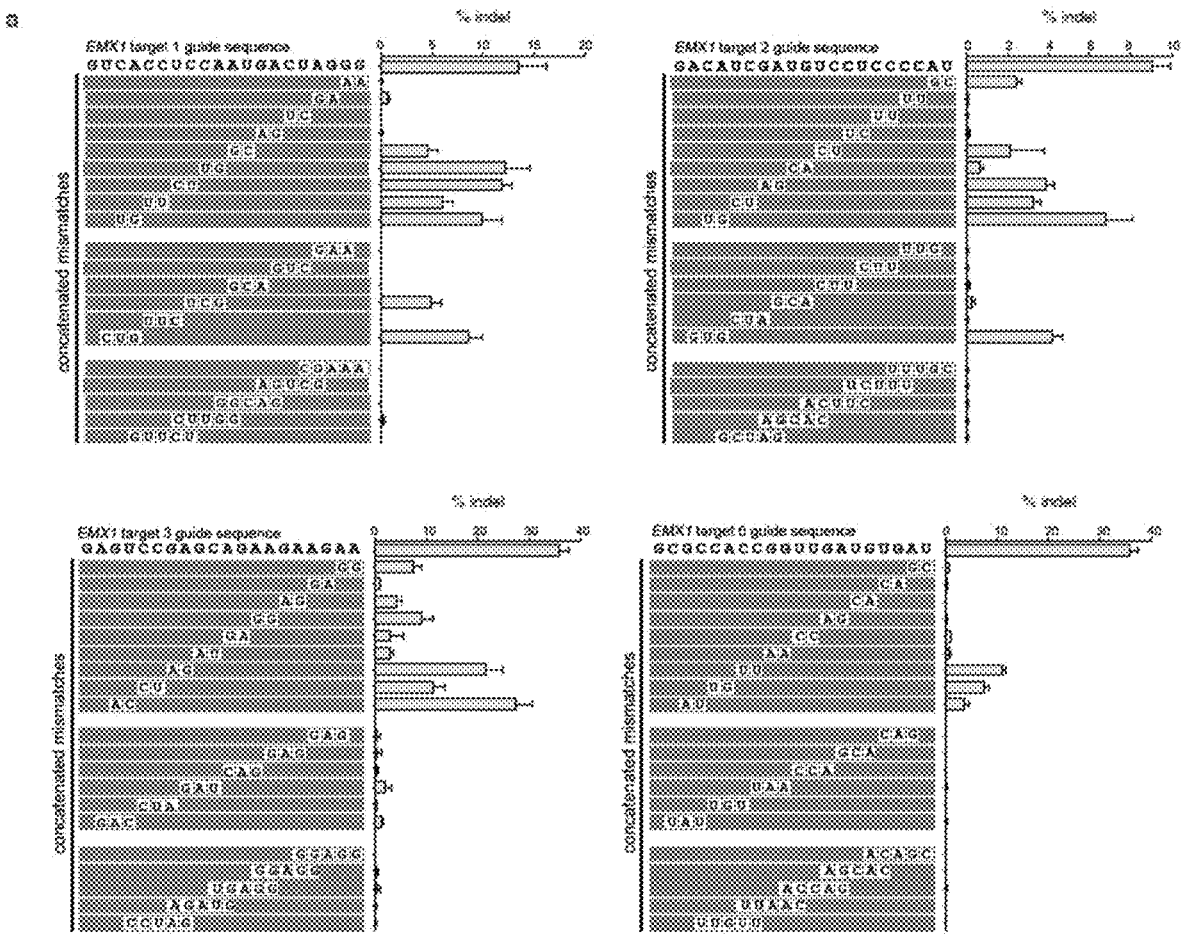
FIG. 26A-C shows the multiple mismatch specificity of SpCas9. (a) SpCas9 cleavage efficiency with guide RNAs containing a, consecutive mismatches of 2, 3, or 5 bases, or (b, c) multiple mismatches separated by different numbers of unmutated bases for EMX1 targets 1, 2, 3, and 6. Rows represent each mutated guide RNA; nucleotide substitutions are shown in white cells; grey cells denote unmutated bases. All indel frequencies are absolute and analyzed by deep sequencing from 2 biological replicas. Error bars indicate Wilson intervals (Example 7, Methods and Materials)

Applicants next explored the effect of multiple base mismatches on SpCas9 target activity. For four targets within the EMX1 gene, Applicants designed sets of guide RNAs that contained varying combinations of mismatches to investigate the effect of mismatch number, position, and spacing on SpCas9 target cleavage activity (FIG. 26a, b).

In general, Applicants observed that the total number of mismatched base-pairs is a key determinant for SpCas9 cleavage efficiency. Two mismatches, particularly those occurring in a PAM-proximal region, significantly reduced SpCas9 activity whether these mismatches are concatenated or interspaced (FIG. 26a, b); this effect is further magnified for three concatenated mismatches (FIG. 20a). Furthermore, three or more interspaced (FIG. 26c) and five concatenated (FIG. 26a) mismatches eliminated detectable SpCas9 cleavage in the vast majority of loci.

Figure 26B:
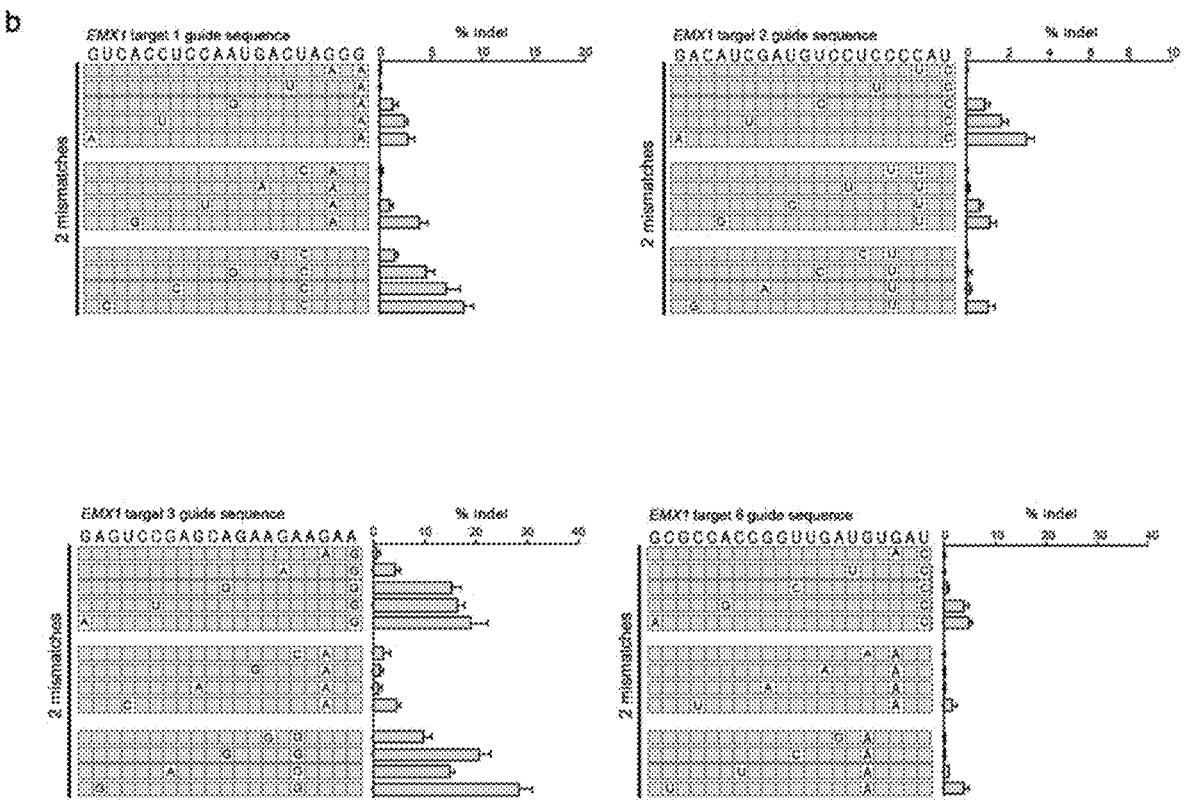
Figure 26C:
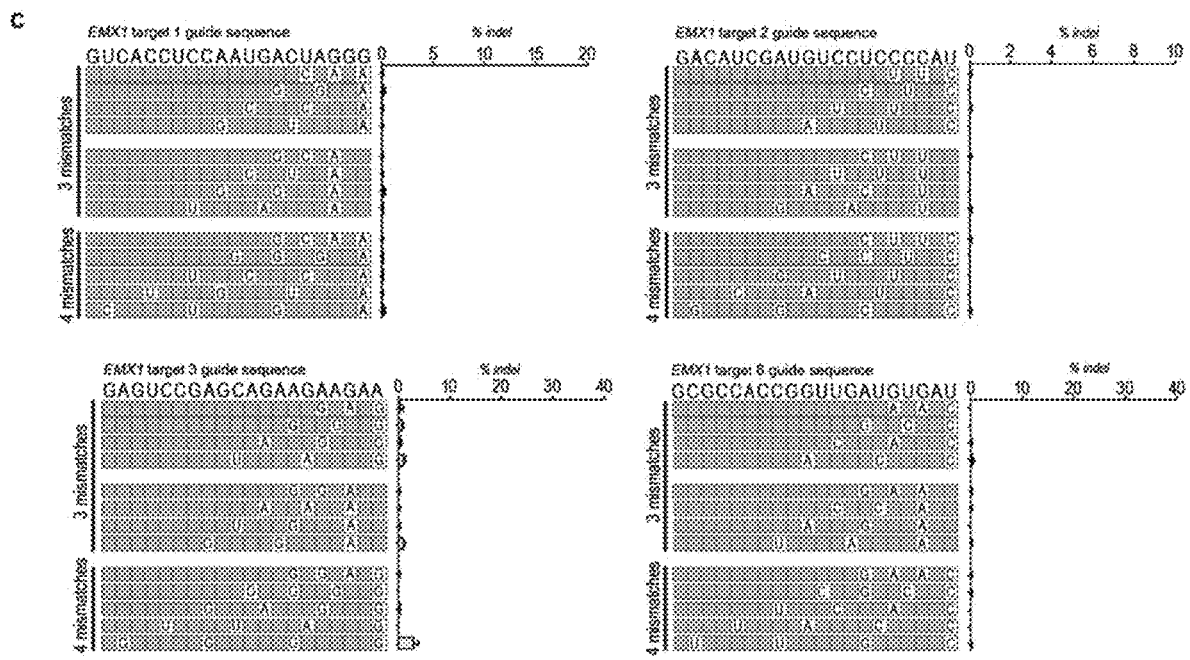

The position of mismatches within the guide sequence also affected the activity of SpCas9: PAM-proximal mismatches are less tolerated than PAM-distal counterparts (FIG. 26a), recapitulating Applicants' observations from the single base-pair mismatch data (FIG. 25c). This effect is particularly salient in guide sequences bearing a small number of total mismatches, whether those are concatenated (FIG. 26a) or interspaced (FIG. 26b). Additionally, guide sequences with mismatches spaced four or more bases apart also mediated SpCas9 cleavage in some cases (FIG. 26c). Thus, together with the identity of mismatched base-pairing, Applicants observed that many off-target cleavage effects can be explained by a combination of mismatch number and position.

Given these mismatched guide RNA results, Applicants expected that for any particular sgRNA, SpCas9 may cleave genomic loci that contain small numbers of mismatched bases. For the four EMX1 targets described above, Applicants computationally identified 117 candidate off-target sites in the human genome that are followed by a 5'-NRG PAM and meet any of the additional following criteria: 1. up to 5 mismatches, 2. short insertions or deletions, or 3. mismatches only in the PAM-distal region. Additionally, Applicants assessed off-target loci of high sequence similarity without the PAM requirement. The majority of off-target sites tested for each sgRNA (30/31, 23/23, 48/51, and 12/12 sites for EMX1 targets 1, 2, 3, and 6, respectively) exhibited modification efficiencies at least 100-fold lower than that of corresponding on-targets (FIG. 27a, b). Of the four off-target sites identified, three contained only mismatches in the PAM-distal region, consistent with the Applicants' multiple mismatch sgRNA observations (FIG. 26). Notably, these three loci were followed by 5'-NAG PAMs, demonstrating that off-target analyses of SpCas9 must include 5'-NAG as well as 5'-NGG candidate loci.

Enzymatic specificity and activity strength are often highly dependent on reaction conditions, which at high reaction concentration might amplify off-target activity (26, 27). One potential strategy for minimizing non-specific cleavage is to limit the enzyme concentration, namely the level of SpCas9-sgRNA complex. Cleavage specificity, measured as a ratio of on- to off-target cleavage, increased dramatically as Applicants decreased the equimolar amounts of SpCas9 and sgRNA transfected into 293FT cells (FIG. 27c, d) from $7.1 \times 10^{-10}$ to $1.8 \times 10^{-11}$ nmoL/cell (400 ng to 10 ng of Cas9-sgRNA plasmid). qRT-PCR assay confirmed that the level of hSpCas9 mRNA and sgRNA decreased proportionally to the amount of transfected DNA. Whereas specificity increased gradually by nearly 4-fold as Applicants decreased the transfected DNA amount from $7.1 \times 10^{-10}$ to $9.0 \times 10^{-11}$ nmol/cell (400 ng to 50 ng plasmid), Applicants observed a notable additional 7-fold increase in specificity upon decreasing transfected DNA from $9.0 \times 10^{-11}$ to $1.8 \times 10^{-11}$ nmol/cell (50 ng to 10 ng plasmid; FIG. 27c). These findings suggest that Applicants may minimize the level of off-target activity by titrating the amount of SpCas9 and sgRNA DNA delivered. However, increasing specificity by reducing the amount of transfected DNA also leads to a reduction in on-target cleavage. These measurements enable quantitative integration of specificity and efficiency criteria into dosage choice to optimize SpCas9 activity for different applications. Applicants further explore modifications in SpCas9 and sgRNA design that may improve the intrinsic specificity without sacrificing cleavage efficiency. FIG. 29 shows data for EMX1 target 2 and target 6. For the tested sites in FIGS. 27 and 29 (in this case, sites with 3 mismatches or less), there were no off-target sites identified (defined as off-target site cleavage within 100-fold of the on-target site cleavage).

The ability to program SpCas9 to target specific sites in the genome by simply designing a short sgRNA holds enormous potential for a variety of applications. Applicants' results demonstrate that the specificity of SpCas9-mediated DNA cleavage is sequence- and locus-dependent and governed by the quantity, position, and identity of mismatching bases. Importantly, while the PAM-proximal 8-12 bp of the guide sequence generally defines specificity, the PAM-distal sequences also contribute to the overall specificity of SpCas9-mediated DNA cleavage. Although there may be off-target cleavage for a given guide sequence, they can be predicted and likely minimized by following general design guidelines.

To maximize SpCas9 specificity for editing a particular gene, one should identify potential 'off-target' genomic sequences by considering the following four constraints: First and foremost, they should not be followed by a PAM with either 5'-NGG or 5'-NAG sequences. Second, their global sequence similarity to the target sequence should be minimized, and guide sequences with genomic off-target loci that have fewer than 3 mismatches should be avoided. Third, at least 2 mismatches should lie within the PAM-proximal region of the off-target site. Fourth, a maximal number of mismatches should be consecutive or spaced less than four bases apart. Finally, the amount of SpCas9 and sgRNA may be titrated to optimize on- to off-target cleavage ratio.

Figure 30:
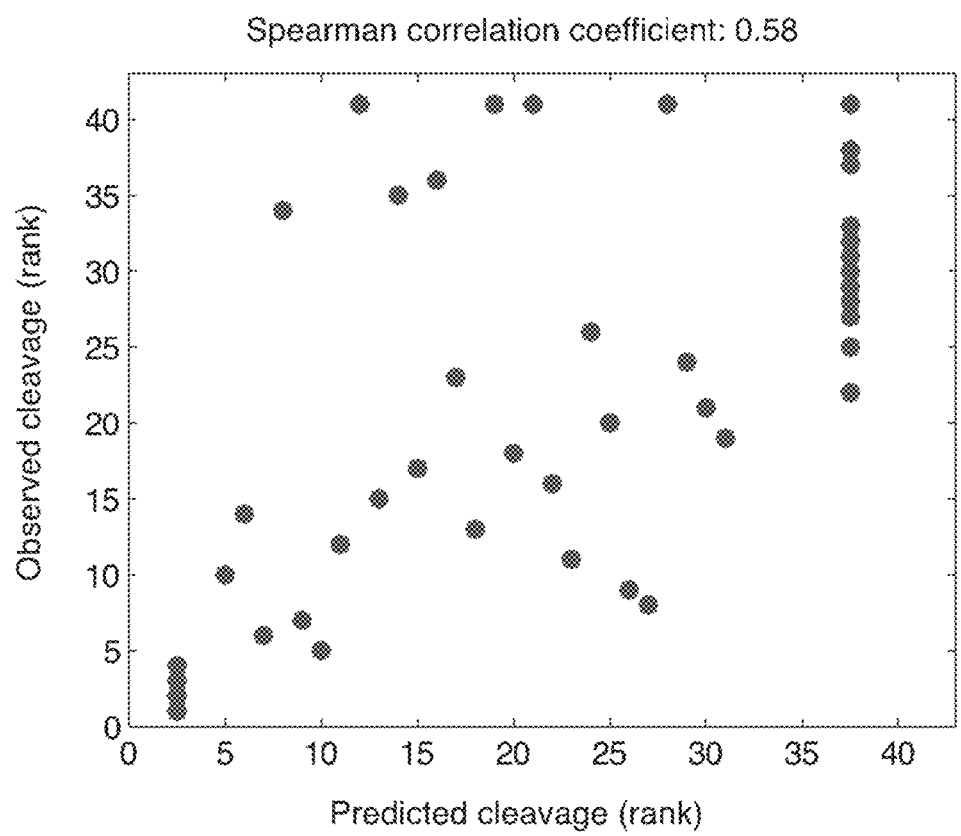
FIG. 30 shows predicted and observed cutting frequency-ranks among genome-wide targets.

Using these criteria, Applicants formulated a simple scoring scheme to integrate the contributions of mismatch location, density, and identity for quantifying their contribution to SpCas9 cutting. Applicants applied the aggregate cleavage efficiencies of single-mismatch guide RNAs to test this scoring scheme separately on genome-wide targets. Applicants found that these factors, taken together, accounted for more than 50% of the variance in cutting-frequency rank among the genome-wide targets studied (FIG. 30).

Implementing the guidelines delineated above, Applicants designed a computational tool to facilitate the selection and validation of sgRNAs as well as to predict off-target loci for specificity analyses; this tool may be accessed at the website genome-engineering.org/tools. These results and tools further extend the SpCas9 system as a powerful and versatile alternative to ZFNs and TALENs for genome editing applications. Further work examining the thermodynamics and in vivo stability of sgRNA-DNA duplexes will likely yield additional predictive power for off-target activity, while exploration of SpCas9 mutants and orthologs may yield novel variants with improved specificity. Accession codes All raw reads can be accessed at NCBI BioProject, accession number SRP023129.

Methods and Materials:

Cell culture and transfection—Human embryonic kidney (HEK) cell line 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 µg/mL streptomycin at 37° C. with 5% CO2 incubation.

293FT cells were seeded either onto 6-well plates, 24-well plates, or 96-well plates (Corning) 24 hours prior to transfection. Cells were transfected using Lipofectamine 2000 (Life Technologies) at 80-90% confluence following the manufacturer's recommended protocol. For each well of a 6-well plate, a total of 1 ug of Cas9+sgRNA plasmid was used. For each well of a 24-well plate, a total of 500 ng Cas9+sgRNA plasmid was used unless otherwise indicated. For each well of a 96-well plate, 65 ng of Cas9 plasmid was used at a 1:1 molar ratio to the U6-sgRNA PCR product.

Human embryonic stem cell line HUES9 (Harvard Stem Cell Institute core) was maintained in feeder-free conditions on GelTrex (Life Technologies) in mTesR medium (Stemcell Technologies) supplemented with 100 ug/ml Normocin (InvivoGen). HUES9 cells were transfected with Amaxa P3 Primary Cell 4-D Nucleofector Kit (Lonza) following the manufacturer's protocol.

SURVEYOR Nuclease Assay for Genome Modification 293FT cells were transfected with plasmid DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes and 98° C. for 10 minutes.

The genomic region flanking the CRISPR target site for each gene was PCR amplified (primers listed in Table 2), and products were purified using QiaQuick Spin Column (Qiagen) following the manufacturer's protocol. 400 ng total of the purified PCR products were mixed with 2 µl 10×Taq DNA Polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities.

Northern blot analysis of tracrRNA expression in human cells: Northern blots were performed as previously described 1. Briefly, RNAs were heated to 95° C. for 5 min before loading on 8% denaturing polyacrylamide gels (SequaGel, National Diagnostics). Afterwards, RNA was transferred to a pre-hybridized Hybond N+ membrane (GE Healthcare) and crosslinked with Stratagene UV Crosslinker (Stratagene). Probes were labeled with [gamma-32P] ATP (Perkin Elmer) with T4 polynucleotide kinase (New England Biolabs). After washing, membrane was exposed to phosphor screen for one hour and scanned with phosphorimager (Typhoon).

Bisulfite sequencing to assess DNA methylation status: HEK 293FT cells were transfected with Cas9 as described above. Genomic DNA was isolated with the DNeasy Blood & Tissue Kit (Qiagen) and bisulfite converted with EZ DNA Methylation-Lightning Kit (Zymo Research). Bisulfite PCR was conducted using KAPA2G Robust HotStart DNA Polymerase (KAPA Biosystems) with primers designed using the Bisulfite Primer Seeker (Zymo Research, Table 6). Resulting PCR amplicons were gel-purified, digested with EcoRI and HindIII, and ligated into a pUC19 backbone prior to transformation. Individual clones were then Sanger sequenced to assess DNA methylation status.

In vitro transcription and cleavage assay: HEK 293FT cells were transfected with Cas9 as described above. Whole cell lysates were then prepared with a lysis buffer (20 mM HEPES, 100 mM KCl, 5 mM MgCl2, 1 mM DTT, 5% glycerol, 0.1% Triton X-100) supplemented with Protease Inhibitor Cocktail (Roche). T7-driven sgRNA was in vitro transcribed using custom oligos (Sequences) and HiScribe T7 In Vitro Transcription Kit (NEB), following the manufacturer's recommended protocol. To prepare methylated target sites, pUC19 plasmid was methylated by M.SssI and then linearized by NheI. The in vitro cleavage assay was performed as follows: for a 20 uL cleavage reaction, 10 uL of cell lysate with incubated with 2 uL cleavage buffer (100 mM HEPES, 500 mM KCl, 25 mM MgCl2, 5 mM DTT, 25% glycerol), the in vitro transcribed RNA, and 300 ng pUC19 plasmid DNA.

Deep sequencing to assess targeting specificity: HEK 293FT cells plated in 96-well plates were transfected with Cas9 plasmid DNA and single guide RNA (sgRNA) PCR cassette 72 hours prior to genomic DNA extraction (FIG. 14). The genomic region flanking the CRISPR target site for each gene was amplified by a fusion PCR method to attach the Illumina P5 adapters as well as unique sample-specific barcodes to the target amplicons. PCR products were purified using EconoSpin 96-well Filter Plates (Epoch Life Sciences) following the manufacturer's recommended protocol.

Barcoded and purified DNA samples were quantified by Quant-iT PicoGreen dsDNA Assay Kit or Qubit 2.0 Fluorometer (Life Technologies) and pooled in an equimolar ratio. Sequencing libraries were then deep sequenced with the Illumina MiSeq Personal Sequencer (Life Technologies).

Sequencing data analysis and indel detection: MiSeq reads were filtered by requiring an average Phred quality (Q score) of at least 23, as well as perfect sequence matches to barcodes and amplicon forward primers. Reads from on- and off-target loci were analyzed by first performing Smith-Waterman alignments against amplicon sequences that included 50 nucleotides upstream and downstream of the target site (a total of 120 bp). Alignments, meanwhile, were analyzed for indels from 5 nucleotides upstream to 5 nucleotides downstream of the target site (a total of 30 bp). Analyzed target regions were discarded if part of their alignment fell outside the MiSeq read itself, or if matched base-pairs comprised less than 85% of their total length.

Negative controls for each sample provided a gauge for the inclusion or exclusion of indels as putative cutting events. For each sample, an indel was counted only if its quality score exceeded $\mu-\sigma$, where $\mu$ was the mean quality-score of the negative control corresponding to that sample and $\sigma$ was the standard deviation of same. This yielded whole target-region indel rates for both negative controls and their corresponding samples. Using the negative control's per-target-region-per-read error rate, q, the sample's observed indel count n, and its read-count R, a maximum-likelihood estimate for the fraction of reads having target-regions with true-indels, p, was derived by applying a binomial error model, as follows.

Letting the (unknown) number of reads in a sample having target regions incorrectly counted as having at least 1 indel be E, Applicants can write (without making any assumptions about the number of true indels)

$$Prob(E \mid p) = \binom{R(1-p)}{E} q^E (1-q)^{R(1-p)-E}$$

since R(1−p) is the number of reads having target-regions with no true indels. Meanwhile, because the number of reads observed to have indels is n, n=E+Rp, in other words the number of reads having target-regions with errors but no true indels plus the number of reads whose target-regions correctly have indels. Applicants can then re-write the above $$Prob(E \mid p) = Prob(n = E + Rp \mid p) = \binom{R(1-p)}{n-Rp} q^{n-Rp}(1-q)^{R-n}$$

Taking all values of the frequency of target-regions with true-indels p to be equally probable a priori, $Prob(n|p) \propto Prob(p|n)$. The maximum-likelihood estimate (MLE) for the frequency of target regions with true-indels was therefore set as the value of p that maximized Prob(n|p). This was evaluated numerically.

In order to place error bounds on the true-indel read frequencies in the sequencing libraries themselves, Wilson score intervals (2) were calculated for each sample, given the MLE-estimate for true-indel target-regions, Rp, and the number of reads R. Explicitly, the lower bound l and upper bound u were calculated as $$l = \left(Rp + \frac{z^2}{2} - z\sqrt{Rp(1-p) + z^2/4}\right) \Big/ (R + z^2)$$

$$u = \left(Rp + \frac{z^2}{2} + z\sqrt{Rp(1-p) + z^2/4}\right) \Big/ (R + z^2)$$

where z, the standard score for the confidence required in normal distribution of variance 1, was set to 1.96, meaning a confidence of 95%.

qRT-PCR analysis of relative Cas9 and sgRNA expression: 293FT cells plated in 24-well plates were transfected as described above. 72 hours post-transfection, total RNA was harvested with miRNeasy Micro Kit (Qiagen). Reverse-strand synthesis for sgRNAs was performed with qScript Flex cDNA kit (VWR) and custom first-strand synthesis primers (Table 6). qPCR analysis was performed with Fast SYBR Green Master Mix (Life Technologies) and custom primers (Table 2), using GAPDH as an endogenous control. Relative quantification was calculated by the $\Delta\Delta$CT method.

TABLE 1

Target site sequences. Tested target sites for *S. pyogenes* type II CRISPR system with the requisite PAM. Cells were transfected with Cas9 and either crRNA-tracrRNA or chimeric sgRNA for each target.

| Target site ID | genomic target | Target site sequence (5' to 3') | PAM | strand |
|---|---|---|---|---|
| 1 | EMX1 | GTCACCTCCAATGACTAGGG | TGG | + |
| 2 | EMX1 | GACATCGATGTCCTCCCCAT | TGG | − |
| 3 | EMX1 | GAGTCCGAGCAGAAGAAGAA | GGG | + |
| 6 | EMX1 | GCGCCACCGGTTGATGTGAT | GGG | − |
| 10 | EMX1 | GGGGCACAGATGAGAAACTC | AGG | − |
| 11 | EMX1 | GTACAAACGGCAGAAGCTGG | AGG | + |
| 12 | EMX1 | GGCAGAAGCTGGAGGAGGAA | GGG | + |
| 13 | EMX1 | GGAGCCCTTCTTCTTCTGCT | CGG | − |
| 14 | EMX1 | GGGCAACCACAAACCCACGA | GGG | + |
| 15 | EMX1 | GCTCCCATCACATCAACCGG | TGG | + |
| 16 | EMX1 | GTGGCGCATTGCCACGAAGC | AGG | + |
| 17 | EMX1 | GGCAGAGTGCTGCTTGCTGC | TGG | + |
| 18 | EMX1 | GCCCCTGCGTGGGCCCAAGC | TGG | + |
| 19 | EMX1 | GAGTGGCCAGAGTCCAGCTT | GGG | − |
| 20 | EMX1 | GGCCTCCCCAAAGCCTGGCC | AGG | − |
| 4 | PVALB | GGGGCCGAGATTGGGTGTTC | AGG | + |
| 5 | PVALB | GTGGCGAGAGGGGCCGAGAT | TGG | + |
| 1 | SERPINB5 | GAGTGCCGCCGAGGCGGGC | GGG | + |

TABLE 1-continued

Target site sequences. Tested target sites for *S. pyogenes* type II CRISPR system with the requisite PAM. Cells were transfected with Cas9 and either crRNA-tracrRNA or chimeric sgRNA for each target.

| Target site ID | genomic target | Target site sequence (5' to 3') | PAM | strand |
|---|---|---|---|---|
| 2 | SERPINB5 | GGAGTGCCGCCGAGGCGGGG | CGG | + |
| 3 | SERPINB5 | GGAGAGGAGTGCCGCCGAGG | CGG | + |

TABLE 2

Primer sequences

SURVEYOR assay

| primer name | genomic target | primer sequence (5' to 3') |
|---|---|---|
| Sp-EMX1-F1 | EMX1 | AAAACCACCCTTCTCTCTGGC |
| Sp-EMX1-R1 | EMX1 | GGAGATTGGAGACACGGAGAG |
| Sp-EMX1-F2 | EMX1 | CCATCCCCTTCTGTGAATGT |
| Sp-EMX1-R2 | EMX1 | GGAGATTGGAGACACGGAGA |
| Sp-PVALB-F | PVALB | CTGGAAAGCCAATGCCTGAC |
| Sp-PVALB-R | PVALB | GGCAGCAAACTCCTTGTCCT |

| primer name | primer sequence (5' to 3') |
|---|---| qRT-PCR for Cas9 and sgRNA expression

| sgRNA reverse-strand synthesis | AAGCACCGACTCGGTGCCAC |
|---|---|
| EMX1.1 sgRNA qPCR F | TCACCTCCAATGACTAGGGG |
| EMX1.1 sgRNA qPCR R | CAAGTTGATAACGGACTAGCCT |
| EMX1.3 sgRNA qPCR F | AGTCCGAGCAGAAGAAGAAGTTT |
| EMX1.3 sgRNA qPCR R | TTTCAAGTTGATAACGGACTAGCCT |
| Cas9 qPCR F | AAACAGCAGATTCGCCTGGA |
| Cas9 qPCR R | TCATCCGCTCGATGAAGCTC |
| GAPDH qPCR F | TCCAAAATCAAGTGGGGCGA |
| GAPDH qPCR R | TGATGACCCTTTTGGCTCCC |

Bisulfite PCR and sequencing

| Bisulfite PCR F (SERPINB5 locus) | GAGGAATTCTTTTTTTGTTYGAATATGTTGGAGGTTTTTTGGAAG |
|---|---|
| Bisulfite PCR R (SERPINB5 locus) | GAGAAGCTTAAATAAAAAACRACAATACTCAACCCAACAACC |
| pUC19 sequencing | CAGGAAACAGCTATGAC |

TABLE 3

Sequences for primers to test sgRNA architecture. Primers hybridize to the reverse strand of the U6 promoter unless otherwise indicated. The U6 priming site is in bold, the guide sequence is indicated by the stretch of "N"s, the direct repeat sequence is in italics, and the tracrRNA sequence is underlined. The secondary structure of each sgRNA architecture is shown in FIG. 71.

| primer name | primer sequence (5' to 3') |
|---|---|
| U6-Forward | GCCTCTAGAGGTACCTGAGGGCCTATTTCCCATGATTCC |
| I: sgRNA (DR + 12, tracrRNA + 85) | ACCTCTAGA<u>AAAAAAAGCACCGACTCGGTGCCACTTTTTCAAGTTGATAACGGACTAGCCTTATTTTAACTTGCTATTT</u>*CTAGCTCTAAAAC*NNNNNNNNNNNNNNNNNNNNGGTGTTTCGTCCTTTCCACAAG |
| II: sgRNA (DR + 12, tracrRNA + 85) mut2 | ACCTCTAGA<u>AAAAAAAGCACCGACTCGGTGCCACTTTTTCAAGTTGATAACGGACTAGCCTTATATTAACTTGCTATTT</u>*CTAGCTCTAATAC*NNNNNNNNNNNNNNNNNNNNGGTGTTTCGTCCTTTCCACAAG |
| III: sgRNA (DR + 22, tracrRNA + 85) | ACCTCTAGA<u>AAAAAAAGCACCGACTCGGTGCCACTTTTTCAAGTTGATAACGGACTAGCCTTATTTTAACTTGCTATGCTGTTTTGTTTCCAAAACAGCATAGCT</u>*CTAAAAC*NNNNNNNNNNNNNNNNNNNNGGTGTTTCGTCCTTTCCACAAG |
| IV: sgRNA (DR + 22, tracrRNA + 85) mut4 | ACCTCTAGA<u>AAAAAAAGCACCGACTCGGTGCCACTTTTTCAAGTTGATAACGGACTAGCCTTATATTAACTTGCTATGCTGTATTGTTTCCAATACAGCATAGCT</u>*CTAATAC*NNNNNNNNNNNNNNNNNNNNGGTGTTTCGTCCTTTCCACAAG |

TABLE 4

Target sites with alternate PAMs for testing PAM specificity of Cas9. All target sites for PAM specificity testing are found within the human EMX1 locus.

| Target site sequence (5' to 3') | PAM |
|---|---|
| AGGCCCCAGTGGCTGCTCT | NAA |
| ACATCAACCGGTGGCGCAT | NAT |
| AAGGTGTGGTTCCAGAACC | NAC |
| CCATCACATCAACCGGTGG | NAG |
| AAACGGCAGAAGCTGGAGG | NTA |
| GGCAGAAGCTGGAGGAGGA | NTT |
| GGTGTGGTTCCAGAACCGG | NTC |
| AACCGGAGGACAAAGTACA | NTG |
| TTCCAGAACCGGAGGACAA | NCA |
| GTGTGGTTCCAGAACCGGA | NCT |
| TCCAGAACCGGAGGACAAA | NCC |
| CAGAAGCTGGAGGAGGAAG | NCG |

TABLE 4-continued

Target sites with alternate PAMs for testing PAM specificity of Cas9. All target sites for PAM specificity testing are found within the human EMX1 locus.

| Target site sequence (5' to 3') | PAM |
| --- | --- |
| CATCAACCGGTGGCGCATT | NGA |
| GCAGAAGCTGGAGGAGGAA | NGT |
| CCTCCCTCCCTGGCCGAGG | NGC |
| TCATCTGTGCCCCTCCCTC | NAA |
| GGGAGGACATCGATGTCAC | NAT |
| CAAACGGCAGAAGCTGGAG | NAC |
| GGGTGGGCAACCACAAACC | NAG |
| GGTGGGCAACCACAAACCC | NTA |
| GGCTCCCATCACATCAACC | NTT |
| GAAGGGCCTGAGTCCGAGC | NTC |
| CAACCGGTGGCGCATTGCC | NTG |
| AGGAGGAAGGGCCTGAGTC | NCA |
| AGCTGGAGGAGGAAGGGCC | NCT |
| GCATTGCCACGAAGCAGGC | NCC |
| ATTGCCACGAAGCAGGCCA | NCG |
| AGAACCGGAGGACAAAGTA | NGA |
| TCAACCGGTGGCGCATTGC | NGT |
| GAAGCTGGAGGAGGAAGGG | NGC |

Sequences

All sequences are in the 5' to 3' direction. For U6 transcription, the string of underlined Ts serve as the transcriptional terminator.

> U6-short tracrRNA (Streptococcus pyogenes SF370)
gagggcctatttcccatgattccttcatatttgcatatacgatacaagga gttagagagataattggaattaatttgactgtaaacacaaagatattagt acaaaatacgtgacgtagaaagtaataatttcttgggtagtttgcagttt taaaattatgttttaaaatggactatcatatgcttaccgtaacttgaaag tatttcgatttcaggctttatatatcagtggaaaggacgaaacaccGGAA

CCATTCAAAACAGCATACCAACTTAAAATAAGGCTAGTCCGTTATCAACT

TGAAAAAGTGGCACCGAGTCGGTGCTTTTTTT
(tracrRNA sequence is in bold)

> U6-DR-guide sequence-DR (Streptococcus pyogenes SF370)
gagggcctatttcccatgattccttcatatttgcatatacgatacaagga gttagagagataattggaattaatttgactgtaaacacaaagatattagt acaaaatacgtgacgtagaaagtaataatttcttgggtagtttgcagttt taaaattatgttttaaaatggactatcatatgcttaccgtaacttgaaag tatttcgatttcttggctttatatatcagtggaaaggacgaaacaccggg

*ttttagagctatgctgttttgaatggtcccaaaac*NNNNNNNNNNNNNNNN

NNNNNNNNNNNNNNNN*gttttagagctatgctgttttgaatggtcccaaaa*

*c*TTTTTTT
(direct repeat sequence is in italics and the guide sequence is indicated by the stretch of "N"s)

> sgRNA containing + 48 tracrRNA (Streptococcus pyogenes SF370)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatatcttgtggaaaggacgaaacaccN NNNNNNNNNNNNNNNNNNNN*gttttagagcta*gaaatagcaagttaaaata aggctagtccgTTTTTTT
(guide sequence is highlighted in blue and the tracrRNA fragment is in bold)

> sgRNA containing + 54 tracrRNA (Streptococcus pyogenes SF370)
gagggcctatacccatgattccttcatatttgcatatacgatacaaggct gttagagagataattggaattaatttgactgtaaacacaaagatattagt acaaaatacgtgacgtagaaagtaataatttcttgggtagtttgcagttt taaaattatgttttaaaatggactatcatatgcttaccgtaacttgaaag tatttcgatttcttggctttatatatcttgtggaaaggacgaaacaccNN NNNNNNNNNNNNNNNNNNNN*gttttagagcta*gaaatagcaagttaaaataa ggctagtccgttatcaTTTTTTT
(guide sequence is indicated by the stretch of "N"s and the tracrRNA fragment is in bold)

> sgRNA containing + 67 tracrRNA (Streptococcus pyogenes SF370)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagat taaaattatgattaaaatggactatcatatgcttaccgtaacttgaaagt atttcgatttcttggctttatatatcttgtggaaaggacgaaacaccNNN NNNNNNNNNNNNNNNNNNNN*gttttagagcta*gaaatagcaagttaaaataag gctagtccgttatcaactttgaaaaagtgTTTTTTT
(guide sequence is indicated by the stretch of "N"s and the tracrRNA fragment is in bold))

> sgRNA containing + 85 tracrRNA (Streptococcus pyogenes SF370)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgattaaaatggactatcatatgcttaccgtaacttgaaag tatttcgatttcttggctttatatatcttgtggaaaggacgaaacaccNN NNNNNNNNNNNNNNNNNNNNgttttagagctagaaatagcaagttaaaataa
ggctagtccgttatcaacttgaaaaagtggcaccgagtcggtgcTTTTTT
T
(guide sequence is indicated by the stretch of
"N"s and the tracrRNA fragment is in bold)

> CBh-NLS-SpCas9-NLS
CGTTACATAACTTACGGTAAATGGCCCGCCTGGCTGACCGCCCAACGACC
CCCGCCCATTGACGTCAATAATGACGTATGTTCCCATAGTAACGCCAATA
GGGACTTTCCATTGACGTCAATGGGTGGAGTATTTACGGTAAACTGCCCA
CTTGGCAGTACATCAAGTGTATCATATGCCAAGTACGCCCCCTATTGACG
TCAATGACGGTAAATGGCCCGCCTGGCATTATGCCCAGTACATGACCTTA
TGGGACTTTCCTACTTGGCAGTACATCTACGTATTAGTCATCGCTATTAC
CATGGTCGAGGTGAGCCCCACGTTCTGCTTCACTCTCCCCATCTCCCCCC
CCTCCCCACCCCCAATTTTGTATTTATTTATTTTTTAATTATTTTGTGCA
GCGATGGGGGCGGGGGGGGGGGGGGGCGCGCGCCAGGCGGGGCGGGGCG
GGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGG
CGGCCCTATAAAAAGCGAAGCGCGCGGCGGGCGGGAGTCGCTGCGACGCT
GCCTTCGCCCCGTGCCCCGCTCCGCCGCCGCCTCGCGCCGCCCGCCCCGG
CTCTGACTGACCGCGTTACTCCCACAGGTGAGCGGGCGGGACGGCCCTTC
TCCTCCGGGCTGTAATTAGCTGAGCAAGAGGTAAGGGTTTAAGGGATGGT
TGGTTGGTGGGGTATTAATGTTTAATTACCTGGAGCACCTGCCTGAAATC
ACTTTTTTTTCAGGTTGGaccggtgccaccATGGACTATAAGGACCACGAC
GGAGACTACAAGGATCATGATATTGATTACAAAGACGATGACGATAAGAT
GGCCCCAAAGAAGAAGCGGAAGGTCGGTATCCACGGAGTCCCAGCAGCCG
ACAAGAAGTACAGCATCGGCCTGGACATCGGCACCAACTCTGTGGGCTGG
GCCGTGATCACCGACGAGTACAAGGTGCCCAGCAAGAAATTCAAGGTGCT
GGGCAACACCGACCGGCACAGCATCAAGAAGAACCTGATCGGAGCCCTGC
TGTTCGACAGCGGCGAAACAGCCGAGGCCACCCGGCTGAAGAGAACCGCC
AGAAGAAGATACACCAGACGGAAGAACCGGATCTGCTATCTGCAAGAGAT
CTTCAGCAACGAGATGGCCAAGGTGGACGACAGCTTCTTCCACAGACTGG
AAGAGTCCTTCCTGGTGGAAGAGGATAAGAAGCACGAGCGGCACCCCATC
TTCGGCAACATCGTGGACGAGGTGGCCTACCACGAGAAGTACCCCACCAT
CTACCACCTGAGAAAGAAACTGGTGGACAGCACCGACAAGGCCGACCTGC
GGCTGATCTATCTGGCCCTGGCCCACATGATCAAGTTCCGGGGCCACTTC
CTGATCGAGGGCGACCTGAACCCCGACAACAGCGACGTGGACAAGCTGTT
CATCCAGCTGGTGCAGACCTACAACCAGCTGTTCGAGGAAAACCCCATCA
ACGCCAGCGGCGTGGACGCCAAGGCCATCCTGTCTGCCAGACTGAGCAAG
AGCAGACGGCTGGAAAATCTGATCGCCCAGCTGCCCGGCGAGAAGAAGAA
TGGCCTGTTCGGCAACCTGATTGCCCTGAGCCTGGGCCTGACCCCCAACT
TCAAGAGCAACTTCGACCTGGCCGAGGATGCCAAACTGCAGCTGAGCAAG
GACACCTACGACGACGACCTGGACAACCTGCTGGCCCAGATCGGCGACCA
GTACGCCGACCTCTTTCTGGCCGCCAAGAACCTGTCCGACGCCATCCTGC
TGAGCGACATCCTGAGAGTGAACACCGAGATCACCAAGGCCCCCCTGAGC
GCCTCTATGATCAAGAGATACGACGAGCACCACCAGGACCTGACCCTGCT
GAAAGCTCTCGTGCGGCAGCAGCTGCCTGAGAAGTACAAAGAGATTTTCT
TCGACCAGAGCAAGAACGGCTACGCCGGCTACATTGACGGCGGAGCCAGC
CAGGAAGAGTTCTACAAGTTCATCAAGCCCATCCTGGAAAAGATGGACGG
CACCGAGGAACTGCTCGTGAAGCTGAACAGAGAGGACCTGCTGCGGAAGC
AGCGGACCTTCGACAACGGCAGCATCCCCCACCAGATCCACCTGGGAGAG
CTGCACGCCATTCTGCGGGGGCAGGAAGATTTTTACCCATTCCTGAAGGA
CAACCGGGAAAAGATCGAGAAGATCCTGACCTTCCGCATCCCCTACTACG
TGGGCCCTCTGGCCAGGGGAAACAGCAGATTCGCCTGGATGACCAGAAAG
AGCGAGGAAACCATCACCCCCTGGAACTTCGAGGAAGTGGTGGACAAGGG
CGCTTCCGCCCAGAGCTTCATCGAGCGGATGACCAACTTCGATAAGAACC
TGCCCAACGAGAAGGTGCTGCCCAAGCACAGCCTGCTGTACGAGTACTTC
ACCGTGTATAACGAGCTGACCAAAGTGAAATAGGTGACCGAGGGAATGAG
AAAGCCCGCCTTCCTGAGCGGCGAGCAGAAAAAGGCCATCGTGGACCTGC
TGTTCAAGACCAACCGGAAAGTGACCGTGAAGCAGCTGAAAGAGGACTAC
TTCAAGAAAATCGAGTGCTTCGACTCCGTGGAAATCTCCGGCGTGGAAGA
TCGGTTCAACGCCTCCCTGGGCACATACCACGATCTGCTGAAAATTATCA
AGGACAAGGACTTCCTGGACAATGAGGAAAACGAGGACATTCTGGAAGAT
ATCGTGCTGACCCTGACACTGTTTGAGGACAGAGAGATGATCGAGGAACG
GCTGAAAACCTATGCCCACCTGTTCGACGACAAAGTGATGAAGCAGCTGA
AGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTC
CGACGGCTTCGCCAACAGAAACTTCATGCAGCTGATCCACGACGACAGCC
TGACCTTTAAAGAGGACATCCAGAAAGCCCAGGTGTCCGGCCAGCGCGAT
AGCCTGCACGAGCACATTGCCAATCTGGCCGGCAGCCCCGCCATTAAGAA
GGGCATCCTGCAGACAGTGAAGGTGGTGGACGAGCTCGTGAAAGTGATGG
GCCGGCACAAGCCCGAGAACATCGTGATCGAAATGGCCAGAGAGAACCAG
ACCACCCAGAAGGGACAGAAGAACAGCCGCGAGAGAATGAAGCGGATCGA
AGAGGGCATCAAAGAGCTGGGCAGCCAGATCCTGAAAGAACACCCCGTGG
AAAACACCCAGCTGCAGAACGAGAAGCTGTACCTGTACTACCTGCAGAAT
GGGCGGGATATGTACGTGGACCAGGAACTGGACATCAACCGGCTGTCCGA
CTACGATGTGGACCATATCGTGCCTCAGAGCTTTCTGAAGGACGACTCCA
TCGACAACAAGGTGCTGACCAGAAGCGACAAGAACCGGGGCAAGAGCGAC
AACGTGCCCTCCGAACAGGTCGTGAAGAAGATGAAGAACTACTGGCGGCA
GCTGCTGAACGCCAAGCTGATTACCCAGAGAAAGTTCGACAATCTGACCA
AGGCCGAGAGAGGCGGCCTGAGCGAACTGGATAAGGCCGGCTTCATCAAG
AGACAGCTGGTGGAAACCCGGCAGATCACAAAGCACGTGGCACAGATCCT
GGACTCCCGGATGAACACTAAGTACGACGAGAATGACAAGCTGATCCGGG -continued
AAGTGAAAGTGATCACCCTGAAGTCCAAGCTGGTGTCCGATTTCCGGAAG

GATTTCCAGTTTTACAAAGTGCGCGAGATCAACAACTACCACCACGCCCA

CGACGCCTACCTGAACGCCGTCGTGGGAACCGCCCTGATCAAAAAGTACC

CTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAA

GTACTTCTTCTACAGCAACATCATGAACTTTTTCAAGACCGAGATTACCC

TGGCCAACGGCGAGATCCGGAAGCGGCCTCTGATCGAGACAAACGGCGAA

ACCGGGGAGATCGTGTGGGATAAGGGCCGGGATTTTGCCACCGTGCGGAA

AGTGCTGAGCATGCCCCAAGTGAATATCGTGAAAAAGACCGAGGTGCAGA

CAGGCGGCTTCAGCAAAGAGTCTATCCTGCCCAAGAGGAACAGCGATAAG

CTGATCGCCAGAAAGAAGGACTGGGACCCTAAGAAGTACGGCGGCTTCGA

CAGCCCCACCGTGGCCTATTCTGTGCTGGTGGTGGCCAAAGTGGAAAAGG

GCAAGTCCAAGAAACTGAAGAGTGTGAAAGAGCTGCTGGGGATCACCATC

ATGGAAAGAAGCAGCTTCGAGAAGAATCCCATCGACTTTCTGGAAGCCAA

GGGCTACAAAGAAGTGAAAAAGGACCTGATCATCAAGCTGCCTAAGTACT

CCCTGTTCCAGCTGGAAAACGGCCGGAAGAGAATGCTGGCCTCTGCCGGC

GAACTGCAGAAGGGAAACGAACTGGCCCTGCCCTCCAAATATGTGAACTT

CCTGTACCTGGCCAGCCACTATGAGAAGCTGAAGGGCTCCCCCGAGGATA

ATGAGCAGAAACAGCTGTTTGTGGAACAGCACAAGCACTACCTGGACGAG

ATCATCGAGCAGATCAGCGAGTTCTCCAAGAGAGTGATCCTGGCCGACGC

TAATCTCGACAAAGTGCTGTCCGCCTACAACAAGCACGGGATAAGCCCA

TCAGAGAGCAGGCCGAGAATATCATCCACCTGTTTACCCTGACCAATCTG

GGAGCCCCTGCCGCCTTCAAGTACTTTGACACCACCATCGACCGGAAGAG

GTACACCAGCACCAAAGAGGTGCTGGACGCCACCCTGATCCACCAGAGCA

TCACCGGCCTGTACGAGACACGGATCGACCTGTCTCAGCTGGGAGGCGAC

TTTCTTTTTCTTAGCTTGACCAGCTTTCTTAGTAGCAGCAGGACGCTTTA

A
(NLS-hSpCas9-NLS is in bold)

> Sequencing amplicon for EMX1 guides 1.1, 1.14,
1.17
CCAATGGGGAGGACATCGATGTCACCTCCAATGACTAGGGTGGGCAACCA

CAAACCCACGAGGGCAGAGTGCTGCTTGCTGCTGGCCAGGCCCCTGCGTG

GGCCCAAGGTGGACTCTGGCCAC

> Sequencing amplicon for EMX1 guides 1.2, 1.16
CGAGCAGAAGAAGAAGGGCTCCCATCACATCAACCGGTGGCGCATTGCCA

CGAAGCAGGCCAATGGGGAGGACATCGATGTCACCTCCAATGACTAGGGT

GGGCAACCACAAACCCACGAG

> Sequencing amplicon for EMX1 guides 1.3, 1.13,
1.15
GGAGGACAAAGTACAAACGGCAGAAGCTGGAGGAGGAAGGGCCTGAGTCC

GAGCAGAAGAAGAAGGGCTCCCATCACATCAACCGGTGGCGCATTGCCAC

GAAGCAGGCCAATGGGGAGGACATCGAT

> Sequencing amplicon for EMX1 guides 1.6
AGAAGCTGGAGGAGGAAGGGCCTGAGTCCGAGCAGAAGAAGAAGGGCTCC

CATCACATCAACCGGTGGCGCATTGCCACGAAGCAGGCCAATGGGGAGGA

CATCGATGTCACCTCCAATGACTAGGGTGG

> Sequencing amplicon for EMX1 guides 1.10
CCTCAGTCTTCCCATCAGGCTCTCAGCTCAGCCTGAGTGTTGAGGCCCCA

GTGGCTGCTGTGGGGGCCTCCTGAGTTTCTCATCTGTGCCCCTCCCTCCC

TGGCCCAGGTGAAGGTGTGGTTCCA

> Sequencing amplicon for EMX1 guides 1.11, 1.12
TCATCTGTGCCCCTCCCTCCCTGGCCCAGGTGAAGGTGTGGTTCCAGAAC

CGGAGGACAAAGTACAAACGGCAGAAGCTGGAGGAGGAAGGGCCTGAGTC

CGAGCAGAAGAAGAAGGGCTCCCATCACA

> Sequencing amplicon for EMX1 guides 1.18, 1.19
CTCCAATGACTAGGGTGGGCAACCACAAACCCACGAGGGCAGAGTGCTGC

TTGCTGCTGGCCAGGCCCCTGCGTGGGCCCAAGCTGGACTCTGGCCACTC

CCTGGCCAGGCTTTGGGGAGGCCTGGAGT

> Sequencing amplicon for EMX1 guides 1.20
CTGCTTGCTGCTGGCCAGGCCCCTGCGTGGGCCCAAGCTGGACTCTGGCC

ACTCCCTGGCCAGGCTTTGGGGAGGCCTGGAGTCATGGCCCCACAGGGCT

TGAAGCCCGGGGCCGCCATTGACAGAG

> T7 promoter F primer for annealing with target
strand
GAAATTAATACGACTCACTATAGGG > oligo containing pUC19 target site 1 for
methylation (T7 reverse)
AAAAAAGCACCGACTCGGTGCCACTTTTTCAAGTTGATAACGGACTAGCC

TTATTTTAACTTTGCTATTTCTAGCTCTAAAACAACGACGAGCGTGACAC

CACCCTATAGTGAGTCGTATTAATTTC

> oligo containing pUC19 target site 2 for
methylation (T7 reverse)
AAAAAAGCACCGACTCGGTGCCACTTTTTCAAGTTGATAACGGACTAGCC

TTATTTTAACTTGCTATTTCTAGCTCTAAAACGCAACAATTAATAGACTG

GACCTATAGTGAGTCGTATTAATTTC

Example 7

Base Pair Mismatching Investigations

Applicants have tested several mismatch guide sequences have been tested to probe cas9 protein off-target effect (Hsu et al., DNA targeting specificity of RNA-guided Cas9 nucleases. Nat Biotechnol. 2013 September; 31(9):827-32). However the number of mismatch guide sequences used may have been far less than the complete set of all possible mismatch guide sequences. In order to predict off target cutting efficiency of non-tested guide-target pairs, a thermodynamic model is built to fit existing experimental data and is used to predict new guide target pair.

Applicants tested cutting frequency data for tested guide target pair collected from Hsu P. D et al., 2013. Applicants collected the nearest neighbor thermodynamic parameters for nucleic acid pairing from ViennaRNA package distribution. Applicants obtained first bi-base pair thermal dynamical parameters per position for each guide target pair. These parameters were referred to as features. Data, comprising of cutting frequency and features for each guide target pair, was divided into 5 groups randomly in order to perform 5 fold cross validation. In each training session, 4 groups of data were used as training data. A modified radial basis kernel that consisted of radial basis kernel with an additive term accounting for different PAM was used in nonlinear regression. In each testing session, the remaining 1 group was used to test the model. Coarse grid search for fitting parameters was performed. The best fitting parameters were used to generate new parameters in fine grid search.

The Applicants' algorithm flows as follows:
1. Choose data with duplicate.
2. Calculate confidence interval for cutting frequency based on binomial distribution. Select data with p value passing a threshold.
3. Calculate thermal dynamic parameters for each guide-target pair to obtain its feature.
4. Transform non-linearly cutting frequency data in order to balance high and low cutting frequency contributions in model fitting.
5. Divide data into 5 groups.
6. Perform coarse grid search for fitting parameter using 5 fold cross validation.
7. Best parameters are selected, and fine grid search is performed.

Figure 36:
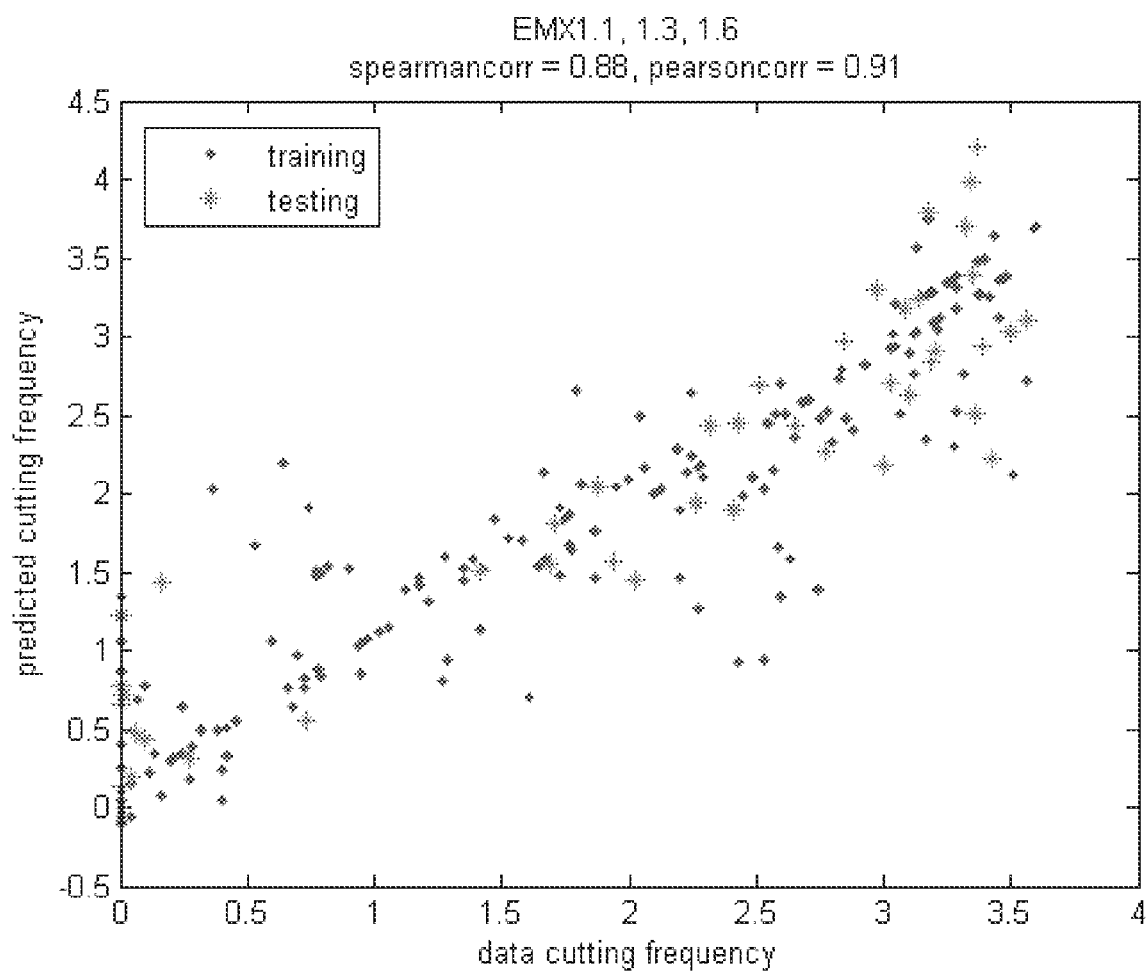
FIG. 36 shows a scatter plot of unfitted training data and testing data.
Figure 37:
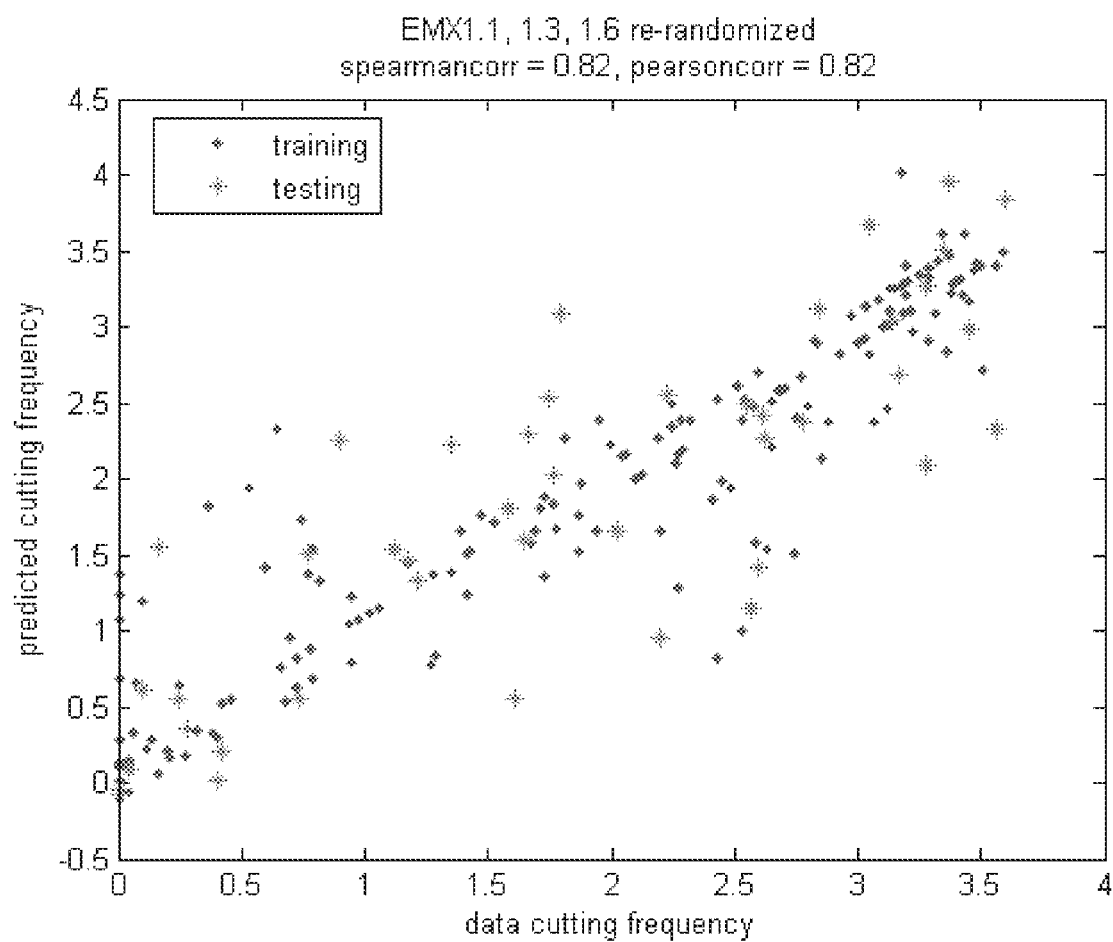
FIG. 37 shows a scatter plot of fitted training data and testing data.

Result: Training data and testing data are shown as blue dots and red dots respectively in the scatter plot. Spearman correlation coefficient is 0.88, and Pearson correlation coefficient is 0.91 (FIG. 36). It demonstrates good model prediction of the data. In order to check model over fitting, data was randomized again, trained and tested using the same parameters. The result is 0.82 for both correlation coefficients (FIG. 37).

REFERENCES

1. Cong, L. et al. Multiplex genome engineering using CRISPR/Cas systems. Science 339, 819-823 (2013)
2. Mali, P. et al. RNA-Guided Human Genome Engineering via Cas9. Science 339, 823-826 (2013).
3. Jinek, M. et al. RNA-programmed genome editing in human cells. eLife 2, e00471 (2013).
4. Cho, S. W., Kim, S., Kim, J. M. & Kim, J. S. Targeted genome engineering in human cells with the Cas9 RNA-guided endonuclease. Nat Biotechnol 31, 230-232 (2013).
5. Deltcheva, E. et al. CRISPR RNA maturation by trans-encoded small RNA and host factor RNase III. Nature 471, 602-607 (2011).
6. Jinek, M. et al. A programmable dual-RNA-guided DNA endonuclease in adaptive bacterial immunity. Science 337, 816-821 (2012).
7. Wang, H. et al. One-Step Generation of Mice Carrying Mutations in Multiple Genes by CRISPR/Cas-Mediated Genome Engineering. Cell 153, 910-918 (2013).
8. Guschin, D. Y. et al. A rapid and general assay for monitoring endogenous gene modification. Methods Mol Biol 649, 247-256 (2010).
9. Bogenhagen, D. F. & Brown, D. D. Nucleotide sequences in Xenopus 5S DNA required for transcription termination. Cell 24, 261-270 (1981).
10. Hwang, W. Y. et al. Efficient genome editing in zebrafish using a CRISPR-Cas system. Nat Biotechnol 31, 227-229 (2013).
11. Bultmann, S. et al. Targeted transcriptional activation of silent oct4 pluripotency gene by combining designer TALEs and inhibition of epigenetic modifiers. Nucleic Acids Res 40, 5368-5377 (2012).
12. Valton, J. et al. Overcoming transcription activator-like effector (TALE) DNA binding domain sensitivity to cytosine methylation. J Biol Chem 287, 38427-38432 (2012).
13. Christian, M. et al. Targeting DNA double-strand breaks with TAL effector nucleases. Genetics 186, 757-761 (2010).
14. Miller, J. C. et al. A TALE nuclease architecture for efficient genome editing. Nat Biotechnol 29, 143-148 (2011).
15. Mussolino, C. et al. A novel TALE nuclease scaffold enables high genome editing activity in combination with low toxicity. Nucleic acids research 39, 9283-9293 (2011).
16. Hsu, P. D. & Zhang, F. Dissecting neural function using targeted genome engineering technologies. ACS chemical neuroscience 3, 603-610 (2012).
17. Sanjana, N. E. et al. A transcription activator-like effector toolbox for genome engineering. Nature protocols 7, 171-192 (2012).
18. Porteus, M. H. & Baltimore, D. Chimeric nucleases stimulate gene targeting in human cells. Science 300, 763 (2003).
19. Miller, J. C. et al. An improved zinc-finger nuclease architecture for highly specific genome editing. Nat Biotechnol 25, 778-785 (2007).
20. Sander, J. D. et al. Selection-free zinc-finger-nuclease engineering by context-dependent assembly (CoDA). Nat Methods 8, 67-69 (2011).
21. Wood, A. J. et al. Targeted genome editing across species using ZFNs and TALENs.
Science 333, 307 (2011).
22. Bobis-Wozowicz, S., Osiak, A., Rahman, S. H. & Cathomen, T. Targeted genome editing in pluripotent stem cells using zinc-finger nucleases. Methods 53, 339-346 (2011).
23. Jiang, W., Bikard, D., Cox, D., Zhang, F. & Marraffini, L. A. RNA-guided editing of bacterial genomes using CRISPR-Cas systems. Nat Biotechnol 31, 233-239 (2013).
24. Qi, L. S. et al. Repurposing CRISPR as an RNA-Guided Platform for Sequence-Specific Control of Gene Expression. Cell 152, 1173-1183 (2013).
25. Michaelis, L. M., Maud "Die kinetik der invertinwirkung.". Biochem. z (1913).
26. Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).
27. Wilson, E. B. Probable inference, the law of succession, and statistical inference. J Am Stat Assoc 22, 209-212 (1927).
28. Ding, Q. et al. A TALEN genome-editing system for generating human stem cell-based disease models. Cell Stem Cell 12, 238-251 (2013).
29. Soldner, F. et al. Generation of isogenic pluripotent stem cells differing exclusively at two early onset Parkinson point mutations. Cell 146, 318-331 (2011).
30. Carlson, D. F. et al. Efficient TALEN-mediated gene knockout in livestock. Proc Natl Acad Sci USA 109, 17382-17387 (2012).
31. Geurts, A. M. et al. Knockout Rats via Embryo Microinjection of Zinc-Finger Nucleases. Science 325, 433-433 (2009).

32. Takasu, Y. et al. Targeted mutagenesis in the silkworm *Bombyx mori* using zinc finger nuclease mRNA injection. Insect Biochem Molec 40, 759-765 (2010).

33. Watanabe, T. et al. Non-transgenic genome modifications in a hemimetabolous insect using zinc-finger and TAL effector nucleases. Nat Commun 3 (2012).

34. Reyon, D. et al. FLASH assembly of TALENs for high-throughput genome editing. Nat Biotechnol 30, 460-465 (2012).

35. Boch, J. et al. Breaking the code of DNA binding specificity of TAL-type 111 effectors. Science 326, 1509-1512 (2009).

36. Moscou, M. J. & Bogdanove, A. J. A simple cipher governs DNA recognition by TAL effectors. Science 326, 1501 (2009).

37. Deveau, H., Garneau, J. E. & Moineau, S. CRISPR/Cas system and its role in phage-bacteria interactions. Annu Rev Microbiol 64, 475-493 (2010).

38. Horvath, P. & Barrangou, R. CRISPR/Cas, the immune system of bacteria and archaea. Science 327, 167-170 (2010).

39. Makarova, K. S. et al. Evolution and classification of the CRISPR-Cas systems. Nat Rev Microbiol 9, 467-477 (2011).

40. Bhaya, D., Davison, M. & Barrangou, R. CRISPR-Cas systems in bacteria and archaea: versatile small RNAs for adaptive defense and regulation. Annu Rev Genet 45, 273-297 (2011).

41. Garneau, J. E. et al. The CRISPR/Cas bacterial immune system cleaves bacteriophage and plasmid DNA. Nature 468, 67-71 (2010).

42. Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).

43. Urnov, F. D., Rebar, E. J., Holmes, M. C., Zhang, H. S. & Gregory, P. D. Genome editing with engineered zinc finger nucleases. Nat Rev Genet 11, 636-646 (2010).

44. Perez, E. E. et al. Establishment of HIV-1 resistance in CD4(+) T cells by genome editing using zinc-finger nucleases. Nat Biotechnol 26, 808-816 (2008).

45. Chen, F. Q. et al. High-frequency genome editing using ssDNA oligonucleotides with zinc-finger nucleases. Nat Methods 8, 753-U796 (2011).

46. Bedell, V. M. et al. In vivo genome editing using a high-efficiency TALEN system. Nature 491, 114-U133 (2012).

47. Saleh-Gohari, N. & Helleday, T. Conservative homologous recombination preferentially repairs DNA double-strand breaks in the S phase of the cell cycle in human cells. Nucleic Acids Res 32, 3683-3688 (2004).

48. Sapranauskas, R. et al. The *Streptococcus thermophilus* CRISPR/Cas system provides immunity in *Escherichia coli*. Nucleic Acids Res 39, 9275-9282 (2011).

49. Shen, B. et al. Generation of gene-modified mice via Cas9/RNA-mediated gene targeting. Cell Res 23, 720-723 (2013).

50. Tuschl, T. Expanding small RNA interference. Nat Biotechnol 20, 446-448 (2002).

51. Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).

52. Thomas, K. R., Folger, K. R. & Capecchi, M. R. High frequency targeting of genes to specific sites in the mammalian genome. Cell 44, 419-428 (1986).

53. Hasty, P., Rivera-Perez, J. & Bradley, A. The length of homology required for gene targeting in embryonic stem cells. Mol Cell Biol 11, 5586-5591 (1991).

54. Wu, S., Ying, G. X., Wu, Q. & Capecchi, M. R. A protocol for constructing gene targeting vectors: generating knockout mice for the cadherin family and beyond. Nat Protoc 3, 1056-1076 (2008).

55. Oliveira, T. Y. et al. Translocation capture sequencing: a method for high throughput mapping of chromosomal rearrangements. J Immunol Methods 375, 176-181 (2012).

56. Tremblay et al., Transcription Activator-Like Effector Proteins Induce the Expression of the Frataxin Gene; Human Gene Therapy. August 2012, 23(8): 883-890.

57. Shalek et al. Nanowire-mediated delivery enables functional interrogation of primary immune cells: application to the analysis of chronic lymphocytic leukemia. Nano Letters, 2012, Dec. 12; 12(12):6498-504.

58. Pardridge et al. Preparation of Trojan horse liposomes (THLs) for gene transfer across the blood-brain barrier; Cold Spring Harb Protoc; 2010; April; 2010 (4)

59. Plosker G L et al. Fluvastatin: a review of its pharmacology and use in the management of hypercholesterolaemia; Drugs 1996, 51(3):433-459).

60. Trapani et al. Potential role of nonstatin cholesterol lowering agents; IUBMB Life, Volume 63, Issue 11, pages 964-971, November 2011

61. Birch A M et al. DGAT1 inhibitors as anti-obesity and anti-diabetic agents; Current Opinion in Drug Discovery & Development, 2010, 13(4):489-496

62. Fuchs et al. Killing of leukemic cells with a BCR/ABL fusion gene by RNA interference (RNAi), Oncogene 2002, 21(37):5716-5724.

63. McManaman J L et al. Perilipin-2 Null Mice are Protected Against Diet-Induced Obesity, Adipose Inflammation and Fatty Liver Disease; The Journal of Lipid Research, jlr.M035063. First Published on Feb. 12, 2013.

64. Tang J et al. Inhibition of SREBP by a Small Molecule, Betulin, Improves Hyperlipidemia and Insulin Resistance and Reduces Atherosclerotic Plaques: Cell Metabolism, Volume 13, Issue 1, 44-56, 5 Jan. 2011.

65. Dumitrache et al. Trex2 enables spontaneous sister chromatid exchanges without facilitating DNA double-strand break repair; Genetics. 2011 August; 188(4): 787-797

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method for selecting and producing an engineered CRISPR complex for targeting and/or cleavage of a candidate target nucleic acid sequence within a eukaryotic cell, comprising the steps of:
   (a) determining amount, location and nature of mismatch(es) of guide sequence of potential CRISPR complex(es) and the candidate target nucleic acid sequence,
   (b) determining contribution of each of the amount, location and nature of mismatch(es) to hybridization free energy of binding between the target nucleic acid sequence and the guide sequence of potential CRISPR complex(es) from a training data set,
   (c) based on the contribution analysis of step (b), predicting cleavage at the location(s) of the mismatch(es) of the target nucleic acid sequence by the potential CRISPR complex(es),
   (d) selecting the CRISPR complex from potential CRISPR complex(es) based on whether the prediction of step (c) indicates that it is more likely than not that cleavage will occur at location(s) of mismatch(es) by the CRISPR complex;
   (e) producing the selected CRISPR complex or nucleic acid molecule(s) encoding the selected CRISPR complex for targeting and/or cleavage of the candidate target nucleic acid sequence within the eukaryotic cell; and
   (f) delivering the selected CRISPR complex or nucleic acid molecule(s) encoding the selected CRISPR complex into the eukaryotic cell, wherein the selected CRISPR complex targets and/or cleaves the candidate target nucleic acid sequence within the eukaryotic cell.

2. The method of claim 1 wherein the candidate target sequence is a DNA sequence, and the mismatch(es) are of RNA of potential CRISPR complex(es) and the DNA.

3. The method of claim 1, wherein step (b) is performed by
   determining known local free energies, $\Delta Gij(k)$, between every guide RNA sequence i and target DNA nucleic acid sequence j at position k,
   calculating values of the effective free-energy $Z_{ij}$ using the relationship $p_{ij} \propto e^{-\beta Z_{ij}}$, where $p_{ij}$ is measured cutting frequency by guide RNA sequence i on target DNA nucleic acid sequence j in the training set and $\beta$ is a positive constant of proportionality,
   determining the weights which are position-dependent weights $\alpha_k$ by fitting the known value of $\Delta Gij(k)$ and the calculated value of $Z_{ij}$ across each guide RNA/target DNA sequence pair in the training set in the sum across all N bases of the guide-sequence $$Z_{ij} = \sum_{k=1}^{N} \alpha_k \Delta G_{ij}(k)$$

by writing the above equation in the matrix form $\vec{Z} = G \vec{\alpha}$ and wherein, step (c) is performed by
   estimating the effective free-energy Zest using the determined position dependent weights in the equation $$\vec{Z_{est}} = G \vec{\alpha}$$

and determining estimated spacer-target cutting frequencies $p_{est} \propto e^{-\beta Zest}$, to thereby predict cleavage.

4. The method of claim 2 wherein the distance, in bp, between the first and last base of the target sequence is 18.

5. The method of claim 1 wherein predicting cleavage comprises predicting whether cleavage is more likely than not to occur at location(s) of mismatch(es), and thereby predicting cleavage.

6. The method of claim 1, further comprising normalizing the calculated values of the effective free energy of hybridization Z for each guide RNA/target DNA sequence pair in the training set.

7. The method of claim 1, further comprising filtering out calculated value of the effective free energy of hybridization Z for each guide RNA/target DNA sequence pair in the training set which have a sequencing depth which is below a minimum sequencing depth.

8. The method of claim 1, wherein the method is implemented by a computer system comprising:
   a. a memory unit configured to receive and/or store sequence information of the candidate target nucleic acid sequence; and
   b. one or more processors alone or in combination programmed to perform steps (a) to (d).

9. The method of claim 1, wherein step (b) is performed by:
   defining a thermodynamic model having a set of weights linking effective free energy of hybridization Z to local free energies G;
   defining a training set of the guide sequence/target DNA sequence pairs;
   inputting known values of local free energies G for each guide sequence/target DNA sequence pair in the training set;
   calculating a value of effective free energy of hybridization Z for each guide sequence/target DNA sequence pair in the training set;
   determining the weights using a machine learning algorithm, and
   outputting the weights whereby the weights can be used to estimate the free energy of hybridization for any sequence.

10. The method of claim 1 wherein the guide sequence is comprised within a single guide RNA (sgRNA) or within a CRISPR-Cas system chimera RNA (chiRNA).

11. The method of claim 1, wherein the selected CRISPR complex generates a cleavage within the candidate target nucleic acid sequence within the eukaryotic cell.

* * * * *

SEQUENCE LISTING

<160> NUMBER OF SEQ ID NOS: 1076

<210> SEQ ID NO 1
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
guuuuagagc ua                                                         12

<210> SEQ ID NO 2
<211> LENGTH: 7
<212> TYPE: PRT
<213> ORGANISM: Simian virus 40

<400> SEQUENCE: 2

Pro Lys Lys Lys Arg Lys Val
1               5

<210> SEQ ID NO 3
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 5

Arg Gln Arg Arg Asn Glu Leu Lys Arg Ser Pro
1               5                   10

<210> SEQ ID NO 6
<211> LENGTH: 38
<212> TYPE: PRT
<213> ORGANISM: Homo sapiens

<400> SEQUENCE: 6

```
Asn Gln Ser Ser Asn Phe Gly Pro Met Lys Gly Gly Asn Phe Gly Gly
1               5                  10                  15

Arg Ser Ser Gly Pro Tyr Gly Gly Gly Gln Tyr Phe Ala Lys Pro
            20                  25                  30

Arg Asn Gln Gly Gly Tyr
        35
```

<210> SEQ ID NO 7
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 7

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
        35                  40
```

<210> SEQ ID NO 8
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 8

```
Val Ser Arg Lys Arg Pro Arg Pro
1               5
```

<210> SEQ ID NO 9
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 9

```
Pro Pro Lys Lys Ala Arg Glu Asp
1               5
```

<210> SEQ ID NO 10
<211> LENGTH: 8
<212> TYPE: PRT
<213> ORGANISM: Homo sapiens

<400> SEQUENCE: 10

```
Pro Gln Pro Lys Lys Lys Pro Leu
1               5
```

<210> SEQ ID NO 11
<211> LENGTH: 12
<212> TYPE: PRT
<213> ORGANISM: Mus musculus

<400> SEQUENCE: 11

-continued

Ser Ala Leu Ile Lys Lys Lys Lys Met Ala Pro
1               5                   10

<210> SEQ ID NO 12
<211> LENGTH: 5
<212> TYPE: PRT
<213> ORGANISM: Influenza virus

<400> SEQUENCE: 12

Asp Arg Leu Arg Arg
1               5

<210> SEQ ID NO 13
<211> LENGTH: 7
<212> TYPE: PRT
<213> ORGANISM: Influenza virus

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Hepatitus delta virus

<400> SEQUENCE: 14

Arg Lys Leu Lys Lys Lys Ile Lys Lys Leu
1               5                   10

<210> SEQ ID NO 15
<211> LENGTH: 10
<212> TYPE: PRT
<213> ORGANISM: Mus musculus

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens

<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 27
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 18
nnnnnnnnnn nnnnnnnnnn nnagaaw                                             27

<210> SEQ ID NO 19
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 19
nnnnnnnnnn nnnnagaaw                                                      19

<210> SEQ ID NO 20
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 20
nnnnnnnnnn nnnnnnnnnn nnagaaw                                             27

<210> SEQ ID NO 21
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other
```

-continued

<400> SEQUENCE: 21
nnnnnnnnnn nnnagaaw                                                   18

<210> SEQ ID NO 22
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 22
nnnnnnnnnn nnnnnnnnnn gttttttgtac tctcaagatt tagaaataaa tcttgcagaa     60
gctacaaaga taaggcttca tgccgaaatc aacaccctgt cattttatgg cagggtgttt    120
tcgttattta attttt                                                    137

<210> SEQ ID NO 23
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 23
nnnnnnnnnn nnnnnnnnnn gttttttgtac tctcagaaat gcagaagcta caaagataag     60
gcttcatgcc gaaatcaaca ccctgtcatt ttatggcagg gtgttttcgt tatttaattt    120
ttt                                                                  123

<210> SEQ ID NO 24
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 24
nnnnnnnnnn nnnnnnnnnn gttttttgtac tctcagaaat gcagaagcta caaagataag     60
gcttcatgcc gaaatcaaca ccctgtcatt ttatggcagg gtgttttttt                110

<210> SEQ ID NO 25
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:

<221> NAME/KEY: modified_base
<222> LOCATION: (1)..(20)
<223> OTHER INFORMATION: a, c, t, g, unknown or other

<400> SEQUENCE: 25
nnnnnnnnnn nnnnnnnnnn gttttagagc tagaaatagc aagttaaaat aaggctagtc    60
cgttatcaac ttgaaaaagt ggcaccgagt cggtgctttt tt    102

<210> SEQ ID NO 26
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 26
nnnnnnnnnn nnnnnnnnnn gttttagagc tagaaatagc aagttaaaat aaggctagtc    60
cgttatcaac ttgaaaaagt gtttttttt    88

<210> SEQ ID NO 27
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 27
nnnnnnnnnn nnnnnnnnnn gttttagagc tagaaatagc aagttaaaat aaggctagtc    60
cgttatcatt tttttt    76

<210> SEQ ID NO 28
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 28
aggccccagt ggctgctctn aa    22

<210> SEQ ID NO 29
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 29
acatcaaccg gtggcgcatn at    22

```
<210> SEQ ID NO 30
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 30
aaggtgtggt tccagaaccn ac                                              22

<210> SEQ ID NO 31
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 31
ccatcacatc aaccggtggn ag                                              22

<210> SEQ ID NO 32
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 32
aaacggcaga agctggaggn ta                                              22

<210> SEQ ID NO 33
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 33
ggcagaagct ggaggaggan tt                                              22

<210> SEQ ID NO 34
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 34
ggtgtggttc cagaaccggn tc                                              22

<210> SEQ ID NO 35
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
```

```
<400> SEQUENCE: 35
aaccggagga caaagtacan tg                                              22

<210> SEQ ID NO 36
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 36
ttccagaacc ggaggacaan ca                                              22

<210> SEQ ID NO 37
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 37
gtgtggttcc agaaccggan ct                                              22

<210> SEQ ID NO 38
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 38
tccagaaccg gaggacaaan cc                                              22

<210> SEQ ID NO 39
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 39
cagaagctgg aggaggaagn cg                                              22

<210> SEQ ID NO 40
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 40
catcaaccgg tggcgcattn ga                                              22

<210> SEQ ID NO 41
<211> LENGTH: 22
<212> TYPE: DNA
<213> ORGANISM: Homo sapiens
```

```
<220> FEATURE:
<221> NAME/KEY: modified_base
<222> LOCATION: (20)..(20)
<223> OTHER INFORMATION: a, c, t, g, unknown or other

<400> SEQUENCE: 41
gcagaagctg gaggaggaan gt                                              22

<210> SEQ ID NO 42
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 42
cctccctccc tgcccaggn gc                                               22

<210> SEQ ID NO 43
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 43
tcatctgtgc ccctccctcn aa                                              22

<210> SEQ ID NO 44
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 44
gggaggacat cgatgtcacn at                                              22

<210> SEQ ID NO 45
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 45
caaacggcag aagctggagn ac                                              22

<210> SEQ ID NO 46
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 46
gggtgggcaa ccacaaaccn ag                                              22
```

```
<210> SEQ ID NO 47
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 47
ggtgggcaac cacaaacccn ta                                              22

<210> SEQ ID NO 48
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 48
ggctcccatc acatcaaccn tt                                              22

<210> SEQ ID NO 49
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 49
gaagggcctg agtccgagcn tc                                              22

<210> SEQ ID NO 50
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 50
caaccggtgg cgcattgccn tg                                              22

<210> SEQ ID NO 51
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 51
aggaggaagg gcctgagtcn ca                                              22

<210> SEQ ID NO 52
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other
```

```
<400> SEQUENCE: 52
agctggagga ggaagggccn ct                                              22

<210> SEQ ID NO 53
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 53
gcattgccac gaagcaggcn cc                                              22

<210> SEQ ID NO 54
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 54
attgccacga agcaggccan cg                                              22

<210> SEQ ID NO 55
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 55
agaaccggag gacaaagtan ga                                              22

<210> SEQ ID NO 56
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 56
tcaaccggtg gcgcattgcn gt                                              22

<210> SEQ ID NO 57
<211> LENGTH: 22
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t, g, unknown or other

<400> SEQUENCE: 57
gaagctggag gaggaagggn gc                                              22

<210> SEQ ID NO 58
<211> LENGTH: 23
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gccaaattgg acgaccctcg cgg                                              23

<210> SEQ ID NO 59
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cgaggagacc cccgtttcgg tgg                                              23

<210> SEQ ID NO 60
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
cccgccgccg ccgtggctcg agg                                              23

<210> SEQ ID NO 61
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
tgagctctac gagatccaca agg                                              23

<210> SEQ ID NO 62
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ctcaaaattc ataccggttg tgg                                              23

<210> SEQ ID NO 63
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
cgttaaacaa caaccggact tgg                                              23
```

<210> SEQ ID NO 64
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ttcaccccgc ggcgctgaat ggg                                          23

<210> SEQ ID NO 65
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
accactacca gtccgtccac agg                                          23

<210> SEQ ID NO 66
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
cactgcttaa gcctcgctcg agg                                          23

<210> SEQ ID NO 67
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
tcaccagcaa tattcgctcg agg                                          23

<210> SEQ ID NO 68
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
caccagcaat attccgctcg agg                                          23

<210> SEQ ID NO 69
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

```
        Synthetic oligonucleotide"

<400> SEQUENCE: 69
tagcaacaga catacgctcg agg                                          23

<210> SEQ ID NO 70
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gggcagtagt aatacgctcg agg                                          23

<210> SEQ ID NO 71
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ccaattccca tacattattg tac                                          23

<210> SEQ ID NO 72
<211> LENGTH: 33
<212> TYPE: DNA
<213> ORGANISM: Homo sapiens

<400> SEQUENCE: 72
ggacatcgat gtcacctcca atgactaggg tgg                               33

<210> SEQ ID NO 73
<211> LENGTH: 33
<212> TYPE: DNA
<213> ORGANISM: Homo sapiens

<400> SEQUENCE: 73
cattggaggt gacatcgatg tcctccccat tgg                               33

<210> SEQ ID NO 74
<211> LENGTH: 33
<212> TYPE: DNA
<213> ORGANISM: Homo sapiens

<400> SEQUENCE: 74
ggaagggcct gagtccgagc agaagaagaa ggg                               33

<210> SEQ ID NO 75
<211> LENGTH: 33
<212> TYPE: DNA
<213> ORGANISM: Homo sapiens

<400> SEQUENCE: 75
ggtggcgaga ggggccgaga ttgggtgttc agg                               33

<210> SEQ ID NO 76
<211> LENGTH: 33
<212> TYPE: DNA
<213> ORGANISM: Homo sapiens
```

```
<400> SEQUENCE: 76
atgcaggagg gtggcgagag gggccgagat tgg                                    33

<210> SEQ ID NO 77
<211> LENGTH: 23
<212> TYPE: DNA
<213> ORGANISM: Homo sapiens

<400> SEQUENCE: 77
gtcacctcca atgactaggg tgg                                               23

<210> SEQ ID NO 78
<211> LENGTH: 23
<212> TYPE: DNA
<213> ORGANISM: Homo sapiens

<400> SEQUENCE: 78
gacatcgatg tcctccccat tgg                                               23

<210> SEQ ID NO 79
<211> LENGTH: 23
<212> TYPE: DNA
<213> ORGANISM: Homo sapiens

<400> SEQUENCE: 79
gagtccgagc agaagaagaa ggg                                               23

<210> SEQ ID NO 80
<211> LENGTH: 23
<212> TYPE: DNA
<213> ORGANISM: Homo sapiens

<400> SEQUENCE: 80
gcgccaccgg ttgatgtgat ggg                                               23

<210> SEQ ID NO 81
<211> LENGTH: 23
<212> TYPE: DNA
<213> ORGANISM: Homo sapiens

<400> SEQUENCE: 81
ggggcacaga tgagaaactc agg                                               23

<210> SEQ ID NO 82
<211> LENGTH: 23
<212> TYPE: DNA
<213> ORGANISM: Homo sapiens

<400> SEQUENCE: 82
gtacaaacgg cagaagctgg agg                                               23

<210> SEQ ID NO 83
<211> LENGTH: 23
<212> TYPE: DNA
<213> ORGANISM: Homo sapiens

<400> SEQUENCE: 83
ggcagaagct ggaggaggaa ggg                                               23

<210> SEQ ID NO 84
<211> LENGTH: 23
<212> TYPE: DNA
```

-continued

```
<213> ORGANISM: Homo sapiens

<400> SEQUENCE: 84
ggagcccttc ttcttctgct cgg                                              23

<210> SEQ ID NO 85
<211> LENGTH: 23
<212> TYPE: DNA
<213> ORGANISM: Homo sapiens

<400> SEQUENCE: 85
gggcaaccac aaacccacga ggg                                              23

<210> SEQ ID NO 86
<211> LENGTH: 23
<212> TYPE: DNA
<213> ORGANISM: Homo sapiens

<400> SEQUENCE: 86
gctcccatca catcaaccgg tgg                                              23

<210> SEQ ID NO 87
<211> LENGTH: 23
<212> TYPE: DNA
<213> ORGANISM: Homo sapiens

<400> SEQUENCE: 87
gtggcgcatt gccacgaagc agg                                              23

<210> SEQ ID NO 88
<211> LENGTH: 23
<212> TYPE: DNA
<213> ORGANISM: Homo sapiens

<400> SEQUENCE: 88
ggcagagtgc tgcttgctgc tgg                                              23

<210> SEQ ID NO 89
<211> LENGTH: 23
<212> TYPE: DNA
<213> ORGANISM: Homo sapiens

<400> SEQUENCE: 89 gccccctgcgt gggcccaagc tgg                                             23

<210> SEQ ID NO 90
<211> LENGTH: 23
<212> TYPE: DNA
<213> ORGANISM: Homo sapiens

<400> SEQUENCE: 90
gagtggccag agtccagctt ggg                                              23

<210> SEQ ID NO 91
<211> LENGTH: 23
<212> TYPE: DNA
<213> ORGANISM: Homo sapiens

<400> SEQUENCE: 91
ggcctcccca aagcctggcc agg                                              23

<210> SEQ ID NO 92
<211> LENGTH: 23
```

```
<212> TYPE: DNA
<213> ORGANISM: Homo sapiens

<400> SEQUENCE: 92
ggggccgaga ttgggtgttc agg                                          23

<210> SEQ ID NO 93
<211> LENGTH: 23
<212> TYPE: DNA
<213> ORGANISM: Homo sapiens

<400> SEQUENCE: 93
gtggcgagag gggccgagat tgg                                          23

<210> SEQ ID NO 94
<211> LENGTH: 23
<212> TYPE: DNA
<213> ORGANISM: Homo sapiens

<400> SEQUENCE: 94
gagtgccgcc gaggcggggc ggg                                          23

<210> SEQ ID NO 95
<211> LENGTH: 23
<212> TYPE: DNA
<213> ORGANISM: Homo sapiens

<400> SEQUENCE: 95
ggagtgccgc cgaggcgggg cgg                                          23

<210> SEQ ID NO 96
<211> LENGTH: 23
<212> TYPE: DNA
<213> ORGANISM: Homo sapiens

<400> SEQUENCE: 96
ggagaggagt gccgccgagg cgg                                          23

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
aaaaccaccc ttctctctgg c                                            21

<210> SEQ ID NO 98
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
ggagattgga gacacggaga g                                            21

<210> SEQ ID NO 99
<211> LENGTH: 20
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
ccatcccctt ctgtgaatgt                                             20

<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
ggagattgga gacacggaga                                             20

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
ctggaaagcc aatgcctgac                                             20

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
ggcagcaaac tccttgtcct                                             20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
aagcaccgac tcggtgccac                                             20

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
tcacctccaa tgactagggg                                             20

<210> SEQ ID NO 105
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
caagttgata acggactagc ct                                              22

<210> SEQ ID NO 106
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
agtccgagca gaagaagaag ttt                                             23

<210> SEQ ID NO 107
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
tttcaagttg ataacggact agcct                                           25

<210> SEQ ID NO 108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
aaacagcaga ttcgcctgga                                                 20

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
tcatccgctc gatgaagctc                                                 20

<210> SEQ ID NO 110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 110
tccaaaatca agtggggcga                                            20

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
tgatgaccct tttggctccc                                            20

<210> SEQ ID NO 112
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
gaggaattct tttttgtty gaatatgttg gaggtttttt ggaag                 45

<210> SEQ ID NO 113
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
gagaagctta aataaaaaac racaatactc aacccaacaa cc                   42

<210> SEQ ID NO 114
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
caggaaacag ctatgac                                               17

<210> SEQ ID NO 115
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
gcctctagag gtacctgagg gcctatttcc catgattcc                       39

<210> SEQ ID NO 116
<211> LENGTH: 133

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (92)..(111)
<223> OTHER INFORMATION: a, c, t, g, unknown or other

<400> SEQUENCE: 116
acctctagaa aaaaagcacc gactcggtgc cacttttca agttgataac ggactagcct    60 tatttaact tgctatttct agctctaaaa cnnnnnnnnn nnnnnnnnnn nggtgtttcg   120
tcctttccac aag                                                    133

<210> SEQ ID NO 117
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (92)..(111)
<223> OTHER INFORMATION: a, c, t, g, unknown or other

<400> SEQUENCE: 117
acctctagaa aaaaagcacc gactcggtgc cacttttca agttgataac ggactagcct    60
tatattaact tgctatttct agctctaata cnnnnnnnnn nnnnnnnnnn nggtgtttcg   120
tcctttccac aag                                                    133

<210> SEQ ID NO 118
<211> LENGTH: 153
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (112)..(131)
<223> OTHER INFORMATION: a, c, t, g, unknown or other

<400> SEQUENCE: 118
acctctagaa aaaaagcacc gactcggtgc cacttttca agttgataac ggactagcct    60 tatttaact tgctatgctg ttttgtttcc aaaacagcat agctctaaaa cnnnnnnnnn   120
nnnnnnnnnn nggtgtttcg tcctttccac aag                              153

<210> SEQ ID NO 119
<211> LENGTH: 153
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (112)..(131)
<223> OTHER INFORMATION: a, c, t, g, unknown or other

<400> SEQUENCE: 119
```

```
acctctagaa aaaaagcacc gactcggtgc cacttttttca agttgataac ggactagcct    60
tatattaact tgctatgctg tattgtttcc aatacagcat agctctaata cnnnnnnnnn   120
nnnnnnnnnn nggtgtttcg tcctttccac aag                                153

<210> SEQ ID NO 120
<211> LENGTH: 335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg gaaccattca aaacagcata gcaagttaaa ataaggctag tccgttatca   300
acttgaaaaa gtggcaccga gtcggtgctt ttttt                              335

<210> SEQ ID NO 121
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (288)..(317)
<223> OTHER INFORMATION: a, c, t, g, unknown or other

<400> SEQUENCE: 121
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccg ggttttagag ctatgctgtt ttgaatggtc ccaaaacnnn nnnnnnnnn   300 nnnnnnnnnn nnnnnnngtt ttagagctat gctgttttga atggtcccaa aactttttttt   360

<210> SEQ ID NO 122
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 122
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
```

```
atgcttaccg taacttgaaa gtatttcgat ttcttggctt tatatatctt gtggaaagga    240
cgaaacaccn nnnnnnnnnn nnnnnnnnng ttttagagct agaaatagca agttaaaata    300
aggctagtcc gttttttt                                                  318
```

```
<210> SEQ ID NO 123
<211> LENGTH: 325
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 123
```

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng ttttagagct agaaatagca agttaaaata    300
aggctagtcc gttatcattt ttttt                                         325
```

```
<210> SEQ ID NO 124
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 124
```

```
gagggcctat ttcccatgat tccttcatat ttgcatatac gatacaaggc tgttagagag    60
ataattggaa ttaatttgac tgtaaacaca aagatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacaccn nnnnnnnnn nnnnnnnnng ttttagagct agaaatagca agttaaaata    300
aggctagtcc gttatcaact tgaaaagtg tttttt                              337
```

```
<210> SEQ ID NO 125
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 125
```

```
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccn nnnnnnnnnn nnnnnnnnng ttttagagct agaaatagca agttaaaata     300
aggctagtcc gttatcaact tgaaaaagtg gcaccgagtc ggtgcttttt tt             352
```

<210> SEQ ID NO 126
<211> LENGTH: 5101
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtcgag gtgagcccca cgttctgctt cactctcccc atctcccccc cctccccacc     360
cccaattttg tatttattta ttttttaatt attttgtgca gcgatggggg cggggggggg     420 ggggggggcgc gcgccaggcg gggcggggcg gggcgagggg cggggcgggg cgaggcggag     480
aggtgcggcg gcagccaatc agagcggcgc gctccgaaag tttccttttta tggcgaggcg     540 gcggcggcgg cggccctata aaaagcgaag cgcgcggcgg cgggagtcg ctgcgacgct      600 gccttcgccc cgtgccccgc tccgccgccg cctcgcgccg cccgccccgg ctctgactga     660
ccgcgttact cccacaggtg agcgggcggg acggcccttc tcctccgggc tgtaattagc     720
tgagcaagag gtaagggttt aagggatggt tggttggtgg gtattaatg tttaattacc     780 tggagcacct gcctgaaatc actttttttc aggttggacc ggtgccacca tggactataa     840
ggaccacgac ggagactaca aggatcatga tattgattac aaagacgatg acgataagat     900 ggcccccaaag aagaagcgga aggtcggtat ccacggagtc ccagcagccg acaagaagta     960
cagcatcggc ctggacatcg gcaccaactc tgtgggctgg gccgtgatca ccgacgagta    1020
caaggtgccc agcaagaaat tcaaggtgct gggcaacacc gaccggcaca gcatcaagaa    1080
gaacctgatc ggagccctgc tgttcgacag cggcgaaaca gccgaggcca cccggctgaa    1140
gagaaccgcc agaagaagat acaccagacg gaagaaccgg atctgctatc tgcaagagat    1200
cttcagcaac gagatggcca aggtggacga cagcttcttc cacagactgg aagagtcctt    1260
cctggtggaa gaggataaga agcacgagcg gcaccccatc ttcggcaaca tcgtggacga    1320
ggtggcctac cacgagaagt accccaccat ctaccacctg agaaagaaac tggtggacag    1380
caccgacaag gccgacctgc ggctgatcta tctggccctg gcccacatga tcaagttccg    1440
gggccacttc ctgatcgagg gcgacctgaa ccccgacaac agcgacgtgg acaagctgtt    1500
catccagctg gtgcagacct acaaccagct gttcgaggaa aaccccatca acgccagcgg    1560
cgtggacgcc aaggccatcc tgtctgccag actgagcaag agcagacggc tggaaaatct    1620
gatcgcccag ctgcccggcg agaagaagaa tggcctgttc ggcaacctga ttgccctgag    1680
```

```
cctgggcctg accccaact  tcaagagcaa cttcgacctg gccgaggatg ccaaactgca    1740
gctgagcaag gacacctacg acgacgacct ggacaacctg ctggcccaga tcggcgacca    1800
gtacgccgac ctgtttctgg ccgccaagaa cctgtccgac gccatcctgc tgagcgacat    1860
cctgagagtg aacaccgaga tcaccaaggc ccccctgagc gcctctatga tcaagagata    1920
cgacgagcac caccaggacc tgaccctgct gaaagctctc gtgcggcagc agctgcctga    1980
gaagtacaaa gagattttct tcgaccagag caagaacggc tacgccggct acattgacgg    2040
cggagccagc caggaagagt tctacaagtt catcaagccc atcctggaaa agatggacgg    2100
caccgaggaa ctgctcgtga agctgaacag agaggacctg ctgcggaagc agcggacctt    2160
cgacaacggc agcatccccc accagatcca cctgggagag ctgcacgcca ttctgcggcg    2220
gcaggaagat tttacccat  tcctgaagga caaccgggaa aagatcgaga gatcctgac    2280 cttccgcatc ccctactacg tgggccctct ggccagggga acagcagat  cgcctggat    2340 gaccagaaag agcgaggaaa ccatcacccc ctggaacttc gaggaagtgg tggacaaggg    2400
cgcttccgcc cagagcttca tcgagcggat gaccaacttc gataagaacc tgcccaacga    2460
gaaggtgctg cccaagcaca gcctgctgta cgagtacttc accgtgtata acgagctgac    2520
caaagtgaaa tacgtgaccg agggaatgag aaagcccgcc ttcctgagcg gcgagcagaa    2580
aaaggccatc gtggacctgc tgttcaagac caaccggaaa gtgaccgtga agcagctgaa    2640
agaggactac ttcaagaaaa tcgagtgctt cgactccgtg gaaatctccg gcgtggaaga    2700
tcggttcaac gcctccctgg gcacatacca cgatctgctg aaaattatca aggacaagga    2760
cttcctggac aatgaggaaa acgaggacat tctggaagat atcgtgctga ccctgacact    2820
gtttgaggac agagagatga tcgaggaacg gctgaaaacc tatgcccacc tgttcgacga    2880
caaagtgatg aagcagctga agcggcggag atacaccggc tggggcaggc tgagccggaa    2940
gctgatcaac ggcatccggg acaagcagtc cggcaagaca atcctggatt tcctgaagtc    3000
cgacggcttc gccaacagaa acttcatgca gctgatccac gacgacagcc tgacctttaa    3060
agaggacatc cagaaagccc aggtgtccgg ccagggcgat agcctgcacg agcacattgc    3120
caatctggcc ggcagccccg ccattaagaa gggcatcctg cagacagtga aggtggtgga    3180
cgagctcgtg aaagtgatgg gccggcacaa gcccgagaac atcgtgatcg aaatggccag    3240
agagaaccag accacccaga agggacagaa gaacagccgc gagagaatga gcggatcga    3300 agagggcatc aaagagctgg gcagccagat cctgaaagaa caccccgtgg aaaacaccca    3360
gctgcagaac gagaagctgt acctgtacta cctgcagaat gggcgggata tgtacgtgga    3420
ccaggaactg gacatcaacc ggctgtccga ctacgatgtg gaccatatcg tgcctcagag    3480
ctttctgaag gacgactcca tcgacaacaa ggtgctgacc agaagcgaca agaaccgggg    3540
caagagcgac aacgtgccct ccgaagaggt cgtgaagaag atgaagaact actggcggca    3600
gctgctgaac gccaagctga ttacccagag aaagttcgac aatctgacca aggccgagag    3660
aggcggcctg agcgaactgg ataaggccgg cttcatcaag agacagctgg tggaaacccg    3720
gcagatcaca aagcacgtgg cacagatcct ggactcccgg atgaacacta agtacgacga    3780
gaatgacaag ctgatccggg aagtgaaagt gatcaccctg aagtccaagc tggtgtccga    3840
tttccggaag gatttccagt tttacaaagt gcgcgagatc aacaactacc accacgccca    3900
cgacgcctac ctgaacgccg tcgtgggaac cgccctgatc aaaaagtacc ctaagctgga    3960
aagcgagttc gtgtacggcg actacaaggt gtacgacgtg cggaagatga tcgccaagag    4020
```

```
cgagcaggaa atcggcaagg ctaccgccaa gtacttcttc tacagcaaca tcatgaactt    4080
tttcaagacc gagattaccc tggccaacgg cgagatccgg aagcggcctc tgatcgagac    4140
aaacggcgaa accggggaga tcgtgtggga taagggccgg gattttgcca ccgtgcggaa    4200
agtgctgagc atgccccaag tgaatatcgt gaaaaagacc gaggtgcaga caggcggctt    4260
cagcaaagag tctatcctgc caagaggaa cagcgataag ctgatcgcca gaaagaagga    4320
ctgggaccct aagaagtacg gcggcttcga cagccccacc gtggcctatt ctgtgctggt    4380
ggtggccaaa gtggaaaagg gcaagtccaa gaaactgaag agtgtgaaag agctgctggg    4440
gatcaccatc atggaaagaa gcagcttcga gaagaatccc atcgactttc tggaagccaa    4500
gggctacaaa gaagtgaaaa aggacctgat catcaagctg cctaagtact ccctgttcga    4560
gctggaaaac ggccggaaga aatgctggc ctctgccggc gaactgcaga agggaaacga    4620
actggccctg ccctccaaat atgtgaactt cctgtacctg gccagccact atgagaagct    4680
gaagggctcc cccgaggata tgagcagaa acagctgttt gtggaacagc acaagcacta    4740
cctggacgag atcatcgagc agatcagcga gttctccaag agagtgatcc tggccgacgc    4800
taatctggac aaagtgctgt ccgcctacaa caagcaccgg gataagccca tcagagagca    4860
ggccgagaat atcatccacc tgtttaccct gaccaatctg ggagcccctg ccgccttcaa    4920
gtactttgac accaccatcg accggaagag gtacaccagc accaaagagg tgctggacgc    4980
caccctgatc caccagagca tcaccggcct gtacgagaca cggatcgacc tgtctcagct    5040
gggaggcgac tttcttttc ttagcttgac cagctttctt agtagcagca ggacgcttta    5100
a                                                                    5101

<210> SEQ ID NO 127
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127
ccaatgggga ggacatcgat gtcacctcca atgactaggg tgggcaacca caaacccacg     60
agggcagagt gctgcttgct gctggccagg cccctgcgtg ggcccaagct ggactctggc    120
cac                                                                  123

<210> SEQ ID NO 128
<211> LENGTH: 121
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128
cgagcagaag aagaagggct cccatcacat caaccggtgg cgcattgcca cgaagcaggc     60
caatggggag gacatcgatg tcacctccaa tgactagggt gggcaaccac aaacccacga    120
g                                                                    121

<210> SEQ ID NO 129
<211> LENGTH: 128
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 129
ggaggacaaa gtacaaacgg cagaagctgg aggaggaagg gcctgagtcc gagcagaaga    60
agaagggctc ccatcacatc aaccggtggc gcattgccac gaagcaggcc aatggggagg   120
acatcgat                                                            128

<210> SEQ ID NO 130
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
agaagctgga ggaggaaggg cctgagtccg agcagaagaa gaagggctcc catcacatca    60
accggtggcg cattgccacg aagcaggcca atggggagga catcgatgtc acctccaatg   120
actagggtgg                                                          130

<210> SEQ ID NO 131
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131
cctcagtctt cccatcaggc tctcagctca gcctgagtgt tgaggcccca gtggctgctc    60
tgggggcctc ctgagtttct catctgtgcc cctccctccc tggcccaggt gaaggtgtgg   120
ttcca                                                               125

<210> SEQ ID NO 132
<211> LENGTH: 129
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132
tcatctgtgc ccctccctcc ctggcccagg tgaaggtgtg gttccagaac cggaggacaa    60
agtacaaacg gcagaagctg gaggaggaag ggcctgagtc cgagcagaag aagaagggct   120
cccatcaca                                                           129

<210> SEQ ID NO 133
<211> LENGTH: 129
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133
```
ctccaatgac tagggtgggc aaccacaaac ccacgagggc agagtgctgc ttgctgctgg    60
ccaggcccct gcgtgggccc aagctggact ctggccactc cctggccagg ctttggggag   120
gcctggagt                                                          129

<210> SEQ ID NO 134
<211> LENGTH: 127
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
ctgcttgctg ctggccaggc ccctgcgtgg gcccaagctg gactctggcc actccctggc    60 caggcttttgg ggaggcctgg agtcatggcc ccacagggct tgaagcccgg ggccgccatt  120
gacagag                                                            127

<210> SEQ ID NO 135
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
gaaattaata cgactcacta taggg                                         25

<210> SEQ ID NO 136
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 136
aaaaaagcac cgactcggtg ccacttttte aagttgataa cggactagcc ttattttaac    60
ttgctatttc tagctctaaa acaacgacga gcgtgacacc accctatagt gagtcgtatt   120
aatttc                                                             126

<210> SEQ ID NO 137
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 137
aaaaaagcac cgactcggtg ccacttttte aagttgataa cggactagcc ttattttaac    60
ttgctatttc tagctctaaa acgcaacaat taatagactg gacctatagt gagtcgtatt   120
aatttc                                                             126

<210> SEQ ID NO 138
<211> LENGTH: 102
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 138
gttttagagc tatgctgttt tgaatggtcc caaaacggaa gggcctgagt ccgagcagaa      60
gaagaagttt tagagctatg ctgttttgaa tggtcccaaa ac                       102

<210> SEQ ID NO 139
<211> LENGTH: 100
<212> TYPE: DNA
<213> ORGANISM: Homo sapiens

<400> SEQUENCE: 139
cggaggacaa agtacaaacg gcagaagctg gaggaggaag ggcctgagtc cgagcagaag      60
aagaagggct cccatcacat caaccggtgg cgcattgcca                          100

<210> SEQ ID NO 140
<211> LENGTH: 50
<212> TYPE: DNA
<213> ORGANISM: Homo sapiens

<400> SEQUENCE: 140
agctggagga ggaagggcct gagtccgagc agaagaagaa gggctcccac                50

<210> SEQ ID NO 141
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gaguccgagc agaagaagaa guuuuagagc                                      30

<210> SEQ ID NO 142
<211> LENGTH: 49
<212> TYPE: DNA
<213> ORGANISM: Homo sapiens

<400> SEQUENCE: 142
agctggagga ggaagggcct gagtccgagc agaagagaag ggctcccat                 49

<210> SEQ ID NO 143
<211> LENGTH: 53
<212> TYPE: DNA
<213> ORGANISM: Homo sapiens

<400> SEQUENCE: 143
ctggaggagg aagggcctga gtccgagcag aagaagaagg gctcccatca cat            53

<210> SEQ ID NO 144
<211> LENGTH: 52
<212> TYPE: DNA
<213> ORGANISM: Homo sapiens

<400> SEQUENCE: 144
ctggaggagg aagggcctga gtccgagcag aagagaaggg ctcccatcac at             52

<210> SEQ ID NO 145
```

<211> LENGTH: 54
<212> TYPE: DNA
<213> ORGANISM: Homo sapiens

<400> SEQUENCE: 145
ctggaggagg aagggcctga gtccgagcag aagaaagaag ggctcccatc acat    54

<210> SEQ ID NO 146
<211> LENGTH: 50
<212> TYPE: DNA
<213> ORGANISM: Homo sapiens

<400> SEQUENCE: 146
ctggaggagg aagggcctga gtccgagcag aagaagggct cccatcacat    50

<210> SEQ ID NO 147
<211> LENGTH: 47
<212> TYPE: DNA
<213> ORGANISM: Homo sapiens

<400> SEQUENCE: 147
ctggaggagg aagggcctga gcccgagcag aagggctccc atcacat    47

<210> SEQ ID NO 148
<211> LENGTH: 23
<212> TYPE: DNA
<213> ORGANISM: Homo sapiens

<400> SEQUENCE: 148
gtcacctcca atgactaggg tgg    23

<210> SEQ ID NO 149
<211> LENGTH: 23
<212> TYPE: DNA
<213> ORGANISM: Homo sapiens

<400> SEQUENCE: 149
gcgccaccgg ttgatgtgat ggg    23

<210> SEQ ID NO 150
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 150
nnnnnnnnnn nnnnnnnnnn guuuuagagc uagaaauagc aaguuaaaau aaggcuaguc    60
cguuaucaac uugaaaaagu ggcaccgagu cggugcuuu    99

<210> SEQ ID NO 151
<211> LENGTH: 64
<212> TYPE: DNA
<213> ORGANISM: Homo sapiens

<400> SEQUENCE: 151
caagaggctt gagtaggaga ggagtgccgc cgaggcgggg cggggcgggg cgtggagctg    60
ggct    64

```
<210> SEQ ID NO 152
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gucaccucca augacuaggg                                                    20

<210> SEQ ID NO 153
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
gucaccucca augacuaaga                                                    20

<210> SEQ ID NO 154
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
gucaccucca augauuagga                                                    20

<210> SEQ ID NO 155
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
gucaccucca gugacuagga                                                    20

<210> SEQ ID NO 156
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
gucacuucca augacuagga                                                    20

<210> SEQ ID NO 157
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 157
aucaccucca augacuagga                                                  20

<210> SEQ ID NO 158
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
gucaccucca augaccaagg                                                  20

<210> SEQ ID NO 159
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
gucaccucca auaacuaagg                                                  20

<210> SEQ ID NO 160
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gucaccucua augacuaagg                                                  20

<210> SEQ ID NO 161
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
gucgccucca augacuaagg                                                  20

<210> SEQ ID NO 162
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
gucaccucca auggccaggg                                                  20

<210> SEQ ID NO 163
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gucaccucca gugaccaggg                                                     20

<210> SEQ ID NO 164
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
gucaccccca augaccaggg                                                     20

<210> SEQ ID NO 165
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
gccaccucca augaccaggg                                                     20

<210> SEQ ID NO 166
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
gucaccucca augaccaaga                                                     20

<210> SEQ ID NO 167
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gucaccucca auggcuggga                                                     20

<210> SEQ ID NO 168
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
```

```
gucaccucca acgaccagga                                              20
```

<210> SEQ ID NO 169
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169

```
gucaccuccg augauuagga                                              20
```

<210> SEQ ID NO 170
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170

```
gucaccucca auggccaagg                                              20
```

<210> SEQ ID NO 171
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171

```
gucaccucca acgauuaagg                                              20
```

<210> SEQ ID NO 172
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172

```
gucaccuccg auggcuaagg                                              20
```

<210> SEQ ID NO 173
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173

```
gucaccuuca auaacuaagg                                              20
```

<210> SEQ ID NO 174
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 174
gucaccucca auggccaaga                                                  20

<210> SEQ ID NO 175
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gucaccucca guggcuggga                                                  20

<210> SEQ ID NO 176
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gucaccuuca acgaccagga                                                  20

<210> SEQ ID NO 177
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gucaucuccg augauuagga                                                  20

<210> SEQ ID NO 178
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gccaccuuca auggcuagga                                                  20

<210> SEQ ID NO 179
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gucaccucca augacuagaa                                                  20

<210> SEQ ID NO 180
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gucaccucca augacugagg                                                 20

<210> SEQ ID NO 181
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gucaccucca augaucaggg                                                 20

<210> SEQ ID NO 182
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
gucaccucca auagcuaggg                                                 20

<210> SEQ ID NO 183
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
gucaccucca gcgacuaggg                                                 20

<210> SEQ ID NO 184
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gucaccucug augacuaggg                                                 20

<210> SEQ ID NO 185
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
```

```
gucacccuca augacuaggg                                              20

<210> SEQ ID NO 186
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gucauuucca augacuaggg                                              20

<210> SEQ ID NO 187
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
guugccucca augacuaggg                                              20

<210> SEQ ID NO 188
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
accaccucca augacuaggg                                              20

<210> SEQ ID NO 189
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gucaccucca augacugaag                                              20

<210> SEQ ID NO 190
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gucaccucca auggcaggg                                               20

<210> SEQ ID NO 191
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 191
gucaccucca gcaacuaggg                                                 20

<210> SEQ ID NO 192
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gucaccuuug augacuaggg                                                 20

<210> SEQ ID NO 193
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
gucauuccca augacuaggg                                                 20

<210> SEQ ID NO 194
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gcugccucca augacuaggg                                                 20

<210> SEQ ID NO 195
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gucaccucca augaccgaaa                                                 20

<210> SEQ ID NO 196
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
gucaccucca auagucgggg                                                 20
```

```
<210> SEQ ID NO 197
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
gucaccuccg gcagcuaggg                                              20

<210> SEQ ID NO 198
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
gucacccuug gugacuaggg                                              20

<210> SEQ ID NO 199
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gucguucuca augacuaggg                                              20

<210> SEQ ID NO 200
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
acugucucca augacuaggg                                              20

<210> SEQ ID NO 201
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
gcgccaccgg uugaugugau                                              20

<210> SEQ ID NO 202
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 202
gcgccaccgg uugauguaac                                              20

<210> SEQ ID NO 203
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gcgccaccgg uugacgugac                                              20

<210> SEQ ID NO 204
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
gcgccaccgg cugaugugac                                              20

<210> SEQ ID NO 205
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
gcgccgccgg uugaugugac                                              20

<210> SEQ ID NO 206
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
acgccaccgg uugaugugac                                              20

<210> SEQ ID NO 207
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gcgccaccgg uugauauaau                                              20

<210> SEQ ID NO 208
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 208
gcgccaccgg uuaauguaau                                                    20

<210> SEQ ID NO 209
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
gcgccaccag uugauguaau                                                    20

<210> SEQ ID NO 210
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gcgucaccgg uugauguaau                                                    20

<210> SEQ ID NO 211
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gcgccaccgg uugguaugau                                                    20

<210> SEQ ID NO 212
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gcgccaccgg cugauaugau                                                    20

<210> SEQ ID NO 213
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
gcgccaucgg uugauaugau                                                    20
```

<210> SEQ ID NO 214
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
gugccaccgg uugauaugau                                            20

<210> SEQ ID NO 215
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gcgccaccgg uugauauaac                                            20

<210> SEQ ID NO 216
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
gcgccaccgg uuggugcgac                                            20

<210> SEQ ID NO 217
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
gcgccaccgg ucgauaugac                                            20

<210> SEQ ID NO 218
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
gcgccaccga uugacgugac                                            20

<210> SEQ ID NO 219
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 219
gcgccaccgg uugguauaau                                              20

<210> SEQ ID NO 220
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 220
gcgccaccgg ucgacguaau                                              20

<210> SEQ ID NO 221
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
gcgccaccga uugguguaau                                              20

<210> SEQ ID NO 222
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
gcgccacugg uuaauguaau                                              20

<210> SEQ ID NO 223
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gcgccaccgg uugguauaac                                              20

<210> SEQ ID NO 224
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gcgccaccgg cuggugcgac                                              20

<210> SEQ ID NO 225
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gcgccacugg ucgauaugac                                                   20

<210> SEQ ID NO 226
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
gcgcuaccga uugacgugac                                                   20

<210> SEQ ID NO 227
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gugccacugg uuggugugac                                                   20

<210> SEQ ID NO 228
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
gcgccaccgg uugauguggc                                                   20

<210> SEQ ID NO 229
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
gcgccaccgg uugaugcaau                                                   20

<210> SEQ ID NO 230
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
```
gcgccaccgg uugacaugau                                               20

<210> SEQ ID NO 231
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
gcgccaccgg uuagugugau                                               20

<210> SEQ ID NO 232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
gcgccaccgg ccgaugugau                                               20

<210> SEQ ID NO 233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
gcgccaccaa uugaugugau                                               20

<210> SEQ ID NO 234
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
gcgccauugg uugaugugau                                               20

<210> SEQ ID NO 235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
gcgcugccgg uugaugugau                                               20

<210> SEQ ID NO 236
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 236
gcaucaccgg uugaugugau                                                 20

<210> SEQ ID NO 237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
augccaccgg uugaugugau                                                 20

<210> SEQ ID NO 238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gcgccaccgg uugaugcagu                                                 20

<210> SEQ ID NO 239
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gcgccaccgg uuggcaugau                                                 20

<210> SEQ ID NO 240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gcgccaccgg ccaaugugau                                                 20

<210> SEQ ID NO 241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gcgccacuaa uugaugugau                                                 20

<210> SEQ ID NO 242
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gcgcugucgg uugaugugau                                              20

<210> SEQ ID NO 243
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
guaucaccgg uugaugugau                                              20

<210> SEQ ID NO 244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
gcgccaccgg uugauacagc                                              20

<210> SEQ ID NO 245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gcgccaccgg uuagcacgau                                              20

<210> SEQ ID NO 246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gcgccaccga ccagugugau                                              20

<210> SEQ ID NO 247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
```

```
gcgccauuaa cugaugugau                                                    20

<210> SEQ ID NO 248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gcguuguugg uugaugugau                                                    20

<210> SEQ ID NO 249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
auauuaccgg uugaugugau                                                    20

<210> SEQ ID NO 250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
gucaccucca augacuaggg                                                    20

<210> SEQ ID NO 251
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
gucaccugga augacuaggg                                                    20

<210> SEQ ID NO 252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
gucacgacca augacuaggg                                                    20

<210> SEQ ID NO 253
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 253
gucugcucca augacuaggg                                              20

<210> SEQ ID NO 254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
gagaccucca augacuaggg                                              20

<210> SEQ ID NO 255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gucaccagga augacuaggg                                              20

<210> SEQ ID NO 256
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
gucuggucca augacuaggg                                              20

<210> SEQ ID NO 257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
gaguccucca augacuaggg                                              20

<210> SEQ ID NO 258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gucacgagga augacuaggg                                              20
```

```
<210> SEQ ID NO 259
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
gucuggacca augacuaggg                                                     20

<210> SEQ ID NO 260
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gagugcucca augacuaggg                                                     20

<210> SEQ ID NO 261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
gucugcugga augacuaggg                                                     20

<210> SEQ ID NO 262
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
gagacgacca augacuaggg                                                     20

<210> SEQ ID NO 263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gagaccugga augacuaggg                                                     20

<210> SEQ ID NO 264
<211> LENGTH: 40
<212> TYPE: DNA
<213> ORGANISM: Homo sapiens

<400> SEQUENCE: 264
ggacatcgat gtcacctcca atgactaggg tgggcaacca                               40
```

```
<210> SEQ ID NO 265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
gucaccucca augacuaggg                                                   20

<210> SEQ ID NO 266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (20)..(20)
<223> OTHER INFORMATION: a, c, u, g, unknown or other

<400> SEQUENCE: 266
gucaccucca augacuaggn                                                   20

<210> SEQ ID NO 267
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (19)..(19)
<223> OTHER INFORMATION: a, c, u, g, unknown or other

<400> SEQUENCE: 267
gucaccucca augacuagng                                                   20

<210> SEQ ID NO 268
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (18)..(18)
<223> OTHER INFORMATION: a, c, u, g, unknown or other

<400> SEQUENCE: 268
gucaccucca augacuangg                                                   20

<210> SEQ ID NO 269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (17)..(17)
<223> OTHER INFORMATION: a, c, u, g, unknown or other

<400> SEQUENCE: 269
gucaccucca augacungggg                                              20

<210> SEQ ID NO 270
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (16)..(16)
<223> OTHER INFORMATION: a, c, u, g, unknown or other

<400> SEQUENCE: 270
gucaccucca augacnaggg                                               20

<210> SEQ ID NO 271
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (15)..(15)
<223> OTHER INFORMATION: a, c, u, g, unknown or other

<400> SEQUENCE: 271
gucaccucca auganuaggg                                               20

<210> SEQ ID NO 272
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (14)..(14)
<223> OTHER INFORMATION: a, c, u, g, unknown or other

<400> SEQUENCE: 272
gucaccucca augncuaggg                                               20

<210> SEQ ID NO 273
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (13)..(13)
<223> OTHER INFORMATION: a, c, u, g, unknown or other

<400> SEQUENCE: 273
gucaccucca aunacuaggg                                               20
```

```
<210> SEQ ID NO 274
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: a, c, u, g, unknown or other

<400> SEQUENCE: 274
gucaccucca angacuaggg                                               20

<210> SEQ ID NO 275
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(11)
<223> OTHER INFORMATION: a, c, u, g, unknown or other

<400> SEQUENCE: 275
gucaccucca nugacuaggg                                               20

<210> SEQ ID NO 276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(10)
<223> OTHER INFORMATION: a, c, u, g, unknown or other

<400> SEQUENCE: 276
gucaccuccn augacuaggg                                               20

<210> SEQ ID NO 277
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (9)..(9)
<223> OTHER INFORMATION: a, c, u, g, unknown or other

<400> SEQUENCE: 277
gucaccucna augacuaggg                                               20

<210> SEQ ID NO 278
<211> LENGTH: 20
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: a, c, u, g, unknown or other

<400> SEQUENCE: 278
gucaccunca augacuaggg                                                    20

<210> SEQ ID NO 279
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(7)
<223> OTHER INFORMATION: a, c, u, g, unknown or other

<400> SEQUENCE: 279
gucaccncca augacuaggg                                                    20

<210> SEQ ID NO 280
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, u, g, unknown or other

<400> SEQUENCE: 280
gucacnucca augacuaggg                                                    20

<210> SEQ ID NO 281
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(5)
<223> OTHER INFORMATION: a, c, u, g, unknown or other

<400> SEQUENCE: 281
gucancucca augacuaggg                                                    20

<210> SEQ ID NO 282
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(4)
<223> OTHER INFORMATION: a, c, u, g, unknown or other
```

```
<400> SEQUENCE: 282
gucnccucca augacuaggg                                            20

<210> SEQ ID NO 283
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(3)
<223> OTHER INFORMATION: a, c, u, g, unknown or other

<400> SEQUENCE: 283
gunaccucca augacuaggg                                            20

<210> SEQ ID NO 284
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (2)..(2)
<223> OTHER INFORMATION: a, c, u, g, unknown or other

<400> SEQUENCE: 284
gncaccucca augacuaggg                                            20

<210> SEQ ID NO 285
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
gucaccucca augacuaggg                                            20

<210> SEQ ID NO 286
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
gacaucgaug uccucccau                                             20

<210> SEQ ID NO 287
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
```
gcgccaccgg uugaugugau                                            20

<210> SEQ ID NO 288
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
gucaccucca augacuaggg                                            20

<210> SEQ ID NO 289
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
gucaccucca augacuagaa                                            20

<210> SEQ ID NO 290
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
gucaccucca augacugagg                                            20

<210> SEQ ID NO 291
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
gucaccucca augaucaggg                                            20

<210> SEQ ID NO 292
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
gucaccucca auagcuaggg                                            20

<210> SEQ ID NO 293
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 293
gucaccucca gcgacuaggg                                                   20

<210> SEQ ID NO 294
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
gucaccucug augacuaggg                                                   20

<210> SEQ ID NO 295
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
gucacccuca augacuaggg                                                   20

<210> SEQ ID NO 296
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gucauuucca augacuaggg                                                   20

<210> SEQ ID NO 297
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
guugccucca augacuaggg                                                   20

<210> SEQ ID NO 298
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
accaccucca augacuaggg                                                   20
```

```
<210> SEQ ID NO 299
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
gucaccucca augacugaag                                                  20

<210> SEQ ID NO 300
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
gucaccucca auggucaggg                                                  20

<210> SEQ ID NO 301
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
gucaccucca gcaacuaggg                                                  20

<210> SEQ ID NO 302
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
gucaccuuug augacuaggg                                                  20

<210> SEQ ID NO 303
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
gucauuccca augacuaggg                                                  20

<210> SEQ ID NO 304
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 304
gcugccucca augacuaggg                                           20

<210> SEQ ID NO 305
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
gucaccucca augaccgaaa                                           20

<210> SEQ ID NO 306
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gucaccucca auagucgggg                                           20

<210> SEQ ID NO 307
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
gucaccuccg gcagcuaggg                                           20

<210> SEQ ID NO 308
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
gucacccuug gugacuaggg                                           20

<210> SEQ ID NO 309
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
gucguucuca augacuaggg                                           20

<210> SEQ ID NO 310
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 310
acugucucca augacuaggg                                              20

<210> SEQ ID NO 311
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
gcgccaccgg uugaugugau                                              20

<210> SEQ ID NO 312
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
gcgccaccgg uugauguggc                                              20

<210> SEQ ID NO 313
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
gcgccaccgg uugaugcaau                                              20

<210> SEQ ID NO 314
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
gcgccaccgg uugacaugau                                              20

<210> SEQ ID NO 315
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
gcgccaccgg uuagugugau                                              20
```

-continued

```
<210> SEQ ID NO 316
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
gcgccaccgg ccgaugugau                                                    20

<210> SEQ ID NO 317
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gcgccaccaa uugaugugau                                                    20

<210> SEQ ID NO 318
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gcgccauugg uugaugugau                                                    20

<210> SEQ ID NO 319
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
gcgcugccgg uugaugugau                                                    20

<210> SEQ ID NO 320
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gcaucaccgg uugaugugau                                                    20

<210> SEQ ID NO 321
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 321
augccaccgg uugaugugau                                              20

<210> SEQ ID NO 322
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
gcgccaccgg uugaugcagu                                              20

<210> SEQ ID NO 323
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
gcgccaccgg uuggcaugau                                              20

<210> SEQ ID NO 324
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
gcgccaccgg ccaaugugau                                              20

<210> SEQ ID NO 325
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
gcgccacuaa uugaugugau                                              20

<210> SEQ ID NO 326
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gcgcugucgg uugaugugau                                              20

<210> SEQ ID NO 327
<211> LENGTH: 20
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
guaucaccgg uugaugugau                                               20

<210> SEQ ID NO 328
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
gcgccaccgg uugauacagc                                               20

<210> SEQ ID NO 329
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
gcgccaccgg uuagcacgau                                               20

<210> SEQ ID NO 330
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
gcgccaccga ggagugugau                                               20

<210> SEQ ID NO 331
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
gcgccauuaa gugaugugau                                               20

<210> SEQ ID NO 332
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
gcguuguugg uugaugugau                                               20
```

```
<210> SEQ ID NO 333
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
auauuaccgg uugaugugau                                                 20

<210> SEQ ID NO 334
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
gucaccucca augacuaggg                                                 20

<210> SEQ ID NO 335
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
gucaccucca augacuaaga                                                 20

<210> SEQ ID NO 336
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gucaccucca augauuagga                                                 20

<210> SEQ ID NO 337
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
gucaccucca gugacuagga                                                 20

<210> SEQ ID NO 338
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 338
gucacuucca augacuagga                                              20

<210> SEQ ID NO 339
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
aucaccucca augacuagga                                              20

<210> SEQ ID NO 340
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
gucaccucca augacuaggg                                              20

<210> SEQ ID NO 341
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
gucaccucca augaccaaga                                              20

<210> SEQ ID NO 342
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
gucaccucca auggcuggga                                              20

<210> SEQ ID NO 343
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
gucaccucca acgaccagga                                              20

<210> SEQ ID NO 344
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
gucaccuccg augauuagga                                                  20

<210> SEQ ID NO 345
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
gucaccucca auggccaagg                                                  20

<210> SEQ ID NO 346
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
gucaccucca acgauuaagg                                                  20

<210> SEQ ID NO 347
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
gucaccuccg auggcuaagg                                                  20

<210> SEQ ID NO 348
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
gucaccuuca auaacuaagg                                                  20

<210> SEQ ID NO 349
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
```
gucaccucca auggccaaga                                              20

<210> SEQ ID NO 350
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
gucaccucca guggcuggga                                              20

<210> SEQ ID NO 351
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gucaccuuca acgaccagga                                              20

<210> SEQ ID NO 352
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gucaucuccg augauuagga                                              20

<210> SEQ ID NO 353
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
gccaccuuca auggcuagga                                              20

<210> SEQ ID NO 354
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gcgccaccgg uugaugugau                                              20

<210> SEQ ID NO 355
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 355
gcgccaccgg uugauguaac                                                 20

<210> SEQ ID NO 356
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
gcgccaccgg uugacgugac                                                 20

<210> SEQ ID NO 357
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
gcgccaccgg cugaugugac                                                 20

<210> SEQ ID NO 358
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gcgccgccgg uugaugugac                                                 20

<210> SEQ ID NO 359
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
acgccaccgg uugaugugac                                                 20

<210> SEQ ID NO 360
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
gcgccaccgg uugaugugau                                                 20

<210> SEQ ID NO 361
```

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
gcgccaccgg uugauauaac                                              20

<210> SEQ ID NO 362
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
gcgccaccgg uuggugcgac                                              20

<210> SEQ ID NO 363
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
gcgccaccgg ucgauaugac                                              20

<210> SEQ ID NO 364
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
gcgccaccga uugacgugac                                              20

<210> SEQ ID NO 365
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
gcgccaccgg uugguauaau                                              20

<210> SEQ ID NO 366
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
```
gcgccaccgg ucgacguaau                                              20

<210> SEQ ID NO 367
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
gcgccaccga uugguguaau                                              20

<210> SEQ ID NO 368
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
gcgccacugg uuaauguaau                                              20

<210> SEQ ID NO 369
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
gcgccaccgg uugguauaac                                              20

<210> SEQ ID NO 370
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
gcgccaccgg cuggugcgac                                              20

<210> SEQ ID NO 371
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
gcgccacugg ucgauaugac                                              20

<210> SEQ ID NO 372
<211> LENGTH: 20
<212> TYPE: RNA
<213> ORGANISM: Artificial Sequence
<220> FEATURE:

<210> SEQ ID NO 373
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
gcgcuaccga uugacgugac                                         20

<210> SEQ ID NO 373
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
gugccacugg uuggugugac                                         20

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 374
gaguccgagc agaagaagaa ggg                                     23

<210> SEQ ID NO 375
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 375
gauuccuacc agaagaagaa tgg                                     23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 376
aaguccgagg agaggaagaa agg                                     23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 377
aaguccgaga agaagcagaa aag                                          23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
gaguuccaga agaagaagaa gag                                          23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
gagucugaac ggaagaagaa aag                                          23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
gaguuugagu agaagaagaa gag                                          23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
gagucccaga agaagaaaaa aag                                          23

<210> SEQ ID NO 382
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 382
gacuccgagc agcagaagga tgg                                          23

<210> SEQ ID NO 383

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
gagucagagc agaacuagaa ggg                                           23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
gaggccgagc agaagaaaga cgg                                           23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
gagucagacc aggagaagaa gag                                           23

<210> SEQ ID NO 386
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 386
gaguccaaga agaauaagaa tag                                           23

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
gaguaagaga agaagaagaa ggg                                           23

<210> SEQ ID NO 388
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 388
gaguaggagg agaagaagaa agg                                               23

<210> SEQ ID NO 389
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 389
aagucugagc acaagaagaa tgg                                               23

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
gagcccgagc agaaggagga ggg                                               23

<210> SEQ ID NO 391
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
gaguuagagc agaagaagaa agg                                               23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
gagucagaac agaagaacaa cag                                               23

<210> SEQ ID NO 393
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 393
acgucugagc agaagaagaa tgg                                            23

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
gaguacuaga agaagaagaa aag                                            23

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
aagucugagc agaagaagca cag                                            23

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
gagucccagc agaggaagca gag                                            23

<210> SEQ ID NO 397
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
gagucugggc aggagaagaa gag                                            23

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
gaguccuagc aggagaagaa gag                                            23

<210> SEQ ID NO 399
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
gaggaggagc agaagaagaa aag                                              23

<210> SEQ ID NO 400
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
gaguccgaga aaaugaagaa gag                                              23

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
gaggcccagc agaggaagaa gag                                              23

<210> SEQ ID NO 402
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
gaauccaagc agaagaagag aag                                              23

<210> SEQ ID NO 403
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 403
gacuccuagc aaaagaagaa tgg                                              23

<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 404
gagucccagc aaaagaagaa aag                                          23

<210> SEQ ID NO 405
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
gagucuaagc agaagaagaa gag                                          23

<210> SEQ ID NO 406
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
aagucagagg agaagaagaa ggg                                          23

<210> SEQ ID NO 407
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 407
gaguccaagc agaagaagga tag                                          23

<210> SEQ ID NO 408
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
gagacugaga agaagaagaa agg                                          23

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
gagucccagg agaagaagag agg                                          23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 410
gagucccagg agaagaaaaa cag                                              23

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 411
gagagcaagc agaagaagaa aag                                              23

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 412
gaguccaagc auaagaaaaa cag                                              23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 413
gaguccaagc aguagaggaa ggg                                              23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 414
gaguccggga aggagaagaa agg                                              23

<210> SEQ ID NO 415
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

-continued

```
       Synthetic oligonucleotide"

<400> SEQUENCE: 415
gcgccaccgg uugaugugau                                              20

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 416
gggccauggg uugaugugau gag                                          23

<210> SEQ ID NO 417
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 417
gtcacctcca atgactaggg tgg                                          23

<210> SEQ ID NO 418
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 418
gcuacctcca gtgactaggg agg                                          23

<210> SEQ ID NO 419
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 419
gtgacctcca atgcctagag ggg                                          23

<210> SEQ ID NO 420
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 420
gtcacctcca ctucctaggg cag                                              23

<210> SEQ ID NO 421
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 421
utcacctcca aaaactaggg aag                                              23

<210> SEQ ID NO 422
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 422
gtcaactcca atggctuggg agg                                              23

<210> SEQ ID NO 423
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 423
gtcacctuaa atgactuggg aag                                              23

<210> SEQ ID NO 424
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 424
gtcacutcca aggactagag aag                                      23

<210> SEQ ID NO 425
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 425
gtcacctcca ggguctaggg cag                                      23

<210> SEQ ID NO 426
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 426
gtcacctcca ctguataggg agg                                      23

<210> SEQ ID NO 427
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 427
gtcaactcca atgautagga cag                                      23

<210> SEQ ID NO 428
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
gtggtgtcac gctcgtcgtt tgg                                      23

<210> SEQ ID NO 429
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 429
tccagtctat taattgttgc cgg                                              23

<210> SEQ ID NO 430
<211> LENGTH: 12
<212> TYPE: DNA
<213> ORGANISM: Homo sapiens

<400> SEQUENCE: 430
tagcgggtaa gc                                                          12

<210> SEQ ID NO 431
<211> LENGTH: 12
<212> TYPE: DNA
<213> ORGANISM: Homo sapiens

<400> SEQUENCE: 431
tcggtcacat gt                                                          12

<210> SEQ ID NO 432
<211> LENGTH: 12
<212> TYPE: DNA
<213> ORGANISM: Homo sapiens

<400> SEQUENCE: 432
actccccgta gg                                                          12

<210> SEQ ID NO 433
<211> LENGTH: 12
<212> TYPE: DNA
<213> ORGANISM: Homo sapiens

<400> SEQUENCE: 433
actgcgtgtt aa                                                          12

<210> SEQ ID NO 434
<211> LENGTH: 12
<212> TYPE: DNA
<213> ORGANISM: Homo sapiens

<400> SEQUENCE: 434
acgtcgcctg at                                                          12

<210> SEQ ID NO 435
<211> LENGTH: 12
<212> TYPE: DNA
<213> ORGANISM: Homo sapiens

<400> SEQUENCE: 435
taggtcgacc ag                                                          12

<210> SEQ ID NO 436
<211> LENGTH: 12
<212> TYPE: DNA
<213> ORGANISM: Homo sapiens

<400> SEQUENCE: 436
ggcgttaatg at                                                          12
```

```
<210> SEQ ID NO 437
<211> LENGTH: 12
<212> TYPE: DNA
<213> ORGANISM: Homo sapiens

<400> SEQUENCE: 437
tgtcgcatgt ta                                                          12

<210> SEQ ID NO 438
<211> LENGTH: 12
<212> TYPE: DNA
<213> ORGANISM: Homo sapiens

<400> SEQUENCE: 438
atggaaacgc at                                                          12

<210> SEQ ID NO 439
<211> LENGTH: 12
<212> TYPE: DNA
<213> ORGANISM: Homo sapiens

<400> SEQUENCE: 439
gccgaattcc tc                                                          12

<210> SEQ ID NO 440
<211> LENGTH: 12
<212> TYPE: DNA
<213> ORGANISM: Homo sapiens

<400> SEQUENCE: 440
gcatggtacg ga                                                          12

<210> SEQ ID NO 441
<211> LENGTH: 12
<212> TYPE: DNA
<213> ORGANISM: Homo sapiens

<400> SEQUENCE: 441
cggtactctt ac                                                          12

<210> SEQ ID NO 442
<211> LENGTH: 12
<212> TYPE: DNA
<213> ORGANISM: Homo sapiens

<400> SEQUENCE: 442
gcctgtgccg ta                                                          12

<210> SEQ ID NO 443
<211> LENGTH: 12
<212> TYPE: DNA
<213> ORGANISM: Homo sapiens

<400> SEQUENCE: 443
tacggtaagt cg                                                          12

<210> SEQ ID NO 444
<211> LENGTH: 12
<212> TYPE: DNA
<213> ORGANISM: Homo sapiens

<400> SEQUENCE: 444
cacgaaatta cc                                                          12
```

<210> SEQ ID NO 445
<211> LENGTH: 12
<212> TYPE: DNA
<213> ORGANISM: Homo sapiens

<400> SEQUENCE: 445
aaccaagata cg                                                          12

<210> SEQ ID NO 446
<211> LENGTH: 12
<212> TYPE: DNA
<213> ORGANISM: Homo sapiens

<400> SEQUENCE: 446
gagtcgatac gc                                                          12

<210> SEQ ID NO 447
<211> LENGTH: 12
<212> TYPE: DNA
<213> ORGANISM: Homo sapiens

<400> SEQUENCE: 447
gtctcacgat cg                                                          12

<210> SEQ ID NO 448
<211> LENGTH: 12
<212> TYPE: DNA
<213> ORGANISM: Homo sapiens

<400> SEQUENCE: 448
tcgtcgggtg ca                                                          12

<210> SEQ ID NO 449
<211> LENGTH: 12
<212> TYPE: DNA
<213> ORGANISM: Homo sapiens

<400> SEQUENCE: 449
actccgtagt ga                                                          12

<210> SEQ ID NO 450
<211> LENGTH: 12
<212> TYPE: DNA
<213> ORGANISM: Homo sapiens

<400> SEQUENCE: 450
caggacgtcc gt                                                          12

<210> SEQ ID NO 451
<211> LENGTH: 12
<212> TYPE: DNA
<213> ORGANISM: Homo sapiens

<400> SEQUENCE: 451
tcgtatccct ac                                                          12

<210> SEQ ID NO 452
<211> LENGTH: 12
<212> TYPE: DNA
<213> ORGANISM: Homo sapiens

<400> SEQUENCE: 452

```
tttcaaggcc gg                                                          12

<210> SEQ ID NO 453
<211> LENGTH: 12
<212> TYPE: DNA
<213> ORGANISM: Homo sapiens

<400> SEQUENCE: 453
cgccggtgga at                                                          12

<210> SEQ ID NO 454
<211> LENGTH: 12
<212> TYPE: DNA
<213> ORGANISM: Homo sapiens

<400> SEQUENCE: 454
gaacccgtcc ta                                                          12

<210> SEQ ID NO 455
<211> LENGTH: 12
<212> TYPE: DNA
<213> ORGANISM: Homo sapiens

<400> SEQUENCE: 455
gattcatcag cg                                                          12

<210> SEQ ID NO 456
<211> LENGTH: 12
<212> TYPE: DNA
<213> ORGANISM: Homo sapiens

<400> SEQUENCE: 456
acaccggtct tc                                                          12

<210> SEQ ID NO 457
<211> LENGTH: 12
<212> TYPE: DNA
<213> ORGANISM: Homo sapiens

<400> SEQUENCE: 457
atcgtgccct aa                                                          12

<210> SEQ ID NO 458
<211> LENGTH: 12
<212> TYPE: DNA
<213> ORGANISM: Homo sapiens

<400> SEQUENCE: 458
gcgtcaatgt tc                                                          12

<210> SEQ ID NO 459
<211> LENGTH: 12
<212> TYPE: DNA
<213> ORGANISM: Homo sapiens

<400> SEQUENCE: 459
ctccgtatct cg                                                          12

<210> SEQ ID NO 460
<211> LENGTH: 12
<212> TYPE: DNA
<213> ORGANISM: Homo sapiens

<400> SEQUENCE: 460
```
ccgattcctt cg                                            12

<210> SEQ ID NO 461
<211> LENGTH: 12
<212> TYPE: DNA
<213> ORGANISM: Homo sapiens

<400> SEQUENCE: 461
tgcgcctcca gt                                            12

<210> SEQ ID NO 462
<211> LENGTH: 12
<212> TYPE: DNA
<213> ORGANISM: Homo sapiens

<400> SEQUENCE: 462
taacgtcgga gc                                            12

<210> SEQ ID NO 463
<211> LENGTH: 12
<212> TYPE: DNA
<213> ORGANISM: Homo sapiens

<400> SEQUENCE: 463
aaggtcgccc at                                            12

<210> SEQ ID NO 464
<211> LENGTH: 12
<212> TYPE: DNA
<213> ORGANISM: Homo sapiens

<400> SEQUENCE: 464
ctcggggact at                                            12

<210> SEQ ID NO 465
<211> LENGTH: 12
<212> TYPE: DNA
<213> ORGANISM: Homo sapiens

<400> SEQUENCE: 465
ttcgagcgat tt                                            12

<210> SEQ ID NO 466
<211> LENGTH: 12
<212> TYPE: DNA
<213> ORGANISM: Homo sapiens

<400> SEQUENCE: 466
tgagtcgtcg ag                                            12

<210> SEQ ID NO 467
<211> LENGTH: 12
<212> TYPE: DNA
<213> ORGANISM: Homo sapiens

<400> SEQUENCE: 467
tttacgcaga gg                                            12

<210> SEQ ID NO 468
<211> LENGTH: 12
<212> TYPE: DNA
<213> ORGANISM: Homo sapiens

```
<400> SEQUENCE: 468
aggaagtatc gc                                                          12

<210> SEQ ID NO 469
<211> LENGTH: 12
<212> TYPE: DNA
<213> ORGANISM: Homo sapiens

<400> SEQUENCE: 469
actcgatacc at                                                          12

<210> SEQ ID NO 470
<211> LENGTH: 12
<212> TYPE: DNA
<213> ORGANISM: Homo sapiens

<400> SEQUENCE: 470
cgctacatag ca                                                          12

<210> SEQ ID NO 471
<211> LENGTH: 12
<212> TYPE: DNA
<213> ORGANISM: Homo sapiens

<400> SEQUENCE: 471
ttcataaccg gc                                                          12

<210> SEQ ID NO 472
<211> LENGTH: 12
<212> TYPE: DNA
<213> ORGANISM: Homo sapiens

<400> SEQUENCE: 472
ccaaacggtt aa                                                          12

<210> SEQ ID NO 473
<211> LENGTH: 12
<212> TYPE: DNA
<213> ORGANISM: Homo sapiens

<400> SEQUENCE: 473
cgattccttc gt                                                          12

<210> SEQ ID NO 474
<211> LENGTH: 12
<212> TYPE: DNA
<213> ORGANISM: Homo sapiens

<400> SEQUENCE: 474
cgtcatgaat aa                                                          12

<210> SEQ ID NO 475
<211> LENGTH: 12
<212> TYPE: DNA
<213> ORGANISM: Homo sapiens

<400> SEQUENCE: 475
agtggcgatg ac                                                          12

<210> SEQ ID NO 476
<211> LENGTH: 12
<212> TYPE: DNA
<213> ORGANISM: Homo sapiens
```

```
<400> SEQUENCE: 476
cccctacggc ac                                                        12

<210> SEQ ID NO 477
<211> LENGTH: 12
<212> TYPE: DNA
<213> ORGANISM: Homo sapiens

<400> SEQUENCE: 477
gccaacccgc ac                                                        12

<210> SEQ ID NO 478
<211> LENGTH: 12
<212> TYPE: DNA
<213> ORGANISM: Homo sapiens

<400> SEQUENCE: 478
tgggacaccg gt                                                        12

<210> SEQ ID NO 479
<211> LENGTH: 12
<212> TYPE: DNA
<213> ORGANISM: Homo sapiens

<400> SEQUENCE: 479
ttgactgcgg cg                                                        12

<210> SEQ ID NO 480
<211> LENGTH: 12
<212> TYPE: DNA
<213> ORGANISM: Homo sapiens

<400> SEQUENCE: 480
actatgcgta gg                                                        12

<210> SEQ ID NO 481
<211> LENGTH: 12
<212> TYPE: DNA
<213> ORGANISM: Homo sapiens

<400> SEQUENCE: 481
tcacccaaag cg                                                        12

<210> SEQ ID NO 482
<211> LENGTH: 12
<212> TYPE: DNA
<213> ORGANISM: Homo sapiens

<400> SEQUENCE: 482
gcaggacgtc cg                                                        12

<210> SEQ ID NO 483
<211> LENGTH: 12
<212> TYPE: DNA
<213> ORGANISM: Homo sapiens

<400> SEQUENCE: 483
acaccgaaaa cg                                                        12

<210> SEQ ID NO 484
<211> LENGTH: 12
<212> TYPE: DNA
```

```
<213> ORGANISM: Homo sapiens

<400> SEQUENCE: 484
cggtgtattg ag                                                        12

<210> SEQ ID NO 485
<211> LENGTH: 12
<212> TYPE: DNA
<213> ORGANISM: Homo sapiens

<400> SEQUENCE: 485
cacgaggtat gc                                                        12

<210> SEQ ID NO 486
<211> LENGTH: 12
<212> TYPE: DNA
<213> ORGANISM: Homo sapiens

<400> SEQUENCE: 486
taaagcgacc cg                                                        12

<210> SEQ ID NO 487
<211> LENGTH: 12
<212> TYPE: DNA
<213> ORGANISM: Homo sapiens

<400> SEQUENCE: 487
cttagtcggc ca                                                        12

<210> SEQ ID NO 488
<211> LENGTH: 12
<212> TYPE: DNA
<213> ORGANISM: Homo sapiens

<400> SEQUENCE: 488
cgaaaacgtg gc                                                        12

<210> SEQ ID NO 489
<211> LENGTH: 12
<212> TYPE: DNA
<213> ORGANISM: Homo sapiens

<400> SEQUENCE: 489
cgtgccctga ac                                                        12

<210> SEQ ID NO 490
<211> LENGTH: 12
<212> TYPE: DNA
<213> ORGANISM: Homo sapiens

<400> SEQUENCE: 490
tttaccatcg aa                                                        12

<210> SEQ ID NO 491
<211> LENGTH: 12
<212> TYPE: DNA
<213> ORGANISM: Homo sapiens

<400> SEQUENCE: 491
cgtagccatg tt                                                        12

<210> SEQ ID NO 492
<211> LENGTH: 12
```

```
<212> TYPE: DNA
<213> ORGANISM: Homo sapiens

<400> SEQUENCE: 492
cccaaacggt ta                                                      12

<210> SEQ ID NO 493
<211> LENGTH: 12
<212> TYPE: DNA
<213> ORGANISM: Homo sapiens

<400> SEQUENCE: 493
gcgttatcag aa                                                      12

<210> SEQ ID NO 494
<211> LENGTH: 12
<212> TYPE: DNA
<213> ORGANISM: Homo sapiens

<400> SEQUENCE: 494
tcgatggtaa ac                                                      12

<210> SEQ ID NO 495
<211> LENGTH: 12
<212> TYPE: DNA
<213> ORGANISM: Homo sapiens

<400> SEQUENCE: 495
cgactttttg ca                                                      12

<210> SEQ ID NO 496
<211> LENGTH: 12
<212> TYPE: DNA
<213> ORGANISM: Homo sapiens

<400> SEQUENCE: 496
tcgacgactc ac                                                      12

<210> SEQ ID NO 497
<211> LENGTH: 12
<212> TYPE: DNA
<213> ORGANISM: Homo sapiens

<400> SEQUENCE: 497
acgcgtcaga ta                                                      12

<210> SEQ ID NO 498
<211> LENGTH: 12
<212> TYPE: DNA
<213> ORGANISM: Homo sapiens

<400> SEQUENCE: 498
cgtacggcac ag                                                      12

<210> SEQ ID NO 499
<211> LENGTH: 12
<212> TYPE: DNA
<213> ORGANISM: Homo sapiens

<400> SEQUENCE: 499
ctatgccgtg ca                                                      12

<210> SEQ ID NO 500
```

```
<211> LENGTH: 12
<212> TYPE: DNA
<213> ORGANISM: Homo sapiens

<400> SEQUENCE: 500
cgcgtcagat at                                                              12

<210> SEQ ID NO 501
<211> LENGTH: 12
<212> TYPE: DNA
<213> ORGANISM: Homo sapiens

<400> SEQUENCE: 501
aagatcggta gc                                                              12

<210> SEQ ID NO 502
<211> LENGTH: 12
<212> TYPE: DNA
<213> ORGANISM: Homo sapiens

<400> SEQUENCE: 502
cttcgcaagg ag                                                              12

<210> SEQ ID NO 503
<211> LENGTH: 12
<212> TYPE: DNA
<213> ORGANISM: Homo sapiens

<400> SEQUENCE: 503
gtcgtggact ac                                                              12

<210> SEQ ID NO 504
<211> LENGTH: 12
<212> TYPE: DNA
<213> ORGANISM: Homo sapiens

<400> SEQUENCE: 504
ggtcgtcatc aa                                                              12

<210> SEQ ID NO 505
<211> LENGTH: 12
<212> TYPE: DNA
<213> ORGANISM: Homo sapiens

<400> SEQUENCE: 505
gttaacagcg tg                                                              12

<210> SEQ ID NO 506
<211> LENGTH: 12
<212> TYPE: DNA
<213> ORGANISM: Homo sapiens

<400> SEQUENCE: 506
tagctaaccg tt                                                              12

<210> SEQ ID NO 507
<211> LENGTH: 12
<212> TYPE: DNA
<213> ORGANISM: Homo sapiens

<400> SEQUENCE: 507
agtaaaggcg ct                                                              12
```

```
<210> SEQ ID NO 508
<211> LENGTH: 12
<212> TYPE: DNA
<213> ORGANISM: Homo sapiens

<400> SEQUENCE: 508
ggtaatttcg tg                                                           12

<210> SEQ ID NO 509
<211> LENGTH: 20
<212> TYPE: DNA
<213> ORGANISM: Mus musculus

<400> SEQUENCE: 509
gactgattca gctagaccgg                                                   20

<210> SEQ ID NO 510
<211> LENGTH: 20
<212> TYPE: DNA
<213> ORGANISM: Mus musculus

<400> SEQUENCE: 510
ggcacaaacg cgttcaatac                                                   20

<210> SEQ ID NO 511
<211> LENGTH: 20
<212> TYPE: DNA
<213> ORGANISM: Mus musculus

<400> SEQUENCE: 511
aacgcgttca ataccggtct                                                   20

<210> SEQ ID NO 512
<211> LENGTH: 20
<212> TYPE: DNA
<213> ORGANISM: Rattus norvegicus

<400> SEQUENCE: 512
gctaggagga tctcgggcgg                                                   20

<210> SEQ ID NO 513
<211> LENGTH: 20
<212> TYPE: DNA
<213> ORGANISM: Rattus norvegicus

<400> SEQUENCE: 513
gttccagccc gcgactaagc                                                   20

<210> SEQ ID NO 514
<211> LENGTH: 20
<212> TYPE: DNA
<213> ORGANISM: Rattus norvegicus

<400> SEQUENCE: 514 gtgaggggt tgcaacgagg                                                    20

<210> SEQ ID NO 515
<211> LENGTH: 20
<212> TYPE: DNA
<213> ORGANISM: Rattus norvegicus

<400> SEQUENCE: 515
accgcaactc ttggcgcgtc                                                   20
```

```
<210> SEQ ID NO 516
<211> LENGTH: 20
<212> TYPE: DNA
<213> ORGANISM: Rattus norvegicus

<400> SEQUENCE: 516
accagatgcg gttgcagtcg                                              20

<210> SEQ ID NO 517
<211> LENGTH: 20
<212> TYPE: DNA
<213> ORGANISM: Rattus norvegicus

<400> SEQUENCE: 517
tacttcggcg cgtatttta                                               20

<210> SEQ ID NO 518
<211> LENGTH: 20
<212> TYPE: DNA
<213> ORGANISM: Rattus norvegicus

<400> SEQUENCE: 518
aaatgtgaga ttccggacta                                              20

<210> SEQ ID NO 519
<211> LENGTH: 20
<212> TYPE: DNA
<213> ORGANISM: Rattus norvegicus

<400> SEQUENCE: 519
tgtgaccgcg cttgcgaact                                              20

<210> SEQ ID NO 520
<211> LENGTH: 20
<212> TYPE: DNA
<213> ORGANISM: Rattus norvegicus

<400> SEQUENCE: 520
tctcgggcac cgcgagccgg                                              20

<210> SEQ ID NO 521
<211> LENGTH: 20
<212> TYPE: DNA
<213> ORGANISM: Rattus norvegicus

<400> SEQUENCE: 521
cgctcctggc tggtccgcaa                                              20

<210> SEQ ID NO 522
<211> LENGTH: 20
<212> TYPE: DNA
<213> ORGANISM: Rattus norvegicus

<400> SEQUENCE: 522
tgagggtagt tgagcgccgt                                              20

<210> SEQ ID NO 523
<211> LENGTH: 20
<212> TYPE: DNA
<213> ORGANISM: Rattus norvegicus

<400> SEQUENCE: 523
tgagattggg accgccacgc                                              20
```

<210> SEQ ID NO 524
<211> LENGTH: 20
<212> TYPE: DNA
<213> ORGANISM: Rattus norvegicus

<400> SEQUENCE: 524
ttgatataga ctttacgtgc                                               20

<210> SEQ ID NO 525
<211> LENGTH: 20
<212> TYPE: DNA
<213> ORGANISM: Rattus norvegicus

<400> SEQUENCE: 525
agctaactac cccccgggt                                                20

<210> SEQ ID NO 526
<211> LENGTH: 20
<212> TYPE: DNA
<213> ORGANISM: Rattus norvegicus

<400> SEQUENCE: 526
cacctccagc atcgggcgag                                               20

<210> SEQ ID NO 527
<211> LENGTH: 20
<212> TYPE: DNA
<213> ORGANISM: Rattus norvegicus

<400> SEQUENCE: 527
aggcggcgtc gtcgggatgt                                               20

<210> SEQ ID NO 528
<211> LENGTH: 20
<212> TYPE: DNA
<213> ORGANISM: Rattus norvegicus

<400> SEQUENCE: 528
ccgtttggcc cccagttcgg                                               20

<210> SEQ ID NO 529
<211> LENGTH: 20
<212> TYPE: DNA
<213> ORGANISM: Rattus norvegicus

<400> SEQUENCE: 529
ttccagcccg cgactaagcg                                               20

<210> SEQ ID NO 530
<211> LENGTH: 20
<212> TYPE: DNA
<213> ORGANISM: Rattus norvegicus

<400> SEQUENCE: 530
agagtgaggg ggttgcaacg                                               20

<210> SEQ ID NO 531
<211> LENGTH: 20
<212> TYPE: DNA
<213> ORGANISM: Rattus norvegicus

<400> SEQUENCE: 531
ccgcaactct tggcgcgtcg                                               20

<210> SEQ ID NO 532
<211> LENGTH: 20
<212> TYPE: DNA
<213> ORGANISM: Rattus norvegicus

<400> SEQUENCE: 532
tgatcccgct cgcccgatgc                                               20

<210> SEQ ID NO 533
<211> LENGTH: 20
<212> TYPE: DNA
<213> ORGANISM: Rattus norvegicus

<400> SEQUENCE: 533
ctggaagagg cggcgtcgtc                                               20

<210> SEQ ID NO 534
<211> LENGTH: 20
<212> TYPE: DNA
<213> ORGANISM: Rattus norvegicus

<400> SEQUENCE: 534
aaccccgctt agtcgcgggc                                               20

<210> SEQ ID NO 535
<211> LENGTH: 20
<212> TYPE: DNA
<213> ORGANISM: Rattus norvegicus

<400> SEQUENCE: 535
attgggaccg ccacgccggt                                               20

<210> SEQ ID NO 536
<211> LENGTH: 20
<212> TYPE: DNA
<213> ORGANISM: Rattus norvegicus

<400> SEQUENCE: 536
tccagaaccg cgtctcgacg                                               20

<210> SEQ ID NO 537
<211> LENGTH: 20
<212> TYPE: DNA
<213> ORGANISM: Rattus norvegicus

<400> SEQUENCE: 537
cgcgcacaga acgcgtacgc                                               20

<210> SEQ ID NO 538
<211> LENGTH: 20
<212> TYPE: DNA
<213> ORGANISM: Rattus norvegicus

<400> SEQUENCE: 538
gtgaaacccc gcttagtcgc                                               20

<210> SEQ ID NO 539
<211> LENGTH: 20
<212> TYPE: DNA
<213> ORGANISM: Rattus norvegicus

<400> SEQUENCE: 539
ccccgacgcg ccaagagttg    20

<210> SEQ ID NO 540
<211> LENGTH: 20
<212> TYPE: DNA
<213> ORGANISM: Rattus norvegicus

<400> SEQUENCE: 540
accgcgtctc gacgcggaga    20

<210> SEQ ID NO 541
<211> LENGTH: 20
<212> TYPE: DNA
<213> ORGANISM: Rattus norvegicus

<400> SEQUENCE: 541
ccgcgcacag aacgcgtacg    20

<210> SEQ ID NO 542
<211> LENGTH: 20
<212> TYPE: DNA
<213> ORGANISM: Rattus norvegicus

<400> SEQUENCE: 542
ggtgaaaccc cgcttagtcg    20

<210> SEQ ID NO 543
<211> LENGTH: 20
<212> TYPE: DNA
<213> ORGANISM: Rattus norvegicus

<400> SEQUENCE: 543
actcttggcg cgtcggggca    20

<210> SEQ ID NO 544
<211> LENGTH: 20
<212> TYPE: DNA
<213> ORGANISM: Rattus norvegicus

<400> SEQUENCE: 544
tccttctccg cgtcgagacg    20

<210> SEQ ID NO 545
<211> LENGTH: 20
<212> TYPE: DNA
<213> ORGANISM: Rattus norvegicus

<400> SEQUENCE: 545
acggtccgga cctccgaact    20

<210> SEQ ID NO 546
<211> LENGTH: 20
<212> TYPE: DNA
<213> ORGANISM: Rattus norvegicus

<400> SEQUENCE: 546
ggcgccagcc gctcgctcta    20

<210> SEQ ID NO 547
<211> LENGTH: 20
<212> TYPE: DNA
<213> ORGANISM: Rattus norvegicus

<400> SEQUENCE: 547
gacttccgag ttcgcaagcg                                                  20

<210> SEQ ID NO 548
<211> LENGTH: 20
<212> TYPE: DNA
<213> ORGANISM: Rattus norvegicus

<400> SEQUENCE: 548
tgcgaactcg gaagtccaat                                                  20

<210> SEQ ID NO 549
<211> LENGTH: 20
<212> TYPE: DNA
<213> ORGANISM: Rattus norvegicus

<400> SEQUENCE: 549
tctggaagag gcggcgtcgt                                                  20

<210> SEQ ID NO 550
<211> LENGTH: 20
<212> TYPE: DNA
<213> ORGANISM: Rattus norvegicus

<400> SEQUENCE: 550
tcttagcccc gagacccggt                                                  20

<210> SEQ ID NO 551
<211> LENGTH: 20
<212> TYPE: DNA
<213> ORGANISM: Rattus norvegicus

<400> SEQUENCE: 551
ccctccggcg ccgtgttttc                                                  20

<210> SEQ ID NO 552
<211> LENGTH: 20
<212> TYPE: DNA
<213> ORGANISM: Rattus norvegicus

<400> SEQUENCE: 552
ccagaaaaca cggcgccgga                                                  20

<210> SEQ ID NO 553
<211> LENGTH: 17
<212> TYPE: DNA
<213> ORGANISM: Danio rerio

<400> SEQUENCE: 553
atcaatatct cgcccag                                                     17

<210> SEQ ID NO 554
<211> LENGTH: 17
<212> TYPE: DNA
<213> ORGANISM: Danio rerio

<400> SEQUENCE: 554
attaaacgtg ttccact                                                     17

<210> SEQ ID NO 555
<211> LENGTH: 17
<212> TYPE: DNA
<213> ORGANISM: Danio rerio

```
<400> SEQUENCE: 555
acgtttaatc gctttct                                                       17

<210> SEQ ID NO 556
<211> LENGTH: 17
<212> TYPE: DNA
<213> ORGANISM: Danio rerio

<400> SEQUENCE: 556
caagatgcgt acggtca                                                       17

<210> SEQ ID NO 557
<211> LENGTH: 17
<212> TYPE: DNA
<213> ORGANISM: Danio rerio

<400> SEQUENCE: 557
tctgtgtact cgaatat                                                       17

<210> SEQ ID NO 558
<211> LENGTH: 17
<212> TYPE: DNA
<213> ORGANISM: Danio rerio

<400> SEQUENCE: 558
tcctgacttc tgggcac                                                       17

<210> SEQ ID NO 559
<211> LENGTH: 17
<212> TYPE: DNA
<213> ORGANISM: Danio rerio

<400> SEQUENCE: 559
cccggtgccc agaagtc                                                       17

<210> SEQ ID NO 560
<211> LENGTH: 17
<212> TYPE: DNA
<213> ORGANISM: Danio rerio

<400> SEQUENCE: 560
ccggagatcc attcatg                                                       17

<210> SEQ ID NO 561
<211> LENGTH: 17
<212> TYPE: DNA
<213> ORGANISM: Danio rerio

<400> SEQUENCE: 561
tgatgaccca gaatcaa                                                       17

<210> SEQ ID NO 562
<211> LENGTH: 17
<212> TYPE: DNA
<213> ORGANISM: Danio rerio

<400> SEQUENCE: 562
tgaatgaccg gtcctcc                                                       17

<210> SEQ ID NO 563
<211> LENGTH: 17
<212> TYPE: DNA
```

<213> ORGANISM: Danio rerio

<400> SEQUENCE: 563
tccaaagggg cttcgga                                                17

<210> SEQ ID NO 564
<211> LENGTH: 17
<212> TYPE: DNA
<213> ORGANISM: Danio rerio

<400> SEQUENCE: 564
cttcagttcg ctgtgca                                                17

<210> SEQ ID NO 565
<211> LENGTH: 17
<212> TYPE: DNA
<213> ORGANISM: Danio rerio

<400> SEQUENCE: 565
gatacacgcc ggcataa                                                17

<210> SEQ ID NO 566
<211> LENGTH: 17
<212> TYPE: DNA
<213> ORGANISM: Danio rerio

<400> SEQUENCE: 566
cacacgagga tacacgc                                                17

<210> SEQ ID NO 567
<211> LENGTH: 17
<212> TYPE: DNA
<213> ORGANISM: Danio rerio

<400> SEQUENCE: 567
tcgctgtcct cttcact                                                17

<210> SEQ ID NO 568
<211> LENGTH: 17
<212> TYPE: DNA
<213> ORGANISM: Danio rerio

<400> SEQUENCE: 568
ttaaagtgat tcccagt                                                17

<210> SEQ ID NO 569
<211> LENGTH: 17
<212> TYPE: DNA
<213> ORGANISM: Danio rerio

<400> SEQUENCE: 569
cagctgatcc tccaact                                                17

<210> SEQ ID NO 570
<211> LENGTH: 17
<212> TYPE: DNA
<213> ORGANISM: Danio rerio

<400> SEQUENCE: 570
atatttagag taagaat                                                17

<210> SEQ ID NO 571
<211> LENGTH: 17

```
<212> TYPE: DNA
<213> ORGANISM: Drosophila melanogaster

<400> SEQUENCE: 571
aatttttatc attcagt                                                    17

<210> SEQ ID NO 572
<211> LENGTH: 20
<212> TYPE: DNA
<213> ORGANISM: Drosophila melanogaster

<400> SEQUENCE: 572
gattcttcca tgatcggcca                                                 20

<210> SEQ ID NO 573
<211> LENGTH: 20
<212> TYPE: DNA
<213> ORGANISM: Drosophila melanogaster

<400> SEQUENCE: 573
cgattgaaaa tccacataaa                                                 20

<210> SEQ ID NO 574
<211> LENGTH: 20
<212> TYPE: DNA
<213> ORGANISM: Drosophila melanogaster

<400> SEQUENCE: 574
gctgatttcg gacaaaagtc                                                 20

<210> SEQ ID NO 575
<211> LENGTH: 20
<212> TYPE: DNA
<213> ORGANISM: Drosophila melanogaster

<400> SEQUENCE: 575
aaacggatga cgtgcaacgt                                                 20

<210> SEQ ID NO 576
<211> LENGTH: 20
<212> TYPE: DNA
<213> ORGANISM: Drosophila melanogaster

<400> SEQUENCE: 576
cgttttgtgt gcgtgcgcac                                                 20

<210> SEQ ID NO 577
<211> LENGTH: 20
<212> TYPE: DNA
<213> ORGANISM: Drosophila melanogaster

<400> SEQUENCE: 577
ggaataatct tcgtctatcc                                                 20

<210> SEQ ID NO 578
<211> LENGTH: 20
<212> TYPE: DNA
<213> ORGANISM: Drosophila melanogaster

<400> SEQUENCE: 578
ttcgctcacg aacaccaaca                                                 20

<210> SEQ ID NO 579
```

-continued

```
<211> LENGTH: 20
<212> TYPE: DNA
<213> ORGANISM: Drosophila melanogaster

<400> SEQUENCE: 579
acaaagtaca tagggtgttt                                            20

<210> SEQ ID NO 580
<211> LENGTH: 20
<212> TYPE: DNA
<213> ORGANISM: Drosophila melanogaster

<400> SEQUENCE: 580
ccatcccccg taaagagggt                                            20

<210> SEQ ID NO 581
<211> LENGTH: 20
<212> TYPE: DNA
<213> ORGANISM: Drosophila melanogaster

<400> SEQUENCE: 581 tattttagt tggtaaatta                                             20

<210> SEQ ID NO 582
<211> LENGTH: 17
<212> TYPE: DNA
<213> ORGANISM: Drosophila melanogaster

<400> SEQUENCE: 582
attcactctg ggttatg                                               17

<210> SEQ ID NO 583
<211> LENGTH: 20
<212> TYPE: DNA
<213> ORGANISM: Drosophila melanogaster

<400> SEQUENCE: 583
ctgctttcct tggccgatca                                            20

<210> SEQ ID NO 584
<211> LENGTH: 20
<212> TYPE: DNA
<213> ORGANISM: Drosophila melanogaster

<400> SEQUENCE: 584
gattatttgc tccatttatg                                            20

<210> SEQ ID NO 585
<211> LENGTH: 20
<212> TYPE: DNA
<213> ORGANISM: Drosophila melanogaster

<400> SEQUENCE: 585
ctctgtacag aatattttct                                            20

<210> SEQ ID NO 586
<211> LENGTH: 20
<212> TYPE: DNA
<213> ORGANISM: Drosophila melanogaster

<400> SEQUENCE: 586
gcagcggcag tgagagacgt                                            20
```

```
<210> SEQ ID NO 587
<211> LENGTH: 20
<212> TYPE: DNA
<213> ORGANISM: Drosophila melanogaster

<400> SEQUENCE: 587
tgtgcgcacg cacacaaaac                                           20

<210> SEQ ID NO 588
<211> LENGTH: 20
<212> TYPE: DNA
<213> ORGANISM: Drosophila melanogaster

<400> SEQUENCE: 588
aattcgctaa ttgggcagcc                                           20

<210> SEQ ID NO 589
<211> LENGTH: 20
<212> TYPE: DNA
<213> ORGANISM: Drosophila melanogaster

<400> SEQUENCE: 589
caaggaaatt gacagatgta                                           20

<210> SEQ ID NO 590
<211> LENGTH: 20
<212> TYPE: DNA
<213> ORGANISM: Drosophila melanogaster

<400> SEQUENCE: 590
gctctagcaa ccacgtcaga                                           20

<210> SEQ ID NO 591
<211> LENGTH: 20
<212> TYPE: DNA
<213> ORGANISM: Drosophila melanogaster

<400> SEQUENCE: 591
acaatacgaa tgcgagaagg                                           20

<210> SEQ ID NO 592
<211> LENGTH: 20
<212> TYPE: DNA
<213> ORGANISM: Drosophila melanogaster

<400> SEQUENCE: 592
aaataaaaat tagtgtccgc                                           20

<210> SEQ ID NO 593
<211> LENGTH: 17
<212> TYPE: DNA
<213> ORGANISM: Drosophila melanogaster

<400> SEQUENCE: 593
agagtgaata aattaca                                              17

<210> SEQ ID NO 594
<211> LENGTH: 20
<212> TYPE: DNA
<213> ORGANISM: Drosophila melanogaster

<400> SEQUENCE: 594
ttattcaaga cttacaccat                                           20
```

<210> SEQ ID NO 595
<211> LENGTH: 20
<212> TYPE: DNA
<213> ORGANISM: Drosophila melanogaster

<400> SEQUENCE: 595
attatgacgt tttttggtac                                              20

<210> SEQ ID NO 596
<211> LENGTH: 20
<212> TYPE: DNA
<213> ORGANISM: Drosophila melanogaster

<400> SEQUENCE: 596
ttcgggcggt ctaaagcagt                                              20

<210> SEQ ID NO 597
<211> LENGTH: 20
<212> TYPE: DNA
<213> ORGANISM: Drosophila melanogaster

<400> SEQUENCE: 597
tgttactttt tcgaacgttg                                              20

<210> SEQ ID NO 598
<211> LENGTH: 20
<212> TYPE: DNA
<213> ORGANISM: Drosophila melanogaster

<400> SEQUENCE: 598
gttttgtgtg cgtgcgcaca                                              20

<210> SEQ ID NO 599
<211> LENGTH: 20
<212> TYPE: DNA
<213> ORGANISM: Drosophila melanogaster

<400> SEQUENCE: 599
tgcccaatta gcgaattagg                                              20

<210> SEQ ID NO 600
<211> LENGTH: 20
<212> TYPE: DNA
<213> ORGANISM: Drosophila melanogaster

<400> SEQUENCE: 600
cgccccaaaa gaaaatacgt                                              20

<210> SEQ ID NO 601
<211> LENGTH: 20
<212> TYPE: DNA
<213> ORGANISM: Drosophila melanogaster

<400> SEQUENCE: 601
gctgcggctt tcgtgaaatg                                              20

<210> SEQ ID NO 602
<211> LENGTH: 20
<212> TYPE: DNA
<213> ORGANISM: Drosophila melanogaster

<400> SEQUENCE: 602
aaaaggagga gaacatatct                                              20

<210> SEQ ID NO 603
<211> LENGTH: 17
<212> TYPE: DNA
<213> ORGANISM: Drosophila melanogaster

<400> SEQUENCE: 603
atgtaattta ttcactc                                                    17

<210> SEQ ID NO 604
<211> LENGTH: 20
<212> TYPE: DNA
<213> ORGANISM: Drosophila melanogaster

<400> SEQUENCE: 604
agaactaagc acgtattttt                                                 20

<210> SEQ ID NO 605
<211> LENGTH: 20
<212> TYPE: DNA
<213> ORGANISM: Drosophila melanogaster

<400> SEQUENCE: 605
acaaacaatc caaataaaag                                                 20

<210> SEQ ID NO 606
<211> LENGTH: 20
<212> TYPE: DNA
<213> ORGANISM: Drosophila melanogaster

<400> SEQUENCE: 606
caacaaaaaa gtgagctctg                                                 20

<210> SEQ ID NO 607
<211> LENGTH: 20
<212> TYPE: DNA
<213> ORGANISM: Drosophila melanogaster

<400> SEQUENCE: 607
cgttgttcgt ttttgtagtt                                                 20

<210> SEQ ID NO 608
<211> LENGTH: 20
<212> TYPE: DNA
<213> ORGANISM: Drosophila melanogaster

<400> SEQUENCE: 608
ctctttctgg taaatgctgt                                                 20

<210> SEQ ID NO 609
<211> LENGTH: 20
<212> TYPE: DNA
<213> ORGANISM: Drosophila melanogaster

<400> SEQUENCE: 609
ttaggtggga ttttcgtgta                                                 20

<210> SEQ ID NO 610
<211> LENGTH: 20
<212> TYPE: DNA
<213> ORGANISM: Drosophila melanogaster

<400> SEQUENCE: 610
ctacaaaact acacgaatta                                                  20

<210> SEQ ID NO 611
<211> LENGTH: 20
<212> TYPE: DNA
<213> ORGANISM: Drosophila melanogaster

<400> SEQUENCE: 611
gctctcgctc tgcctcgctg                                                  20

<210> SEQ ID NO 612
<211> LENGTH: 20
<212> TYPE: DNA
<213> ORGANISM: Drosophila melanogaster

<400> SEQUENCE: 612
aaaggaggag aacatatctt                                                  20

<210> SEQ ID NO 613
<211> LENGTH: 17
<212> TYPE: DNA
<213> ORGANISM: Drosophila melanogaster

<400> SEQUENCE: 613
aatcaaatcg gtacatt                                                     17

<210> SEQ ID NO 614
<211> LENGTH: 20
<212> TYPE: DNA
<213> ORGANISM: Drosophila melanogaster

<400> SEQUENCE: 614
atttcagctc tcaacgcaaa                                                  20

<210> SEQ ID NO 615
<211> LENGTH: 20
<212> TYPE: DNA
<213> ORGANISM: Drosophila melanogaster

<400> SEQUENCE: 615
attctgaaac cacttttatt                                                  20

<210> SEQ ID NO 616
<211> LENGTH: 20
<212> TYPE: DNA
<213> ORGANISM: Drosophila melanogaster

<400> SEQUENCE: 616
gagctctgcg gtagtgacgc                                                  20

<210> SEQ ID NO 617
<211> LENGTH: 20
<212> TYPE: DNA
<213> ORGANISM: Drosophila melanogaster

<400> SEQUENCE: 617
ctacaaaaac gaacaacgca                                                  20

<210> SEQ ID NO 618
<211> LENGTH: 20
<212> TYPE: DNA
<213> ORGANISM: Drosophila melanogaster

<400> SEQUENCE: 618

```
tactaaacac atactaaaac                                              20

<210> SEQ ID NO 619
<211> LENGTH: 20
<212> TYPE: DNA
<213> ORGANISM: Drosophila melanogaster

<400> SEQUENCE: 619
gtcgatttgt agaactggtg                                              20

<210> SEQ ID NO 620
<211> LENGTH: 20
<212> TYPE: DNA
<213> ORGANISM: Drosophila melanogaster

<400> SEQUENCE: 620
tggtactttt ctctcgtaca                                              20

<210> SEQ ID NO 621
<211> LENGTH: 20
<212> TYPE: DNA
<213> ORGANISM: Drosophila melanogaster

<400> SEQUENCE: 621
ttccatgctt ctttagtgca                                              20

<210> SEQ ID NO 622
<211> LENGTH: 20
<212> TYPE: DNA
<213> ORGANISM: Drosophila melanogaster

<400> SEQUENCE: 622
attaaaagcg tatttttagt                                              20

<210> SEQ ID NO 623
<211> LENGTH: 17
<212> TYPE: DNA
<213> ORGANISM: Drosophila melanogaster

<400> SEQUENCE: 623
ggttcgacac gcagaaa                                                 17

<210> SEQ ID NO 624
<211> LENGTH: 20
<212> TYPE: DNA
<213> ORGANISM: Drosophila melanogaster

<400> SEQUENCE: 624
tggagcaaat aatccattca                                              20

<210> SEQ ID NO 625
<211> LENGTH: 20
<212> TYPE: DNA
<213> ORGANISM: Drosophila melanogaster

<400> SEQUENCE: 625
gctctgtaca gaatattttc                                              20

<210> SEQ ID NO 626
<211> LENGTH: 20
<212> TYPE: DNA
<213> ORGANISM: Drosophila melanogaster
```

```
<400> SEQUENCE: 626
atgttacttt ttcgaacgtt                                                  20

<210> SEQ ID NO 627
<211> LENGTH: 20
<212> TYPE: DNA
<213> ORGANISM: Drosophila melanogaster

<400> SEQUENCE: 627
atcccgttag tgtgtgagat                                                  20

<210> SEQ ID NO 628
<211> LENGTH: 20
<212> TYPE: DNA
<213> ORGANISM: Drosophila melanogaster

<400> SEQUENCE: 628
taggtgggat tttcgtgtag                                                  20

<210> SEQ ID NO 629
<211> LENGTH: 20
<212> TYPE: DNA
<213> ORGANISM: Drosophila melanogaster

<400> SEQUENCE: 629
tctttatgta cacgagtata                                                  20

<210> SEQ ID NO 630
<211> LENGTH: 20
<212> TYPE: DNA
<213> ORGANISM: Drosophila melanogaster

<400> SEQUENCE: 630
ttccatgcac taaagaagca                                                  20

<210> SEQ ID NO 631
<211> LENGTH: 20
<212> TYPE: DNA
<213> ORGANISM: Drosophila melanogaster

<400> SEQUENCE: 631
ggtcgcgtcg ataccatttt                                                  20

<210> SEQ ID NO 632
<211> LENGTH: 20
<212> TYPE: DNA
<213> ORGANISM: Drosophila melanogaster

<400> SEQUENCE: 632
ctttcttcct cttcttcggg                                                  20

<210> SEQ ID NO 633
<211> LENGTH: 20
<212> TYPE: DNA
<213> ORGANISM: Drosophila melanogaster

<400> SEQUENCE: 633
catgttactt tttcgaacgt                                                  20

<210> SEQ ID NO 634
<211> LENGTH: 20
<212> TYPE: DNA
<213> ORGANISM: Drosophila melanogaster
```

<400> SEQUENCE: 634
tccccaatct cacacactaa                                          20

<210> SEQ ID NO 635
<211> LENGTH: 20
<212> TYPE: DNA
<213> ORGANISM: Drosophila melanogaster

<400> SEQUENCE: 635 tgtagggtc cctatagtag                                           20

<210> SEQ ID NO 636
<211> LENGTH: 20
<212> TYPE: DNA
<213> ORGANISM: Drosophila melanogaster

<400> SEQUENCE: 636
cacaaagtac atagggtgtt                                          20

<210> SEQ ID NO 637
<211> LENGTH: 20
<212> TYPE: DNA
<213> ORGANISM: Drosophila melanogaster

<400> SEQUENCE: 637
tcccccatcc cccgtaaaga                                          20

<210> SEQ ID NO 638
<211> LENGTH: 20
<212> TYPE: DNA
<213> ORGANISM: Drosophila melanogaster

<400> SEQUENCE: 638
ctttagaccg cccgaagaag                                          20

<210> SEQ ID NO 639
<211> LENGTH: 20
<212> TYPE: DNA
<213> ORGANISM: Drosophila melanogaster

<400> SEQUENCE: 639
tacaaaaacg aacaacgcaa                                          20

<210> SEQ ID NO 640
<211> LENGTH: 20
<212> TYPE: DNA
<213> ORGANISM: Drosophila melanogaster

<400> SEQUENCE: 640
gttgaatcgc ctgtctttaa                                          20

<210> SEQ ID NO 641
<211> LENGTH: 20
<212> TYPE: DNA
<213> ORGANISM: Drosophila melanogaster

<400> SEQUENCE: 641
ccgcgctgct catccaaact                                          20

<210> SEQ ID NO 642
<211> LENGTH: 20
<212> TYPE: DNA

-continued

<213> ORGANISM: Drosophila melanogaster

<400> SEQUENCE: 642
cttcagcgca caaagtacat                                            20

<210> SEQ ID NO 643
<211> LENGTH: 20
<212> TYPE: DNA
<213> ORGANISM: Drosophila melanogaster

<400> SEQUENCE: 643
gcaacaatac gaatgcgaga                                            20

<210> SEQ ID NO 644
<211> LENGTH: 20
<212> TYPE: DNA
<213> ORGANISM: Drosophila melanogaster

<400> SEQUENCE: 644
gccggcagag gcagtgaccg                                            20

<210> SEQ ID NO 645
<211> LENGTH: 20
<212> TYPE: DNA
<213> ORGANISM: Drosophila melanogaster

<400> SEQUENCE: 645
cgcaagggag caatgggtac                                            20

<210> SEQ ID NO 646
<211> LENGTH: 20
<212> TYPE: DNA
<213> ORGANISM: Drosophila melanogaster

<400> SEQUENCE: 646
ttgaatcgcc tgtctttaat                                            20

<210> SEQ ID NO 647
<211> LENGTH: 20
<212> TYPE: DNA
<213> ORGANISM: Drosophila melanogaster

<400> SEQUENCE: 647
agaaactttc acggcaccgt                                            20

<210> SEQ ID NO 648
<211> LENGTH: 20
<212> TYPE: DNA
<213> ORGANISM: Drosophila melanogaster

<400> SEQUENCE: 648
gcaagcgaaa tggcgcttcg                                            20

<210> SEQ ID NO 649
<211> LENGTH: 20
<212> TYPE: DNA
<213> ORGANISM: Drosophila melanogaster

<400> SEQUENCE: 649
agaggcagtg accgaggcag                                            20

<210> SEQ ID NO 650
<211> LENGTH: 20

```
<212> TYPE: DNA
<213> ORGANISM: Drosophila melanogaster

<400> SEQUENCE: 650
ggaaaaaacc cattaaagac                                               20

<210> SEQ ID NO 651
<211> LENGTH: 20
<212> TYPE: DNA
<213> ORGANISM: Drosophila melanogaster

<400> SEQUENCE: 651
atgcacggaa taagctccaa                                               20

<210> SEQ ID NO 652
<211> LENGTH: 20
<212> TYPE: DNA
<213> ORGANISM: Drosophila melanogaster

<400> SEQUENCE: 652
tgtaccacca accctcttta                                               20

<210> SEQ ID NO 653
<211> LENGTH: 20
<212> TYPE: DNA
<213> ORGANISM: Drosophila melanogaster

<400> SEQUENCE: 653
gaaatcttca ttccctccaa                                               20

<210> SEQ ID NO 654
<211> LENGTH: 20
<212> TYPE: DNA
<213> ORGANISM: Drosophila melanogaster

<400> SEQUENCE: 654
aaggaaattg acagatgtat                                               20

<210> SEQ ID NO 655
<211> LENGTH: 20
<212> TYPE: DNA
<213> ORGANISM: Drosophila melanogaster

<400> SEQUENCE: 655
gtaccaccaa ccctctttac                                               20

<210> SEQ ID NO 656
<211> LENGTH: 20
<212> TYPE: DNA
<213> ORGANISM: Drosophila melanogaster

<400> SEQUENCE: 656
cgcaaaaagc ctctactata                                               20

<210> SEQ ID NO 657
<211> LENGTH: 20
<212> TYPE: DNA
<213> ORGANISM: Drosophila melanogaster

<400> SEQUENCE: 657
taccaccaac cctctttacg                                               20

<210> SEQ ID NO 658
```

-continued

```
<210> SEQ ID NO 658
<211> LENGTH: 20
<212> TYPE: DNA
<213> ORGANISM: Drosophila melanogaster

<400> SEQUENCE: 658
tcgcaaaaag cctctactat                                                 20

<210> SEQ ID NO 659
<211> LENGTH: 20
<212> TYPE: DNA
<213> ORGANISM: Drosophila melanogaster

<400> SEQUENCE: 659
accaccaacc ctctttacgg                                                 20

<210> SEQ ID NO 660
<211> LENGTH: 20
<212> TYPE: DNA
<213> ORGANISM: Drosophila melanogaster

<400> SEQUENCE: 660
ccaaccctct ttacggggga                                                 20

<210> SEQ ID NO 661
<211> LENGTH: 20
<212> TYPE: DNA
<213> ORGANISM: Drosophila melanogaster

<400> SEQUENCE: 661
caaccctctt tacgggggat                                                 20

<210> SEQ ID NO 662
<211> LENGTH: 20
<212> TYPE: DNA
<213> ORGANISM: Drosophila melanogaster

<400> SEQUENCE: 662 atccccatc ccccgtaaag                                                  20

<210> SEQ ID NO 663
<211> LENGTH: 17
<212> TYPE: DNA
<213> ORGANISM: Caenorhabditis elegans

<400> SEQUENCE: 663
aagagagtca gattgga                                                    17

<210> SEQ ID NO 664
<211> LENGTH: 17
<212> TYPE: DNA
<213> ORGANISM: Caenorhabditis elegans

<400> SEQUENCE: 664
tctgactctc ttgtgtt                                                    17

<210> SEQ ID NO 665
<211> LENGTH: 17
<212> TYPE: DNA
<213> ORGANISM: Caenorhabditis elegans

<400> SEQUENCE: 665
acacaagaga gtcagat                                                    17
```

```
<210> SEQ ID NO 666
<211> LENGTH: 17
<212> TYPE: DNA
<213> ORGANISM: Caenorhabditis elegans

<400> SEQUENCE: 666
attttcaggt aaaagtt                                                    17

<210> SEQ ID NO 667
<211> LENGTH: 17
<212> TYPE: DNA
<213> ORGANISM: Caenorhabditis elegans

<400> SEQUENCE: 667
gaagacgctc gaattct                                                    17

<210> SEQ ID NO 668
<211> LENGTH: 17
<212> TYPE: DNA
<213> ORGANISM: Caenorhabditis elegans

<400> SEQUENCE: 668
tatgtgacgt cttatct                                                    17

<210> SEQ ID NO 669
<211> LENGTH: 17
<212> TYPE: DNA
<213> ORGANISM: Caenorhabditis elegans

<400> SEQUENCE: 669
tgttcctctt gatcatc                                                    17

<210> SEQ ID NO 670
<211> LENGTH: 17
<212> TYPE: DNA
<213> ORGANISM: Caenorhabditis elegans

<400> SEQUENCE: 670
aagaggaaca taatcta                                                    17

<210> SEQ ID NO 671
<211> LENGTH: 17
<212> TYPE: DNA
<213> ORGANISM: Caenorhabditis elegans

<400> SEQUENCE: 671
tctaggccac gtcttgc                                                    17

<210> SEQ ID NO 672
<211> LENGTH: 17
<212> TYPE: DNA
<213> ORGANISM: Caenorhabditis elegans

<400> SEQUENCE: 672
agtattctat attcagt                                                    17

<210> SEQ ID NO 673
<211> LENGTH: 17
<212> TYPE: DNA
<213> ORGANISM: Caenorhabditis elegans

<400> SEQUENCE: 673
tgcatggttt gaatctt                                                    17
```

```
<210> SEQ ID NO 674
<211> LENGTH: 17
<212> TYPE: DNA
<213> ORGANISM: Caenorhabditis elegans

<400> SEQUENCE: 674
gcaactgatg tgtttct                                                    17

<210> SEQ ID NO 675
<211> LENGTH: 17
<212> TYPE: DNA
<213> ORGANISM: Caenorhabditis elegans

<400> SEQUENCE: 675
gatgtgtttc taggctc                                                    17

<210> SEQ ID NO 676
<211> LENGTH: 17
<212> TYPE: DNA
<213> ORGANISM: Caenorhabditis elegans

<400> SEQUENCE: 676
aagttctaga tcacgag                                                    17

<210> SEQ ID NO 677
<211> LENGTH: 17
<212> TYPE: DNA
<213> ORGANISM: Caenorhabditis elegans

<400> SEQUENCE: 677
tcccaaatca tccttga                                                    17

<210> SEQ ID NO 678
<211> LENGTH: 17
<212> TYPE: DNA
<213> ORGANISM: Caenorhabditis elegans

<400> SEQUENCE: 678
tgggttttaa accatca                                                    17

<210> SEQ ID NO 679
<211> LENGTH: 17
<212> TYPE: DNA
<213> ORGANISM: Caenorhabditis elegans

<400> SEQUENCE: 679
gacgggttgg aggcaga                                                    17

<210> SEQ ID NO 680
<211> LENGTH: 17
<212> TYPE: DNA
<213> ORGANISM: Caenorhabditis elegans

<400> SEQUENCE: 680
cctccaaccc gtccaat                                                    17

<210> SEQ ID NO 681
<211> LENGTH: 17
<212> TYPE: DNA
<213> ORGANISM: Caenorhabditis elegans

<400> SEQUENCE: 681
aaaccgattg gacgggt                                                    17
```

<210> SEQ ID NO 682
<211> LENGTH: 17
<212> TYPE: DNA
<213> ORGANISM: Caenorhabditis elegans

<400> SEQUENCE: 682
ttggaaaccg attggac                                                    17

<210> SEQ ID NO 683
<211> LENGTH: 17
<212> TYPE: DNA
<213> ORGANISM: Caenorhabditis elegans

<400> SEQUENCE: 683
tgtctattgt acaagct                                                    17

<210> SEQ ID NO 684
<211> LENGTH: 17
<212> TYPE: DNA
<213> ORGANISM: Caenorhabditis elegans

<400> SEQUENCE: 684
gtctattgta caagctt                                                    17

<210> SEQ ID NO 685
<211> LENGTH: 17
<212> TYPE: DNA
<213> ORGANISM: Caenorhabditis elegans

<400> SEQUENCE: 685
tctattgtac aagcttg                                                    17

<210> SEQ ID NO 686
<211> LENGTH: 17
<212> TYPE: DNA
<213> ORGANISM: Caenorhabditis elegans

<400> SEQUENCE: 686
tagcactcga cccgaaa                                                    17

<210> SEQ ID NO 687
<211> LENGTH: 17
<212> TYPE: DNA
<213> ORGANISM: Caenorhabditis elegans

<400> SEQUENCE: 687
cactcgaccc gaaacgg                                                    17

<210> SEQ ID NO 688
<211> LENGTH: 17
<212> TYPE: DNA
<213> ORGANISM: Caenorhabditis elegans

<400> SEQUENCE: 688
actcgacccg aaacggt                                                    17

<210> SEQ ID NO 689
<211> LENGTH: 16
<212> TYPE: DNA
<213> ORGANISM: Caenorhabditis elegans

<400> SEQUENCE: 689
acccgaaacg gtggga                            16

<210> SEQ ID NO 690
<211> LENGTH: 17
<212> TYPE: DNA
<213> ORGANISM: Caenorhabditis elegans

<400> SEQUENCE: 690
cccgaaacgg tgggaag                           17

<210> SEQ ID NO 691
<211> LENGTH: 17
<212> TYPE: DNA
<213> ORGANISM: Caenorhabditis elegans

<400> SEQUENCE: 691
ccgaaacggt gggaagg                           17

<210> SEQ ID NO 692
<211> LENGTH: 17
<212> TYPE: DNA
<213> ORGANISM: Caenorhabditis elegans

<400> SEQUENCE: 692
aacggtggga aggggggg                          17

<210> SEQ ID NO 693
<211> LENGTH: 17
<212> TYPE: DNA
<213> ORGANISM: Caenorhabditis elegans

<400> SEQUENCE: 693 cccctteccca ccgtttc                          17

<210> SEQ ID NO 694
<211> LENGTH: 17
<212> TYPE: DNA
<213> ORGANISM: Caenorhabditis elegans

<400> SEQUENCE: 694
cccccttccc accgttt                           17

<210> SEQ ID NO 695
<211> LENGTH: 17
<212> TYPE: DNA
<213> ORGANISM: Caenorhabditis elegans

<400> SEQUENCE: 695 gggggagga catccgc                            17

<210> SEQ ID NO 696
<211> LENGTH: 17
<212> TYPE: DNA
<213> ORGANISM: Caenorhabditis elegans

<400> SEQUENCE: 696
taggtgactg actccgg                           17

<210> SEQ ID NO 697
<211> LENGTH: 17
<212> TYPE: DNA
<213> ORGANISM: Caenorhabditis elegans

<400> SEQUENCE: 697
ttgtaggtga ctgactc                                                        17

<210> SEQ ID NO 698
<211> LENGTH: 17
<212> TYPE: DNA
<213> ORGANISM: Caenorhabditis elegans

<400> SEQUENCE: 698
ggattagctg ctccaat                                                        17

<210> SEQ ID NO 699
<211> LENGTH: 17
<212> TYPE: DNA
<213> ORGANISM: Caenorhabditis elegans

<400> SEQUENCE: 699
attagctgct ccaattg                                                        17

<210> SEQ ID NO 700
<211> LENGTH: 17
<212> TYPE: DNA
<213> ORGANISM: Caenorhabditis elegans

<400> SEQUENCE: 700
acttagcaca ccccaat                                                        17

<210> SEQ ID NO 701
<211> LENGTH: 17
<212> TYPE: DNA
<213> ORGANISM: Caenorhabditis elegans

<400> SEQUENCE: 701
aattgtctat gtttaat                                                        17

<210> SEQ ID NO 702
<211> LENGTH: 17
<212> TYPE: DNA
<213> ORGANISM: Caenorhabditis elegans

<400> SEQUENCE: 702
taatgggtgt atcgtat                                                        17

<210> SEQ ID NO 703
<211> LENGTH: 17
<212> TYPE: DNA
<213> ORGANISM: Caenorhabditis elegans

<400> SEQUENCE: 703 agcactttt gagtggt                                                         17

<210> SEQ ID NO 704
<211> LENGTH: 17
<212> TYPE: DNA
<213> ORGANISM: Caenorhabditis elegans

<400> SEQUENCE: 704
aggaagtgag agtcact                                                        17

<210> SEQ ID NO 705
<211> LENGTH: 17
<212> TYPE: DNA
<213> ORGANISM: Caenorhabditis elegans

```
<400> SEQUENCE: 705
ggaagtgaga gtcacta                                                   17

<210> SEQ ID NO 706
<211> LENGTH: 17
<212> TYPE: DNA
<213> ORGANISM: Caenorhabditis elegans

<400> SEQUENCE: 706
gaatggataa agccacg                                                   17

<210> SEQ ID NO 707
<211> LENGTH: 17
<212> TYPE: DNA
<213> ORGANISM: Caenorhabditis elegans

<400> SEQUENCE: 707
ccacgtggca atcatat                                                   17

<210> SEQ ID NO 708
<211> LENGTH: 17
<212> TYPE: DNA
<213> ORGANISM: Caenorhabditis elegans

<400> SEQUENCE: 708
gtttatagta ggatttt                                                   17

<210> SEQ ID NO 709
<211> LENGTH: 20
<212> TYPE: DNA
<213> ORGANISM: Sus scrofa

<400> SEQUENCE: 709 aggataccte aacgactacg                                                20

<210> SEQ ID NO 710
<211> LENGTH: 20
<212> TYPE: DNA
<213> ORGANISM: Sus scrofa

<400> SEQUENCE: 710
gcgctgcccg acgtgtggca                                                20

<210> SEQ ID NO 711
<211> LENGTH: 20
<212> TYPE: DNA
<213> ORGANISM: Sus scrofa

<400> SEQUENCE: 711
cttcaagcaa tagggtcccg                                                20

<210> SEQ ID NO 712
<211> LENGTH: 20
<212> TYPE: DNA
<213> ORGANISM: Sus scrofa

<400> SEQUENCE: 712
atgacgcata tcaaatcgca                                                20

<210> SEQ ID NO 713
<211> LENGTH: 20
<212> TYPE: DNA
<213> ORGANISM: Sus scrofa
```

```
<400> SEQUENCE: 713
tattgctcta tagtcggctt                                                 20

<210> SEQ ID NO 714
<211> LENGTH: 20
<212> TYPE: DNA
<213> ORGANISM: Sus scrofa

<400> SEQUENCE: 714
ataaccgact tagcgaattc                                                 20

<210> SEQ ID NO 715
<211> LENGTH: 20
<212> TYPE: DNA
<213> ORGANISM: Sus scrofa

<400> SEQUENCE: 715
aggctgctga ccgtattgcc                                                 20

<210> SEQ ID NO 716
<211> LENGTH: 20
<212> TYPE: DNA
<213> ORGANISM: Sus scrofa

<400> SEQUENCE: 716
ggatacctca acgactacgc                                                 20

<210> SEQ ID NO 717
<211> LENGTH: 20
<212> TYPE: DNA
<213> ORGANISM: Sus scrofa

<400> SEQUENCE: 717
ctcagccccg tgcaggccta                                                 20

<210> SEQ ID NO 718
<211> LENGTH: 20
<212> TYPE: DNA
<213> ORGANISM: Sus scrofa

<400> SEQUENCE: 718
taggaaagcg gctcggattg                                                 20

<210> SEQ ID NO 719
<211> LENGTH: 20
<212> TYPE: DNA
<213> ORGANISM: Sus scrofa

<400> SEQUENCE: 719
ggcatagacg ggcgttaagt                                                 20

<210> SEQ ID NO 720
<211> LENGTH: 20
<212> TYPE: DNA
<213> ORGANISM: Sus scrofa

<400> SEQUENCE: 720
gcggtcccta gacccaaccg                                                 20

<210> SEQ ID NO 721
<211> LENGTH: 20
<212> TYPE: DNA
```

```
<213> ORGANISM: Sus scrofa

<400> SEQUENCE: 721
agcccgggag tctttcgcta                                               20

<210> SEQ ID NO 722
<211> LENGTH: 20
<212> TYPE: DNA
<213> ORGANISM: Sus scrofa

<400> SEQUENCE: 722
ctgctagtgg cggccgttta                                               20

<210> SEQ ID NO 723
<211> LENGTH: 20
<212> TYPE: DNA
<213> ORGANISM: Sus scrofa

<400> SEQUENCE: 723
gatacctcaa cgactacgcg                                               20

<210> SEQ ID NO 724
<211> LENGTH: 20
<212> TYPE: DNA
<213> ORGANISM: Sus scrofa

<400> SEQUENCE: 724
ttttcccagc aatagggtcg                                               20

<210> SEQ ID NO 725
<211> LENGTH: 20
<212> TYPE: DNA
<213> ORGANISM: Sus scrofa

<400> SEQUENCE: 725
cgaatgcccg ggtacgaggg                                               20

<210> SEQ ID NO 726
<211> LENGTH: 20
<212> TYPE: DNA
<213> ORGANISM: Sus scrofa

<400> SEQUENCE: 726
ggaaagaaag tctgcgcgtc                                               20

<210> SEQ ID NO 727
<211> LENGTH: 20
<212> TYPE: DNA
<213> ORGANISM: Sus scrofa

<400> SEQUENCE: 727
cgggccccgc gtagtcgttg                                               20

<210> SEQ ID NO 728
<211> LENGTH: 20
<212> TYPE: DNA
<213> ORGANISM: Sus scrofa

<400> SEQUENCE: 728
ggtctcctcg accctattgc                                               20

<210> SEQ ID NO 729
<211> LENGTH: 20
```

```
<212> TYPE: DNA
<213> ORGANISM: Sus scrofa

<400> SEQUENCE: 729
tttatgaacg gattgcactc                                        20

<210> SEQ ID NO 730
<211> LENGTH: 20
<212> TYPE: DNA
<213> ORGANISM: Sus scrofa

<400> SEQUENCE: 730
gcagaggccg gcgggtgtaa                                        20

<210> SEQ ID NO 731
<211> LENGTH: 20
<212> TYPE: DNA
<213> ORGANISM: Sus scrofa

<400> SEQUENCE: 731
ggcgtcgcca tcgtagacgg                                        20

<210> SEQ ID NO 732
<211> LENGTH: 20
<212> TYPE: DNA
<213> ORGANISM: Sus scrofa

<400> SEQUENCE: 732
gtctctgcga cgcgatccag                                        20

<210> SEQ ID NO 733
<211> LENGTH: 20
<212> TYPE: DNA
<213> ORGANISM: Sus scrofa

<400> SEQUENCE: 733
tcacccacca accgttcatt                                        20

<210> SEQ ID NO 734
<211> LENGTH: 20
<212> TYPE: DNA
<213> ORGANISM: Sus scrofa

<400> SEQUENCE: 734
cgtctacgat ggcgacgccg                                        20

<210> SEQ ID NO 735
<211> LENGTH: 20
<212> TYPE: DNA
<213> ORGANISM: Sus scrofa

<400> SEQUENCE: 735
agtctctgcg acgcgatcca                                        20

<210> SEQ ID NO 736
<211> LENGTH: 20
<212> TYPE: DNA
<213> ORGANISM: Sus scrofa

<400> SEQUENCE: 736
gtaggtgcct aatgaacggt                                        20

<210> SEQ ID NO 737
```

```
<211> LENGTH: 20
<212> TYPE: DNA
<213> ORGANISM: Sus scrofa

<400> SEQUENCE: 737
tggctacatc aacggcgacg                                          20

<210> SEQ ID NO 738
<211> LENGTH: 20
<212> TYPE: DNA
<213> ORGANISM: Sus scrofa

<400> SEQUENCE: 738
gagtctctgc gacgcgatcc                                          20

<210> SEQ ID NO 739
<211> LENGTH: 20
<212> TYPE: DNA
<213> ORGANISM: Sus scrofa

<400> SEQUENCE: 739
ggggcccacg gttgggtcta                                          20

<210> SEQ ID NO 740
<211> LENGTH: 20
<212> TYPE: DNA
<213> ORGANISM: Sus scrofa

<400> SEQUENCE: 740
acctccgccg tcgccgtcgg                                          20

<210> SEQ ID NO 741
<211> LENGTH: 20
<212> TYPE: DNA
<213> ORGANISM: Sus scrofa

<400> SEQUENCE: 741
ttggcagagg atgcgaggcg                                          20

<210> SEQ ID NO 742
<211> LENGTH: 20
<212> TYPE: DNA
<213> ORGANISM: Sus scrofa

<400> SEQUENCE: 742
cccgggccct gagcgcgcct                                          20

<210> SEQ ID NO 743
<211> LENGTH: 20
<212> TYPE: DNA
<213> ORGANISM: Sus scrofa

<400> SEQUENCE: 743
cggcacgctt gcggcgagtg                                          20

<210> SEQ ID NO 744
<211> LENGTH: 20
<212> TYPE: DNA
<213> ORGANISM: Bos taurus

<400> SEQUENCE: 744
cctgccagta tctcaaaccg                                          20
```

```
<210> SEQ ID NO 745
<211> LENGTH: 23
<212> TYPE: DNA
<213> ORGANISM: Homo sapiens

<400> SEQUENCE: 745
cacatcgatg tcctccccat tcc                                              23

<210> SEQ ID NO 746
<211> LENGTH: 20
<212> TYPE: DNA
<213> ORGANISM: Homo sapiens

<400> SEQUENCE: 746
atggggagga catcgatgtc                                                  20

<210> SEQ ID NO 747
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
cacaucgaug uccuccccau                                                  20

<210> SEQ ID NO 748
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
caccgacatc gatgtcctcc ccat                                             24

<210> SEQ ID NO 749
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
aaacatgggg aggacatcga tgtc                                             24

<210> SEQ ID NO 750
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
gagggcctat ttcccatgat tccttc                                           26

<210> SEQ ID NO 751
<211> LENGTH: 125
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 751
aaaaaaagca ccgactcggt gccactttt caagttgata acggactagc cttattttaa    60
cttgctattt ctagctctaa aacatggga ggacatcgat gtcggtgttt cgtccttttcc  120 acaag                                                              125

<210> SEQ ID NO 752
<211> LENGTH: 23
<212> TYPE: DNA
<213> ORGANISM: Homo sapiens

<400> SEQUENCE: 752
cacataggtg tcctccccat agg                                           23

<210> SEQ ID NO 753
<211> LENGTH: 23
<212> TYPE: DNA
<213> ORGANISM: Homo sapiens

<400> SEQUENCE: 753
gaaatcaagg tcctccccat agg                                           23

<210> SEQ ID NO 754
<211> LENGTH: 23
<212> TYPE: DNA
<213> ORGANISM: Homo sapiens

<400> SEQUENCE: 754
aacttccatc tcctccccat ggg                                           23

<210> SEQ ID NO 755
<211> LENGTH: 23
<212> TYPE: DNA
<213> ORGANISM: Homo sapiens

<400> SEQUENCE: 755
gccttctctg tcctccccat ggg                                           23

<210> SEQ ID NO 756
<211> LENGTH: 23
<212> TYPE: DNA
<213> ORGANISM: Homo sapiens

<400> SEQUENCE: 756
gagacccatt tcctccccat tag                                           23

<210> SEQ ID NO 757
<211> LENGTH: 23
<212> TYPE: DNA
<213> ORGANISM: Homo sapiens

<400> SEQUENCE: 757
aaaaacaatg tcctccccat tag                                           23

<210> SEQ ID NO 758
<211> LENGTH: 23
<212> TYPE: DNA
<213> ORGANISM: Homo sapiens
```

```
<400> SEQUENCE: 758
gccctcgctg ccctccccat cag                                          23

<210> SEQ ID NO 759
<211> LENGTH: 23
<212> TYPE: DNA
<213> ORGANISM: Homo sapiens

<400> SEQUENCE: 759
cacggctgtg tcctccccat tgg                                          23

<210> SEQ ID NO 760
<211> LENGTH: 23
<212> TYPE: DNA
<213> ORGANISM: Homo sapiens

<400> SEQUENCE: 760
tgcttcactg tcctccccat agg                                          23

<210> SEQ ID NO 761
<211> LENGTH: 23
<212> TYPE: DNA
<213> ORGANISM: Homo sapiens

<400> SEQUENCE: 761
gtcaacgttg tcctcctcat tgg                                          23

<210> SEQ ID NO 762
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 762
gagggcctat ttcccatgat tcc                                          23

<210> SEQ ID NO 763
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
gagggcctat ttcccatgat tcc                                          23

<210> SEQ ID NO 764
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
cttgtggaaa ggacgaaaca cc                                           22

<210> SEQ ID NO 765
```

```
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (4)..(23)
<223> OTHER INFORMATION: a, c, t, g, unknown or other

<400> SEQUENCE: 765
aacnnnnnnn nnnnnnnnnn nnnggtgttt cgtcctttcc acaag              45

<210> SEQ ID NO 766
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(25)
<223> OTHER INFORMATION: a, c, t, g, unknown or other

<400> SEQUENCE: 766
caccgnnnnn nnnnnnnnnn nnnnn                                    25

<210> SEQ ID NO 767
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(24)
<223> OTHER INFORMATION: a, c, t, g, unknown or other

<400> SEQUENCE: 767
aaacnnnnnn nnnnnnnnnn nnnnc                                    25

<210> SEQ ID NO 768
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
aacaccgggt cttcgagaag acctgtttta gagctagaaa tagcaagtta aaat    54

<210> SEQ ID NO 769
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
gaguccgagc agaagaagaa                                          20
```

```
<210> SEQ ID NO 770
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
gucaccucca augacuaggg                                                   20

<210> SEQ ID NO 771
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
gucaccucca augacuagaa                                                   20

<210> SEQ ID NO 772
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
gucaccucca augacugagg                                                   20

<210> SEQ ID NO 773
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
gucaccucca augaucaggg                                                   20

<210> SEQ ID NO 774
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
gucaccucca auagcuaggg                                                   20

<210> SEQ ID NO 775
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 775
gucaccucca gcgacuaggg                                             20

<210> SEQ ID NO 776
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
gucaccucug augacuaggg                                             20

<210> SEQ ID NO 777
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
gucacccuca augacuaggg                                             20

<210> SEQ ID NO 778
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
gucauuucca augacuaggg                                             20

<210> SEQ ID NO 779
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
guugccucca augacuaggg                                             20

<210> SEQ ID NO 780
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
gucaccucca augacugaag                                             20

<210> SEQ ID NO 781
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
gucaccucca auggucaggg                                              20

<210> SEQ ID NO 782
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
gucaccucca gcaacuaggg                                              20

<210> SEQ ID NO 783
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
gucaccuucg augacuaggg                                              20

<210> SEQ ID NO 784
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
gucauuccca augacuaggg                                              20

<210> SEQ ID NO 785
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
gcugccucca augacuaggg                                              20

<210> SEQ ID NO 786
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
```
gucaccucca augaccgaaa					20

<210> SEQ ID NO 787
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
gucaccucca auagucgggg					20

<210> SEQ ID NO 788
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
gucaccuccg gcagcuaggg					20

<210> SEQ ID NO 789
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
gucacccuug gugacuaggg					20

<210> SEQ ID NO 790
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
gucguucuca augacuaggg					20

<210> SEQ ID NO 791
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
gacaucgaug uccuccccau					20

<210> SEQ ID NO 792
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 792
gacaucgaug uccucccgc                                                   20

<210> SEQ ID NO 793
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
gacaucgaug uccuccuuau                                                  20

<210> SEQ ID NO 794
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
gacaucgaug uccuuuccau                                                  20

<210> SEQ ID NO 795
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
gacaucgaug ucuccccau                                                   20

<210> SEQ ID NO 796
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
gacaucgaug cucuccccau                                                  20

<210> SEQ ID NO 797
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
gacaucgaca uccuccccau                                                  20

<210> SEQ ID NO 798
```

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
gacaucagug uccucccccau                                                  20

<210> SEQ ID NO 799
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
gacacugaug uccuccccau                                                   20

<210> SEQ ID NO 800
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
gaugucgaug uccuccccau                                                   20

<210> SEQ ID NO 801
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
gacaucgaug uccuccuugu                                                   20

<210> SEQ ID NO 802
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
gacaucgaug ucccuuccau                                                   20

<210> SEQ ID NO 803
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
```
gacaucgaug cuuucccccau				20

<210> SEQ ID NO 804
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
gacaucggca uccuccccau				20

<210> SEQ ID NO 805
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
gacacuaaug uccuccccau				20

<210> SEQ ID NO 806
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
ggugucgaug uccuccccau				20

<210> SEQ ID NO 807
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
gacaucgaug uccucuuugc				20

<210> SEQ ID NO 808
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
gacaucgaug ucucuuucau				20

<210> SEQ ID NO 809
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic
      oligonucleotide"

<400> SEQUENCE: 809
gacaucgaua cuucccccau                                              20

<210> SEQ ID NO 810
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
gacaucagca cccuccccau                                              20

<210> SEQ ID NO 811
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
gacgcuagug uccuccccau                                              20

<210> SEQ ID NO 812
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
gaguccgagc agaagaagaa                                              20

<210> SEQ ID NO 813
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
gaguccgagc agaagaaggg                                              20

<210> SEQ ID NO 814
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
gaguccgagc agaagagaaa                                              20
```

<210> SEQ ID NO 815
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 815
gaguccgagc agaaagagaa                    20

<210> SEQ ID NO 816
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 816
gaguccgagc aggggaagaa                    20

<210> SEQ ID NO 817
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 817
gaguccgagc gaaagaagaa                    20

<210> SEQ ID NO 818
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 818
gaguccgaau agaagaagaa                    20

<210> SEQ ID NO 819
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 819
gaguccaggc agaagaagaa                    20

<210> SEQ ID NO 820
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 820
gagucugagc agaagaagaa                                          20

<210> SEQ ID NO 821
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
gaacccgagc agaagaagaa                                          20

<210> SEQ ID NO 822
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
gaguccgagc agaagagaga                                          20

<210> SEQ ID NO 823
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
gaguccgagc agagagagaa                                          20

<210> SEQ ID NO 824
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
gaguccgagc gagagaagaa                                          20

<210> SEQ ID NO 825
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
gaguccggau agaagaagaa                                          20

<210> SEQ ID NO 826
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
gagucuaagc agaagaagaa                                                    20

<210> SEQ ID NO 827
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
ggacccgagc agaagaagaa                                                    20

<210> SEQ ID NO 828
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
gaguccgagc agaagggagg                                                    20

<210> SEQ ID NO 829
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
gaguccgagc agggagggaa                                                    20

<210> SEQ ID NO 830
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
gaguccgagu gagggaagaa                                                    20

<210> SEQ ID NO 831
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
gaguccagau ggaagaagaa                                                    20
```

<210> SEQ ID NO 832
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
gagccuaggc agaagaagaa                                                  20

<210> SEQ ID NO 833
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
gcgccaccgg uugaugugau                                                  20

<210> SEQ ID NO 834
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
gcgccaccgg uugauguggc                                                  20

<210> SEQ ID NO 835
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
gcgccaccgg uugaugcaau                                                  20

<210> SEQ ID NO 836
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
gcgccaccgg uugacaugau                                                  20

<210> SEQ ID NO 837
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 837
gcgccaccgg uuagugugau                                        20

<210> SEQ ID NO 838
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
gcgccaccgg ccgaugugau                                        20

<210> SEQ ID NO 839
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
gcgccaccaa uugaugugau                                        20

<210> SEQ ID NO 840
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
gcgccauugg uugaugugau                                        20

<210> SEQ ID NO 841
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
gcgcugccgg uugaugugau                                        20

<210> SEQ ID NO 842
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
gcaucaccgg uugaugugau                                        20

<210> SEQ ID NO 843
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
gcgccaccgg uugaugcagu                                              20

<210> SEQ ID NO 844
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
gcgccaccgg uuggcaugau                                              20

<210> SEQ ID NO 845
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
gcgccaccgg ccaaugugau                                              20

<210> SEQ ID NO 846
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
gcgccacuaa uugaugugau                                              20

<210> SEQ ID NO 847
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
gcgcugucgg uugaugugau                                              20

<210> SEQ ID NO 848
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
```
guaucaccgg uugaugugau 20

<210> SEQ ID NO 849
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
gcgccaccgg uugauacagc 20

<210> SEQ ID NO 850
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
gcgccaccgg uuagcacgau 20

<210> SEQ ID NO 851
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
gcgccaccga ccagugugau 20

<210> SEQ ID NO 852
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
gcgccauuaa cugaugugau 20

<210> SEQ ID NO 853
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
gcguuguugg uugaugugau 20

<210> SEQ ID NO 854
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 854
gucaccucca augacuaggg                                                   20

<210> SEQ ID NO 855
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
gucaccucca augacuaaga                                                   20

<210> SEQ ID NO 856
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
gucaccucca augauuagga                                                   20

<210> SEQ ID NO 857
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
gucaccucca gugacuagga                                                   20

<210> SEQ ID NO 858
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
gucacuucca augacuagga                                                   20

<210> SEQ ID NO 859
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
aucaccucca augacuagga                                                   20

<210> SEQ ID NO 860
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
gucaccucca augaccaagg                                                   20

<210> SEQ ID NO 861
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
gucaccucca auaacuaagg                                                   20

<210> SEQ ID NO 862
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
gucaccucua augacuaagg                                                   20

<210> SEQ ID NO 863
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
gucgccucca augacuaagg                                                   20

<210> SEQ ID NO 864
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
gucaccucca auggccaggg                                                   20

<210> SEQ ID NO 865
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
```

```
gucaccucca gugaccaggg                                              20

<210> SEQ ID NO 866
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
gucaccccca augaccaggg                                              20

<210> SEQ ID NO 867
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
gccaccucca augaccaggg                                              20

<210> SEQ ID NO 868
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
gacaucgaug uccuccccau                                              20

<210> SEQ ID NO 869
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
gacaucgaug uccucccuag                                              20

<210> SEQ ID NO 870
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
gacaucgaug uccuucccag                                              20

<210> SEQ ID NO 871
<211> LENGTH: 20
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 871
gacaucgaug cccuccccag                                                     20

<210> SEQ ID NO 872
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
gacauugaug uccuccccag                                                     20

<210> SEQ ID NO 873
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
aacaucgaug uccuccccag                                                     20

<210> SEQ ID NO 874
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
gacaucgaug uccucucuau                                                     20

<210> SEQ ID NO 875
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
gacaucgaug ucuucccuau                                                     20

<210> SEQ ID NO 876
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
gacaucgacg uccucccuau                                                     20

```
<210> SEQ ID NO 877
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
gacgucgaug uccucccuau                                                   20

<210> SEQ ID NO 878
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
gacaucgaug uccccuccau                                                   20

<210> SEQ ID NO 879
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
gacaucgaug cccucuccau                                                   20

<210> SEQ ID NO 880
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
gacaucaaug uccucuccau                                                   20

<210> SEQ ID NO 881
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
ggcaucgaug uccucuccau                                                   20

<210> SEQ ID NO 882
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 882
gaguccgagc agaagaagaa                                              20

<210> SEQ ID NO 883
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
gaguccgagc agaagaaaag                                              20

<210> SEQ ID NO 884
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
gaguccgagc agaaaaagag                                              20

<210> SEQ ID NO 885
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
gaguccgagc ggaagaagag                                              20

<210> SEQ ID NO 886
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
gagucugagc agaagaagag                                              20

<210> SEQ ID NO 887
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
aaguccgagc agaagaagag                                              20

<210> SEQ ID NO 888
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 888
gaguccgagc agaagcaaaa                                                      20

<210> SEQ ID NO 889
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
gaguccgagc aggagaaaaa                                                      20

<210> SEQ ID NO 890
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
gaguccgaac agaagaaaaa                                                      20

<210> SEQ ID NO 891
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
gagcccgagc agaagaaaaa                                                      20

<210> SEQ ID NO 892
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
gaguccgagc agagggagaa                                                      20

<210> SEQ ID NO 893
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
gaguccgagc ggaaggagaa                                                      20
```

<210> SEQ ID NO 894
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
gaguccaagc agaaggagaa                                              20

<210> SEQ ID NO 895
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 895
ggguccgagc agaaggagaa                                              20

<210> SEQ ID NO 896
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
gcgccaccgg uugaugugau                                              20

<210> SEQ ID NO 897
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
gcgccaccgg uugauguaac                                              20

<210> SEQ ID NO 898
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
gcgccaccgg uugaugugac                                              20

<210> SEQ ID NO 899
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 899
gcgccaccgg cugaugugac                                           20

<210> SEQ ID NO 900
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
gcgccgccgg uugaugugac                                           20

<210> SEQ ID NO 901
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
acgccaccgg uugaugugac                                           20

<210> SEQ ID NO 902
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
gcgccaccgg uugauauaau                                           20

<210> SEQ ID NO 903
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
gcgccaccgg uuaauguaau                                           20

<210> SEQ ID NO 904
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
gcgccaccag uugauguaau                                           20

<210> SEQ ID NO 905
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
gcgucaccgg uugauguaau                                                   20

<210> SEQ ID NO 906
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
gcgccaccgg uugguaugau                                                   20

<210> SEQ ID NO 907
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
gcgccaccgg cugauaugau                                                   20

<210> SEQ ID NO 908
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
gcgccaucgg uugauaugau                                                   20

<210> SEQ ID NO 909
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
gugccaccgg uugauaugau                                                   20

<210> SEQ ID NO 910
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
```

-continued gucaccucca augacuaggg           20

<210> SEQ ID NO 911
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 911
gucaccucca augaccaaga           20

<210> SEQ ID NO 912
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
gucaccucca auggcuggga           20

<210> SEQ ID NO 913
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
gucaccucca acgaccagga           20

<210> SEQ ID NO 914
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
gucaccuccg augauuagga           20

<210> SEQ ID NO 915
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 915
gucaccucca auggccaagg           20

<210> SEQ ID NO 916
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 916
gucaccucca acgauuaagg                                               20

<210> SEQ ID NO 917
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
gucaccuccg auggcuaagg                                               20

<210> SEQ ID NO 918
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
gucaccuuca auaacuaagg                                               20

<210> SEQ ID NO 919
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
gucaccucca auggccaaga                                               20

<210> SEQ ID NO 920
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
gucaccucca guggcuggga                                               20

<210> SEQ ID NO 921
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
gucaccuuca acgaccagga                                               20
```

<210> SEQ ID NO 922
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 922
gucaucuccg augauuagga                                               20

<210> SEQ ID NO 923
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 923
gccaccuuca auggcuagga                                               20

<210> SEQ ID NO 924
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 924
gacaucgaug uccuccccau                                               20

<210> SEQ ID NO 925
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 925
gacaucgaug uccucucuag                                               20

<210> SEQ ID NO 926
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 926
gacaucgaug uccccccucag                                              20

<210> SEQ ID NO 927
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 927
gacaucgaug uucucuccag                                           20

<210> SEQ ID NO 928
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
gacaucgaua uccuuccag                                            20

<210> SEQ ID NO 929
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
gacaucgaug uccccucuau                                           20

<210> SEQ ID NO 930
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
gacaucgaug uucuuccuau                                           20

<210> SEQ ID NO 931
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
gacaucgaua ucccccuau                                            20

<210> SEQ ID NO 932
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
gacaucggug ucaucccuau                                           20

<210> SEQ ID NO 933
<211> LENGTH: 20
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
gacaucgaug uccccucuag                                                20

<210> SEQ ID NO 934
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
gacaucgaug cccccccucag                                               20

<210> SEQ ID NO 935
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
gacaucggug uucucuccag                                                20

<210> SEQ ID NO 936
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic  oligonucleotide"

<400> SEQUENCE: 936
gacaccgaua uccuucccag                                                20

<210> SEQ ID NO 937
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
ggcaucggug uccccccccag                                               20

<210> SEQ ID NO 938
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
gaguccgagc agaagaagaa                                                20

<210> SEQ ID NO 939
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
gaguccgagc agaaggaaag                                             20

<210> SEQ ID NO 940
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic
      oligonucleotide"

<400> SEQUENCE: 940
gaguccgagc agaggaggag                                             20

<210> SEQ ID NO 941
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
gaguccgagc aaaaggagag                                             20

<210> SEQ ID NO 942
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
gaguccgagu agaaaaagag                                             20

<210> SEQ ID NO 943
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
gaguccgagc agagggaaaa                                             20

<210> SEQ ID NO 944
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 944 gauccgagc aaaaaaaaaa                                                   20

<210> SEQ ID NO 945
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945 gauccgagu agaggaaaaa                                                   20

<210> SEQ ID NO 946
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946 gauccgggc aggagaaaaa                                                   20

<210> SEQ ID NO 947
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947 gauccgagc agagggaaag                                                   20

<210> SEQ ID NO 948
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948 gauccgagc ggaggaggag                                                   20

<210> SEQ ID NO 949
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949 gauccgggc aaaaggagag                                                   20

<210> SEQ ID NO 950
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
gaguucgagu agaaaaagag                                                     20

<210> SEQ ID NO 951
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 951
ggguccgggc agaggaagag                                                     20

<210> SEQ ID NO 952
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
gcgccaccgg uugaugugau                                                     20

<210> SEQ ID NO 953
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
gcgccaccgg uugauauaac                                                     20

<210> SEQ ID NO 954
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
gcgccaccgg uuggugcgac                                                     20

<210> SEQ ID NO 955
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
```

-continued gcgccaccgg ucgauaugac                                              20

<210> SEQ ID NO 956
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
gcgccaccga uugacgugac                                              20

<210> SEQ ID NO 957
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
gcgccaccgg uugguauaau                                              20

<210> SEQ ID NO 958
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
gcgccaccgg ucgacguaau                                              20

<210> SEQ ID NO 959
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
gcgccaccga uugguguaau                                              20

<210> SEQ ID NO 960
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
gcgccacugg uuaauguaau                                              20

<210> SEQ ID NO 961
<211> LENGTH: 20
<212> TYPE: RNA
<213> ORGANISM: Artificial Sequence
<220> FEATURE:

-continued

<221> NAME/KEY: source
<223> OTHER INFORMATION: /note="Description of Artificial Sequence:
      Synthetic oligonucleotide"

<400> SEQUENCE: 961
gcgccaccgg uugguauaac                                                    20

<210> SEQ ID NO 962
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
gcgccaccgg cuggugcgac                                                    20

<210> SEQ ID NO 963
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
gcgccacugg ucgauaugac                                                    20

<210> SEQ ID NO 964
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
gcgcuaccga uugacgugac                                                    20

<210> SEQ ID NO 965
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
gugccacugg uuggugugac                                                    20

<210> SEQ ID NO 966
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
gucaccucca augacuaggg                                                    20

```
<210> SEQ ID NO 967
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 967
gucaccucca augacuaggg tgg                                              23

<210> SEQ ID NO 968
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 968
gucaacucca augatuagga cag                                              23

<210> SEQ ID NO 969
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 969
gucaccucca cutccuaggg cag                                              23

<210> SEQ ID NO 970
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 970
gucactucca aggacuagag aag                                              23

<210> SEQ ID NO 971
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
                          Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 971
gucaccucca gggtcuaggg cag                                           23

<210> SEQ ID NO 972
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 972
gucaacucca augacutggg agg                                           23

<210> SEQ ID NO 973
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 973
gucaccutaa augacutggg aag                                           23

<210> SEQ ID NO 974
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 974
tucaccucca aaaacuaggg aag                                           23

<210> SEQ ID NO 975
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 975
```
gctaccucca gugacuaggg aag                     23

<210> SEQ ID NO 976
<211> LENGTH: 12
<212> TYPE: DNA
<213> ORGANISM: Homo sapiens

<400> SEQUENCE: 976
tgactagggt gg                                 12

<210> SEQ ID NO 977
<211> LENGTH: 11
<212> TYPE: DNA
<213> ORGANISM: Homo sapiens

<400> SEQUENCE: 977
tgactgggtg g                                  11

<210> SEQ ID NO 978
<211> LENGTH: 14
<212> TYPE: DNA
<213> ORGANISM: Homo sapiens

<400> SEQUENCE: 978
tgactatagg gtgg                               14

<210> SEQ ID NO 979
<211> LENGTH: 12
<212> TYPE: DNA
<213> ORGANISM: Homo sapiens

<400> SEQUENCE: 979
tgactaggga ag                                 12

<210> SEQ ID NO 980
<211> LENGTH: 11
<212> TYPE: DNA
<213> ORGANISM: Homo sapiens

<400> SEQUENCE: 980
tgactgggaa g                                  11

<210> SEQ ID NO 981
<211> LENGTH: 14
<212> TYPE: DNA
<213> ORGANISM: Homo sapiens

<400> SEQUENCE: 981
tgactatagg gaag                               14

<210> SEQ ID NO 982
<211> LENGTH: 14
<212> TYPE: DNA
<213> ORGANISM: Homo sapiens

<400> SEQUENCE: 982
tgactggagg gaag                               14

<210> SEQ ID NO 983
<211> LENGTH: 13
<212> TYPE: DNA
<213> ORGANISM: Homo sapiens

```
<400> SEQUENCE: 983
tgactacggg aag                                                          13

<210> SEQ ID NO 984
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
gaguccgagc agaagaagaa                                                   20

<210> SEQ ID NO 985
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
gaguccgagc agaagaagaa ggg                                               23

<210> SEQ ID NO 986
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
gaggccgagc agaagaaaga cgg                                               23

<210> SEQ ID NO 987
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
gagucccagc agaggaagca gag                                               23

<210> SEQ ID NO 988
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 988
gaguccaagc agaggaagga tag                                               23
```

-continued

```
<210> SEQ ID NO 989
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 989
gagucagagc agaactagaa ggg                                            23

<210> SEQ ID NO 990
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
gagucccagg agaagaagag agg                                            23

<210> SEQ ID NO 991
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 991
gaguccaagc agtagaggaa ggg                                            23

<210> SEQ ID NO 992
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 992
gaguccgaga aaatgaagaa gag                                            23

<210> SEQ ID NO 993
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
```
gagucccaga agaagaaaaa aag 23

<210> SEQ ID NO 994
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
gagucccagg agaagaaaaa cag 23

<210> SEQ ID NO 995
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
gagucagaac agaagaacaa cag 23

<210> SEQ ID NO 996
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 996
gaguccaaga agaataagaa tag 23

<210> SEQ ID NO 997
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
gaauccaagc agaagaagag aag 23

<210> SEQ ID NO 998
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
gagucagacc aggagaagaa gag 23

<210> SEQ ID NO 999
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
aaguccgaga agaagcagaa aag                                         23

<210> SEQ ID NO 1000
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1000
gaguctgggc aggagaagaa gag                                         23

<210> SEQ ID NO 1001
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1001
gaguctgaac ggaagaagaa aag                                         23

<210> SEQ ID NO 1002
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1002
aaguctgagc agaagaagca cag                                         23

<210> SEQ ID NO 1003
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
aaguccgagg agaggaagaa agg                                         23
```

```
<210> SEQ ID NO 1004
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
gaggcccagc agaggaagaa gag                                              23

<210> SEQ ID NO 1005
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1005
gagutccaga agaagaagaa gag                                              23

<210> SEQ ID NO 1006
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1006
gaguactaga agaagaagaa aag                                              23

<210> SEQ ID NO 1007
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1007
gacucctagc aaaagaagaa tgg                                              23

<210> SEQ ID NO 1008
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

<223> OTHER INFORMATION: /note="Description of Combined DNA/RNA
      Molecule: Synthetic oligonucleotide"

<400> SEQUENCE: 1008
gaguuugagu agaagaagaa gag                                              23

<210> SEQ ID NO 1009
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
gaguaagaga agaagaagaa ggg                                              23

<210> SEQ ID NO 1010
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
gaguaggagg agaagaagaa agg                                              23

<210> SEQ ID NO 1011
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1011
gaguccuagc aggagaagaa gag                                              23

<210> SEQ ID NO 1012
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1012
gatuccuacc agaagaagaa tgg                                              23

<210> SEQ ID NO 1013
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
                      Synthetic oligonucleotide"

<400> SEQUENCE: 1013
gagucccagc aaaagaagaa aag                                              23

<210> SEQ ID NO 1014
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
gagagcaagc agaagaagaa ggg                                              23

<210> SEQ ID NO 1015
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
aagucagagg agaagaagaa aag                                              23

<210> SEQ ID NO 1016
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1016
gaguctaagc agaagaagaa gag                                              23

<210> SEQ ID NO 1017
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1017
acguctgagc agaagaagaa tgg                                              23

<210> SEQ ID NO 1018
<211> LENGTH: 12
<212> TYPE: DNA
<213> ORGANISM: Homo sapiens

<400> SEQUENCE: 1018
gaagaagaag gg                                                          12
```

```
<210> SEQ ID NO 1019
<211> LENGTH: 13
<212> TYPE: DNA
<213> ORGANISM: Homo sapiens

<400> SEQUENCE: 1019
gaagaaggaa ggg                                                          13

<210> SEQ ID NO 1020
<211> LENGTH: 13
<212> TYPE: DNA
<213> ORGANISM: Homo sapiens

<400> SEQUENCE: 1020
gaagaaagaa ggg                                                          13

<210> SEQ ID NO 1021
<211> LENGTH: 15
<212> TYPE: DNA
<213> ORGANISM: Homo sapiens

<400> SEQUENCE: 1021
gaagaattag aaggg                                                        15

<210> SEQ ID NO 1022
<211> LENGTH: 14
<212> TYPE: DNA
<213> ORGANISM: Homo sapiens

<400> SEQUENCE: 1022
gaagaacaga aggg                                                         14

<210> SEQ ID NO 1023
<211> LENGTH: 11
<212> TYPE: DNA
<213> ORGANISM: Homo sapiens

<400> SEQUENCE: 1023
gaagagaagg g                                                            11

<210> SEQ ID NO 1024
<211> LENGTH: 11
<212> TYPE: DNA
<213> ORGANISM: Homo sapiens

<400> SEQUENCE: 1024
gaagaaaagg g                                                            11

<210> SEQ ID NO 1025
<211> LENGTH: 12
<212> TYPE: DNA
<213> ORGANISM: Homo sapiens

<400> SEQUENCE: 1025
gaagaaagac gg                                                           12

<210> SEQ ID NO 1026
<211> LENGTH: 11
<212> TYPE: DNA
<213> ORGANISM: Homo sapiens

<400> SEQUENCE: 1026
```

```
gaagaagacg g                                                          11

<210> SEQ ID NO 1027
<211> LENGTH: 13
<212> TYPE: DNA
<213> ORGANISM: Homo sapiens

<400> SEQUENCE: 1027
gaagaaaaga cgg                                                        13

<210> SEQ ID NO 1028
<211> LENGTH: 13
<212> TYPE: DNA
<213> ORGANISM: Homo sapiens

<400> SEQUENCE: 1028
gaagaataga cgg                                                        13

<210> SEQ ID NO 1029
<211> LENGTH: 13
<212> TYPE: DNA
<213> ORGANISM: Homo sapiens

<400> SEQUENCE: 1029
gaagaacaga cgg                                                        13

<210> SEQ ID NO 1030
<211> LENGTH: 14
<212> TYPE: DNA
<213> ORGANISM: Homo sapiens

<400> SEQUENCE: 1030
gaagaataag acgg                                                       14

<210> SEQ ID NO 1031
<211> LENGTH: 12
<212> TYPE: DNA
<213> ORGANISM: Homo sapiens

<400> SEQUENCE: 1031
ggagaagaag ag                                                         12

<210> SEQ ID NO 1032
<211> LENGTH: 13
<212> TYPE: DNA
<213> ORGANISM: Homo sapiens

<400> SEQUENCE: 1032
ggagaaagaa gag                                                        13

<210> SEQ ID NO 1033
<211> LENGTH: 11
<212> TYPE: DNA
<213> ORGANISM: Homo sapiens

<400> SEQUENCE: 1033
ggagagaaga g                                                          11

<210> SEQ ID NO 1034
<211> LENGTH: 11
<212> TYPE: DNA
<213> ORGANISM: Homo sapiens

<400> SEQUENCE: 1034
```

```
ggagaaaaga g                                                              11

<210> SEQ ID NO 1035
<211> LENGTH: 14
<212> TYPE: DNA
<213> ORGANISM: Homo sapiens

<400> SEQUENCE: 1035
ggagaataga agag                                                           14

<210> SEQ ID NO 1036
<211> LENGTH: 12
<212> TYPE: DNA
<213> ORGANISM: Homo sapiens

<400> SEQUENCE: 1036
gaagaagaag ag                                                             12

<210> SEQ ID NO 1037
<211> LENGTH: 13
<212> TYPE: DNA
<213> ORGANISM: Homo sapiens

<400> SEQUENCE: 1037
gaagaaagaa gag                                                            13

<210> SEQ ID NO 1038
<211> LENGTH: 11
<212> TYPE: DNA
<213> ORGANISM: Homo sapiens

<400> SEQUENCE: 1038
gaagagaaga g                                                              11

<210> SEQ ID NO 1039
<211> LENGTH: 11
<212> TYPE: DNA
<213> ORGANISM: Homo sapiens

<400> SEQUENCE: 1039
gaagaaaaga g                                                              11

<210> SEQ ID NO 1040
<211> LENGTH: 384
<212> TYPE: DNA
<213> ORGANISM: Homo sapiens

<400> SEQUENCE: 1040
cccagtggct gctctggggg cctcctgagt ttctcatctg tgcccctccc tccctggccc         60
aggtgaaggt gtggttccag aaccggagga caaagtacaa acggcagaag ctggaggagg        120
aagggcctga gtccgagcag aagaagaagg gctcccatca catcaaccgg tggcgcattg        180
ccacgaagca ggccaatggg gaggacatcg atgtcacctc caatgactag ggtgggcaac        240
cacaaaccca cgagggggca gagtgctgct tgctgctggc caggcccctg cgtgggccca        300
agctggactc tggccactcc ctggccaggc tttggggagg cctggagtca tggccccaca        360
gggcttgaag cccggggccg ccat                                               384

<210> SEQ ID NO 1041
<211> LENGTH: 23
<212> TYPE: DNA
```

<213> ORGANISM: Homo sapiens

<400> SEQUENCE: 1041
gtcacctcca atgactaggg tgg                                          23

<210> SEQ ID NO 1042
<211> LENGTH: 23
<212> TYPE: DNA
<213> ORGANISM: Homo sapiens

<400> SEQUENCE: 1042
gacatcgatg tcctccccat tgg                                          23

<210> SEQ ID NO 1043
<211> LENGTH: 23
<212> TYPE: DNA
<213> ORGANISM: Homo sapiens

<400> SEQUENCE: 1043
gagtccgagc agaagaagaa ggg                                          23

<210> SEQ ID NO 1044
<211> LENGTH: 23
<212> TYPE: DNA
<213> ORGANISM: Homo sapiens

<400> SEQUENCE: 1044
gcgccaccgg ttgatgtgat ggg                                          23

<210> SEQ ID NO 1045
<211> LENGTH: 23
<212> TYPE: DNA
<213> ORGANISM: Homo sapiens

<400> SEQUENCE: 1045
ggggcacaga tgagaaactc agg                                          23

<210> SEQ ID NO 1046
<211> LENGTH: 23
<212> TYPE: DNA
<213> ORGANISM: Homo sapiens

<400> SEQUENCE: 1046
gtacaaacgg cagaagctgg agg                                          23

<210> SEQ ID NO 1047
<211> LENGTH: 23
<212> TYPE: DNA
<213> ORGANISM: Homo sapiens

<400> SEQUENCE: 1047
ggcagaagct ggaggaggaa ggg                                          23

<210> SEQ ID NO 1048
<211> LENGTH: 23
<212> TYPE: DNA
<213> ORGANISM: Homo sapiens

<400> SEQUENCE: 1048
ggagcccttc ttcttctgct cgg                                          23

<210> SEQ ID NO 1049
<211> LENGTH: 23

<212> TYPE: DNA
<213> ORGANISM: Homo sapiens

<400> SEQUENCE: 1049
gggcaaccac aaacccacga ggg                                              23

<210> SEQ ID NO 1050
<211> LENGTH: 23
<212> TYPE: DNA
<213> ORGANISM: Homo sapiens

<400> SEQUENCE: 1050
gctcccatca catcaaccgg tgg                                              23

<210> SEQ ID NO 1051
<211> LENGTH: 23
<212> TYPE: DNA
<213> ORGANISM: Homo sapiens

<400> SEQUENCE: 1051
gtggcgcatt gccacgaagc agg                                              23

<210> SEQ ID NO 1052
<211> LENGTH: 23
<212> TYPE: DNA
<213> ORGANISM: Homo sapiens

<400> SEQUENCE: 1052
ggcagagtgc tgcttgctgc tgg                                              23

<210> SEQ ID NO 1053
<211> LENGTH: 23
<212> TYPE: DNA
<213> ORGANISM: Homo sapiens

<400> SEQUENCE: 1053
gcccctgcgt gggcccaagc tgg                                              23

<210> SEQ ID NO 1054
<211> LENGTH: 23
<212> TYPE: DNA
<213> ORGANISM: Homo sapiens

<400> SEQUENCE: 1054
gagtggccag agtccagctt ggg                                              23

<210> SEQ ID NO 1055
<211> LENGTH: 23
<212> TYPE: DNA
<213> ORGANISM: Homo sapiens

<400> SEQUENCE: 1055
ggcctcccca aagcctggcc agg                                              23

<210> SEQ ID NO 1056
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1056

```
gacaucgaug uccuccccau                                              20
```

```
<210> SEQ ID NO 1057
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1057
gacaucgaug uccuccccau tgg                                          23
```

```
<210> SEQ ID NO 1058
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1058
gacaucgaua gccuccccac tgg                                          23
```

```
<210> SEQ ID NO 1059
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1059
gacaccgaug ucaucuccau cag                                          23
```

```
<210> SEQ ID NO 1060
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1060
gacaugaaug accuccccau cag                                          23
```

```
<210> SEQ ID NO 1061
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1061
gaaaucaagg uccuccccau agg                                          23
```

<210> SEQ ID NO 1062
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1062
cacauaggug uccuccccau agg                                              23

<210> SEQ ID NO 1063
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1063
gcgccaccgg uugaugugau                                                  20

<210> SEQ ID NO 1064
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1064
gcgccaccgg uugaugugau tgg                                              23

<210> SEQ ID NO 1065
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 1065
gggccatggg uugaugugac gag                                              23

<210> SEQ ID NO 1066
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1066
gcccgggtgg aactggtagc catgaat                                          27

<210> SEQ ID NO 1067
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1067
gttgaagatg aagcccagag cggagt                                    26

<210> SEQ ID NO 1068
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1068
gcttccgacg aggtggccat caaggat                                   27

<210> SEQ ID NO 1069
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1069
gcaccatctc tccgtggtac cccgggt                                   27

<210> SEQ ID NO 1070
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1070
ggtggaactg gtagccatga atgaga                                    26

<210> SEQ ID NO 1071
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1071
gccatgaatg agaccgaccc aaagagc                                   27

<210> SEQ ID NO 1072
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 1072
gcatcctcgt gggcacttcc gacgagg                                               27

<210> SEQ ID NO 1073
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1073
gcagagcgga gtgctgttct cccaagt                                               27

<210> SEQ ID NO 1074
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1074
ggtcggtctc attcatggct accagt                                                26

<210> SEQ ID NO 1075
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1075
gcaataaaag gtgctattgc tatagt                                                26

<210> SEQ ID NO 1076
<211> LENGTH: 20
<212> TYPE: DNA
<213> ORGANISM: Sus scrofa

<400> SEQUENCE: 1076
gggagtcttt cgctagggtg                                                       20
```